US007906289B2

(12) United States Patent
Juo

(10) Patent No.: US 7,906,289 B2
(45) Date of Patent: Mar. 15, 2011

(54) USING GENETIC POLYMORPHISMS OF THE BICD1 GENE AS A METHOD FOR DIAGNOSING AND TREATING MYOPIA

(75) Inventor: Suh-Hang Hank Juo, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 12/180,820

(22) Filed: Jul. 28, 2008

(65) Prior Publication Data

US 2010/0021889 A1 Jan. 28, 2010

(51) Int. Cl.

*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search ........................ None
See application file for complete search history.

(56) References Cited

OTHER PUBLICATIONS

Lucentin J. The Scientist (Dec. 20, 2004) "Gene assocaition stidues typically wrong", p. 20.*
Hegele R.A. Arterioscler Thromb Vasc Biol. 2002;22:1058-1061.*
Data Changes that Occur Between Builds, from www.ncbi.nlm.nih.gov, printed on Oct. 28, 2008, pp. 1-3.*
Hacker U.T. et al. Gut (May 1997), vol. 40 No. 5, pp. 623-627.*
Juppner H. Bone (Aug. 1995) vol. 17 No. 2, Supplement pp. 39S-42S.*

* cited by examiner

*Primary Examiner* — Stephen Kapushoc
(74) *Attorney, Agent, or Firm* — Pai Patent & Trademark Law Firm; Chao-Chang David Pai

(57) ABSTRACT

Using the BICD1 gene as a method for diagnosing myopia and/or myopia related complications is provided. The method includes obtaining a biological sample from a subject, and determining at least one SNP genotype in the BICD1 gene in the biological sample, wherein the presence of the SNP genotype indicates that the subject is susceptible to myopia. The SNP genotype is selected from the group consisting of SNPs rs7966276, rs1151029, rs2650122, and rs10771923. In addition, the present invention also provides a method of screening a material for preventing, treating myopia, and a method of assessing a subject for probability of response to a myopia therapeutic agent.

2 Claims, 1 Drawing Sheet

SEQUENCE LISTING

```
<160> NUMBER OF SEQ ID NOS: 1

<210> SEQ ID NO 1
<211> LENGTH: 270957
<212> TYPE: DNA
<213> ORGANISM: Homo sapiens
<220> FEATURE:
<222> LOCATION: Intron 8, Chromosome 12q11
<223> OTHER INFORMATION: Bicaudal D Homolog 1 (Drosophila) (BICD1) gene

<400> SEQUENCE: 1

atttccttct ccctttcccc gccagcttcg catccatctc ccccaccccg taaccccctc     60

ctgcctccat ccaccggggc tatggccgca gaagaggtat tgcagacggt ggaccattat    120

aagactgaga tagagaggct aaccaaggag ctcacggaga ccacccacga gaagatccag    180

gctgccgagt acgggctggt ggtgctggag gagaagctga ccctcaaaca gcagtatgat    240

gaactggagg ctgagtacga cagcctcaaa caggagctgg agcagctcaa agaggtgagt    300

tgcctgtcac ctctcccttt cctggccctc actcccccca cccgcaaggc ccactcatca    360

tgatcaagaa gtcataaagg aggtgattga aaggactgtt ttttcttcta gggccctttg    420

ttggtaagag aagattgaaa gagtccattg tttcctcccc caagagaaaa attgcctaag    480

aaatgaatat ataagctgga atttgggagg caatggctgt ttggcctgcg ggggagggag    540

attagtaaga gtcatcaagt ctcagcactc taagacgaca ttcaagtggg ttggaatgta    600

taaatcaaac ttctcaaaac cgctgttatc tcaaacccag gtttcagcga caatttcgta    660
```

-continued

```
gtccacaaaa gtgatgaggt ttgtgcctga ggacccacaa tttcaggatt tagactgtgt    720
ggcacctcag ctttcctctg gatgtaacca ctccttggtg agagagggaa ctcctcacca    780
atcccatttg acaaaggcta ggcaatcttc attctgcttg gctttagtca ttcttgtcat    840
tgggctgcag aagaaaaaca actttgctgg gtgatcccac tgccttgatt tcacctcgga    900
gcgaggctgg gccatgtcca agtcttatga ggtcaccctg actagaaaaa attgaactca    960
cctacaaata gtctgaaaga gtggtgtata tcaaatacgt gggtagtgtt gcatttcaaa   1020
tgaggctctt ctggttgaaa tgatatattt ataaaaccag aatatcaaaa atgggtgatg   1080
tataatgtct ctttagtttt ttggtatttg gcctctttta aagcctgtcg gatgtatggg   1140
agaaaacaat gaacgtgctt tgatttccta tcagtcactc ttaagaacat acatattgtt   1200
taagtaactc ggtctttttt atctgattct tgaggcacta tgggtagcaa ataaccactt   1260
acaaatttaa atgtaatata cactcctttt ctgtgtgtca agtccttatt tttaggtgca   1320
tattgacatt taaatgttaa ttattgtttg gcatataata tcaaaaatct attatttatt   1380
ttatgctgtt acagttaaaa gatgtgattt atgacatact gaatcaactt gccttccaat   1440
ttagtgtgta atatggtaag catttatact tttagatatg tcttattttt atttggatgc   1500
ctgtctacca aaaaataaat gtactaccta tgattaaaaa tcccaactag gaatctaatt   1560
tttgtgtgtc aggctgtaaa tttctggttc ctattttact taccatgtac ctgtctggtc   1620
ttaacaacag ctggacttgt ttatattttc caacttagat taggctgaca tgtttaaatg   1680
cagtgatgct aaaccttgtg aagtgaggaa gcaggatgat gactgtcatt ctcagagatg   1740
ttttgatatt gtctatacct atcaacactg ctttgccaag atagggaagt gcaaaccaga   1800
aagtggtaag ccatcacctt cttgataaag gagatggact taatttaatg aaatgtacct   1860
cttactgact ttgctgcttg atttaaacaa tccttctagg gatatttctg tcattgcact   1920
taccttgcat agcaaacctt aatgcaattg tgttttgcct ttgctacacc atgagctttg   1980
catcccaagt ctttaacaca aaagctagca cacagtgggc atgaaatatt ttatgaaaga   2040
atcagtttgt actagaagaa ggcacacttt tatcaagggt tcactagtca atattgatta   2100
gtgttagata aatactaaga aaattaggat gtataggaag tgacagatgt taataaaact   2160
acctgtatta gtttcaccag cagtaatgag aaaaatgtga aaaaaacgtt ttgtaggaat   2220
aatgtaactg tggtttctta atacagaata atgcaaatac caactaaaat tttttctata   2280
aatattttaa tatatatttt gttctatata gcaggaggtt aataaaaatt taccagcatt   2340
atttttacta aacgattctt gttcatatat ttattttcag ttgcatttag cataagtgaa   2400
attcgagatt cctaaaaaac tggtttatac agttatataa aaatgtattt taggtaataa   2460
aattattata gttgattatt tgatagtgag gcctattatt tttattcttt aaacatagaa   2520
tatactttag ttggaaatat aacttaaatg agttaaattg atttcaagta acatttcttg   2580
tatgaaaagt aaatccaaaa taattgtgca aactgaggtg ttccaacacc tcagttttga   2640
aaaatatttt gtgagtgttt tgatttttca aaagaaagtt ttgctcatca ggtatgtata   2700
gtaaatgatg ttgcattata tctataaagc caagcataaa ataaatcttt gcttatttct   2760
aggatttttg aacaaatatg atttatttaa aaataattga accagtttat gggaatgtca   2820
acagaaaact actgtattaa gtccaaattg gacattagta atttgcagta tagcaacatg   2880
gctcagtctt tgcagatcat tttgttttcc agagtcagta cccaccaatg ttgctacctt   2940
ccttcccagg ctaggtactg ctgtgacaat aatgcaagtc ggcagtgttg cctaaagatg   3000
tgcaaaatca agaagatgaa attcattaaa tttttttcct agttatttct tccctcaact   3060
```

-continued

```
caattgtttt ttgacctggc ctgatgttgt ttagtgctct gcatggacta ctgtaattca   3120
gctcacagaa gaacacactt gaaagaatag tactaaggat ttgaaaaaag gatgacttct   3180
gacatcatca aagtgttctc cttttcatga ttctttgggc agctggacag agcagtatgt   3240
ccactagaat acttgagtct ggttttgtga tttcacaagt aacacttgct cttcagtgac   3300
ctgagtgagg gtcacccatg cccagttatg ttcagggcct ggctgattat atgtttggga   3360
tgtacgtaaa tcagcactgt gcgcctgtca cccaggccag aatagtgttt gaagaagagt   3420
catagctcca aaataacctg aaaactaaaa atatacatat ataaaaatac cttggatcta   3480
aacttaagag tttttttac accgcatgtt ctcactcata gatgggaatt gaacaatgag   3540
aacacatgga cacaggaagg ggaacatcac actctgggga ctgttgtggg gtggggggag   3600
gggggatgga tagcattagg agatatacct aatgctaaat gacgagttaa tgggtgcagc   3660
acaccagcat ggcacatgta tacatatgta actaatctgc acgttgtgca catgtaccct   3720
aaaacttaaa gtataataat aaaaaaaaag agttttttt taacttaaaa atggttgaaa   3780
tttaaaatgt tgtaaagttg aaaaagagcc ccttagaaag gaatgattca gcattactga   3840
tggcatttta aaaaggaaat gtatctgtga gacagcttta gaaaagtttt gcagcttgga   3900
taccgtaaac tatgcactaa tgagcttcaa cccattttct tgcttatttt gtcaaccctg   3960
acaccaagga tagttaccag ctgctgaaga agcactttct ggacattggg cagctttttc   4020
ttttggagcc aactctattc tttttcaggg ttatagttaa atcattcaac acaaaaaatat   4080
gtacttacac agttttagag cttgtcacat tggtgacctg atgaatgcca cttaaattac   4140
ctagattcat ctttaagcag aattgttttc ccttcagatg cttagaaaga ttgttagttt   4200
cttttatatc tttaagttct aaatcacaaa atcatatggc aagaaaaacc ccagatttct   4260
tttccaatct atgaataaac ataaagagac agttaatact taattgatct atctgaacta   4320
tgatttttaa cttctctcat tgtttttatt tttttatttt attttatttt attttgagat   4380
ggagtctcgc actttcaccc agcctggagt gcggtggtgt gatctcggct cactgcaagc   4440
tccacctccc gggttcacgc cattctcctg cctcagcctc cggagtagct gagactacac   4500
gcattcacca ccacacctgg ctaatttttc gtatttttag tagagatggg ctttcacctt   4560
gttagccagg atggtctcga tgtttttaaa gaaaaaatat ttacatttat tatcaaatta   4620
atcttaaaat ctaaaataca ttaagatatg cttttggaaa ctgtttacaa acaacctcaa   4680
caaataaaca tcatcgcttt caatcacatt tcttttttc tggacccagt tgctctaact   4740
tgcactatcc ctttttttt ttttttttt tttgagatgg agtttcactc ttgttgccca   4800
ggctggagtg caatggtgtg atctcggctc accgcaaatt ctgcctcttg ggttcaagtg   4860
attcttctgc ttcagcctcc cgagtagcta ggattacagg catgcgccac cacacctggc   4920
cagttttgta tttttagtag agatagcgtt tcttcatgtt ggtgaggttg gtcttgaact   4980
cccgacctca ggtgatccgc ctgcctcagc ctcccaaagt gctgggatta caggcgtgag   5040
cccccacgcc cagccccttc tttttatttg aaatcaagat ttcgtctctg gcgaagttat   5100
ttctcagata taacttagca agaatttatc atcttttatc acattcccca tgtttatgtg   5160
aacatgtatg acagcgatgg tttgaaggtt tcttcagaac tttctgcttg caaatatttt   5220
gccctatcat ccccttaaat atagttgtac tcatggatat tgctttccaa atttgaaaat   5280
acggtaatta attacttgca tgttgaaata tacataaagg acttgcccac acataagatt   5340
ccacctgtaa ttatggcttt gaggagagga gggcatgaag ggctgcatag tcttagtatt   5400
aaataattca ttacgctaaa ggagaatgca cgtaaagtca agtggcagga gatgcaattg   5460
```

-continued

```
tgaaagggcc atggccacat tttgtcttgg ggatgtggag ccattgaaaa taaatgaaac   5520

agtcactgtg tttaatctca ccagtcttca aaacaattca gagggcttac tgctcatttt   5580

tactgataag aagataataa aaataataaa gcattgactt aggtacaagg ctccatttag   5640

aactaggttc tttacaagcc tcacctctaa ttcatgcagc aatccttact caaggtaggt   5700

gtttcttgca ttatacagaa gaggaaactg ggtcttagag aggtttaggt ctcttcccag   5760

ggccacaaaa ctaaacgatg aaacttggaa gaagcccact ttttttcac tgcatcatac    5820

taccttgaat atgaaatatc tctgccaagt ctacaagtgc agtatagaag gttatggtga   5880

tggtcatagt gggtggattg aggctgtgtg gtgggacaga cagtggcagt agggatcgtg   5940

aggaggggc acgtctaaga gctatttggg aggtagggtg gaacaggcat tggatgttac    6000

tatatgtgga aagtgaggaa gacagtggag ctgagaatct tctcaggctg gataggaggt   6060

ggttctattt acaaaggaag gtattatggg gcagagcagt tttagagggt gaaattgatg   6120

ctcaagttac atgagtttct gttgtttttg acacagggtt tctctctgtc acccaggctg   6180

gagtgcagtg gtgctgttac agctcaccgc aaccttaact aaccatcctg gctcaagtga   6240

tcctcccatc tcagcctccc aaggagctgg gaatacagac ccatgccacc atgcctggct   6300

aattttttt tgagactgag tctccctctg tttccccagc tggagtgcag tggcatgatc    6360

tcagcccact gcaacctttg cctcctgggt tcaagtgatt ctcctgcctc agcctcccaa   6420

gtaactggga ctacaggagc ataccaccat gcttgggtaa ttttttttt tttttttgag    6480

ctggaatctc actctatcac ccaggctgga gtgcagtggt ctgatctcag ctcactgcaa   6540

cctccacctc ccaggttcaa gcgattctcc tgcctcagcc tcctgaatag gtgggactac   6600

aggtgcctgc caccatgcct gaataatttt tttttttcca agacagaatc tcgctctgtc   6660

gcctaggctg gagtgcagtg gcgcaatctc ggcttactgc aacctctgcc tcccgggttc   6720

aagtgattct cctgcgtcag ccacctgtag atgggattat aggcgcgcgc caccacgcct   6780

ggctagtttt tgtatttttt ttagtagaga cagggtttca ccatgttggc cagagtggtc   6840

ttgatcttct gacctcgtga tccacccacc ttggcctccg aaagtgctgg gattataggc   6900

atgagccacc gcgcccagcc taatttttgt acttttagta gagagaagat ttcaaacatg   6960

ttgcccaggc tggtctgaaa ttcctgagct cgagcgatct gcctgccttg ccctcgtaaa   7020

gtgtggagat tacaggcatg agccattgtg cccagccaca taagtccttt taattcatgt   7080

tttctttgct ggggaagcgt acattgcatg atggattcag atcctcaact ttcttttttt   7140

tctttttttg agatggggtc tcattttgtc acctaggctg gagtacagtg gtgtgatcgt   7200

ggcttactgc agccttgacc tcctgggctc aagcaatcct catgcctcag cccccaagta   7260

gctgggacta caggtgcaca ccgccatgcc tgactaattt ttgtattttt tttgtagaca   7320

cagggttttg ccatgtaagc caggttggtc tagaactctt gagctaagga cagtccgcct   7380

gttttggcct cccaaagtgc taggattaca ggctaacttt caatttaata aaaaaaatta   7440

atttgtgcaa ttggttgtta ttttatagaa gcctaatttc tagaatatgg gatataaaca   7500

atttaataat gttttcacca gttagtttga ttgctttcta aattaggaaa aatgaaaaca   7560

aataaacgat gggcaaaaaa gctgactggg gacagtaagg tctaagaagg cagcctaagt   7620

ggaaaattag cccttactca ccatttaggg ttatgggggc tgggagcaac agtcctcact   7680

gctcactgac taatctttat caatcttatt taatctttat tgaagatgca ttagcatttt   7740

taatttaagt gggttttttt cctcttttct tttggtgggg ggtgtgggcg gcgggggagt   7800

ttcaatatgt tgaccaggct ggtcttgaac tcctggcctc aagcgattct ccctcctcag   7860
```

-continued

```
cctcccaaag tgctgggatt acaggcatga gccattgcac ccagcctttt ctatttttca   7920
tttcaagagt ttgcttttta agaattaaaa ttgtgtaatt atgacagttt ttattgcagt   7980
actccaagct agagaaaagc atatataaat taatagtttt cccttcttct cccacagttc   8040
tgtctctgtt gttaacactt tgctgagtat tcttctgtac ttgttttaaa tgtctttaaa   8100
catataggca gggtttttgt gtgtgtggtg tttttggttt tttttttttt gctgtttttc   8160
ttcctttgtt tttataaaaa caggatcttg cagcctggtg ttttaaattt agtagtatgt   8220
cctttcaaaa ggcaggtatt tacgagacaa agctgcattt ttaaagcact ggtgaagtgt   8280
gaagaaaatg agaccgatta gggaagaaaa cccgagaagc tcagagtttg ggtgaccctg   8340
gggatgtggg aaggtggtga aaatggtacc ctgagggtag catggatggt aagtgaaaga   8400
ggaaaaggtg taggtttgca taaaagaaac tgatggaatt tggatgccca atagcagacc   8460
caggggaatg ataccagggg aaaagatgga cagttttgtg ggtaaattag cagtgatttt   8520
gattccttgt cttgttagct gctgatggag atacgtgtat cagcataata cctggctagt   8580
ttccatggcc ggcaagagcc agtcctgcag tgtgaccaca tcctgtccat tctgggtctt   8640
ggtggcaagc caggatgatt caggcagttg ggctttatta cgttatccct tctttgccct   8700
ctgaaagctg agttttgaaa tagttaggat cttatacaac atctcagatt cagcatgctg   8760
tgcaggaggt ggggagaaaa gggtacaaaa gaggaaaatg ttcagtgaag gtgttattac   8820
aatggagggg aatatgaaag tggaaattga taccttttcc tcttgggatt taattaagtc   8880
tataaaatta aggtgttgca atacataatg tctatgattt ttttttacca gctctaaatc   8940
tctgagatgg ctgtgtttta gagctgcatg ttctgcttat ttactgcctg tcctttacat   9000
ttcaaattca ttcaatattt ttccaaagta cagaatagtt ttgcctagtt gcagtaattt   9060
tcacctagac ttcagggatc ttccatcaac tcttttatgt atttttctc ctttgttttt   9120
ccactctggt cactcagttc tagccaagat agtccacctt attttagcac ttgtactatg   9180
tctctgtctc tgtctgtctg tctgtctgtc tgtctctctc tctctctctc tctctctctc   9240
tttctctctc tctctctctc tatatatata tatatatatg taattttgag atggagtctc   9300
actctgtcgc tctgactgaa gtacagtggt gcgattacag cccactgcag ccttgacctc   9360
acaggttcaa gtaatcctcc cacctcagcc tccagagtag ctgggaccac aggtgcacac   9420
cactatgctg gctatttttt tttttttaa cctgattttg tttttactgg aggctcaggt   9480
ggcccaacta atttttagaa attattattt gcagagatga ggttttgtta tgttgctcag   9540
gctggtcttg aacttctggg ctcaagtgat tctcccacct cagcctccca aagtgttggg   9600
attgtaggtg tgaactactg tgcctggcct tctacatttt ttttttaacc atttcatagt   9660
tcccttttc tttgaacact tggtccaaac tcacttttct tctggattca tattttctga   9720
tctcacctat tatgttatag aactgatatg ttacgtttgt tttcattgat gcgtctgtac   9780
ttggcttcag agagcagaac aaggccctgt gagtcactgg gagccagatt ttggatcaaa   9840
ataaatcact ttctgacaag tgtagttgtc tagtaatgga atgaggcagt cttcttagga   9900
agtaatgaat tccctgtcac caaaagggag aagctagtga gccacttgct gagaatactc   9960
tatggggagt tgtccttagg aaggggtata tctagaatga tctctaaggt tcattcttat  10020
tcggatttct ttgattttta tcattccagg tgttccaaat aatttgataa gtttatgttt  10080
tttatacttt tcccaccacc agagcagtgt ttccaacatg gttaaattgt tctgctttaa  10140
tgtttggcat ttcacactat ttgatgactg taaacatttg gaatgttttc acagtgtctc  10200
aaaactttat tttgatttat gttttgcttt attttcagaa gaaaactaat gggtaatata  10260
```

-continued

```
aagctttaag atgagtgtat ctctaaattt ggagagcttt cagtgaaact gtacattttg  10320
aagctacgtg gttgcattga gggaggtcta cagcctccag aatcttcttt ttcacacaca  10380
cgggcacatg tgcatgtgca tgactttata ttttgtcatt tacgcttagt catatatata  10440
tatatataca caaatatata tacacacaca cacacacaca cacacatata tatatatata  10500
tatatatatt ttttttaag accatatttc gctctcgttg tccaggctgg agtgcaatgg  10560
catgatctca gctcaccgca acctccacct cccagtttca agcaattctc ctgcctcagg  10620
ctcccgagta gctgggatta caggcatgca ccaccatgcc cagctaattt tgtattttta  10680
gtagagacag ggtttctcca tgttggtcag gctggtcgcg aactcctgac ctcaggtgat  10740
ctgctcgcct cggcctccca aagtgctggg attacaggcg tgagccatcg caccggcccg  10800
cttagtccaa tattttattt tattttattt tattttattt attttttttg agatggagtc  10860
tcactctgtc gcccaggctg gagtgcagtg gcgcgaactc ggctcactgc aagctccgct  10920
tccctgggtt catgccattc tcctgtctca gcctcccaag tagctgggac tacaggtgcc  10980
cgccactacg cctggccaat tttgtattt ttagtacaga tggggtttca ccgtgttagc  11040
caggatggtc tcgatctctt gaccttgtga tccgcccgcc tcggcctccc aaagtgctgg  11100
gattacaggt gtgagccacc gagcctggcc tagtccaata ttttataatc tgcatcgtca  11160
actagtcagg ccccagaatc tgtgggttca gcatccttgg attctgcatc cttggattga  11220
aaatatttgg aaaaaaaatt gcatcggtac taaacgtata caggcttttt ttggtcattg  11280
ttccctgaat aattcagcat aacagctatt tacatagcat ttacatcgta ttaggtatta  11340
taagtaatct agagatgatt taatgtatac tggaggatgt gtgtaggtta catgcaaata  11400
ctacactatt ttatctcaga gacttgagca tctgtggatt ttggtatctg caggggggtcc  11460
tggaaccccc acaccctcac ccagactgag ggatgactgt atttacgtta tctaccactc  11520
tgatgttttc tttttgcttt agattgccca ttacctcttc atctgtttca tttattcatt  11580
caaaaatttg tattgagtgg ctactgtgtc gggcatggtg ccacttgctg gagatacagc  11640
gttgaacaag acagacccaa tggggctgcc tgggtggagc ttatgtttca gactgggaag  11700
agagtcaacg aacatccaca catatttcag ttgtgagagg tgccatgagg gaagagacag  11760
actggctggg gaaagcgtga tcaggcagtc ttccccagga ggtgagactt gagcccagac  11820
ctgaatgatg acaaggagcc agtcatgtgg agactgggga atgtgatttt taagaagagg  11880
acaagtgcca agatctgcga actctgttgt agttgttagg ggaagggatg ggttaccatg  11940
ctctgtaaaa atgaccattc atatttgaaa tatgaccatt ctgtaacaca gtgtattgcc  12000
tactggattt ttctaatgag gtattgggtc tcaacattgg aaatgtttga gcagaccttg  12060
gatatctccc tgaggtcttc tctgagaaga ggtgggtagg aactagtgac tttcaataca  12120
gactgtatgt tagaatcacc tgggtgattt ataaaactac tgctgcctgg accccactcc  12180
gggagagtta aatcactcat tggaagtgga gcctggcttc agcatgtgaa tcccacttcc  12240
cttagagatg cagccagggt aaagaacccc tcttctatat ttccaacttg aggactaaat  12300
gaccccatgg gcgtagaagt gtttagtaag aaaatctagt tccgggtgca gtggctcatg  12360
cctgtaatgc cagcacttag ggagaccaag gcagatggat catatgaggc caggagtttg  12420
agaccagcct gaccaacgtg gcgaaacccc atctctatta aaaatacaga attagctggg  12480
catgctggca tgcgcctgta gtcccagcta ttcgggagac tgaggcatga gaattgcttg  12540
aacccaggag gtggaggttg cagtgagctg agatcgtgac acttcactcc agcttgggcg  12600
acagaacaag actctgtctc aaaacaaaac aaaacaaaaa actgggaagt tatgagctaa  12660
```

-continued

```
tacataaacc ttcattgcac agtcttttaa aatttgttgt ttctactttc tgaaaatgaa  12720
aatattaaat ccttcctgaa aacagaaaat atcaaaaact taactgcatt agacagagat  12780
atatgttaac tttgagtgca tttaattttg tattcttgag tactgtttaa agtgtctttt  12840
aaaagttctc tcttattgtg tctatttatt ttattctgtt tgcagttttt atgccaactt  12900
tacacatttg taaatagaat atttaaaaag aatttttttt gagggattga tctctaactt  12960
cttggtgact tatagttgtt cttttggttg tacatcttta ctgttttcca acattttaag  13020
gagaaaaagc actactctca aatgtaatat ttaactgctg tgtttctatc tttaaatata  13080
gaattgaaaa tgagaacctg tttatattta tgggagcaat agcaatatgt gtacaataac  13140
agtagcaatt tccttaagaa tgttctgttg cagtttggcg tgggtctgtg atagaaggtt  13200
cagaatgatg ggtctttgtt tttctcttgc atactgcaga gtaatgtgga atcaaatacc  13260
actattgaag agctcttagt catcaatttt tgaaactgaa agaggtttat attgtaagaa  13320
ggatgggccc tgttgataag cctcactgat tgctacttgc tagatggttt taggagatat  13380
cttgaagttg accttgtgtg aggttactgg atggaaacag catgagttta atcttgtaca  13440
tgacttcttt tgttgagctg gagatactat tgtcttgcag attatctctt tggcacgcat  13500
gaccattttt tttttgtctt ttaaatcaca aactggcttt ctttctgcta aggttggtgt  13560
gcttagattc tttaagctcc aaatctcaag aaaatatagg aaggaaaatc aaccattaga  13620
gagagagaga gagagagaga gagagaaaaa aaaaaggaaa aaatataatg tgctccaaac  13680
tgattataaa tagcttttga attgttggct ccatagaatt tttttttttt ttttttgaga  13740
cggagtctcg cgctattgcc caggctggag tgcagtggcg tgatctcagc tcactgcagc  13800
caccgcctcc tgggttcaag tgattctcct gcctcagcct cccgagtagc tgggattaca  13860
ggcgtgtgcc accatgcctg gctaagtttt tgtatcttta gtagagacgg ggtttcacca  13920
tgttggccag cctggtcttg aacctctgac ctcatgatcc acctgtctca gagtgctggg  13980
agtacaggcg tgagccacag cacctggcgt ccatagataa ttttaaaaat tcataccaga  14040
tcttaattaa tgttggcatt aaaaactaat ggtggctcat gcctgtaatc ccagaatttt  14100
gggaggccaa ggtgggtgga tcacttgagg tcaggagttc aagaccagcc tggccaacat  14160
ggtgaaaccc tctctctact aaaaatataa aaattagctg gatgtgatca tgcgtgtctg  14220
taatcccagc tacttgggag gctgaggcag gagaaactct tgaacctggg aggcggaggt  14280
tgcagtgagc taagatcact ccattgcact ccagcctggg cgagagtctt gttctgtctc  14340
caaaaataaa aataaaaata aaaataaaaa taaaaataaa agcgctgagg tggaaggatg  14400
gcttgagccc aggaggcaga gactgcagac agccaagatc gcaacactgc actccagcct  14460
gggcaacaga acaagactct atctcaaaca aacaaacaaa caaagaaaac ctacggttaa  14520
tgatatagtg atctgaacaa cagaagatct cagtttgtca aatttttttt tttttttttt  14580
tgagacaggg tctcactctc ttgcccaggc tggagtgcaa tggtgcaatc tcggctcact  14640
gcagctttga cttcccaggc tcaagtgatc ctcctgcctc agcctcctga gtagctggga  14700
ctacaggtgt gagtcaccac acccagctaa tttttttgta ttttttgtag agacagtgtc  14760
tcacaatgtt gtgcaggctc gtctcaaact gttggactca agacatctac ctgcctcagc  14820
ctccaaaggt gctgggatta caggtgtgta ccactgtacc cagcctcagt ttgttaatat  14880
tttacaataa tttagaagta gaacccttc ttaaggctgg gcgcgctggc tcacacctgt  14940
aatcccagca ctttgggagg ccgaggtggg tggatcacga ggtcaggaaa tcgagaccat  15000
cctaacacag atcgagacca tcctaacaca gatcgagacc atcctgacta acatggtgaa  15060
```

```
acccccgtct ctatgaaaaa tacaaaaaat tagccgggct tggtggtggg cgcctgtagt  15120
cccagctact caggaggctg aggcaggaga atggtgtgaa cctgggaggc ggagcttgca  15180
gtgagctgag atcgcgccac tgcagtccag cctgggcgac agagcaagac tccgtttcaa  15240
aaaaaaaaaa aaacaaataa caaaaaaaga agtagaaccc tttcttaaga gcattctcag  15300
gtcttctatc ttaattactg tagttatttc cagtcatgtt ttataatcag gtgctatttt  15360
tcattgtggc ataataagta atatattttt gtaaatcatg ttgaagtgct tgagacaata  15420
caagcaatta tttgctaaaa tttagaccag ggtctcaaaa caacaattac atttttagat  15480
aatggtcaca gtaagtcttt tcagaaaaaa gcaacgaaga aagctctaga ccaatgagat  15540
tttagtcatc attaatcaat gccaagcgaa aaaatcttaa gatgtattta aatttgtgat  15600
gccagtgtga ttcagaaatt tgaaaaatgg atttcaaagt aatgctgtga gcagataggt  15660
cattgtataa acataactaa tggttcattc attcattcct acaataatga ttcagtgtca  15720
gatttgggtg ttgaaaatac agcagagaac aaacacaaca gaaggtccat atttgcggag  15780
cctacatttt gtgggggaag agagatgata aacaaaatga atgagttaag tagatagcac  15840
gttagatcat ccaaaatgct atggggggaa aaaaccctgg gaatagggag atggcatgtg  15900
aagtggaaga aggttatgat tttcaataga gtgatcagag aaagcctcat tgagaagaca  15960
cactaaggag gccatgtggc tggaggggac tgagttaggg ggtgaatagt aggtgagacc  16020
agagggggcc acatgatgta gcagcttcta gattatcagg actttggctt ttgctctgag  16080
tgagatggga aactttcaga gagctttgag cagaaaagtc acaatgttct gcactttttc  16140
cttcattgag ataacctctg catacattca agcacgacta agaccccctt cagggaaaag  16200
aagttttcat taactcagta tcccatgagg tatatggcat tctcttcctt cccaccatag  16260
caggtgttta ataggtggtt atggtattgc actgatttag gctgggaaaa aattaaagat  16320
gaagttatta agacagccag ttgtggtcgg gcacagtggc gcacgccggt aatcccagca  16380
gtttgggagg ctgaggcggg cggatcacct gaggtcagga gttcaagacc agcctggcca  16440
acatggtgaa accccatctc tattaaaaat acaaaaaata agccaggcgt ggtggcaggt  16500
gcctgtaatc ccagctaccc gggggctgag ccaggagaat agcttgaacc tgggagatgg  16560
aggttgcagt gagccgagat tgcgccactg cactccatcc tgggcgacag agcaagactc  16620
cgtctgaaaa gaaaaaaaaa aaagacagcc agttatttga aaagaggttg gagtagacca  16680
cttgttttaa aaataaccac ttgtttgcct aggttaaacc catttactca aaagacactg  16740
cgctgacttg cctggttcct tgtacctgaa tctttaccta agtgtcttgt gctctctgtc  16800
ctttattctc cataatgcga gctatccagt agaccctagc caaaggggac ataaagacag  16860
tctcaacatt gtattactgg ttctgtgcta cagttgtcat tcaagttcct gagaaaatgg  16920
aatgaatgtc tgttattcat ttatttatta aatctttaga gagcatcatc tatatgccag  16980
gtattatgca ggctatacaa aaattaggaa gacgtgatct ttatttttaa gttacttatt  17040
tgttgttgga ggcaacagag ataaatgaat tgtgatattt tactggaaac aatatgagtt  17100
tttgagttaa gaacagactg tgtttgaaat ccctttagca gctatgtgac cttaggccaa  17160
tatttgaaat gatgtgaacg ttggtttcct cctcagtaaa atggagaatg ataataacta  17220
taagtggtaa ggaaaaatgc atgtgaagga tttaatacag tatctgacac atgacaagca  17280
cttgataaat gatggatgtg atggtgacaa taatagtaat aataataaaa taataatgtg  17340
ttggctgtgc tcgataggag tggagggtag caaactcagc ttgaatcaga gtaatctcct  17400
gatcaggcaa catttgaggg ggctttgaag aataagtagg gattttccgg ggagagaaga  17460
```

```
ggggcaaagt cattcaggaa gatgaaacag cctgtagaag agggaaggct ggagagagtg  17520
ctgcttgtca gtgtctgtgt tgttgcagta gggaggtaga tggaatgggg tgagagggga  17580
ggtgagcctg gagagatggt ttggggccag atggggaaag ctgtgttatg gggcttgtca  17640
gtttctgcca gccaaggctt cagcatagct gactgtaaca aagttgggaa ggccttgctt  17700
ttgagagcca gaccaggagt acctgtgact aacaaggggt ctgggaggat ctgctgctcc  17760
catgccctcc tttgtatatt ttaaatctgt ttgagccttc tgggctcctg tgaattaggg  17820
agaggcagct cctcagtcta actcctactg tgaccaggtt gcctaattgg ccctttggtt  17880
tgggcaccca ctgtcctctg cgtggttgga tagatgctgc tcccaatgtc cctgatctct  17940
tacagacccc tctgattctt cactcttggc tttgagagcc cctgatgccc tgcagtcttg  18000
actgagcttc taatggttga tcagaccctt gaatgttgag ctctttccat actagacttg  18060
aatattctcc tgcccatttg atttgttaat taggattcat tggctgtttc tctgctctcc  18120
tcttttctct ctgttcctgc tggttcaagt ttaacctcca ttttctttct cctctgggaa  18180
gtttccctta tgcctcttga acagggtcaa gagcacttag gagctcagat ttacactgta  18240
tatcatgaga aaagcattga aagtttcaaa gcaggagagt gacataatta gctttatgtt  18300
ttaaagcgga tttttgactt tagattctgg caatacagtg gtcctgtggt ctaagacatc  18360
tgactaacct tcctgctagc aacaattaaa aatgctgagt gcaataaaaa actagccctt  18420
aaatggaatg aatgagtcga ctacttggta aggatgctca gaggctaaaa ctgaatcaaa  18480
gcaggaactc ttagaagtaa gcagtgtgtt ggctaggcgc agtggctcag cctgtaatcc  18540
caacactttg ggaagccaag gcaggtggat cacttgagct caggagtttg agacctgccg  18600
gggcaacatg gcaagacccc gtctctaaaa aaaaaaaaaa atgccaaaat taggcagaca  18660
tggtggcaca cacttgtagt cccagctgct cgggagcctg aggtgggaga atcgcttgag  18720
cccaggaggt ggagtttgca gttagctgag attgtgtcac tgcactccag cctgggcaac  18780
agagcaagac tccatctcaa aaaaaaaaaa aaaaaaaaag cagtgcatca aatctgactt  18840
ttgccttgaa tgcatttgct gaatcagtat tggttcaata ctgagcatta gttttccggc  18900
cacttagagt agaggaaata ggagataaag cctagaatct ccccagattt gggctccaga  18960
ggaccctaca actattgtgg ggggaactgg atgtggtggg aaaaattgta tacctcttct  19020
cagacttcat accccaccaa tgggctctca ccacggtttg cagactgttc acaccgagtt  19080
tgtgtagaaa ggatgaaatc ttaagattag aatgagagtg aacgcaggtt ggtcatgcct  19140
gcagctctct ttgaagacac tcgctatcat ggtgggctag aaatagtcac catagatagt  19200
attcttaaaa aaaaaaaagt tgctggccgg gtatggtggc tcacacctgt aatcttagca  19260
ttttgggagg ccgaggcggg tggatcactt gataccagga gttcgagatc agcctggcca  19320
acatagtgaa accttgtttc tactaaaaat acaaaaatta gtttggcatg gtgatgcaag  19380
cctgtaatcc cagctacttg ggaggctgag gcaggagaat tgcttgaacc cgggaggtga  19440
aggttgcagt gagccgagat cagatcacgc cactgcactc tagcctgggc gacagagtga  19500
gactctgttt aaaaaaaaag aaaaagaccc tgcagaaatt aaaattgtaa aaatataaat  19560
atacaaggaa caggcaccag gcacctttgg ctccacatcc ttgtcatcac ttcatacctt  19620
gtggctctag tttgcatttt tgtggctgct tatgaggtcg tgcctcttca gtatttacag  19680
gcatttatga ctatcctgca ctgaaatgca tttcatgtct ttgctcattt accattggat  19740
tgtttacatt tttcttcctg atttgtaaga gtatacacct atactcatat tctgtatact  19800
aagccttttt agttatttag atatgttgga aatatctttt cctagtccat gggttgtctt  19860
```

```
tttactcttt ctgtggtatc ctttgaagaa gagaagttta taattttaat ttagttgatt  19920

tatcactctt ttgtgtttct aggttgtatt tttctattct taagaaatcc tttccatgaa  19980

gtcataaaaa catgcaccta tattgtcttc tgaatatctt atggtttgac ttttatattt  20040

aaatctttaa ttctccctgg aattgagttt tgtgtttggt gtgaggtaga aatctaattt  20100

aaatttttttc ccatgattcc accccacccc ccaataaaat tagccagtga tctcagtacc  20160

acaggttact gaacagttga tctttcctgc actaatttcc aatgtgtgtt ttgtgataaa  20220

tcaagttttt atatatgcat gggtctattt ttggactatt ctgttacatt ggtttgttgg  20280

tctattcttg tgcaaatgcc acactgtctt actcttacca ttttaatata agttcttggt  20340

agctgatgga ataattcttc ttattttgtt cttccccagg agtcactggc tttggacacc  20400

ttccttgctg tcataggctc tttgctttgg aaagctctca acatttacaa ggaagtgaca  20460

agtgtgaacg aaggcagatc acactgttta tttccgtttc cccaataagc attaaggagg  20520

aggatattga gggtctagtt gtggttgtct tagactttgc acatgttttt ataagcaaag  20580

cagacaagct ccagcaaggg aactcaattg tctaattaga tgttaccaga aatcttattg  20640

gggctgtgat ctaattcttt tttttttttt tgagacagac tcttgctgtg tcatccaggc  20700

tgcagtgcag tggcgcgatc tcagttcact gcagcctctg cctccgaggc tccagtgatt  20760

ctcctgcctc agcctcctag gtagcgggga ttacaggtgc atgccaccac acccggctaa  20820

tttttgtatt tttagtagag acagggtttc accgtgttgg ccaggctggt ctcaaactcc  20880

tgacctcagg tgatctgccc gcctccgcct cccaaagtgt tgggatcaca ggcgtgagcc  20940

accgcacccg gcctgagcta attcttaaga agtcactttg gaaaaaaata ttatttaagg  21000

gcttttcata aagtattcaa aaaggtacaa gttctaatct aacagttcta tttgtgattt  21060

ttgaggaagc atatgcgtat ttccacttaa gcatctgaaa tattgcctct agtgctgaac  21120

aaattcttcc cttggttatt ttcctcttat ctcagtccct ggaagaataa atgcctgtac  21180

taattctcta tatacataaa tggtctcttt aggtataaat aacctcataa tcacataaaa  21240

gttaaagttt taatggaaaa ggctgagatg aaatattacc taagtaggaa ttaattgctt  21300

tttatcactt tacattattt catttttagt attatgaaaa atataattgt tccttttctt  21360

aaaaaaaaac cagcgtaatt tgtgcttagt tttaaaccaa aattttttcct atatgtttat  21420

agtttatatt ttcaagccaa aatacttgag ttttttttcct gtcataatat atcaatatga  21480

gaaatgtatt gttactttag aatcttttaa aacttctttt tattcctttt tttgtttttt  21540

aagatagggt attgttttgt tgcgcaggct agaatgcaag ggcacgatct tggcttactg  21600

tagcctcagc ctcccaggtt caagcaaccc tcccacatca gccatacaag tagccgggac  21660

tacaggcatg caccaccatg tccaactaat tttttttttc tttttttttg agacagaatc  21720

tcgctctgtt gcccaggctg gagtgcagtg gcacgatctt ggctcactgc aacctctgcc  21780

tcccagattc aagagattct cctgcctcag cctcccgagt agctgggatt atgcaccatt  21840

gtgcctggct aatttttgta tttttataga gatggggttt caccatgttg tccaggctgg  21900

tctcgaactc ctgacctcag gtgatccgcc tgcctcagct ccccaaagtg ctggggttag  21960

aggcccaact aattttttaa aaattttttg taggccgggc atggtggctt atgcctgtaa  22020

tcccagcact ttgggagtcc aggcagacgg atcacctgag gtcaggagtt ggagaccagc  22080

ctggccaaca tagtgaaatc ctgtctctac taaaaataaa aaaaattagc caggtatggt  22140

ggcacatgcc tatagtccca gctacttggg aggctgaggc aggacaattg cttgaaccca  22200

ggaggtggag gttgcagtga gctgagatgg cgcaactata ctccagcctg ggcgacagag  22260
```

```
cgagattcca tctcaaaaaa aaaaaaaaaa aaaaaaattc tgtaaacaca aggtgtcact  22320
atgtttccca ggctggtctc aaactctggg ctcaaccgat cttcccacct cagcctccca  22380
cagtcctggg attatagaca tgagccaccg cacctggcct aaaactcttt cttcaacatt  22440
aagaaataag acttttccag tctctttctt aaccctgtac ccttttcttt ctcatcttct  22500
tttatcccct cccttcatta actttacatt gcaataccaa ggacttaatg gtttgttaaa  22560
aaaatgaatt ctactcagta gaaaattcct gagaatattt attaaatgtc actgggagga  22620
aatttcccta agcaagatac aaaacttaga atcaaaaggg aggactgact tatttggttt  22680
tagaaatgaa aaagaacagt ttggaagaaa tagtgcgatg tggatgactt acaaacaatt  22740
attattccta aaatataggt acaatgagtt tattgaaaac aacataatgc aataggaaaa  22800
aaggacaaag agcaactagt cagagaggat ttgcaagtaa atcagtaaat gggaagagat  22860
gttcaatctg agtagtcagt gaatgtaaat taaggaagtt tacttttttt cccattaatt  22920
tacaaaaatt ttaaatatga taatatacag tgacaaaatt tttttttttt ttgagatgga  22980
gtctcgctct gtcgcccagg ctggagtgca ctgggcaatc tcggctcact gcaagctccg  23040
cctctcgggt tcatgccctt ctcctgcctc agcctcccaa gtagctggga ctacaggcgc  23100
ctgccaccgc gctcggctaa ctttttgtgt ttttagtaga gacggggttt caccgtggtc  23160
tcgatctcct gacctcgtga tctgcctgcc tcagcctccc aaagtgctgg gattacaggc  23220
gtgagccacc acgcccggcc ccaaaatttt taaataatga taatatacag tgtcggaaag  23280
tgtgtagagg tagaagtgtg aattgctgtg aactttgaga acgtggattg gcagtctgta  23340
ttaagatcta aaatgcatac agtgcttggg cccagcagtc tcacagaagc cataggtgat  23400
tgtatgtcag ttcccaaata ccactcgtta gagagaagca ctgtttaaca tctagtatct  23460
catttagacc ctgtttgagc atagatcata tgtgtgtgga acataaaagt aatcgaagta  23520
tgctcattct ttttttaaca tatctttcca ggcttctata tagttaaata aataatgctc  23580
cttgacattt atgtatttat ttatttagat ggagtctatt tctgtcgccc aggttggagt  23640
tcagtggtgt gatctcagct cactgcaacc tctgcctttc gggttcaagc aattctcctg  23700
ccttagcctc tcaagctggg actataggca tgcaccacca ttcccggcta atttttgtat  23760
ttttagtaga gacggggttt cgtcatgttg gccaggctgg tctcgaactc ctgacctcag  23820
gtgatctgcc cgcctcagcc tcccaaagtg ctgggattac aggtgtgagt caccacgcca  23880
ggctgctccg tgacatttaa ataaaatcat attttaaagt ccagttgtaa gcctatacat  23940
ccccttatc acttatctct aattcacttc tagacctggt ttgaactttg gatttagtgc  24000
tttcaaagtg tgattttttt aaaaaaatta tttttctgtt gccgtatatt tcagctcttc  24060
tcggtcttga aaagatttgt gagccttttt gacaaaaggt ggtgctcatt ttctatttcg  24120
gtggctccag taaagggagc tgctctctca tcggatgatt attgccccca gaagtggtcc  24180
taccatagct ttactggtca gttagccaga atttacacat ttactctgag gcttacaaaa  24240
atactgtgtt cataaaaagc cctccttcac attttgtgaa acagttgcat ggtgatttgg  24300
gatattttaa gtttaccatc acctctctgt cctctgcaaa aataaaaatt gtggaatgta  24360
aaacaactct gttgcacaaa aaggggaact tggtgtagga aaaaataact agaaatgata  24420
actacgagac actgcactcc caaattgaag atttaaaaaa attcctgatc gtaaataaga  24480
aaaattatgg agacatttat ccactgcata tctgatgact aaacgcttgg tataccccag  24540
ccattgttag gtgccagggt acaaagttcc tgccctcagc gggttgacac acttgtgggg  24600
gagaaaggca acaaaagctt aagcaagtaa atgcataatt ttacagggtg atatgtgcta  24660
```

```
aaaactaaat aaagcaaggt ggaggaataa caagactggc gggggtgctg gctggggtgg  24720
ctatttgaga aatgagggcc aggcatggcc tttcagagga gatgatgttg gagctgaatc  24780
ccaagtggtc agaaggagca aggtgggaaa atatttgagc aagatgggaa aatatttcag  24840
ttcctgggtc aaaagtaaca gtaagtgtaa agatcttgag atgggggctg ggcactgtgg  24900
ctcacacctg taatcccagc tgtttgggag gccaaggtgg gcagatcatg aggtcaggag  24960
ttcgagacca gcttgaccaa tatggtgaaa acctgtctct actaaaaata caaaaattag  25020
ctgggtgtgg tggcaggcgc ttgtaatccc agctactcag gaggctgagg caggagaatt  25080
gcttgaaccc gggaggcgga ggttgcagtg aaccgagatt gtgccactgc actgcagcct  25140
aggcgacaga gcgagactct gtctcaaaaa aaaaaaaaaa aagatcttga gatgagaatg  25200
aactgggttt ttgtgaaaat ggcaaatggc attttgggta ctgcaagcct ttgcggctcg  25260
gaactgtgct gtgcactgtg ggactgtgtg gctcaatgcg ggacggttag catccctagt  25320
cactgtcatt acaaaaacag tcacacattc tagacaccca ctgcccgccc caacgccaag  25380
ggggcagtac tgccttcaac caggacccca aaagactcca gtgtggcagt tgttggggag  25440
ggggaatgtg agaggggcag tggagaggga gtcagcaagc aggttctctg agccctggtg  25500
agaagtctgg attttatttt aagccgcctg agtgatgtga tttcatacat gtttttaaaa  25560
gatcactctg gttattcctt gcagacagtg gaagagtgag ccaagttagg aggctattgc  25620
agtagttcag gtaagagatg atggtggctt agactgagag agaatctact tgagggtaag  25680
aagtgatctg attcagggta tatgttgaaa gatttgctaa ttaattaaat atgggaggca  25740
aaagaaggtg gagaaatcag gatggctcct aggtttctta taaggagcta ggaagaatgt  25800
aaagaaatca tatgataagg agatataaaa aggaataaaa taatatttca cacttaaatt  25860
taggagacga aatatttgct tatttgaatt tgaaaattct tgtggatacc aatattgata  25920
ctttgtctga aaaataattt taagatgagt ctcctggcca ggcggggtgg ctcatgcctg  25980
taatcccagc actttgggag gctgagtcag gtggatcacc tgaggtcagg agtttgagac  26040
cagcctgacc aacatggtga aaccccatct ctactaaaaa tgcaaaaatt agccgggtat  26100
ggtggtgcac acctgtaatc ctagctactc gggaggttga ggcacaagaa tcacttgaac  26160
ctgggaggta gaggttgcag tgagccaaga tcgtgccact gcaagccagc ctgggcgaca  26220
gaacaagact ccatctggga aaaaaaaaaa agatgagtct gccaaaatgt ttctcatttg  26280
gaagggattc atgactttgc cagaaaaaca agcagcattc tatagttata atgctctatg  26340
atgtaattta ctggacctaa gttggctacc tttcatgatg catattaagt gtggagccat  26400
atttcttagt ttctgttata aagctaaact gttaagtcat ttttattcct ataaagtcaa  26460
acaaactagc catggatact ttttaacatt ctgtgaaacc aactttatcc agtttctgaa  26520
atggatgcca gttctttttt tttttttttg agatggagtc ttgctctgtc ccccaggctg  26580
gagtgcagtg gtacgatctc tgatcactgc aacctccgcc tcccgggttc acgccattct  26640
tctgcctcag cctcttgagt agctgggact acaggcgcct gccaccacgc ctggctaatt  26700
ttttgtattt ttagtagaga cggggtttca ctgtgttggc caggatggtc ttgatctcct  26760
gacctggtga tccacccacc tcggcctccc aaagtgctgg gattacaggc ctgagccact  26820
gtgcctggct ggatgccagt actttttaaa ccaaagttaa aataattatt tataggaagc  26880
agttgtgcac tgtagattag gaacatggag actggggcat aaatatattc ttgagctaga  26940
attaaagtaa aacatgtgac tgatggaaat aacagctctc cctgtgccct accatggaac  27000
ttggtaagcc tttgttaact cactggcact gctagatcat gctatggtcc ccgagggcca  27060
```

-continued

```
gggaggcaag tgtgctagtc caagtaaaaa gctgatatga tctttgtatg aacagaaaca  27120
ctgtttgtaa tgtgatgata acgttggttt cttgctcctg ggatattgtg ttctaggtaa  27180
agtggtccag agaccaatgg gtggcagata cagggataca gaggtcaact taatataaaa  27240
aaagaccttc tctaatgtct aagagcagag tgaaagtgag caggccatct gaggagagag  27300
agacttccct gttggctcat catgatgctt aagcagagcc aaaaagctac ttggtaggga  27360
tgtcaaggaa gtgagtcagg tgttttcagc accgcgactc tgtcattgtg tgcctctctc  27420
cttaatacct cagaattaga ataaagtctt gataacagta gtggcaccag tcctgtggtt  27480
tgttttgcga tgactgtgtg gttgttaaac tttctaagtg aaacaccata gtgtcgggag  27540
caatgccgac aagcctggcc acctttggtc tacagcagat attgcaagct gatatcccgt  27600
ggccacagtc aggcttggtg attgataaac attttgattt agggagctgc ttttttcaag  27660
aaacagaatc acataaacag gatttcaggc cagtctcaaa aaactggaag atttcacaga  27720
gccttgggcc cacatttctg tgtggcatca gagggctaga ggtgaatgag tcctcctctc  27780
ctctcctctc cccctcctcc cctccattcc cctcccctcc ccttccccgc tcccctcctt  27840
tatttttttt ttttatgaga cggagtctca ctgtgtcacc caggctggag tgcagtggtg  27900
tggtctcagt tcattgcaac ctccatctcc caggttcaag ccattctcct gcctcagcct  27960
cctgagtagc tgggattaca ggtgcatgcc accatgcctg gctaatttta tatttttagt  28020
agagatgggc tttcaccatg ttggccaggc tggtcttgaa cttgtgacct caggtgatcc  28080
gcctgcctcg gcctcccaaa gtgccgggat tacaggcatg agccaccatg cgtggctttt  28140
tttttttttt tttttttttt tttttgaga cagggtctct tgcgctgtca cctaggctgg  28200
agtgcagtga gacaaacaca gctcactgca gcctagacct gctgggttta agtgatcctt  28260
acatctcagc ctcctgagta cctgggacta caggtgtgca tcaccacacc tggctaattt  28320
ttaaatttat tgtagagaca acacttcact atattggctg gcctggtctc aaattccttg  28380
cctcaagcga tcttctgcct ttacatccca aagtgctgga attacaggca tgaaccttca  28440
cctttctttt agaaagagcg tgaatctcta attcaccaga gtccccacca ttccatctca  28500
tctgagttat ctcactatct ctgttcttcc ctcatttaca tcatctgtca cttacctgtt  28560
gacatgtgag ttttgacttt tgattgagat gctgacaccc tccttccctt ctaggaaagg  28620
aaaataaagg gggaaggaag gtggagaggg acaaaggaga ggcgtgtgga ggatgatagc  28680
gcaggacttg cattctcagt tctgcctctt aaatcttgga acctatttct tcatctaaca  28740
gtataggact gatgtttatt tttgtattag atcatatata taggagtacc tggcatataa  28800
ctttgtccaa agtacacatt ctttagctgg tgctcctctg tgttcccctg taaagactga  28860
ggcaactata atgttccact gttctgtgat tattgatttt caggtctgtt tcctccacca  28920
gattatgtgt gtcttactca actttgtatc accaagcacc tacgtggcat tttttctttt  28980
ttgaaggtag ggaccatggc tttctctttc tttactggac actgtataga tgtcatgcag  29040
gtctgaacgt cacactgtta aataattact taacaactga ccagaactaa ggctgtggtc  29100
tagagctcca aaccagaagc aaaaaggaat ggtgctgggc tggggcactt tcctctaaca  29160
tcacccaaac ccagaaaacg aggatcgtaa gccccttcat gggccaaatg cagggctggg  29220
gcccttgggc taacccttta gtgcctctgg ctgcatcact gtcagagtaa ggtaaccagc  29280
aaggggctgc agggaacaac cagccaggtc cagacatgga caaacataat tggaaggaag  29340
acaggaaatg gacaggtcct gtccagtgta gataaaatga cagcagctaa ggcaggttga  29400
ggggcagagg agaggctggg ggatcggtat tgtagcaatg caggagtcct gtcctgagtg  29460
```

-continued

```
gctgctcagg gtattgacat gccattttga taaatacatg aattaatgag tgagtttcga  29520
gagtaggggg agagagaata actgggcatc cccttctgta gatcctcagt cttctagtct  29580
tatctctcta gaaggatatt cacccatact caccttgtcc actttgtgcc agagttgaac  29640
attcttaaga aattaagaag gtgattcttt gccaaccata ttccagttct ttatttagga  29700
gctatattat cagctttgct tatggctcca gaagtggcca ttaatacctg gagctaaaac  29760
actgttttgg tttagcatga ctctagtttt cactgaatat ttagtatttt taagttaggt  29820
tttttgttg ttgttgtttt tgtttttgtt ttgtttgaga cagtgtctcg ctctgttgcc  29880
cagactggat tgcagtggtg tgatttcagc tcactgcagc ctacactgcc tgggttcaag  29940
aaattcttgt gccccagcca cctgagtagc tgggattaca ggcatgcgcc accacacctg  30000
gttgattttt gtatttttag tagagacagg gttttgccgt gtttgccagg ctggtcttga  30060
actcctggcc tcaagtgatc agcctgcctc ggcctttcaa agtgctggga ttacaggcat  30120
gagccaccgc acctggccta aggttaattg tttttataag caaattattt tgcttttgtg  30180
acccaaagca gtactctcag atacttagtg tagcaattta ttactcagat atataacttt  30240
ttacaaagag aatcatagca gaaaagaaca aggtaacgtg ttgtagggca tatgttctga  30300
aggagcactt gaccttatct tctgacatca tgtaaagatt ttggcattta gtgtcatcat  30360
gtgcaaccat tgttactttt tgctactgta tcataataat acttagtcgt atcagtttga  30420
ttaaatgcct cctttgtatg gttcccagca gcatggctgt agaaagtatt ctcaaattta  30480
tcaggagacc caagttttaa ttcggattcc ctttgtaaaa aggcctccat tactggaggc  30540
caaatataaa aacttttttt tttttgagac agagtctcct tctgtctcct aggctggagt  30600
gcagtggcgc gatctcagtt cactgcaacc tccgcctccc aggttcaagc gattctcctg  30660
cctcagtctc ccaagtagct gggattacag gcacgcatca ccatgcctgg ttaatttttg  30720
gtgtttttag tagggacagg gttttgctat gttggccaag ctggtctcgg actcctgagc  30780
ttaggcaatc cgcctgcctt ggcctcccaa agtgctgaga ttacaggcgt gagccaccgt  30840
gcctggccaa atatataaag tttaaaaata gctcgcttgt gttcattgcc taccacatac  30900
tgggtattgt gctagatatt taatatgcca gatagcatat gcctcattag cctatgaagt  30960
agaggctttt attattattt ccacttacat agatgagaaa attgcagcac agataaatta  31020
atttgtctag cgatggaacc aaaatctcag tcaggcagtg tgacttcaaa gcttgtattg  31080
atagaagttc tccaagtgct ttaaatatat taactcattc agactcacca agctgtgcat  31140
ttttagttta tagagttgat atcagtatta aataggaata tgtatgtgta tgtatttata  31200
tatgtatgca gatggtccct gacttaacga tggttcatct taatgatttt ttgactttat  31260
aattattttt tgactttata attttttgac tttatataaa ccatattttg ggtgcccaca  31320
cgtctattct gtttttcact ttcagtacac cagtcaacaa attacatgag ctattcaaca  31380
ctttacttta aataggcttt gtgttaggtg atttttgccc aaatataggc taatgtaagt  31440
gttttgagca tgtttaaggt aggtgaggct aagtaagctg tatttgatag gttaggcgta  31500
ttaaatgtat ttttgactta tgatattttt caaactatga tgggtttact aggacataat  31560
ctcatcatca gttgaggagc atctgtatat gtatgtgttt agatagatat aattagatat  31620
ctatatataa tagattctat gctatgggca ttgtaagttc taaattgctt cagtggcatt  31680
attgtacatt cttacataag attgaagaat tttgtgattt tgattaattt atatccttca  31740
aagtgaccag gaaggtagag tttgcatgca gaaaatttgc atgtatatta attccataaa  31800
taatgtttgt agttaaattt tcattttgtt taaacatttt ttacaagata gagtttactc  31860
```

```
agtgctgtta tttagcagct gtgtgtatga cttcataatt tagggggctg tctgttttgt  31920
gttctaagcc acgtggctgc tgtggtgact gctttagaaa ctttcagttc cctttgctgt  31980
gaaacaggtt tcagtgcatc gtccctgtgt ataaggtcag gtttcttaca tggactcact  32040
ctgtttctgt aaatttgtct gagaattttc aaggcagtgc tttcatggcc tctcctctaa  32100
ttttgtgtgt gtgtgtttgt gtgtgtctgt gtgtgatgat gaaaaagtca aaagccctaa  32160
aattaaatca gagtttaatc catgtcccta aactagataa gctgctttag accttttcct  32220
tatcccttac acgtcgctca gtaaatactt gctgattgac tttcaaattc agattacttt  32280
tacgctagca tacggtgggc acaaagggtt tttttgttta tttgtttgtt tgagacggag  32340
tctcgctctg tcgccaggct ggagcgcagt ggtgcaatct cggctcactg caacctcctc  32400
ttcctgggtt cgagcgattc ctcgtgcctt agcctcccaa gtagctggga ctacagacaa  32460
gcgccaccac gcccagctga tttttgtatt tttagtaaag acggggtttc accatgttgg  32520
ccaggatgct caaacccctg acctcgcgat ccgcccgcct cggcctccca aagcgctgag  32580
attacaggcg tgagccaccg ctcctggcct gggcacagag ttaaaaaaaa aatactggta  32640
acagaaaact tgttggcgtg tttcagtttt cagagtcttc tataaggtct tataccagcc  32700
gagaagcagc agaaccatct gtccgtgtac cgaggacgga tctcagcagc tctctgttca  32760
gtggctcctg cctttgtagt ggattccctt gctgtgctgt aattaagtca gccggcagga  32820
gttcctgttt tgagggggcc tctcccggct ggagaagtac cactgccttt gtgttacctg  32880
ccatgttatt gtggagtgga taattttttt ttcctgcatg ggtcttggtt taacagcagg  32940
atcctctggg cttcttccaa gaagcaccac atttccctga aaataaatgg cagatgaatt  33000
atttcttgag attatgaaaa tctgttagat gaaagcttgc ctttttctca tgttcaaaac  33060
aatgctaaat gcttataatt atactcccaa tgaattactt ctttcactgg cttcctttgc  33120
tctggcaaag gtggattttt tttccatggc agagaaattt tataaaaaat gtaatatttt  33180
agaaaatgcc taaatgtcaa gaatacaaca tcttgtttgt tgttgttgtt gttgttttgt  33240
ttgttttttg atacggagtc tcgctctgtc gcccaggctg gagtgcagtg gcgcaatctc  33300
agctcaatgc aaccccgcct cccgggttca agcaattcgc tgcctcagcc tcccgagtag  33360
cctccattga aggaagtgcc atagtgtggg aggatctttt tattttctac gcgcaccgta  33420
tttgattctg tgtttacagg aactgtgtct gtagacaaaa agcaaaatgt tggggtttag  33480
tttcttcagg tgaataaaat gttacttgca tctcctcatt gtcacagtgt tcgtattaca  33540
tacttcgtgt gtgtagtttt ggcatttaag gaaacagagc taaaaaaaaa acaaaggaca  33600
ataactgcat caacaacatg ttatacacca gaggaaatgc ggcgacttag gttctgtgat  33660
gggaaacccg gatttttttg ttgtacttga aatcttccgt agaacgtacg tgtttgcatg  33720
acccagaaag gaaaacacat tggaggactt tgtactagtt ccattctaat tctgtaaaat  33780
tctcacaaat tcaggcatct gttaaccctt cgagggcata taagttcaga gccatgtttt  33840
ctgttttgtg tctttccctt tggcggagtg gttacctttt ctgagccctt ggcttgcttt  33900
ctgtgaacat aaggcgctcc atctgccgct ttaaagtgaa gatttataat tcaaacaaga  33960
cagcgtttcg atgttgcact cctgtcttat tagatatcaa cttaaagtta agaaaatgga  34020
attattcaag gccttgttat ctagtttata gcttattcag aatttatatt tctgattttt  34080
ttttgtcctg atgactgcct gtgactaatt tgtgtttttg ttattaagct aagattgtat  34140
gaaaaatatg gcaaaaacaa aattctatat ttctaatgcc ccatgagaaa tctgatttag  34200
aggcccttcc tttggacaca ctttttgttt tgttttgttt ttgagcggag tcttgctctg  34260
```

```
tcgcccaggc tggagtgcag tggtgcaatc tcggctcact gcaccctcca cctcctgggt  34320
tcaagcgatt ctcctgcctc agcctcccga gtagctcgga gtacaggcgc ccgccactac  34380
gcccagctaa tttttctatt tttagtagag gtggggtttc accatgttgg ccaggctggt  34440
ctcaaacccc taaccttaaa tgatccatcc gcctcagcct cccaaagtgc tgggattaca  34500
ggcgtgagcc accgcgcctg gcctggacac ccattttgaa tagcacttac cacagattcc  34560
cgaagccagt ggttttctag ccttttttatt cgccgttcgt tgtaagcttc ttgagtcttg  34620
gtgattcttg tttcatttgt ttttgtttct ccccagagcc tagcacatag taggtgacga  34680
acaaatgttc atcgaatgta tgggctcaac catagtctat tttttcaaa aaggtataaa  34740
tcttatcaat gttttacatt ttgctgaaca aaacaggaga gagcggattc ttttcaaata  34800
ggaaaaatta gggagggaaa agagggattg actgaaactc tattgaagta tgtcaacata  34860
aaagtttatt gacagcctgg cgtgatggct caggcctgta atcccagcac tttaggaggc  34920
caaggtgggc gggtcactag aggtcaggag ttcgagacca gcctggccaa catggtgaaa  34980
ccccgtctct attaaaaata caaaaattag ccaggtgtgg tggcaggcgc ctgtactctg  35040
agctactggg gaggctgaga caggagaatc gcttgaacct gggaggcaga ggttgcagtg  35100
agctgagatc gtgtcaccac acttccagcc tgggcaaaag agtgagactc tgtctaaaaa  35160
aaaaaaaaaa aaaaaaaaaa acaaaaaacc ccacctatct atcctatcta tctatctatc  35220
tatctatcta tctatctatt ggtctatcta tctagataaa aatagcagtc aactaatttt  35280
tcaaattaaa aatgctttat tgttatttat agcatgattg tttttctata aaaaaggcat  35340
attacaacag ccttcgcttc acatctgact cttgcagcat tcttataaag agatctcaca  35400
ccatatttga gggcttcatt agttttctaa gccttaaaaa aatttcatca ttaagattat  35460
tctctcatga agcacccaaa atatagacag cttttcttat tttcttttct tcaattgttg  35520
acagtctaat gctgccagat ctttatctgt cagggacttt tgatgttgtt ggagccatct  35580
cttgtggact ttatgaaatc ttgcatgcag cacaatttga aacttcattg tgcattcaat  35640
ttgcattgcc tttgctgtgt tcacagtggc actccatgag gcttaactat ggagatcctg  35700
gtgctacaag ccgttaaata gttctctctt ctcaacctat tcccctatcc tgcttttctt  35760
ttcttcatag cacttattac ctcctgatta tattttttgt ttgccttttg tctatcacct  35820
gtcattcttt taccagacca tctagtctca tatgtctata taacctttct gaaaaacatc  35880
ctgtgggaaa tataccatat atacagaaaa agtgcacaaa catgaatata cagtttaaca  35940
aataatataa acctgctatt catgtagcca ccacccagat gaaggaaata gaatatcata  36000
agcaccgcac aatctccatt tgtgcccttc tccatcgtag ctttctctgt cccagacaac  36060
cattgtccac aacttgttgt aataatttac ttaattttct tttatagttt tatcacacat  36120
aatttagttt ttgtctgctt tttgaacttt acatgaatgg aataatattg catatattat  36180
ttaatgcttt ttctttcatt taacattttt ttttgtgtgt gtgtgagatt ctccaggttg  36240
ttgtacacag tgctagttat ttcattttgt tatggtatag tatcccattg tatgattgta  36300
ccacagttta tccatttttt agttgatggg ttttgacttg ctttcattgt ttgggctatt  36360
atgaatagtg ctgctctgca cctgttgtac atatagcctg gtgaacatgt ttgcgaattt  36420
ctatgagcgt gatcacggtg gtgtagaatt gccaatcttc aacctgcctg tattttccaa  36480
agcgatcata ccaatttatt taccttccag cagtgtatga gaattctcta ttctcaccat  36540
cattggatat tgtcagattt taacatttgg ctcaactgat gggtgtataa tggtatccta  36600
tggtacttat aatttgcatt atccctagtt actaataagc ttgagcaatt tttcatattt  36660
```

```
ttatttcgat ttcctaattt atgaaatgcc tgtttaagtc ttcagccatt tcaaatgtta  36720
cctgtctttt caaaatgatc tataggagtt ctttgtataa tatatattct ggcccctagt  36780
cctttattct ttgtatgtgt tgcaaatatc ttcatctctg cagtttactc tttttgtggt  36840
gtcctttgat aaaattctca atttggtgaa tgtaattgaa tttattaatt tttctctttg  36900
ttatgtattt ttgtgtcttt aagaaatttt tccctatgta gggaagaagg acaaaaattg  36960
tctttcataa ttagttcttt aacccttcat aactttgagt atataaatta ttgtgaccat  37020
ctttgaatct acagtagttg aattgcatat atagaggctt gagttcttaa attattcttt  37080
ccagggtgaa tattagcata tcacaatagg acagtaggga cagtggcttt ttcgctaatg  37140
aaatctaaga tttttccttt tctgctcatg aaaaatgttt ctgcttaaat tgtaatgagt  37200
gtacaagagg cataaatcca cagtgggtac aaatgtcaaa gattatggtt taaaccagca  37260
aaatatgtct tcttagatat acgaaacatt ttgtcaaata gcccctggca tcatctgggc  37320
taaatgaaga atcaccagga catgtgatac agtgaaacta ttccacttat agtaacagca  37380
cttagtaatt gctttcatta atccaggcag gttaatattc tatctacttg cataacaatg  37440
tcaaaaaatc tattatctac tgaaaccttt tatatagcaa gttaagctcc tatttctttc  37500
ataaagattg agattcaaat attaatccaa actactcaga atcactttct cttcctcact  37560
tttctgatac ccccactgga gagtgactga tcagtgcatt atctgtcacc tcagagctca  37620
gagtgcccct cttttctatt caaatacaaa gccattcatt tactttgatg gacaaatagc  37680
cgtggcatta gtatgggtag gggcaagtgc tgttgtctct tatctaggaa ggagttggtt  37740
cttttctgat ggttgaataa tatacttagg tatagaaaga gacctgagtg tcttgaaagc  37800
aacattcttt catttttgtc aatgttttaa tcagcacccc tgtgcatata ttatctttgc  37860
atatttcagc actttgtatt agacttctac atgttgtggt ctttgcttct gataagggac  37920
agaataaata ggaagaaaga ataaaaaagc cataatgtta agtacatcca ttccatgccc  37980
atagccatac atcacagaag tcacagggaa ggctctgtga cacgagataa tgatgtggat  38040
gtgacagaac atggtagagg aaaaggccac agacaggtgc agagtaggaa gaatgaaaga  38100
attcattgtg gctgtcaaaa tcctatgttt gtgttcccaa atcctatttc tttttctttt  38160
tgacttgtga tgtattgact gtcaattagt tatcaggtac tatgttcagc ccagttattg  38220
cacaagagat cctgaaaatc tttaagtagc tcctggactt ggaagaggga aggaaggagg  38280
agacactaaa ataattacaa tatgttacta ttatacatga caatatgcag aatgcatttg  38340
gaacatagcc aataacttta cacagagata gcagtttttg agctgaattt tagaggacca  38400
agttgataga atttgatgat cagatgaggg gttagggaga ggaagtcttt cagtttattt  38460
taaggctgga gtgaatatta tttttgtaaa tgcaggattt taaggaaaag gacaaaatgc  38520
cagaagacag cagatttcta ttttctgtat atttgtacat catgacaata catttataga  38580
tacactaatt cttgtacata aataattcat ataatgtttg tctttatcag tctgaattgt  38640
cagctttggt catagggaat tggaaccaag tgtttactga gcatctacta tatgtgaggc  38700
actatattag gtgctgggca tgcagtgatg agcaaaacag ggatgggtcc agctcttata  38760
gaacttagag ttgagtggga aaaacagaat taatcaaatt tccatattta taattagaaa  38820
tgacatatac atatgaacaa aggctctctc agaacccaat tattcttccc tttcactctt  38880
cttcctaatc atactaccag cgttaagttg acagttattt atcaggcata tttagcagcc  38940
agccttacag ttttctcttg cacactgtta acaattactg tcacatggtc actgttacat  39000
gttagccaat agtgcctcac attcactgtg gcttccaaag cttgggcttg gggaagcagg  39060
```

```
tggatggtga tatcatgagc tcagatagag atcatgggag aagagatttg agatgtttta  39120
aaaaagtgtt ttgagcagat gaagttaaag agttaaaggg aactatggtc aagtggaggt  39180
gctggtaggc aggtggaaat atacttctga atctcaggat gactaatgaa aagcaagaaa  39240
atgaacaaca agggactatt aatgtgtgtt atgctgtgct tatgcatttt gtctggtttc  39300
aaatcattgt atttaagtag ttcttaaagt cacaggagtg aatgagatta agtagaggaa  39360
gaaggaaaag aggtacagat ggagacctag ggagtgccag gcctcagagc agacagagga  39420
agggcacgca gtgacagagc ccacgaagtg tggccagaga gcagtgatga ggaggattac  39480
cgagtggctc atggaaacca gcgtggaagc tttcttattt cttcttctcc ttctgcttct  39540
ctttctccct tcctcctttc ctccctccct ccctccctcc ctcccttcct tccttccttc  39600
tcctcctcct tctccttcct cttcttcttc ctcctcctcc tcttcttctt ctttctcttc  39660
ttcttccttc ttcctccttc ctcctccttc ttcttccttt ttctttttttg agacagtctt  39720
gctctgtcac ccaggctgga atgtagtggt atgatcatag ctcactgcag cctcgacctc  39780
cccaggctta ggtgatcctc tcaccttagc ctcccgagga gctaagacca taggtgtgag  39840
ccaccatgcc cagctaatgt tttaattttt gtagacatgg gacctcccta tgttgcccag  39900
gctaatcttg aactcaagtg atcctcctgc ctcagcttcc caaagtgctg ggattacata  39960
tatgagccac tgtgcccggc tgtgggaagc tttcaagaac aagagagacc aatgttgcca  40020
gacaggccaa gtaatattag gactggaaag cagctagatt gagagactca caggaacaag  40080
aacagagaat tctgaattct aaaatccaca acgctcattt cactgaaagg tcgttcaggt  40140
ggcggtggtg gatttttttc ccttagccgt cattttggat atttgattaa ttatcgacca  40200
ttatatttcc ttcttcttgt tagttacgat ttactaagaa gaatttttat gctattttaa  40260
agttaaatga tctgtgattg taaaatcatt cattatttac ctcaactgct cacttaattt  40320
tttaaaaaca tcttcaaggc tccttcagag tttttatgtt gataatttta aaaaatcttt  40380
ttcaagtttt ctagaaacat gaataagtac acaataattt agttaatgtg ggcagtaaat  40440
acacagttgt gatagtgaaa tgtcttctat gaactagaaa ataagaaaat agacacttaa  40500
agttcagagt agagaaggaa actcaaagag acagaatggt tccagggcag cctaactgta  40560
cagtaccctt aagaaaagta ttcgtatcta tatctctact gcagtaggcc aagtgctgtg  40620
gcacacgcct aaaattgtag cactttggga ggctgaagtg ggaggactgc ttgagcctag  40680
gtgtttgagg ccagccctag caatataggg agaccccccca tctctacaaa aaataagaaa  40740
aattagtcag atgtggtggt gcacacctgt ggtcccagct gcttgggagg ctgaggtggg  40800
aggatcactt gagtctggga ggttgaggct acagtgagcc gtgatgacac catcacactc  40860
tagcctgggt gacagagcga gactccgtct ccaaaaaaaa aagaatctga gaagcagata  40920
ctggccatat tcactgaggt gctaagcagg ggtgggcacc ctgcctggct ctgtagtggt  40980
catttctgac aggcctgtgt tgtggagaca gacacactag gttttcagag tctgatgcag  41040
ttacattcga attaggcaaa tctcatactg attctgattc catgttcccc gcaacaggca  41100
cccggtaaac tggctttctg gagagtctgc ctttgagcag agaatgtgat tttcccactg  41160
tccttctctg acctctcggc agttatacaa ttcttattgt aaaataaagc tctattctgg  41220
ttttgtgcat cagtctcctg tgggtttaat tcacatgcaa gagcgtcctc gagcctgaat  41280
gagcctggaa tggaatacag tttcccagcc catgaatcat gacctgaatc atgtcaaatt  41340
caccaagtta tgctcccttt taaggtcact tggcagacag gcaggtagga actttcctgg  41400
tgaaccctcc ctgtatgacc atgcagcttt ccactgggaa cttttacagg ttgctgctat  41460
```

-continued

```
ttttataaaa atgatagact gtaatgttgc cggggacagt ggctcatgcc tgtaatccca  41520
gcagtttagg aggctgaggt gggagaaaca cttgaggtca ggagtttcag accagcctag  41580
gcaacatggt gaaaccctgt ctctactaaa aatacaaaaa ttagctggac atggtggtgc  41640
acacctgtat tcccagctcc tcaggaggat aaggcacgag aatcacttga acccgggagg  41700
tagaggttac agtgagccga gatcacgtca ctgtactcca ccctgggtga cgaagtgagg  41760
ctctgtctcc aaaaaaaaaa aagagttctg taattgtaaa aatgtgacat aggcattctc  41820
taatgtgcaa tgaatagtca tttttaagca tttcatacat tgttcctgta ctgcactggg  41880
tctccttgtg ctgaactgca tgggatagcc catttccata caatctcatc ctctgaataa  41940
ggaaccatga tgctcctaaa gacatactaa atatagatct tgggtaatat tggagtcagt  42000
gctggtcatc aatgattttc tctgtgatga tagagggggt ccactatgaa tgatagcatt  42060
aattttgctg tatgttcttg catcattggt acataataat tcatagactt cataagttat  42120
taatatacaa gttacagaat ttaataatgt aacccacctt tgatatgttt tcatatacat  42180
tatggggaaa ccatattttt ttgaagtcaa gaaatgtata ttgcttcatg ttgcaaaatt  42240
tgtatgctat gtcaaagaag cattgccaga aaatgatctg aaatgtagaa caataaagtt  42300
acattataga tgtcttaggt gaaccaagag aaaaattagt gtcagagtta aaaagatgca  42360
agtcaggaat taaggcaaaa cattgaccct atctgactta ggagaattct ggtcatgtga  42420
tcttaagaag agagagtaac tgacagttct ggagactggg aagtccaaat caaggcatca  42480
gcagattcag tgtctggtgg gagcttgctg tctgcttcac agatggtgcc ttcttatggc  42540
atcctcacat ggtgaaaggg aacaaacagc ctccctcaag cctttttgt aagggcacta  42600
atcccattca tgaaggcaga gcacctactt gtaatactat cgtattcgtt cgttctcatg  42660
ctgctaataa agacataccc acgactgggt aatttattta atggacttgc agttccaggt  42720
ggctgcggag gcctcacagt catggcagaa ggtgaaggaa gaccaaaggt acatcttaca  42780
tggcagcagg caagagggtg tgtgcaggag aactcccctt tataaaacca tcagatctca  42840
tgagacttac tcactatcat gagaatggca tgggaaagac ctgtccccat gattcaatta  42900
ccttccaccg ggtccctcct acaacacatg ggaattatgg gagctacaat tcaagatgag  42960
atttgggtgg ggacacagcc aaactgtatc aactatcata cctcttaata ctatcacatt  43020
ggattttagg ttccaacata caaattttgg gaggacatga acatctggac agtagcaatg  43080
ctagtccatt attctggtct gtctgaaggt tttatctagg cagggaaaag cgtatgtttt  43140
ttccttgacc ttgaaaattt agcttgggct ttctttgtac aaacatgaag atcctaggag  43200
aagcccaatc aattttagag agacaagtgg atgaagatag ggattaaaag aattgtgctt  43260
gactgagcag agagactgat gatctgaaag gacaccaggt aaaatgtttc tttttagctt  43320
tacaaatgca ctgcttgtta acatctatga attcatgtac ttgcttttcc atgctataga  43380
cgggtaactt ccagggctgc tgtgtggcac aagtttgggg agtagggatg gaaatggtac  43440
ccttaaagtt atgcagtgca gacctgcaca acctgacaca ggggccttgg gtcagtccat  43500
gtcggtgagt gtatgatact ctgatatctt aaaaaaaaat aacataagaa tctgtaggct  43560
cttgttcaaa gatattgcag agacaagaac cccttccaca ggtaaagaag gcacgtgaga  43620
ctcatggcaa attcattgac tcttctgtcc gagcattttc ttgtcatttt cattatagcc  43680
cttccttgta atcttaacat caatggtacc ctgcttctta gcaattttga taaatctttg  43740
tatttcagca aatacttgaa aaaaatgtag gatccactgg cttatatctt ctgtgtaggc  43800
atcaaaacag atggtggtgg ggttgttggg aagatggtag cagacagggt tgcttaaaaa  43860
```

```
tataagactt ccttgatgtc caagaatact gagatttata tgattagaaa tttctataca  43920
aagctggaaa cagtggagca tgttcccaca tagaagcaca ggttcccagc tcccccagag  43980
gccctcatac agagctgcag ctgcctgtga tggagcctgc acagattctt ccagtagaca  44040
gtcactttcc ttctttcttg gcagtcttgt gccctgacag cccttctgat ggctctggag  44100
cctctggctg cctgccttcc tactcaccag gtgcaacttg ttaattactt gcatgcaata  44160
tgatcactgg attatggtac agctttggct aaatcactta catttttcat tcttattaat  44220
ttggagacat gcacgtgcca acccaagtac aataaatggc acactgttta ttgcaagcac  44280
taaatagata catcgaaggt tatgttctca ggcatcccta gcttataagt gtacattatg  44340
ttgatttgat attgggtgat gaccaaacac agttggtcaa atcctccctc tgggagttgg  44400
agagacatag aaggaaagga acagaaatgc cagtggtgat aacagggaca gcagaaggaa  44460
gaggagcagg gactgaaagc cactgagtca gagtacactg aggcatatga gcaatacctg  44520
agtggaatct gtggttgcag ggcatcccta cctctgcctg cacatctgct tctttcttcc  44580
ctacccccag tttccctttt tctccttccc tgtggccata gtggaagatg gaggcttcac  44640
agttcctgag actagatgtc ttcagttcaa gcagtcagca gagacttgtt tttttgttgt  44700
tgttgttttt tgtttttgtt ttttgagaca gagtctcgct gtgtctccca ggctggagtg  44760
tagtggcgcg ttctcagctc actgcaacct ctgcctcccg ggttcacgtg attctcctgc  44820
ctcagactcc tgagtagctg ggactacagg cacacgctac catgcctggc caatttttgt  44880
atttttagta gagatggggt ttcgccatgt tgcccaggct ggtcttgaac tcctgacctc  44940
aggtgatcca cctgccttgg cctcccaaag tgctgggatt acaggcagag actagttttt  45000
tttaactttt tttttttttt aacagtcttg ctctgtcaca taggctggtg tgccatggca  45060
tgatcatagc tcactttaac cttgaactcc tgggctcaag tgatcctccc gtcttagcct  45120
cccaagtacc tagggctaca ggtgcatgcc accatgctca gctaattttc ttgccatgat  45180
gctgaggcta gtcttgaact cctggcctca agtgatcctc ctgcctcagc ttcccaaagt  45240
gttgggatta caggcgtgag ccaatgcacc tggctgaggc tggtattttc aaatttcaat  45300
tctagctgtc agggagagag aaattgattg gcccaccagg gaccaggtgt ttgcttctgg  45360
tccattcttc tataaccagg gagacattta tatatataaa cttggctgct gaggcccaac  45420
cctcaaaaca tagagatttg agcaacatta gaataaattc ttttatttat ggaattattt  45480
ctataggcat atgtcataac cttttatttt ctttttaaga aatcaagtct acttaatatg  45540
ataataatat agtcaaagaa gtacacagcc acgtatggct ggatttgatt tcttatccaa  45600
tagctggatc tgagaaaagg ttgttcagtt acattccaga agcttcagta gcaaaactgc  45660
tctttttttcc cccaactttt actttatatt cagagggtac atgtgcaggt tttttactga  45720
ggtatatcgt gtcatgctga ggttttgggt atgaatggtc ccatcaccca gacactgagc  45780
atagtataca gtagttttc aacccttgct ctcctctctc cctctcacct ctaggcatcc  45840
ctagtgccta gtattgccat ctttatgtcc ataagtacct gatgtgtagc tctcatttgt  45900
aagtgagaac atacggtatt tgtttttctt ttcctgcatt tctttgctta gaataatggc  45960
ctccagctgc atctatgttg ctgcaaagga catgattttg attttttatg gctgcataga  46020
attccatggt gtttatatac cacattttct ttatccaagc cactgttgat gggaacctaa  46080
attgattctg tgtctttgct attgtgaata gtgctgcgat aaacatgtga gtgcccttgt  46140
ctttttggta ttaatagagt ggtttgtttt cttacggata tatacctgaa actattcttg  46200
ttaagtgagt caacaaggcc cacctggcag aagaggaaac ccaagaacat taaatcagtt  46260
```

```
aagatggagg ccaaggcggg tggatcactg gagctcacga attcaagacc agcttgggca  46320
acatggcgaa agttcatctc tacaaaaaat acaaaactag ccaggcatga tggcgtgcac  46380
ctgtagtcac agctactcag gaggctgagg tgggaggctg gcttgggtct gggaggcaga  46440
ggttgcagtg agccaagatt gtgcctctgc actccagcct gggtgataga gccagacttt  46500
gtatatatat gtgtgtgtac atatatatat atgtgtgtgt gtgtgtgtat atatgtaata  46560
catatatatt acatatctaa tatatataat atatatgtaa taaacatcat gtatatatga  46620
tgtttattag ccctccaatg cttgaaatca ggggttggaa tcaaggctaa ccaactctgg  46680
tctggtcacc atcactgaat gcttgcggta gccatgtgaa cattgtttat tgtcgtatac  46740
tcctgggaga gtcccaggga tgagctttta taaagttgca gacgggaaag ggactctcac  46800
tttggagaga attaagcatg tcacccagtt gcctaacaag ttattgctgt gcaggcaaaa  46860
aacagacaaa agactcaccc aactctaaga ttttttttgat ggacttctct aagttcatta  46920
tgataaagtt aatattatga tttttccagt tctcaatatt ttgggtctaa cccttttttt  46980
attactttat gtatatgttc tgggctccgt agactctctg gagtgacaag aaaatcttga  47040
aaaataaaag gcgaggtcta ttggagagct gttcgtggat gattctgata cgtgctcttg  47100
gttaagaatc actgctctgg ttttcttccc agtgcctctt acccaccact gttagatcag  47160
ttctttaaac accacttaaa ctcccacttt tgtcagcaac ctcctcttga cagtcaagct  47220
ccttagtctg gcatgtagca ctcaccatta cttggtgtga gtcctgaatt ctgagcagcc  47280
agtgtctcct tatctgtcac attcgtactc atttttatga ctttgcaggt cttgctgaaa  47340
attcttcctt aacttgcctt gagaaccacc ttttccacca agcattccca atgaatgtag  47400
ctcgtggtgt tctttccttc caaattcctg ttctcttatc tctactgctt ataacccaat  47460
acttgactat atattgtctt gtataaatga agtcttttct atcaaagtag atgttcattt  47520
tcttaggagg aggaatgtct ttggtatcct gtacaaaatc tagcatagcc tggtactcaa  47580
agtcacctta atcatacact aaatggtatc tttattgatg ggttgtcgat aaacctcctg  47640
ctttatcctg tatccaatta aaatgatccc tcgtcagttt ttcctctgat tcaaacattt  47700
taccccacat tgtttctgca attagacaga aaaataagca tctgtgaagt caaccttttt  47760
gcttttttta ctctgaagtg ctgctttttt ttttcagtaa gttgtggttt taaaaaaatc  47820
cagttatttg aatgacattt attattttg cagttaataa atgtatttta agtttttaaa  47880
tccacagtgt agataaggcc ctagaagcaa gtgtagactt cgtccacagc tgtactccat  47940
cggccactga cagtcttatt gcattatttc aacggcacaa gcaatcattt acacttgtta  48000
ttacccaggg gcatttcaaa ctgttactga aatgcatcca tccctggagt aaccatctgt  48060
gaatggtaat gccataaggt agagagacta aatctaattg atatgcaaaa aggagaattt  48120
cagctgtcca gctatggaga ttcaaattga acctttaata ggctgaggat ttcagctaaa  48180
tttttaaaat catgatatct agttcaggca ctcatctttt aggtttctca cagattaaag  48240
tacagccgtc ttccttgaag taagaacatc tcaaagtcaa aaatacttgt ttattgtaaa  48300
acaaaatgct acagagaaag gaaagttctt gtaaaataca aagagatcgc ttttgttgct  48360
atataatagc aaagcagctg cacctttcct tggtttttac acttgtttgt gcctcaaatt  48420
gcctgaaaga aaaaaaggga aaataagaaa atgctttcag atttcagttg cattaaaaca  48480
taaaaaaaat tgggagcaac atttgttaag atattaagat atagtcattt acattaagtg  48540
gttttataaa agtgatttat aatcttttaa agttatctcc ccctttctta tgacacgtaa  48600
ccctaaaaga gccatttaaa ttagctgtca ggcaagatgt accaggcctt tccagtgatc  48660
```

-continued

```
ccagcccacc tggacatatc tagcaattct gcagaccagc acatacttct ggaaagatgt  48720
tgcatggtga tttatagatc tgtgtggaca cataacacct ttacaatgga gtgaggtctt  48780
gaaatagccc tgctgttgct gcccattgag agataagtat tctcctgagg tattccccaa  48840
cagctggaaa tgaagtagca gctcttgtca gtctgtgaca ggagtggatt atcagacatt  48900
tgtaaagaga caacagcaga atcaggcctt tttgcaataa aattgcacac atagatatta  48960
ttgctcctcc agcgtttcat atgcagtgtc aaggcacgct acagttcagg cagcaggcaa  49020
gcagctctgt ttgaatggtg ggacaaacat acctctgtgt gtgaggtgcc tgcacttgcc  49080
ctgctttgtc agggaggaca caatgccact ttctctgctc ctcagcatag ctcaattcca  49140
gctcccggga tgaattaata aagagatata gccgagggca gtcttagttg gggctcaggt  49200
taccagctgt cacattactg aaatctcagg atatgcttac agtaattgaa ggaaagcaca  49260
ttagggttat attgactcag aatgaggcac tctctgggag atcaccgtga acagcatttt  49320
gggagcaacc tagatcattt cccctaaaat tctgacattt gctttttggt cttctgggct  49380
ccaggtactt attactcttt cctgaagagc tgttaactgg ctgtcaagtt tacattttga  49440
aatagtgcca tgatggcatc cctatgcttg gtattattta ccccacggag gagatgtgtg  49500
tattgcagaa cactcatgtt tagatcagcc aagagaactg cttggaacaa tcctagaagc  49560
aggcaaagct gcattttatg ttcttcatat attatttgaa aattactagt ggtcaagaaa  49620
cattccaact gtttgaattc tcctctccaa acaggaaaat tctgtaaaat tgtttttcat  49680
atatatatgt ataacacaca tacattttat aacacataca tacacatata agcatatact  49740
aaatgagtta gtaaatatac aacactttga actgttgcct gggatataat tactggcata  49800
attacatgtg ctcgttatta tttttctaaa tcaaaggtct ggttttcata ggcttaaaaa  49860
ataataaaat tggatgttaa tggtacaagt tttgaaaata tttgatattg attcaggaga  49920
tgaaactgtc tagaaattac tcttgtctat tataattaag tccagagtct tattttcaga  49980
gataagtact tgatccctac ttttgtgtgt caatttgaat ttaatttttt aatgcatgtc  50040
ttttaatact accctttatt atagatgcag acgttaatga agaatccagt cccatttgta  50100
caaatgccaa ggagtttacc ctctattgaa gggatgaaat gttggtagag caaatgcagg  50160
tgtattatta tgattacttt tggatacttt gtattaacaa attttcagac acattcctaa  50220
agattctggg gggctggagc aagcaggcaa acagaggtcc acatactcta tgtgtaaata  50280
ctaaaagtga tcaatcaagg gtgctctcca ccctttctgc ttcttctgga agctaccaag  50340
attcctgggt gcccaaggat acctgttggg tggttgcagg ggccacctaa ccccaaattt  50400
ccttgccacc attcccttca tcctctcagc atgacagctg gtttcctact tttcctcttc  50460
ttcccccttt tttctgtctt tggccaaagc ttagtgaatt ttaccttaga gattttactt  50520
ttaacctatt cccatatttt aaatgtttcc acgtattcac tgcagtgtgc tgatggttgg  50580
aggtggtaat acagtttctt ggttaaggtg tggtctttgg aatttgactg cctgtttagg  50640
tcctggctcc ccactattag ctgtgagacc ctgggcaaat tacttaactt ttctgtggct  50700
caggttccag atgtaaaatg aaatttttaa aaaagcaaca cctttaagtt ttcttaagaa  50760
ttaaatgagg ctgggctcag tggctcacac ctgtaatccc agcactttgg gaggcttaca  50820
caggacgata atttgagcct aggggttttt tttttctttt tttttttttt ttgagatgga  50880
gtttcactct tgttgcccag gctggagtgc agtggtgcaa tctcagctcg ctgcaacctc  50940
cgcctcccgg gttcaagcga ttctcctgcc tcagcctcct gagtagctgg gattacaggc  51000
gcccaccccc atgcccggct gatttttgta ctttttaagt agagacaggg ttttgccatg  51060
```

```
ttggccaggc tggtcttgaa cttctgacct ccagtgatct gcccaccttg gcctcccaaa  51120
gtgctgggat tacaggcgtg agccaccgtg cctggcccaa gcccaggaat tgagatcagc  51180
ctgggcgaca cggtgagacc ctgcctgtat aaaaaagaaa aatttaaaaa tttaaaataa  51240
aaaaaaatta agtgagttaa tatgtggaaa gaatacctct ggtatatagg aaacactcaa  51300
caaatattag ctattctttt tcttggaact ctgaaggtgg cagacttgct ccctcttcct  51360
gtgtggagag aagcccatgt actttatttg tggacagtca tctgtgattc tcatgaatgg  51420
ctttgcttcc ttctcatgtg gctttcacac ttatgcagag ctttgttaga acctctgctg  51480
catcctgcag tgtgaaattt acattcccac ctctccatct ccattggttt gtgagccctt  51540
caaaggcaaa aattgtgttc tttggttttg ttttcctagg gccttgcaca gcacttgcca  51600
ctcttgatta agcatgctta agaaatgctt gttgagtgag tgcgtgaaag gggggccaat  51660
aacttgtatg gttatttgta cgccatcaaa cttttttttt tgagatggag tctcgctctg  51720
tcgcccaggc tggaatgcag tggcacaatc tcagcgcact gcaacctccg cttcccgggt  51780
tcaggcaata ctcttgcctc agcctcccga gtagctggaa ttacagtcgc gcaccaccat  51840
gcccagctaa tttttgtatt tttaatagag acggggtttc atcacgttgg ctaggctggt  51900
ctcgaacttc tgacctcatg tgatccaccc accttggcct cccaaagtgc tgatttacag  51960
gcgtgagcca ccgcacctgg ctcatcaaac gtttgattta tcggtttcct agcatataaa  52020
ctagctgcga agatgtgtat ttttttgaga agccatgtgg agagagtagg ggacacagaa  52080
tctgctcttc aggcatgctg acagcaaaaa gtgactacta gtaggccatg agggatggaa  52140
gagagaaata ctataaaaag catagttgtc tggggctatt taaggaagac acaataacac  52200
actgcacatc ccaggacccc tttcaggcat cactataata gcatggtgta agaactgtgt  52260
cctctcagtc ctgttcagct tcagccacta ctatcctttg tctattaata cagcaccaac  52320
cacttggtcc caaaggaacg ttctggcgag aaatgtgcag agagaatcag ttcgccagca  52380
ggtgcgattc tggaattgtt tggctgccag agacccggta tttggtgtgt ccgtcattac  52440
tgggtgtttg tgtccccaag ccagagtcat catgttgacc atcctcctga actggggctc  52500
tggttggatt cccacctgtt tacctggtgc cttaacgttc ttctccactt atcttgccat  52560
acccttcctg gagaggaaag aagacaatta atttctacct gtagtttggg ttctccttca  52620
agagaaatta caaaactgcc tgccttggac ccagagcttt ccttctttag gatggtttgg  52680
gcctgacagc ctgaggtttg aatctggtct ccaccatttc ctagttcata ttcactctca  52740
gcaaatattt aactctctaa gcctcaaatt tctcacccac aaaataggga taataatatc  52800
ctgttgttgt gcccttagat gacgcatatg gcatctaaca catacttagc atgtggttta  52860
gtctggcaca tacttagtat tcagcaaatg gtagctgcta cccctcccac ggccatgtcc  52920
cagctactgg aatagctcac tctggatatt gttcacttct ggaaccaagc ccacctttgc  52980
caggcagcct cggctaatcc cttagagatg tccccacagc aagggaatct ctgctagcat  53040
gccttccatg gcctgttttg acaagatgtt tataattctc caggttgtta agaaaaggtt  53100
ttatctttaa aatgtaaagc catcgttagc taagctagct taaaaattct attgtatact  53160
ttagaaatat ttccacaaat atggctaaaa taaatgtaac cactcttgga gaggcaatgt  53220
tcatttatct tgaaatggaa gtgcctcact tttttttttt taatggagcc tcaatacagt  53280
ctgaaaacca ggtggaaagt gtttttcagt atcaagtgtg gtaaataaga gctaactgat  53340
tcaaattact tttattcctt atcatctgat atgaaaatct gaatcatctt gaaatacagt  53400
ggtgcccctt aaaattgctt ttctgtctta tattcattca ttcatgcagc aatttagggt  53460
```

```
ttattatata caaggtagta aggtgggtag atattcctgt ttgtgactgt tgaaacattt  53520
tttattaagt ttcaggtatc atacacacat acacagatac acacatgtgt gttttgtttt  53580
ttcccctctt attaaaactt aacacatgaa ggtagataat atttcaattg tacttaagca  53640
ctatctaaat ttgctttatg tgcagcaaga ctatgatata accttgtaaa tatctaactt  53700
cattaaaaac acacatttat acagaatagg ttaactctgt ggctctctga gcaatatctt  53760
aacctttagt ctggaagcct taatgacaca ctaatatcta atattgccta taacttcttc  53820
agatccggaa agaaaagtga tataaatgtc attatgtctt gagactcacc taaatgcaat  53880
ctttaacatg acttactgag cccccaacat ggtaaaagat cttagcctga aaacactcct  53940
tgtcaaatca ttgcccatca tagtgctgag tagtaatctc tccaggctga aagatggcat  54000
gccgtataac aaatgaaagg gagctgacac tagaaagaac attagtgaaa tcaatatgat  54060
tcaaccagag acacagactc cgttaatggt atgtcaatat gaccaattat ttccacagca  54120
ctgacatcat gattgtattt ttttcttcat ctttaggaga gaacagtttt acttaaccgt  54180
aattgttgaa ttatagccat tggccgagaa agtcttggat gttttacatt gttatcgtta  54240
ccagtttcaa tttgtcttta tttgatatct aaactcctga tcataactta ccatagtttg  54300
aaggttaaga tcaataaagt ggaccaaaca ttcagtgaat tgtgaattct agaaatgcct  54360
gatggtatcc actgcccagg gaataagatg taatggaagc aggcagaact tgaagagcaa  54420
tcagagattg taaatataat cagaattgaa ttcatatagt tattttgtta atttctgctt  54480
cctcaactag actgtaagct tcttaagtgc agggaagtat atattttact tgtcattgta  54540
tttgtcattc tatgccatgt ctatcacctg gcatagaagg cactggatga atattttttg  54600
aataattttc taacttttca tgaatttttg ttcaattttc tcatattggg aagctgccag  54660
ttttagagtt ataccaacac tgccataata aaaaaaagct gtcaagatca ggaaactgca  54720
gatactttcg caggttccag aaccagcaaa ggaatgcccc ttaccatacc cgtcagcacc  54780
catgaagtaa gggaatggac actgcaactt ctggtagcac catcacagag aagggaagtg  54840
ccttcgtgag caggcttgat ggcagcaaca gccatccctc ggtctcacat ccccctttgt  54900
aatcccacag gcatgtgtct gattggtgga ttctaaacca ccctcagaaa tgtagctgca  54960
aaggagtatg aaatgtgcag gttttaatat tccagcctct gctggaaaga aggcttacag  55020
aaagaagttg gaatggatgt tgagtgccaa tctactgtat ctattctact tccttaaagc  55080
ttacattcca ttaacagtct ttggaagaat gtaatatagg cgaagatttt tcagtgccaa  55140
aaaataactg acatggataa atgacatgag gcagtgatta agtatgggct ccagagtgat  55200
gctgtctgaa gtcaaatcct cttccacctc tatgggaatc catttccata tctataaaat  55260
gggtatcatc tttcttcaaa atatggcttt gaggaataaa taagaaaaac agtacgatat  55320
gcctagcaga gtgcctggct aatggtaatt catcaataga ggttagctat tatacttcca  55380
atccttattc ttcaaatttt tgttttcctg gcaggaaacg gagattcttt aattaaaaat  55440
taaaatttga ggttgggtat ggtggctcat gcctgtaaac ccagcatttt ggcagaccga  55500
ggcaggagga tcgcttgaat tcaggagttt gagaccagcc tgggcaacat agcaagacct  55560
tgctctgcta aaaacaaaca aaaaaattag ccaggcgtag tgatatgtgc ctgtggtccc  55620
agctactcag gaggctgagg caggaggatt gcttgagttt gggaggtgga ggctgcagtg  55680
agctatgatt gtgccattgc actccagact gggagacaaa gtgagactct gtcttaaaaa  55740
aataaaaaat aaaaaatttg atattttata attttaaatt atggttttaa catatttagt  55800
tgaaaaggac tcttccaaag cctcatgaat atctcttaca catgttaaat gataacgcag  55860
```

-continued

```
gggtcttgag ttctgaggat tgttccagta tttctacttg ctttttatta gctccacacc  55920

taagcaaccc caaattgaga acgattttca ttataataga ttttcatata acattttatt  55980

atttaattct tcctgccttc ttttcattaa tttatgcagc atttgagggt ttattatgta  56040

ctagggtact gaggtggata ggtacttctg ttttatttga atgatataaa ttcttatttc  56100

tttaataata tttttattat aagactaata catgtttatt gtggagaatt tgacaataaa  56160

caagtgtata gagaataaca ttaaatcacc tataatccca ctctacaggg ctgttggtag  56220

caaagtgata ttttcctcta gtgtttttct tgcatatcct tactttttag gaagacatta  56280

tgtattcagt ttggtatcct gcttgttcac tcaagactgt attatgagca tgtttctgtg  56340

ccattaaata ttcttggaaa acattttaat ggcttgatag tcttttatta tatgaaatat  56400

aaaaatataa aaattgctgt ttcccgtttt ccagtattgt agtcatgtct ttggaacata  56460

gattctggtg ctcaccaaat attccatgtg gccctttcta tttcctgcct tcctgttttg  56520

ttgagttaga atcatgagac tgatatgagt cagtggccca tgaacagaat ccactagtac  56580

cactcacagg ccaatggtca gaacccaaga cccctgcgtt atcatttcac atgtgtaaga  56640

gatgttcatg aagctttgga ctagtctttt tcaactaaat atgctaaagc caaaattaaa  56700

aactatcaaa tttcaaaatt tttttttat tttctgtttt ttaagacaga gtctcacttt  56760

gtcttccagg ctggagtgca gcagcacaat catagctcac tgcagcctcc atctcccgtg  56820

tgtttccttt cttcccttct tctcttagtg aaacgaactt agaagtggca tatggcgaat  56880

gtcacagcta taagttggag gaggaactac cagtctactt tcaactttac ctagactgat  56940

gttgagtcaa atcattgaga cttacagatt tgtctattat agcagcttgt gttaattatc  57000

ctgataatgt atagaatgta tcttgtttac caatggtatt gatttattgt tatatttttt  57060

aaggaatctt tgcagtttta atggccatgc tattatgccc caattctcat tagcgcactt  57120

aaaaatcagt tctttccacc ctgtaaactg aaaataaatc agaatatatg gttcaaaagt  57180

gaaagactaa agaaagttta ctaccacgca atcctatctt tgtctctttc tcttttttat  57240

tggcgtcaaa ctactcagta ttttagactg caaaatttcc actgcatgga ggaaagtaaa  57300

tggattggga ttatttcctg caggtaaatg aaactttatg gtatttgtta tggaggcaag  57360

tagggtactt agagaaagcc aaatataacc tgtccctccc tatcttttcc ttagttgtga  57420

gggtcaaagg ggcacattac agtctggatt cagaaacccc tttcaacagc acgtagatag  57480

ttaaagagaa agattgttct tcaagggcct ctaaggacaa aagtgaatcc actaacactc  57540

taggaagcag tgtgactact ggaagaaaga cattcaagag gtaaaatgga ttttagaagg  57600

tcacaggagc caattgtcag tgtttgtact cttcatcaaa attattttta atgagctccc  57660

tgacaactgc gcatcctgac agcacgggtg aagtggctca tctggggtca tgcccgtgcc  57720

tgacactgcc ctaattagct gacactgctc tgctttgctg aagcacaggg aggtctctcg  57780

agaaagatcc agaagggacc atgataaatc gggcaaaata ttccttgaga gcctgaggtt  57840

cacatgagag ctcagaggaa ttacaataaa gatggattag gaaaatggaa tattaggagg  57900

ggaaagacta gagttactag aagagatatt tgaaaagaga ttccaggatt tactggacag  57960

gtttgtttaa aagtatttga gttggccggg cgcggtggct catgcctgta atcccagcac  58020

tttgggaggc cgaggcgggc ggatcacgag gtcaggagat tgagaccatc ctggctaaca  58080

cggtgaaaca ccgtctctac tgaaaataca aaaaaattag acgggcgtgg tggcgggcgc  58140

ttgtagtccc agctactcgg gatgttgagg caggagaatg gcgcgaaccc gggaggcgga  58200

gcttgcagtg agccgagatc gagccactgc actccagcct gggcgacaga gcgagactcc  58260
```

gtcacaaaac aaaacaaaac aaaaattagc tgggcgtggt ggtgcgtgcc tatagtccca 58320
gctactcggg aggctgaggc aagataattg cttgaaccag ggagtcggag attgcagtga 58380
gctgagatgc gccactgtac tacagtctgg tgacagagcc agactctgtc tcaaaaaaaa 58440
aaaaaaaaaa gtatttgagt tgatgctctg tcaaaactca tttatcaaga ggatttggtt 58500
ttaggcaacg aaaccttgcc tcaaactcat ttccaactca gcgggtttga agatgtgcaa 58560
ggattcatct gttcaaaagc aaaacatgat aaaacaatgc agaacacctc aaaaccatag 58620
agaagtacct gtggaactgt tcaggagtcc taaaggggct cattctaagt ggaaaattat 58680
tgttactctt tcttgagttg tttctgtgaa ttacgaaaaa ggcctatctc agtgaacaga 58740
ccatgttgat catactatga agcagagatt gtagagattt tattaaactg ccatacttct 58800
cagttcagag ctgttttact ccttctccct gggacatttg gcaatgtctg gagacattta 58860
tttatttatt tatttattta tttatttatt tatttatttt ttggagccag cgtttcgttc 58920
tgtcacccag gctggagtgc agtggcgcaa tctcggctca ctgcagcctc tgtttcctgg 58980
gttcaagcga ttctcctgcc ttagtctccc aagtagctgg gattacaggc gtctgccacc 59040
atgcctggct aatttttgta tttttagtaa agacggggtt tcaccacgtt ggtcaggctg 59100
gtctcaaact cctgacttca ggtgatccac ctgcctccgc cacccaaagt gctgggatta 59160
caggtgtggg ccaccgcgcc aggctatctg gagacatttt tgattgtcac aactgggggg 59220
atgcttctgg catctagtgg gtagaagcta gaggtgctgc taaccatcct acactgcaca 59280
ggacagccaa caggaaagaa tcatccagtc tcaaatgtcg gtagtgccca ggctgagaaa 59340
gcttgagtta aagtaaacct gataacctgt atttaaatga ataaaaggga taagactagg 59400
ggagaataaa gctgtccaca tttgtaagcc tctaccaagc acagtgcctg atgtgggatt 59460
acagacaggc gcctgtctca gtgagatcat agcatcagta atccctgtac cgtatgtagt 59520
cccagattgg aatccttgac cgaaggcaag ttctcaacct ctctaagact cagttacaaa 59580
aaagagggca taatagtgtc tcttgcctta taggttttgg tgaaaattga ataagaaaac 59640
atcagtaagg atgtggcatg gtgcctgaca atctttagat gcccaataag tggtagctag 59700
tatcaacata gaaataaaat tgaaaagata cacacacaat gtttgcattg gttatccttg 59760
ggtaatgggt tttaactttg tttcctagat tttaaatttt tccaccataa cacgtattgc 59820
ctttataata acataattca cttgttttaa gtcgattcag gaagcttctg attctatatt 59880
ataaattcta aatgttccct tctattttcc agagtcaagt ttagattatc tagatcatga 59940
aataatcaga tattttcagc tattacctaa ctcatgagtg tgtggaatgc tgtggctttc 60000
tgttattaga atgaaataaa aatgaaaaat aaattgctta tcaatattct gagatagcaa 60060
agcaatgatg catttatgat agactggatg ataggatttg tttttgctga acttattcat 60120
acatatttgt gttttgctta gactttaaaa ttgtttcttt ttctatgagc acatagcaat 60180
aactgggaag tggctgagaa tcattctttt ttttttaatt tttgagacgg agtcttgcac 60240
tgtcgcccag gctggagtgc agtggtgaga tctcagctca ctgcaacctc tgcctcctgg 60300
gttcaagtga ttctcttgcc tcagcctccc aagtagttag gactacaggc gcatgccacc 60360
atgcctggct aatttttgta tttttggttg aaatggggct tcaccatgtt ggtcaggctg 60420
gtctcaaact cctgacctca ggtgatctgc ccaccttggc ctcccaaagt gctgagatta 60480
caggtgtgac ctaccgcgcc tggcctatca ttcttatttg acagggattt ccctattgct 60540
gggtgctaag tgattgaggg aaacccagaa acagctttgt gttgtggtta acagcacaga 60600
ttctggagcc aggcttcctt gtaccaaatc tcagccctac cgctaactag ctttttgact 60660

```
tcagtgaagt ttcttaactt ccttgtgatt attttcctca tctttgaaaa aggaataatg  60720
tcctcaacag gtaacatgaa ggttaaaagg agatggcgtg tgtgtgtgtg tgtgtgtgtg  60780
tgtgtgtata cttgtgtatc tcatccctaa acaaagcctg gctcatagta ggccctatat  60840
aagtgcttgt tactatgatt gaaagttgga tatattttta aatttctatt tttcaatctt  60900
ttgcaaagaa ggaaaacaca actttgataa aggtaatttt ggtagacatt ctctaacatg  60960
taaactgctt gtgtaaactg ggaaatacca gattgctcta aattaattag ttctatattt  61020
gttcaattac actggattgt gttctgtgtt tttattttgt tttgtttctt gttttctact  61080
cacatggtga gacttggctt gggtgagtca tttctttgaa gaccctcagt tcatactaag  61140
gggcaaaagc agatgagggt ccagggcaag gcatggaagc caactgctca gtggtttcaa  61200
cccgggcttc atgggaaaag gatgggaggg tggggttggg tgtccttgag attgaggtga  61260
gaacagttgc ctgagaacag gaaccagaaa gtcctaacag cggtcgatca ctgataacat  61320
ttgtgctgaa aacatttcag gcccaaactg tctcagccat gctgagcaag gcaggaactt  61380
gggatgtgaa ccactctctt aatcgggtcc actgtgtatc caaagttgac ccttgagggc  61440
caggcacggt ggctcactcc tgtaatccca gcactctggg aggccaaggc aggtggatca  61500
tctgacgtca ggagtttgag tccatcctgg ccaacatggt gaaaccctga taatacaaaa  61560
attagccagg tgtttgtggc gggtacctgt aatcccagct actcgggagg ctgaggcagg  61620
agaatcgctt gaacccggga ggcggaggtt gcattgagcc gagatcgcgc gattgcactc  61680
cagcttgggc aacaagagcg aaacttcatc tcaaacaaac aaacaaacaa acccaaaatt  61740
gaccattgag aaaaaccctt gctttgtgcc catctgttgt gaggagatgg gacagccttg  61800
cccctgcatg gaatctgctc aggagcttta gtttctgtag tagaaggtgg gctctgtgat  61860
taactctgtg gagtttaagg atctgggttc agtgagcact caggctctga tggggaattg  61920
tacctggaac ggttaattat ctcgtaaaaa gatcaatgga aaaattattt tcaagaaaaa  61980
taatagataa aatttaccta ctctgatact tagcacaata aatatttatt gaactgttga  62040
atcttttcta ggtatttgaa gttttatttt caggctagtg gcttttgaat tctgccacag  62100
gagaattcag ttctccttct gaggccttct gaggagggga gagagtgaaa ggaagggaag  62160
aagcagcttg gcctggaccc attttttcca ttaatttttt ttttcttagt agagacgagc  62220
tctctgctat gttgcccagg ctggtctcag actcctgggc tcaagcgatc ctcccgcctc  62280
ggcctctcaa agtgttggga ttacaggcgt gagccactgt gcccagcctg gacccatttt  62340
atatactaga cttttctaga aggttctctt tgaagaaaag ttttctctgc taaccacact  62400
ttgaaaaatt atttctgtag gaaaatgata tattatcctt tgataaccta ggtcgctgga  62460
cagcttttgt taaaaagttc tacccatgtg gctttagctt ccaaagatac acttcctttt  62520
tttgagacag agtctcactg tgttgcccag gctggtcttg aactcctggg ctcaagtgat  62580
cctcctgact tggcctcagc ctcccaaagt gctgggatta caggcatgag ccactgcgcc  62640
tggcccccaa gatacacttt caccaaactg tgtttcaaag ttatgctttt aaattgtatt  62700
taaagttcat ataagaacag gcttagctgt gacactgtag aggcgagaat gtggagttga  62760
cacgggtcct tttcacactt gttccccaca cagggcccac atgaaacctg tccctgagtt  62820
taatcctaag aaaaaccttg tttcactagc aaataattcc cttctctgag aaggcaaatt  62880
aattatttta tttccaactt tctcttaggc atcctgaaat tctgagctca gtttcatgct  62940
ctgaaaaaga aaaaataact gctagagtca cagaaatggt attgactttt tggattggaa  63000
tatttgtttt ctctgttcct tacctgtttc cccctatttt tcttacttcc tttccatttt  63060
```

```
atttttgtatg cctctttgta agctgcctta aatgcttttt ggaatgaggc aggatataca  63120
ttcaataaat aaaatatgtc tgagccactt atgaacaaaa ccttcttggg ccagagccta  63180
aacattactt atataaaaag acctgattcc tcaccttcta caacaatatt atttagtcat  63240
ttctctgcat tgtactcaac tctttaaagg ttatagaatt gtagttagcg tattagaagg  63300
ctcatggatc tagattctat gtcctcagca ggtgaagtct tttttacaca atgccactgt  63360
acggattgta gagttcttgg gctggcataa ttttatgtga ccaaaatttg gcaaagggtc  63420
ttatcagttt gaggagagat tagtggagca ttgaatttca gagtttgaaa tgacattaga  63480
gattatctgg tccagtgatt ctcaaccagg gagacatttg gttatttccg gagatatttt  63540
tggtcacaac tgaggtgggt gctactggct tctagggatg gaggtcagga aagctgccaa  63600
gaacccgaca gtgtacagga cagcccccac accagcatgt cactactgcc gaggacgaga  63660
agccctgatc tagccaatcc tgtcattttt cagactccag ggagtttgtg acctgacctt  63720
caaatataag atttaatatt taattgccca aattcattct taaaatatag caaaatgatg  63780
agaaatttcc cttcaaaact gagaacaaga caaagatgtc tattatgata gaccgttctt  63840
agaagtttac tgctcctcct ggggatgcct ctcaatagag aaattctaca ttcccgcctg  63900
ttgaaagcag acatggttac ttgacttgtt tgggcctatg aaatgtgaac agaggcgaca  63960
cacgtcacga tcaggtggga gacttagtaa cacatgcctg gtgtcccatg cccttttccc  64020
tctgccagtg ttccagggcg tggcaggact gccagcctgg tcttggagtc acagctgggc  64080
cccgaaggcg atgctgtggg acctggaaat aaagctttgc tgttgtttta aaaatggaat  64140
cacattgtaa attaggatcc tggggagcgt ggcactaggt attcttatgc agagctagat  64200
ggtgatgctt tcctttcctt atcacttcaa gtctgcagac acagccttca gggcgttctt  64260
cttctgtggt tcctcagttg gggcaccttg tctggagtac acagtaaggc tatgccacag  64320
tcctgctatg actgagatgg caatatgagt gcttttcttt gttggtggtt tttatattta  64380
tgtttaaaaa attataaact aggctaggca cagtggctca cacctataat ctcagcactt  64440
tgggaggccg aggcggatgg atcactctag gtcaggagct ggagaccagt ctggccaaca  64500
tggtgaagcc cggtctctac taaaaatgta aaaattagct gggcatggtg gcgtgcacct  64560
gtagtcccag ctacttggga ggctgaggca ggagaattgc ttgaacccag gaggcggagg  64620
ttgccctgag ctaagatcat gccactgcac tccagcctgg gtaacaaagc aagacttggt  64680
ctcaaaaaat acacacacac acacacacac acacacacac acacacacac acacacacac  64740
taaaactgct gacattgagc attatacagt aagacagatt ttccttcctt gtttctttgc  64800
atcaattttc tctgcctctc cctccgttcc ttttctgttt gcttctactc aggactgggc  64860
acgaatgcac acattgctgt ctggcttgta tctatgtggt aagtctagaa tgatcagtta  64920
ctgaaagaag agggaatcag tgctagtgaa ggatataggt tgtggttaac tggagttccc  64980
aagtagctgg atcttttgtg acagggattg gctagtttgg ttttatacca gatactagtt  65040
atatagagat gaaaagacaa gtttccttca ctcaaaggaa ccttagctta gagtcttgca  65100
gggaaattga tttgcaagca agctgctttg ctcccttact ctaaactcac acttgaatct  65160
ctgatcttaa cactttgatg gtgaagaaaa agccctccag agaaaaggta gtaagagatc  65220
cagaatctag agcctttccc aaggcttcag gtagatctgg ttgaattcac cttgttctct  65280
cttgccccct attctcttat cagtcattcc cacagcttta agtgttttaa aggagtggaa  65340
agctcccaag actcaggccc ttatgtcact cctgacatgc acttataggg gagtccagag  65400
tgtttagtcc tccagggttt ttatgaatgg tcagtgttac tctcagaaga tgctgacctg  65460
```

```
ggtaggacag gttgttcatc cattcatttg tgtgcttacc atgtgccagg cacagttcca  65520
gaactgggga tccactgcta aataagactg ataaggtctt tgctcttaag gagattccat  65580
gctagacatt aattatatta atcttgactc cagtttatgc cctaagccaa gctatcctct  65640
attctctttc ggcatttttc agttgttaaa ccagcatcac caggttgaca acataaccca  65700
actaatacca acaacataaa gtgcctgagt tcaccagccc gctcagctcc cagctgactg  65760
ccccggagtc ccgccctgtt caggcagagg cagagttttt ttttttgttt tttttggaga  65820
cagcgtctca ctctgtcgcc aggctggagt gcagtggcac gatcgtggat cactgcaacc  65880
tccgcctcca gggttcaagc aattctcctg cctcagcctc ctgagtagct gggactaagg  65940
ctcaccacca cccctggcta atttttttttg tttgttttta gtagagatgg ggtttcacca  66000
tgttgcccag gctggtctca aactcccgag ctcaggcaat ccgcccgcct cggcctccca  66060
aagtgccggg attacaggcc tgagccaccg tgcccggccc aggcagagtt ttaattgacc  66120
accatccctt gtccgactcc tagaaacttt cacctggatt ccttaaagtg atgccttgct  66180
gacctgattg gataactcag tattcattgc tgagtagctg aggtaagcgt gatgttcact  66240
tatttctcag ctatctatga gagctgtagc ttacattgtg atcattctgg taaatgttct  66300
ctaagaaaga aaacgaaaaa ataatggcta gagtcatgtt cacctagttt taacatcttt  66360
agagttttgc ttcttctcag ttcagtagct caaagagaga aaaaacaccc aaagacagca  66420
attcttcact ctaaacccaa tattcttcaa ctttctagaa attattagcc acttaattta  66480
ctttgatttt catctctgaa aaagtattca gacttatata tagttgccag atgtgttcat  66540
caaacacttc tctaagaaat ttgtatattt ttggaattca gtcaacattt tttggataaa  66600
tgaatgtgaa cactttagga attgcttatt ccacaaatga tttcttacca agatttccag  66660
aaactatttt catattgaaa caaaaacaaa acaacacacc actctgcttc ttcccacaga  66720
gttctgagac agcttttaca taatgatctt gaacatattg taatcttgtt tatgacagaa  66780
atgaaaagct gtcatcacat ttctgttttg gagagttcat tgttttccct gtgaattcat  66840
aggagttctt tgtctattat aaatattatc actttgtctt gaaaatagct ttcccttctg  66900
tactctttct ctgtgggctt tatgcatctt ttgtcttata aaatgtatga tgtctacaga  66960
gtcagatgta tctgtttttt ccttttttagc gtctttattt tttgtttaac acaaaaaacat  67020
ctgccagttg gtaagttata gaaatattct taaatttctt ctaaagtttt aatattgtat  67080
ttttcagtta aagtgtaatc cactgagcca ggcgtggtga catacacctg tagtcccaac  67140
cacctgggag gccgaggtgg gaggattgct taagcccagg agtttgaggc tgcagtgtac  67200
aatgttcaca ctactgcact ccagcctggg ccacagagca agaccctgtc tccaaaaaaa  67260
aaagagaaaa aattaatcca ttggattact ctttgttttc ttctagttaa acatccattg  67320
tgtcagcata atcaaactat cttgccctat gaaatgagtt gctatctctt gtctatattc  67380
acatcttttc ccagattttc tgttctattc ccactgatgt atttacaggc cagtatcaca  67440
acctgtgaaa gcattgtctt cagtggaaat tttaaaatag taattactcc tttcattatt  67500
tttttcataa ttttcttggt tatttccaga tctttacttt tcaatgaaca tatttttaaa  67560
tcgcttaaat cattcagatc tgaaacctca ttggcagtct aattggagtg aatcttctga  67620
ttcacaagca tgaaatgtat gtatttctgt ttattcaaac cttcttttag tattttaaat  67680
atgcgttttg ttgtcttttt catgtaggat ctataccttt cctaaatgtt ttatagtttc  67740
ttgtaaatag aattttaaaa ttcccattct atctggttat tgtaactata agacaaagct  67800
attgattttt ttcctcttta ttttctagca tttattattt gcaagcattt attagttgac  67860
```

```
cttttggggt ctgttttctc ttttgaatgt gtaagcacaa ggtagatcat gtttatcttg  67920
tttactagtt tatccccagc attctggcag gacaaatgaa tgaatgcatg aatggatatc  67980
tgaaaaagcg tttgagagga gattcaacaa tctacactac tttccctttt cttcttttta  68040
ccttgtgttt ctaacacata ctaagctttt tttctttttc ttctgaaatg gggttttgct  68100
ctgtcaccca ggctggagtg cagtgtcatg atctaggctc actgcaacct ctgcctcctg  68160
ggttcaaacg attttcctgc ctcagcctcc cgagtagctg ggattacagg tgcacgccac  68220
caagcccagc taatttttgt atttttagta gagacgggat ttcgccatgt tggccaggct  68280
gctgtccaac tgctgacctc gggtgatcca cccacctcgg cctccccaaa gtgctgagac  68340
gacaggcatg agccaccaat cccagcccat tctaagcttt taacatcctt agattactgt  68400
tccaaatacg ttgggaaggt cccccaattt tttccttaac tttttaaaag caactttatt  68460
gaaatatatt ttatatatca taaaaatcac ctatttcaag atgattttag tattcaataa  68520
tttttagtag ctttactgag tgatgcaact gtaatgtaac gatagatgtt caggtttaga  68580
acgttttcat cctcctaata ggatctctca tgtccattta tagttaatcc ctgttcgcac  68640
ctttacccct attcacaagc aatcgttaat ttacttcttg tttcagtgga tttgcctgtt  68700
ctggacattt catataaatg agatggtacc atatgtgaac ttttgtgtct gactgctttc  68760
gcttagcata atgttttcaa ggttcatcta tgttgtcgcc tgtgtcagta ttctcttcct  68820
ctgttgctga ataatattcc cttgtatgca tgtactacat tttgtgtatc tgttcattag  68880
tttttggaca tgtaggttgt ttctactttt tggttattat gagtaatgct ccagtgaact  68940
tcacatgtaa gtctctgtgt ggacatatgt tttcatttct tttcagtagg tacctaggag  69000
cggaattggt ggttcatttt atgtttttttg agaaattgtc aaactatttt ccaaagtggc  69060
cacaccattt tatatttcta gcagtaatgt atgagggttc ctattcctct tttcttaaca  69120
tttttctcac agtttattga tgtatgattg aggtatcatt tacattgagg tataacttac  69180
atatgataaa atgctcagat cttaagtgta cagttcaatt atttttggac acatgtatac  69240
atgcatgtat acaaccactg cgtcaatcaa gatacgaaac atttgcatca ttctagaaag  69300
tcccttgttc cttgccctca gattttgatt tctatcattc tatcatactg ttttgatttc  69360
tatcattgta gattagtgtt tattccagaa tttcatacaa atcaaatcat acagtatgta  69420
ctcctttgtg ttgtcttctt tcactcatcg taagggtttc gagtttcatc agtgttattg  69480
tgtttatctc agttgtttgt tccttttttat tgctgagagc actccattgt atgaatgtcc  69540
cacattttttg tttatccagt tacctgttga tggacatttg agtcattttt catttgtagt  69600
tattaggaac aaaggtacta ttaaacattt atataccagt ctttttgtgg acatgatttc  69660
atttttcttg ggtgaattcc caagagtgta attgctgggt catagggtag ttatatgtta  69720
cttactgttt tttatctagt attaagtcac tttacaaaat tctttaagaa ttacagtttt  69780
ttggccgggc atggtggctc acgcctgtaa tcccagcact ttgggaggct gaggcgggcg  69840
catgccttga ggccaagagt tcaagaccag cctggccaac atggtgaaac cccatctcta  69900
ctagaaatac aaaaattagc caggcgtggt ggtgcgcacc tgtaatccga gctacttggg  69960
aggctgaggc ataagaatct cttgaacccg ggaggtggag attgcagtga gctgagatca  70020
caccatggca ctccagtctg ggcaacacag ctagactcag tctcaaaaaa aaaaaaagaat  70080
gacagtttct aaaatatcgt gtctttgatt ttctaaatta ttatacaatt tgctgatagg  70140
tataattttg agttagatct ttatctgttg atctggagga gtttctggga cttttttttt  70200
ttttaaagaa gcacacaagt tgcccagaaa tgtatatagt ataatccaaa ttttgtaaga  70260
```

```
caaacaataa catgtatgta tatgttcgcg attctatagg caaaagaaaa gatgtgaaag  70320
atgttcactg gcatgctaac catggtttcg tggctggagt ggcggaggtg gttaagggga  70380
ggtgtagagg gttgagttta caaaaaaagg aaacagggat aaagaaaaca cattattaaa  70440
gttaaatgat ttagtagagt ataaatatat aaatatattt atatatttat ataaaatata  70500
tataaatatt ttaatatata tttaatatat aaatatttat aaaaatataa atatttatat  70560
aaaatataaa atatttattg caaaaacttt ttaatgataa aaatattgga accagcataa  70620
agatgagctt accaaagtta tttgcagctg ttaaaaatag tgatatacgt gtgtttagaa  70680
tgtatgttaa attcaaattc agattgcaaa gcagtatgca ttctatggcc ctgactactt  70740
tgtgctaata tgattgtgat tatgggcatt tttgtttact ttttaaaatc ttatggggga  70800
aaaaagcagg agttatttct agaagtatga atcactgaaa cacagtaata ttccttaaat  70860
tatacttttc ttaggatagc tgtaattata taagatttag tcaaatcttt aattagatgg  70920
taggctgatt gagggtaggg atccctcaag attctatttg tcaccgtcag agctcagaat  70980
aattctgact cattcataac atgaagagat caccgttgaa cacagtccat aggaaagtaa  71040
gatctcagca ttaaagagat gcaggtatga gtgttaaaga agagcaggcc ctggtcagag  71100
tattctccaa ttgacgtcaa tcagttctcc acttgattga cctggagagt actttgacag  71160
ggcctgctct tcatttacat aggctcggtg cctacctttt gcagctgaac aggctcggcc  71220
ccagttcttg ctgggttcta agctacagtt tcagggaaaa ggcagaaagc caagataggg  71280
caggaatggg atgaaagggg actggcctgt tggctaggtc agcaaatttg tctgtgattt  71340
acagcactaa gctcaggatt tgacttgatt agaatttgat tgcctttcat ttgattcaag  71400
ttggagccac tgctccgggc tgttctatct agtggatgga ccatagaagc agggatctca  71460
tgacttagca atattaaaac ctcaggcagg tggcttgttg gtctgagcag cctctaaatt  71520
tgtacaaaag cctggtggct ggctgggttg gtaaaaatgg cagttgtcct gcatgctgac  71580
attgggagtt actctgcact gctgcaggct gtcctggcac actgcaggcc gggcatcatt  71640
tcatggtgga ggacgtcact cagttttgca tgaggctctt gcatcacatt tgtatttaag  71700
gaattcacac cttattttag ggaaaacatc tgttccttgg ttaaaacagc attgcacttt  71760
taacagagcg gccacctttt tccacatacg ataggacagg ttttggatat atggagtatt  71820
aactgaaaag agcactatat atttcatagt tctttaaaga ccattgatat gtaaatcaat  71880
gtgtaagaag atatcgttta agaggggtta tggcacatgg tggaaggaat gctgctttgc  71940
atttatccgt gtgaagtaat ctgcctgtgc atctgaagaa acagcaggcc ccgccgcaag  72000
tgatgaagca gttctgtgga gaaacccatt tacaccagtt tccagatgct attccaccag  72060
aaataattcc aagaatatac ttatatttta aataaatgat aaaatcaatt tccagatgaa  72120
gtgtacatta caaagagaaa cttggtatta ttatgtatta atccatatta actaaagttg  72180
aacctgacat caaaatattg atcccttctt aaaatagaca aaaatacttt gagttaaatt  72240
gtttttcttc ctatttgtgc tagccggtgc ttaaagtcta atgatgtgat aattgaatag  72300
taaaggaatc taaatctcta ctttcttgat tcccagtgtg ctaactttac taaaattgtg  72360
ggaataagca aaatattttt catagcagta ataaggattt ttaaaaatta tgtgacaatt  72420
gtgtattaga ctgaagtaat taataccttt gtcacaggga ccgggtgcaa tggctcatgc  72480
ctgttatctt agcactttgg gaggccgaga caggcagatc acttgaggtc aggagtttga  72540
gaccaacctg gccagcatgg tgaagcctca tcttactaaa agtacaaaaa ttagctgggc  72600
atggtggtag gcacctgtaa tcccagctac tcaggaggct gaggcaggag aatttcttga  72660
```

-continued

```
acccaggagg caaagattgc agtgagccga cattgcgcta ctgcactcca gcctgggcaa  72720
caaagcaaga cacgctctca aaaaaaaaaa aaaaaaaatt ggcatgagac taaagaggat  72780
ttaaggtgga ggatttcctc gcagtaggta aagaagcaaa gccctgttta ttcagagcct  72840
gagctcagac ttgaatttct tttttagact ttcattttct ccctttatga agtggcaaag  72900
tcagttaagt atagatgtgg ccgtctatgt ccctgagctt ctgggttcaa taatcagctc  72960
tgcgactcct cttaaagaat ccagaggatt tcctgcctgg accttgaagt cacctccccg  73020
ctacatattt cccagctctg gttttccacc tcctcaggat gaatgtcttc ttgaatgtcc  73080
tctggaagag tgtcagctgc acttaaactt ccatcaaaag ggggactcag aggccttaaa  73140
ataggcatca ggtacacatt ctatttatga ttctgggatt aggcctattt tttggcattt  73200
cctgtggtca aatttttaat ttctgaactt tatcggattt ccaaagatac cgtcccttgg  73260
ctgtcttcat tgatttcttc aaaggatttc ctcggcaaag ttaccctagt cttaactgga  73320
agagcatggc tcccttaaag agtctaaaat aagccttttc ctttagtgac tcccagctct  73380
ggtcttgtca ggttgcattt ttctcctaac cttcttcttt cctaatcctc actcactaat  73440
tcaaaaatgt tattctgcct tccagaacat cacactttgt aaacattttg ttaataataa  73500
aagctagcat tccttgaata ctggttttgt aagctagatt atctcattta accctgtgat  73560
gatgttattc attaaggagc atttgctttc ttaggtctgc aacatcagtc actcctcgcc  73620
catctgtatc ccagctttta acagtttgtt actgctcttt cctatcatat tctcttgtgg  73680
gcaccaaatt ttttttttta attttattgt atctttagag gagttttagg ggagagtaaa  73740
aataaatata tttttcaatc catctttacc cagaaattga aatattactt tttatagtag  73800
aaccagaaat taacttaaga atgtttttgg catttggaga catgcataca aatactaaag  73860
aggtgcttat aaaaaaatta cacttttggc cgggcagagt ggctcacacc tgtaacccca  73920
gcagtttggg aggccgaggg gggtggatca cttgaggtca ggagttcgag accagcctgc  73980
ccaacgtggt gaaaccctgt ctctactaaa aatacaaaaa ttagctggga gtggtggcat  74040
gcgcctgtaa tcctagccac cggggaggct gaggcaggag aatcgcttgg acctgggagg  74100
cagaggttgc ggtgagcaga gatcacccca cggcactcca gcctgggcaa cagagcgaga  74160
ctctgtctca aaaaaaaaaa aatttacttt ttattataaa tttgtcatat ttaatgccat  74220
ggtgcattat agttctggct acaaaatgaa acaatttatt tttaaacttg attttttttc  74280
tctaacattt gaaatcatta aaagttacta tcaggagcct ctcattttat gcatataaat  74340
gcaataaaac agctggttat cttatgctct atatgaaggg taatatttta agtgcatttt  74400
caaattcagc taagctagtg attctatcag aaaatatcat ttttcactca ctggcttttg  74460
aaacataatt agattttctg agcaactgtt gcttataatt ggaatttgct tattatcatt  74520
ttaacagaga aaaacactga cctatgtaat tttagtgcaa ttaaattttt ctccttatgc  74580
ctgtgtgtac ctcatcaatt cagcaaaagc aaaacctgat ctagaagtcc ctgtgcagca  74640
gattgcaggg aaagaagcag tcagctgatt tgtctgggcc ataaaaccgt ggtgtctggc  74700
agaattgtga tagtaattgc tctaagatgc attctgttta caaagactaa cattgcagct  74760
gcttttaatt agctgctaga aatgaaaaac tgtcagggta tgcttgttag atctacctga  74820
atttattcca ttgcaaataa agcagaattt aaagaatatc aatgtaaaac aggaaacttc  74880
tcattgtaaa ccaagttcag aaaggtggtg gtaaatatct gaatgtatcc ttttggtttt  74940
atgggaagca gaaaaacctg atttcctatg acacagacca ttgcattctg tattgtattg  75000
ttttcttttt tctttctttc tttctttctt tttttttttt tttttttttt gagacacagt  75060
```

```
cttgctctgt tgcccaggct ggagtacaat ggtgcaatct cagctcactg caacctccac  75120
ctcccgggtc caggcaattc tcctgcctca gcctccctag tagctgggat tacaggtggg  75180
cgtcaccatg cccaggtaat ttttgtattt ttagtagaga tgggctttca tcatgttggc  75240
caggctggtc ttgaactcct gacctcaagt gatctgccca ccttggagtc ccaaagtact  75300
ggaaatatag gcatgagcca ccatgccccg ctgttttcta catttctttt atatgtaaat  75360
ttctgtcctg agcagatgat tcacttccag agaaaaggat ctttgcattc cctgctgtct  75420
ggcattgtgc ataataaata tatactggca aatacataat ggtagtattt ttatttataa  75480
aagtatgaga aattgctttg agaaaatcaa agggttagaa ataaaagaaa attaaaagca  75540
ttgttacaat ttatcatgaa atttagtgag tattacagag ctttgtacac tgggttagaa  75600
aatttgtgtt tttttctttt tcttttcttt tctttcttt tttttttttt ttttttttta  75660
aagagatagt gtcttgctct gttgacaagg ctggaatgca gtggtgtgat cacagatcac  75720
tgcagccttg acctagactc gagcaatcct tccacctcag cctccagact agctggaact  75780
acaggtgtgc accagtgcac tcagctcatt gttttatttt ttaaatgttt tgtagagacg  75840
gagtcttgct ttgttgccca ggctggtctc aaagtcctgg cctcaagtga tcctcccttc  75900
tcggcctccc aaatcctggg attacagggg tgagccacca cacctggtct taggtttctt  75960
aattttattt ctctgtgttt ctacaggctt ttaggccatt ttactaataa ttactttttt  76020
tttttttttt ttagtttttt tgagacagag tcttgctctg tcaccaggct ggagtgcagt  76080
ggtgcgatct tggctcattg caaccgctgg ttcaagcgat tctcctgcct cagcctccct  76140
agtagctgag attacaggca cgcgcgccat cacgcccagc taatttttgt atttttagta  76200
gagacagggt ttcaccatgt tggccaggct ggtcttgaac tcctgacctt gtgatctgcc  76260
cacctcggcc tcccaaagtg ctggcattat aggcgtgagc cactgttccc agcctgctaa  76320
tagcttttaa aaaggaatat tgattttcat agttgtgtgg cagacacagc tgacaccact  76380
agctaactta agcatactct gagaatgacc ttgcatggca gatgcacctg acacaaaatt  76440
taagcataac ctgaggatga ccctgtagcc taagaagaat gtgtattcag agttcccagc  76500
taataaatcc aggaaggcca actgggagag tcattcctta tctgtgagta acatctgaac  76560
cctcagccca tcctgtggaa cacaggccat ataggggatt gaggcccttt gttttgggtt  76620
agatagaggt tgctaggggg agggtgctaa gcaagaatgc tgtataaact gcatgctttt  76680
tacaagcagt tgccattgtc tagtccagcc cgtcaccact ggaccaccct gtatgtaaat  76740
cctctcagta aaccttgtct catttactgg ctccaggtct ctttgaaagc ctctcaaaca  76800
tggcgccatc cctattgcag ccattagagt ccggcgtggc agtggtcagg actgttgaag  76860
aaggctgaga atttagggca ctgtgaagtg tttaatcatt tatcaaggta tcaatttagt  76920
gtctctcaag gaaaaaacat atttgttgat ttgatttcat gccaacactg atgtttttttg  76980
ctactctatg gccttgaata gtcaggcatt gactgtaacc aaaaggatgt atggaaaata  77040
attgttttct tttttgagat ggaatcttgc tctgtcgcca ggctggagtg cagtggcgcg  77100
atcttggctc actgcaacct ccacctctcg ggttcaagcg attctcctgc ctcagcctcc  77160
cgagtagctg ggattacaga cgcatgccac cacgcccagc taatttttgt atctttatta  77220
gagatggagt ttcaccatgt tggccaggct gctcttgaac tcctgacctc gtgatccacc  77280
cacctcggcc tcccaaagtg ctgggattac aggtgtgagc caccgcgccc ggccaaaata  77340
attgttttct atccttagtg aagagctaaa gagaatttcc ttagaataac agcaaaggaa  77400
cttaaagtgt tcagaaaaac aaagtgagga tggtaggaat cctttcgcct gaaactttgg  77460
```

```
aaaaaggtgg atgaattaca actaagtcat cttttagctt tgctttcttg atcttccttc  77520
aaagtttatg atacctaaat tctctcttca actcataaaa tgtgttttat ggtttaatag  77580
aaaagctata agcacatgac aaaattagtt cttattagct atatgcctac agaaccaatt  77640
ttgtggtttt caatatgata tgttcaattc cagaaggtgt tttataaatc agttggtagg  77700
aacctgtttt atgtgtaagc tgtgtccaga tggatgtttc tttacccttt tatgtacctg  77760
gaccaatagt accagaaacc atgggagcat aaccacccca caagaactcc acccctgcca  77820
cagccttcac tatttggcag gggaagcaga gactctgcca tcttcaagcc actggtagag  77880
ccccttttcac atgacctggg aggtaatttc acaagcaaag aagtctaaag gaaaggttgt  77940
acctaattta aattattgct tttgtcatat tctctaccac tcacaggaat gttttattat  78000
taatcacaaa tcataagcaa tttatactct tgattatttc aaaagagcca catccactgc  78060
tatggttttg aaattattac attatacatt attagtcagc ttagactaaa ttatgctgtg  78120
gtaacaaacc ccaaaatttc aagggcttac aacaataaag gtttgtcttt catgctgtac  78180
attcattgca ggtaactaag acactattcc atgtcactgt cattctgaga tatgggctga  78240
aggaacatcc tctccctgag gctttgctag tgtttcagta gacagaaaaa gaacgcaatg  78300
ggaacacaca caatggttct taaagcttca gcttcaaagc agcacatgtc atggcactca  78360
cactttacaa agcaagtcag acggctgctc tggggacctg cagtcgtgca ggagaggggc  78420
tcccaaatca gacagccact cctggcatca atgacgcagg gatctatagt ccttttatgc  78480
tgaggggtgg tgaatccacc acagttaaca aaatcttgag acttgccata aacaaattct  78540
catctgtttg tgtgatgagg tccagatgat ggcccacttc agtagcaaag acagtgcact  78600
gtgctcacca cgccatttca tcttttccct gggttgatag gaagatggcc ttctcaaccc  78660
ctttgcatct gtgtggggcc aggagactaa acaccgccag ttgattatga ggaggaatga  78720
cgtgtggcac ttccagacct agctcacaaa cgtggcaaaa tccactctcc cccaactcct  78780
tgagcctgtc tctccaaatt gctgcataga ggcaatgttt ccaggagaac ctcacctggc  78840
cagaaacatc tgccttgaac atggttagaa caaatgaaac tttttgtat taaaacactt  78900
gagattctgt ggctcttcgt tactgtgtta ccctatcctg accttgcttt gtggtttatt  78960
taatgatgca catttactag agtggtgtac attcaatagt gaggtggcca catacaacat  79020
acccctaaaa cattgctgaa agtacacagc catttctact ataaaaatat aagtatatga  79080
gtgaagaact gatttttgaa ttttgcttta attaatttaa atttaagtgg tcacatgtgg  79140
gtagtggcca ccgtattgga ccacagaacc ttaagcagta ggaagctttt tgctacgtga  79200
tgtattataa atctttccac tgtctcagca atctaaacat aaaaccaaca tgtctaaatt  79260
tcacactttc tagatgatga agagtcataa aatgaacaga aagtctttat atggtgtttc  79320
agggggacag ttgtgacatt ggagtgctgg tcaaagttct ttattatttt ttatttgttt  79380
ccaaatatgg agtgcagaaa accaaatggt ggaatggaca tttttgccaa agtataattg  79440
tggtctttaa tgatgtaaaa taaaatacca tattcatttc tgaatttttt tcatcgtgaa  79500
gtgtgtgaga tgtgacttga caactttgca aatgtcgtgc ctctgcttaa atctctgcat  79560
tatatttatg gaaatgtttg agatcctgga aaccatttag aggtgttata aaatacttta  79620
tttcttgagg tccaaaagac ttcaaaatag gggctgagtg atataatgga aagaacactg  79680
gattaggagc cagaatatct gggttatgtt gcctgctctc tcactaactg gctcagtgaa  79740
tttgggcagg ttatttgaac tctctggatc tcggtttctt ctatggtgag tttatgggct  79800
tagattaatc acccacctct aaaattccag gtcttttctt ttttctgact ttaggtcagg  79860
```

```
tcttttcttg tgaagtatta aaactgagcc cacccatgtc aatataactt aactctttgt  79920
tccacgaaat tcgtgcccag gaagataaga cagtaaatta ataaataaat tcactgtttg  79980
ctttaggaaa gtcttgcaaa tcaatttatc aggacaaaca gtttgctcat ctgggcaaac  80040
agttgtctta ttaaaacaat atattgctca cctgggcaaa cagcttgaca agtttgtgaa  80100
agaatgtcac tatgcattgt ggttttgaaa atgaatctat gggctgggcg cggtggctca  80160
cgtctgtaat ctcagcactt tgggaggccg aggcgggcag atcacaaggt caggagttgg  80220
agaccagcct gaccaacatg gtgaaacccc gtctgtacta aaaatacaaa aattattcgg  80280
gcgtggtggc gcgctcctat aatcccagct actcaggagg ctgaggcatg aaaatcgctt  80340
gaacctggga ggcggaggtt gcagtgagcc aagattgtgc cccgcactc cagcctgggc  80400
aacagagcga gactccatat caaaaaaaag gaaaaagaaa aaagaaaatg attctatgga  80460
aacagcagac actggggact ccaaaagaag gacaaagatg taagaactac ctattgggta  80520
ctatgtttat tatttgggta aggaattcag caggaaccca aacctcccac atcacacaat  80580
atatccatct aacaaacctg cacatgtacc cctgaatcta aattttgttg ttgttgttgt  80640
tttttgagac ggagtctcgc tctgtcacgc aggctggaat ctactataaa tgcatttttt  80700
ttttttttaga cggagtctcg ctctgttgcc caggctagag tgcaatggca cgatctcggc  80760
tcactgcaac ctccgcctcc cgggttcatg caattctccc acctcagcct cctgaatagc  80820
tgggattaca gaaacctgcc atcatgcctg gctaattttt gtatttttgt agagacgggg  80880
tttcaccatg tgggctgggc tggtcttgaa ctcctgacct caggtgatcc acccacctcg  80940
gcctcccaaa gtactgggat tacagtcatg agccactgcg cctggccaac tataaatgca  81000
attttattta ctatttaact gggagtagaa tatcttagta tgtaagtcta ggtatttttc  81060
caactagcac aacacttcag atagtttata tattggtgag attaattaca agattagtga  81120
gcacatcata gacattgagt taattatgac aaggtgaatg aacaaaacca attttctgtg  81180
tcaaacgtag tttacaactt tatgtaaaca tttatcgtat acattgtaag aaattcagtt  81240
ttctgtaaaa aaatacgtag tcttaagttt acaattcaaa acccatagag gttccctgac  81300
attacctgcc aacatttaag agctacttat tagtttgaag agagacagag tatgtgcaca  81360
tttaaactta aggcagaaat ttgtgtctgt tggcctaagt gttctttgtt cactgggctc  81420
tgaagaccat caaataaaag taattcttaa cttagtgttt ttggcactga atcttgaatt  81480
cctttttttt tttttgagac agagtctcac tctattgccc aggatggagt gcagtggtgc  81540
aatcttggct cactgcaacc tccgcctctg gggctcaagt gattttcctg cctcagcctc  81600
ccgagtagct gggactacag gcgcccacta ccatgcctgg ctaattttg tatgtttta  81660
gtagagacgg ggtttcacca tgttggccag gctggtgcat cctgaattct taaataacca  81720
gtaccaaagt tatttttctt gaaccttctc actaagtatc tttatcgcac atgagttctc  81780
tctttaattt taactaaggc ctaattaaaa tattttcaaa tttataattt ttattttctc  81840
atgaagcctg ataggaaaag ctttgccctt aggctcatag ttttacctga ggaaattcaa  81900
caatggatct gaaagcagct tattgaggac atgcagttag aacttaagaa gaatgtgcct  81960
ttaaggagga ataaccctga gaaatagttc catgacattt aaattctatt gctctgacag  82020
agccattctg acaggtttta agtttcaaag ttatcagaca atgtgcagac aacctcacca  82080
tctcctgagc ttcacctcac tgttaaccag cctatggtaa tgtctttctc tttttctcct  82140
cctcttcctc ctactcccta tccttgccct gtcaatattg gatataatgg caggtcagaa  82200
atggggtgag gcatgaggtg aaaaccaaag agaactgtgc agaaggttaa gggttaaata  82260
```

```
acatcaggca aaccagccaa gtataactag acattagaag ttcagctcta gtataaaagt  82320
taaaagacaa aagtattaaa aatcactata cctgcataat ttgttgatga atacacagta  82380
taaaaaggtg taaagtgtga catcaacacc atagaatggt gggtggggga taagtaaaag  82440
tgtagtaatt tttttttttt ttttttgaga cagggtcttg ctctgttgcc caggctggag  82500
tgcagtggtg caatctcggc tcactgcaac ctctgcctcc cgggttcaag agattctcct  82560
gcctcagcct cccgagtagc tgggactaca ggcacgcacc accatgccag gctaattttt  82620
gtatttgtag tagagatggg gtttcaccat gttggccagg ttggtctcca actcctgacc  82680
tcgagttatc tgctcacctc cgcctcccaa agtgctggga ttacaggcgt gagccaccgc  82740
acctggcaag tgtagaattt ttgtatgcaa ttgaagttga gttgttacca gtttaaacag  82800
aatgttttgt tttatgtaag gtccatggta accccaaaga acctaccttt agtagaaaca  82860
cagaagataa agaaatgaat caaagcatac cactacaaaa aaaaatttaa agtcacaaag  82920
caagactgta agagaggaag aaaggaacaa atgaactgca aaacaaaaca aaatagttaa  82980
gcccttaact ctcaataatt agtttaaatg taaatggatt gaattcccca accaaagata  83040
aacagtggcc aaatggatta aaagaaaacc caagatctaa caatattcgt gtgtacaaga  83100
aattcacttt agacttaagg acatacatag gctgaaagta aagggatgga agaaaatatt  83160
ccacgcaaat agtaatcaaa agagagcagg agtggcttta tttatatcag actaaataga  83220
ctttcagtca aaatctgtca cagaagacaa agaagatcac tatataataa taaagaggtc  83280
agttcatcaa gaggatataa caattataaa tatatgtgca ccccacattg aagcatctaa  83340
atacataaag cacatattaa cagagctgaa gggaaaaaca gacatcaata caacaatagc  83400
aggatgcctc agtacccctt tcaacagtgg gtagattatc cagacagaaa atcaatgagg  83460
aaacagtggc ctgaataaca ttatagacca agtggaccta acagacatac acagaccatc  83520
tcatccaata gcagcagaat acacgttttt ctcaaggacg cttggaacat tcacaagggc  83580
tagattatat gttgggccac aaaacaagac ttaacaaatt taagaagatt ggaatcatct  83640
ccagtacctt ttctgatcat aataacatta gaaattaata acaggaatta tgaaaaatgg  83700
acatatgtag acattaagca cacactcctg aacaactact tggttgaaga agaaatcaaa  83760
agagagatta ggaagtatct tgaggcaaat gcaaatggat acacaacata ccaaaagtta  83820
caggatgcag caaaagcaat tctaagaggg aagtttagag ggataaaggc ctacattcgg  83880
aagaaagatc ttaaacaacc taatttcaca ccccaaggaa ctagaaaaag aagaacaaac  83940
taagcccaaa gtcagcagaa ggagacaaag attggagcaa aaagaagcta aggagacagt  84000
agaaaagatc aacaaaactg agatttgttt tttgaagaga aacaaaattg acaaatcctt  84060
tatctagctt taccaagaaa aaaagagaga actcaaataa atgaaattat aaatgaaaga  84120
agagatacag gcataccttg gtttattgca ctttattgta ctttgcagat attgcatttt  84180
ttacaaattg aaggtttgtg gcaaccctgc atggagcaag tctgttggca acgtttttcc  84240
cgcatgtgct cactctgtgt ctctgtgtcc cattttggta attcacacaa tatatcaaag  84300
tttttcatta ttgtattata tatataatat tatgtatata taatatgtaa tatatataat  84360
acgtatataa tatataatat atgttatata ttatatgtta tatgcaatat atgttatata  84420
taatatatat tatatataat acatatatat tatgatatta ttatatcaca atgctgattg  84480
tgatcagtga tctttgatgt tacaatagta attgctttgg ggtatcacag actgtcccca  84540
tgtaagaagg tgaatttaat caatagatat catgtggtct ctgactacta cagtgtgggc  84600
tctgctactg ttctgactgg cctttccctc tcattgagcc tccctattcc ctgagacaca  84660
```

```
acagtattga gattaaacca attaataacc ctataatggc ctctaattgt tcaagtgaaa  84720
ggaagagtta cacatctctc actttaaatc gaaatgtaga aatgattaag cttagtgaag  84780
aaggcatatt gaaagcccag ataggcctat tgtgtcaaac agtcaagttg tgaaggccaa  84840
gaaacgttct tgaaggaaat taaaagtgct attccagtga acacacaaaa gataaagcag  84900
gccaggtgcg gtggctcacg cctgtaatcc cagcactttg ggaggccaag gtgggcagat  84960
cacaaggtca agagatcgag accatcctgg ctaacatggt gaaaccccat ctctactaaa  85020
aatacaaaaa aaaagtagcc aggcatggtg gcacgtgcct gtagtcccag ctacttggga  85080
ggctgaggtg ggagaattgc ttgaacccag gaggcggagg ttgcagtgag ctaagatcgt  85140
gccattgcac tccagcctgg gtggcagagc gagactctgt taaataaata aataaataaa  85200
taaatagata gatagataga tagatagaca aataaagcaa aaaaacctat tactgatata  85260
cagaaagttt gagtcttctg gatagaagat caaaccaacc acaacattcc gttaagccaa  85320
agcttaatcc agagcaaggt ctttcttcag ttctatgaag actgagagag gcagtgctat  85380
ggaaggagag tttggtacta gcagagactg gttcatgaga tttaaggaaa gaagccattt  85440
ccattacata aaagtgcaaa taagcagcaa atgctgatgt aggggccgca gcaagtcatc  85500
cagaagatct agctaagatt attagtaaag gtggatgatt ttgaggggtt caagacttca  85560
gtggaggaag gaactgcaga tgtggtggaa acagcaagag agctagaatt agaagtgaag  85620
cctgaagatg tgactgaatt gctgcaatct gaggataaaa tgtgaatgaa tgagtacttg  85680
tttcttatgg atgaacatcc ttcttaaaga tggaatctac tcctggtgaa gatgctgtgg  85740
atattgttga agtgacaaca aaagatgtag aatatttcac aaacttagtt gataaccagt  85800
ggcagaattt gagaggattg actccaattt tgaaaaaagt tctactgtgg gtaaaatgct  85860
gccagacagt attgcctatt acagagaaat ctttcacgaa aggaacagtt gatcaatgca  85920
ttaaacttgt cttattttaa gaaattgcca cagccacccc aaccttcaac aaccaccaac  85980
ctgatcagtc agcaggcctc agtaatgaga caagaccttc taccagcaaa aaagattgtg  86040
actcactgaa gacttagatg atcattatca ttttttagca ataaagtatt tttaaggtat  86100
gtacattgtt gttttagaca taatggtatt attgcacatt actagactac agtatagtgt  86160
caacataact ttcatatgca ctgggaaacc aaaaaaatgga tgtgacttgt tttattgtgg  86220
tatttgctct gttgtggtgg tttggaactg gacctgcaat gtatcagagg tatacctgta  86280
ttatagctaa taccaaataa atagaatcat aagagactac tgtgaataat tgtatgccta  86340
caaattggat aacctggaag aaatggatca attcctagaa acatacaacc tacaaagatt  86400
gaatcataaa aaaactagaa aatataaacg accaaataag taaggagatt aaatgagtca  86460
tcaaaaacct ccagcaaaga aaaaccccaa actagatggc ttctttggtg agttctacta  86520
tgcgtttaaa taagaattaa caccaatcct tctcaaactc ttccaagaaa ttcgagagga  86580
gggaacactt ccaaattcat tttatgaggc cagcaacacc ctcataccaa agccagataa  86640
ggacactaca agaaaattcc agatcagtat cactgatgaa catagatgca aaagttctca  86700
acaaaatacc agcgaaccta attcaacagc acactaaaaa catcatacac cataatcaat  86760
gaaatgtatc tctgagatgc aaggatggtt caaatatatg caaattagta aatgtgatat  86820
accacattaa caggatgagg gataaaaatc acatgatcat ctcaatagtt gcagaaaaag  86880
tatttgacaa tattcaacat cctttcatga ttaaaaacta ttaacaaatc agatacagaa  86940
ggaatatacc tcaacataat aaaggccata tatgacaagc tcacaactaa catcctactc  87000
aatggtgaaa agctaaaagc ttttcctcta aaaccaagaa caagagaagg atgcccacac  87060
```

tcaccacttc tgttatacat agtactagaa gtcctagcta gagcaattag gcaagaaaaa 87120
gaaacaaaag acatccaaat tagggaaagc taaatagtct ctgtttgcag atgtcatgat 87180
cttatatatt aaccctaaag attccacagt tagaactaat aaatgaattc agtaaagttg 87240
caggatacaa aattaacata caaatattag ttgcatttct gtatactgac aactaaccag 87300
aaattaagaa aacaatccta tttacaatag catcagaaag aataaaatag gccaggcgtg 87360
gtggctcatg cctgtaatcc caacattttg ggaggccgag gggggtggat cacatgaggt 87420
tgggattttg agaccagcct gaccaacagg gagaaacccc atctctacta aaaatacaaa 87480
aaattagccg ggcgtggtgg cgcatgcctg taatcccagc tactcaggag gctgaggtag 87540
gagaatcgct tgaaccggga ggtggacgtt gcggtgagcc gagatcatgc cattgcactc 87600
ccgcctgggc aacaagagca aaactccatc ccaaaaaata aaataaaaca aaataaaatg 87660
aaataaaata aaatacctag gaataccaag aaggtgaaag atctgtacat tgaaaactgt 87720
aaaatattaa tgaaagaaat tgaaggctgg ggcagaagga ttgcgtgatt ccaggagttt 87780
gaggctgcag taagtcatga ttgtgccact gcactgcagc ctgtgtgaca gagtgagacc 87840
aaaaaaaaaa aaaaaaaaat tgaagacaga aataaatgga aaggtatcct ctgttcaaag 87900
agtggaatag ttaatattgt taaaatgtcc atactactga aagcaacata cagattcaat 87960
gcgatgccta tcaaaatttt aatggcattt ttcacagata tcagaaaaac aatcctaata 88020
tttgtatgga attgcaaaag accccaagta accaaagcaa tcttgagaaa gaaggacaaa 88080
gctggaggaa ccacttcctg gtttcaaact acttcctggt ttcaaactac attacaaagc 88140
tctagtaatt aaaacagtat ggaactggcc taaaaacggc cactagggtc actgggacag 88200
aatagaaaga ctagaaataa acccaaacat atatggtcat ctaatctttg acaagggtgc 88260
caagaataca caatggggaa aagatcatct cttcaataaa tagtgttgga aaaactggat 88320
atctatatgc aaaagattga aattggaccc ttgatttaca acatatacaa caattcaagt 88380
gaattgaaga cttaactgaa tgtgagattt gaaatcgtaa aagtcttgga agaaaacatc 88440
agcaaaaagc tcaaccttgg tcttggcaat gatttttttg gaaatgacaa caaaagcaca 88500
ggcaacaaat gcaaaaataa tgaaatggga ctatgttaaa ctaaaaaaac ttctgcacaa 88560
caaaggaaac aatcaacaaa attaaaagac agcctaaaga atgggacaaa atatttgcaa 88620
gccatatgtt tgataaggag ttaatatcca aaatatataa ggaattcaca taaaggattt 88680
cacataactc attagcaaga aaacataaag cccaatttaa aaacggacaa aggacttgaa 88740
tggacatttt tccaaagaag acatacaaat ggctgacaga catgtgaaaa gttgcccaag 88800
attactaatc atgagagaaa tgcaagtcaa aaccaccatg agctatcacc ttgcacctgt 88860
tataatgact ttatcaaaat gacaagagat agtaagtgtt ggcgaggatg tggagaaaag 88920
agaatttttg tatattgttg gtggaaatat caatttgtac aggaattatc aaaaaacagt 88980
atggacgttc ttccaaaatt taaaaaaaga gctaccatat gatccagcca tcccacttct 89040
gggatgaaat aaaatctgtg tcttgaagag acatctgcac cccatgttca tagcagcact 89100
attcacaata gccaagatat ggaaacaacc taagtatctg tcagccaatg aatgaataaa 89160
gaaaatgtgg tgtgtataca caatggaata ttatttagcc atgaagaagg aaatcctgcc 89220
atttgcaaaa acagaaacga acctggagga catgatggta agtaaaataa gccaaacaca 89280
gcaagacaaa tattgttttg tcttacttat atgtagaatc taaaaagttg aactcttagt 89340
aacagagtag aatggtggtt gccagggtct gggggtgagg gattagggga gatattagtc 89400
agagtgtaca aacttttagt tttaagatga ataagttcag tggatctaat gttcaacatg 89460

-continued

```
gtgaatatag ttgacgatac tgtgtttact tgaaattaga taagaagata gattttaagt  89520
gtcagcactg caaccacaca cagatgataa ctgggtggtg atggatatgt tagttaattt  89580
gattgtggta gtcagtacac actgtgtatg tatatcaaat catcatgttg tacgccttga  89640
atatgtacaa cttttctttg ttaaataagt actttaaaat tttacaaaag acatttacaa  89700
gccacactta ctcatcttgg gaaaagctat cagtcattta aagcaaagca tcctttcctt  89760
ttcaagattt tacttttttt tttttttga gacagagtct caggctagag tgcagtggca  89820
cgatctcagc tcactacaac ctctgcctcc caggttcaag agattcttat gcctcagcct  89880
ccggagtagc tgggattaca ggcatacttc accatgccca actgattttt gtatttttgg  89940
tagaggcggg gtttcaccat gttggccagg ctggtcttga actcctgacc tcaggtgatc  90000
tgcccacctt ggcctcccaa agtgctggga ttacaggctt aaaccactgc acctggcctc  90060
aagattttac ttatatttta aatgtctaca tcttgaattt caattcttat tctacctaga  90120
agctaaaagc attggcaggg ttatgagttg gggtggaaat atttgggcct gtggaagata  90180
aattcatatt gtttgaagaa aataatctgc ttataattat cagtttatta taatcaggcc  90240
caaagaagga aaccaaaagt cttaatattt tcttagtgat aaagtggagg aagtaactga  90300
caaagtaatt ttggctcttt accagggatg cttcatataa aggagggaga acaatttcct  90360
tgacaaccaa ttaatatgta tagcttaagg ctatgactgt attctgcaag aaatagatta  90420
catttctgag gtctgcacat ctgaagatat tataaactag ctaggagatt tttatgatga  90480
tatgatacag atcagcaata cgtaagacag aaagggggtt tcacccagca agagttagga  90540
tttatagtcc cagtatgccc gagttttaca tattgtgaac tttgctaacc ttcaccttta  90600
tcaacaagct gtgagtgact ctccagcaca aagctttgag tatcaagcat gcatatagta  90660
aaaaaaaaaa aattgccagg caccgtggct catgcctgta atcccagcat tttgggaggc  90720
caaggcgggt ggatcacctg aagtggggag ttcgagacca gcctgaccaa tatggagaaa  90780
cctcgtctct actaaaaatg caaaattagc cgggcgtggt ggctcatgcc tgtaatccca  90840
gctactcggg tggctgaggc aagagaatcg cttgaacctg ggaggcagag gttgcggtga  90900
gctgagatcg tgccattgta ctccagcctg ggcatcaaga gcaaaacttc gtctgaaaaa  90960
agaaaaaaaa attatactga tgatttgggg gagagcacca aataccctta aagtttttac  91020
ggcacagact ttttagtaaa tcttatgagg ggatgattat gggaataata tgcatctatc  91080
tatatatata tatatatata tattccaaaa atattggcaa aaataatgaa gaacctgaaa  91140
gtcctccatg gtcagagtta aggtcagggt cagggatgaa tgttgcatta gttggcaata  91200
aaaagcagcc attgtacagt ttgacaggcc tgtgtgaata tcctgctttg tagctgagtg  91260
ttcttgcttg ttaatctgct tcccctatcc ccactctttt ttttttattt aatctggtgg  91320
ttgagaggtg cttccaagcc tacctatttt atttaccact tcctcgttag tttttttgggc  91380
ttcttaaaat ggtcctccac tcttatgact tctggctgtt tgtacacaag aactgtccac  91440
ctctctcctc ctgccgtcaa gggtgttgct aaacctatca tcctcaacct gaagctcctt  91500
ccacatcctt cttgccagct cactatcagt catttcctga gactgacatc acaaaagagt  91560
cattagattt aagccctggt ttcagcaatt actggacctg ttgtgattct agacagggtt  91620
cttaactttt aattttccat gacatttttt cccttgacat cccagtccaa gctgttgact  91680
tttgcattta ctgctcattt ctacctttaa tattccattt tcctctgtta atattatatg  91740
ctgtgaaacc caggagaagt cagcattact atggtcttgg gtagaactga gagagataaa  91800
gacatgaatt tgaggctgtt gggggatgag ttgcagagag gcataaatac gaggcagaaa  91860
```

```
ataagttatg agtgagaata caacttatta atagcttttg taaacttctg gcaaaaaaag  91920
atattgaaga taattagagt tgaaaaatta tataagacat cacttacgat tgggattcaa  91980
tcacatttta tagaaaattc aaataagagt tgcttaagca tgaaagaagt tcagaggtaa  92040
gtagctcagg gcttgtatgg caactccatg gtcacagggg gcccaggttc cttctcacat  92100
tgttttctcc catccttggt gctggcttac atgccaaatg tctcctcatg accacaagat  92160
gctcctggtg ttcccagacc aaactgaggg ttgggctgct atttctcgtg gcccaataac  92220
gagaagcaga tgaactgggg aggaagagtt tttatttctg caactggtta tggggggaag  92280
gcctggaaat tatcaccaga ccaactcaaa attacagttt tccagagctt atataccttc  92340
taagctatat gtctacgtgt aagtgtgcat tcatctaaag acataagtga ttaacttctt  92400
ctaatctata gctaaggtct gagtcctgaa gaccttcctc tggagcctca gtaaatttac  92460
ttaatctaaa tgggtccagc tgctggggtg attaccctta ttatgtctcc tgcttaaatc  92520
acggaggttt ggggagttcc ttcagacctc caataaactt gtttgtggag gtctggggag  92580
tttcttcaga cccacaataa aactcgttta atcctaaatg ggtcctgtta agaattcctt  92640
tgttattttg ttatgcttta aggcccagga aaagcctagg caaaactctt ggtgggcttt  92700
cgttacattc cagcctttgt ataagggcac tggctttttt aacttttaat atttaactta  92760
accactcagt cagtactgaa acagttgtta tggaggcctg cgttagtgag agctggcctg  92820
ccacactggt gctccagcta ttatgtccac gttccaagat ggaagaaagt ataatggcaa  92880
aagtacctat ctctcagctg aatcagtttg ctttaaaggg cttccttggc ttccatccac  92940
ttctgcttac acttccttga acacctccag aaaccaagga ggttgggaaa gctttaggct  93000
gaggacatta tcactccaaa taacatattt ttaagtcagg aagtgggaag agtggatatt  93060
gtgtaggcaa ctcacagtcc cttccaccat agccgaccag gacagagata gctggatgat  93120
ggtttgctct agttgagcct aaacaagctc atggctccct ctccttaaac tacttttata  93180
ttttctttct ctaagttcag agcaaagctt tcatattatt ttatgaatgt ttcttaacaa  93240
gctcatcgtt tctggtgttt tgctgcaatt ctgcagtaga tagtatggta tatttggtgg  93300
acagattcag ggccaccagg ctttgaatag cagtggtgct acttagaagc tgagaggtta  93360
tgaaccttat atgcaaccat agggaatagt gttgttacta taaataatga ttgtactgaa  93420
ccttatatgc aatagtgaat aatgttatta taaataatga ttgtactgaa ccttatatgc  93480
aacataggga ataatgttat tataaataat gattttcaga ctgaggcagt tttctaaaaa  93540
ttcaagtgaa agatcacatt actttacatg aggaccacaa ggcacattca aaagatacgg  93600
ttgattcact ttgttaaaca ataagaatat aagtgtccaa atacagaaca aaggaaataa  93660
tatgtccaag aaacattttt ctttgcttaa tactaaaagc ctcttgatct gtttcctata  93720
tcctagtcac aactgaattt taagaaagtc gaggtcatgt tggtaactcc atgtcaatac  93780
tgctttgtgt actaactgca agatcaggaa tcgtccctca ttacttccat cttggctttc  93840
aaaagagcct actgtaattt tttcttctga aatagtatga aataactttt ttcctgaaag  93900
aaaatctcct ttctatggtt ctttcttctg aaacaaggct ttccttctct gagcttccag  93960
ctagaataat ttcctctgac atactctgat ctaggaggat tgtagtgtgg tcacaatgcc  94020
tcagctgatt tcagttaatt ttcttgagct gaatcaaatg aatgtcttaa caagttgtcc  94080
tttaaaagga tagacgtgct tttatacaaa acttgcattt aaatgaaacc actagacttc  94140
ttcatacaat gtaatgaagt cttggtattc cagcgatttg gcacctaaat gcataggcac  94200
tcagtaaata ttggagggaa ggaggatggt ggaaagaaag aaagggggag cagggaaaat  94260
```

```
taggggggaa attatttttt cttcctgggg ataggtttca tttttaattg ggaaatgtaa  94320
tgtgaaatgt attactttca aacttgagga cccagaatat aacttatgat gatttaagtt  94380
ttcttccttt tatttacatt ttaatgataa agacactcat tggccaagac ccagaaaaaa  94440
agtttaaata aaaatttaca ttttaatgat aaagacactc attggccaag acccagaaaa  94500
aatagtttac ctatatttta tacgtgtttg tttaaaaaaa aaaaacacaa tctttgaaaa  94560
atctggagaa tttatttcgg gttataatag tcagaaaatg tgtgccttta agttttgctt  94620
ctgaatagac atattctgct aagcaagcaa tctcctctta gactgcttgc tgagcacata  94680
tactttccgt atgctgattt ttaaagtgtc tgtatttggt tggtggcttt agtaataaga  94740
gactagcttt taacacagcc agaagaagct gatgtgaacc agcagaaata acactgatca  94800
tatataatac ttatggaaca gtggttgccc accatttttg aacccaagat ttcctgacat  94860
ttatcactgt gccaacaaaa agaaaaacta ggaacctggg gaggacttag agagaggaag  94920
catggacagc tgccagcctg ggcagatggc gtctgtttgg ttgagacaga ttcaccagga  94980
aacaagatca gatcctagtt tgagacccaa aacctggtga gtaagaacaa gtgttcagga  95040
cttcaagggg cccagtaggc aattgtggga aaaaatctgg aggtcctgaa cttgcccaaa  95100
ttacaggggt aggtgagaaa aggtaatcca aggggtaata ttttttctg ctttttggtg  95160
ttatctatat tttctttaac aattatatat attacttaaa ggaaaaaact ctaggtctta  95220
tatattcctg actaagcttc atcaatatgt atttgcttct tttatacaaa gtaacattgt  95280
tttcatttac agattgccat taggatacct tagtaatgat gtccagttat gatgcagata  95340
tttcaaagtt tattgtttat ttatttatta ttattttgga ggcagggtct tactgtgttg  95400
cccaggcttg ggtacagtgg tgtgatcttg gctcactgca gcctcgacct tccaggctca  95460
agcagtcctc ccatctcagc ctcccaagta gctggaacta caggtgtgca ccaccatgcc  95520
tgtctaattt ttatattttt tgtagagatg gggtctcgcc atgttgccca ggctggtctt  95580
gaacacctgg gctcaagaga tctgcccgcc tcagcctccc caaatgctgg gattataggc  95640
gtgagccacc gcaccaggcc caaagttaaa ataacttaat gaataaggtt tggatgatgt  95700
caggtacccc tttttctca ggggaactgg ctcctactta gatatcttat gaccattagt  95760
gggacattat aggatagcct agaaacagaa acactcacgt cagtgtgatt tatggctaag  95820
ctggcactcg acatcagtgg gataggaggg ggtaatacat taaatggtgc atgggaaatt  95880
gattattcgt tcagaaaata attgaaatgg atctgtactt catttcatac acaaaaatca  95940
atttcaggga gattaaggga cttaagttat aaaaggcaaa actttgaaac ttttggaaat  96000
agtataggag aatagcttta tgaccttgga ggagggaagg atttacaaat agtgttagct  96060
ataaggcaaa ggtttggtca ttgagccatc ttaaaatcaa ggaaattact tcatcaaaag  96120
acatcgctaa aagagtggga gagaaaaacc acacactggg agaaaatatg tgccatacat  96180
atgtgtggca ggcacacctg acagcaacaa ccgaagcata ccctgagaat gaccctatgg  96240
tctaagaaga atgtgtgttt ggagttctca gctgaggaac ctggtagtgg ccaacccgga  96300
gactgattcc ttgtctatga ggaacatctg aaccccggc ccatttcgga ttaaaggagg  96360
gttgccaggt gaaggttgca ggagggggagc taagtaaaaa tgctatataa actgcatact  96420
ttttagaaac ggtagtggtt cgtccatcca gcctgctacc actggaccgc tgcatatgta  96480
agtcccctcg agaagcccta tatctcattt gccagctctc ggtctcttct ttggcctctc  96540
ttctttggcc tctcgaacct gtgctatccc tatccaactc aataggggtc tggcacaata  96600
acatgtaact aacaattagg aaacagaaac ctgtctttta gaatgtggga cttctcttca  96660
```

```
tcaaaagcac tgtaaaatga gttaagaaac aacccataaa tacttgagga agatacttgc  96720
catacatgta actgacaaat taataaagga aaaaggtact ctggagaaaa atgaacaaaa  96780
gccttgaata gaaactacac agaagtggaa atgtgaggtt gggcgtggtg gctcacacct  96840
gtaatcccaa cattttggga ggcctagaca ggtggattgc ttgagcccag gagtttgagg  96900
ccagcctggg caacatggtg aaaccccatc tctacaaaaa aatgcataaa ttaactgggt  96960
gtggtggcag acatctgtgg tcccagctac ttgggaggct gaggtgggaa gattgcctga  97020
gcctgggagg tggaggttgc aatgagctgt gatcatgcca ttgcactcta acctgggcaa  97080
cagaggagac cctgtcaaaa aaaaaaaaaa atgaaaatgt gaatggtcaa taaaaatgtg  97140
aaactactta acttcattag taatcaggga aatgcaaatg agaagcacca ggtgatactg  97200
tttcacactc tccggggcgg ccaaaatttt taagtcttaa caaacaaccc taacaatgta  97260
gagtcacaaa caggaatcct tagacactgc tggtggcagt tgaattagta cagccacttt  97320
ggagaactct gcagccttgt caggaagagt tgaagctgtg tgtaatccac aacactgccc  97380
acactccaca gcaatgcttc tcaagcctgg cataatatat tagcatccca aaatgagcat  97440
gttggaaata cttacacctg gcccttaccc cagacctgtg attctcaaat ggtatgccaa  97500
gatgccctgg ggaaccacag caaactcaca gaagacgatg ggatatctta aatgttcaag  97560
gggaatgcag tgatacttgg catctgttga acgcagtgtg aattactagc tcaagacact  97620
tcagttcagt ctcaatgtta ccccacgcat catccctttc tattatgcga agctggattt  97680
tcagtggttg ctgtaacaaa aagcagatat catgaaaatc agtatggaag aggaaataag  97740
ggtgatagag tccaatatga ttccaaagtt taagaagttg tatagtgccc aacgagtgca  97800
cacattccat taataagtaa ttgaggttat ttaagaatga aataaaactt ttttctttgg  97860
tattttcata cagatttttc aaacagctac tgcattgtta ggacaaaaaa gacttgttaa  97920
ctttttttgga cctaactact taaatggaat tgttaggaat ttgttctagg ggtgcctaga  97980
accctgaaaa aattgagcca cttagtagtg tcccttcaac tgagaatatt tgggaatctc  98040
tttcccaaat tagttaactc agaatggaga tggaatctct atgtctttgt ttttaaaaag  98100
ctccccaagt gattctaatg ggttcgtaag gttgagaacc actgcttgag agactcttgc  98160
acatgtgact taggataatg ctactcaaat tgtacctggg ggccagcgct ggtttgcaaa  98220
ttatttccta cagatctgca gcaagtttat atgaatcata ctttcagtga ataatggtac  98280
agtttttgta atcttttgtc ttctgattaa atttactgaa atataatttt atgtcaaatt  98340
ttataatgga aaaattgagg cttgtacttt gtgctttttt ctcatatttt tctaatattt  98400
atgattttac agctttgttg atgtataagt gatcaatttg cactctttaa atatgtgcaa  98460
tatattatat gtcaattttg acatatgtat atacttgcga aatcatcaac acaaccaaga  98520
taatgaacat atccatgact ctctaaagta ttttctcatc cctgtgtaat ctctcccatt  98580
tggccctcca catcccttca taatcctcca ctcctgtccc cgccccagtg caaccactca  98640
tctgcctgtt gtcactatag attagtttgc attctctagc atttcatgta aatggaatgt  98700
tactgaatgt actcttgctt ttgtctggct tcttttactt agcataatgt tttgcaattc  98760
agccatgttg ttggatatgt cagtagttta ctccttttta ttgccgatta gtattccatt  98820
gtatggatat gccacaactt ggttttttat tcaccaattg atggatattt gaaatgtttg  98880
cattttggct gctatgaaca tttgtgtgta aatctttatg tgatcacgtg ctttcatttg  98940
tcttggataa ataaatacct aggagtggaa tggttggatt gcatggtagg aatatgcata  99000
tagtaattta tttttattgc atttcacaaa taaaaagcat tagcccacaa ggattagaaa  99060
```

```
taaaactctc ccaggccggg agcaggggct catgcctgta atcccagcac tttgggaggc  99120

taaggtgggc tgatcacctg atgtcaggag ttcaaggcca gcctggccaa caaggtgaaa  99180

cctcatatcc actaaaaata caaaaattag ctgggtgtgg tggtgcatgc ctgtaatccc  99240

agctactcag gaggctgagg taggagaatc acttgaacct gggagatgga ggttgcagtg  99300

agccgagatc acgccactgc actccagcct gggagacaga gcaagactcc ttctcaaaaa  99360

aaagaaagaa ggaaagaaaa ctcttccttc agcaaatgta ttttgaaaag tactagccta  99420

agttaaatgc ccaacagtgt tcacagctac attgtttata atagcaaaag actggaaaca  99480

atccaatcat ccattgtcaa gagaatggat tattaatatg aagtatatat ccagtagact  99540

actttataac aatgaaaact acattgatgt agctgcagtt tatctactac attaatgtag  99600

ctgcagctac attaatcaga atgaataaac ggaatttaaa gttgagttcc aaaagcaaat  99660

tgcaaaagag tgcatatgga aggatttcat catatgaatt ttacaaacag tattttacta  99720

caatattaaa tagcatttta tttacagaaa catacatata tggtaaacta taaagaaaat  99780

ggtgatacaa aatgcaggat agtgtttact tggggagtgg ccgaaggtac aatgagagag  99840

ataggaccaa ggaggacaga cagaggcctt tgaggctagt gggtcttggt cccgttctta  99900

aactatagga attcatttta atgttacatt ttgtgtttat attttgtcat aaattttttg  99960

tgcatattca atatgtaacc acaaaataca aaaaaactct caacagttga caagggagtt 100020

tattaagcaa atagaggtac caattacaaa ccatcagggt tagaaaaaaa atccaggctt 100080

taagtaaata taaatctaag taataggcta ttgactatta tcttagaaaa acttggggta 100140

ttacaccagg ttatcacaga atatttagtt gagaagtatg gaaaatatga tatgctattt 100200

atttgaatga tactcggtag gcatgtaatg tgatgattaa atcagttaag aatatgtgat 100260

agattttttt taaaaaaaca tctcatttaa aatgcatgtc ttttgttttt atgattattg 100320

aaaaatggtt ttcagaatac aaaatgagaa tcaaaaattg gtaattagat attctgtgtt 100380

tctcaaatgg acggacttta taattgggtg gagttatgtt aaaagctaga aaaactgaag 100440

aagttaagaa agaattgaaa attcccatta agagaaaaaa gaaaaagctg caacctttgc 100500

taatataaac cgtaagagcc tatgcctctt gaaatttctc tgtgtttgtc tttgtacatt 100560

tttaatgact taatgagaaa aaagattcat caggactcct ttcctagcag gaggtttagt 100620

gtttcacaaa tgagtaggga gctgctctca taatgaggta aacggccacc tgattcttgg 100680

ataagtccaa ggaaaacctt tacaccagag gaagcaacag cttgccagtg ttcaatctga 100740

gactttccaa ggtcagaaga gaggaggatt ggtattgata tttaataagc atttactgtg 100800

tccaaggcat tttggtacga attttatatc tcttatctga tatccttgcc ttttaggact 100860

aggctgtttt tacctttaag gtagatgtta ttattctcat tttacacatg aggtaactga 100920

aacatagaac ttaaaaacct tgccaaacat ttcagaggag gcagatttaa acccagatgc 100980

atttgcatta aaccccaatg gatttgattc caaagcacgt cgtctttctg ctaataatag 101040

ccaacagtca ttgagtactt actatattta taccaaggtc tgttccaagt gatacataga 101100

ttttctcttt taagcctcgt ggcagtatga gaaagaagct attattatcc ccattttaca 101160

gatgaaaaaa tggagtcaca gaatgttatg taatttgccc aatgtcacac agtaagtggc 101220

agagttggtc cacctcagga gcccacactc ttaacctctt ttggcctttt atgagtacat 101280

ctgccctttc aaggatcagg cttgagtctg tcagggaggc ctcatgtctc ctattaactt 101340

ttgagccata cgcatcatgg aaactggttt ctcctggctg ggtacttctg agttgcctgg 101400

cctcctgtga gctcttcttt tctaattgaa tctactctct aagactcttt gctgctggaa 101460
```

tatgcagcag tagtttgaga gacacttctc agtcagttct aacatgttta gctaggttct 101520
tcctattttt tgtgcttcat cagatcattt gggctcagtg ttttctttct ttttattttt 101580
ttcttttttt ttgagacagt atctcacgtt gttgcccagg ctgcagtgca gtggtgcaat 101640
ctcagctcac tgcaaccctg cctcctgggt tcaagcgatt ctcctgcgat tctcctgcct 101700
cagccttcag agtagctggg attacaagca cctgccatca cagccggcta atttttgtat 101760
ttttaataga gatggggttt cactatgttg gtcaggtgga ccttaggtga tccacctgcc 101820
tcagcctccc aaactgctgg gattacagac gtgagccacc gcgcccagtc tgggctcagt 101880
gtttttcagt ggaataagga tgaatcatta gaagagcttt catacctctt aaactctcaa 101940
attccatgcc ttaataagga tttttattaa tacttcattt aaaacaaaca gtaattaagc 102000
atcattttaa ccatttgatg tgattataac tcatatgctt tctactccaa aaatatttga 102060
agtagaagaa accaatacaa tgggataaac acaaaaaaat gcagaacaat gtagagaaaa 102120
cagagataat tatacaaaac cttaaggtat tttcgttatt gctgttgagc atttaatgct 102180
gaatttcctg gcagctgagg caacagaaag gtaattggtc agataatttt tgttatatgt 102240
tcaaataaag taaactagtt cattggggag gatagggtac catgtcaggc cactagccaa 102300
ccctttcttt cctacaagtt aaattatatc tgaatatcct ctggagcact cagatcttaa 102360
aatactttag aagagactgt aaagaactgc cagtgattgt ctttaaagag gcgtcatggc 102420
agtgctgtaa ttcttgctta gcaacactta tatctaagct ttcttctctg agggaaaggc 102480
caggttctag gtcactccct cactttgttc cagtctctgc ccaaaggtca cctcttccct 102540
gactgccctt tctatatgag gttcccaccg aacgcatctg ggttgccctc tatccctgtc 102600
caacatagta gtcactagcc atatatgaca attaaaatta attaaatgac aaaataaaaa 102660
attcagtact ttggtcatac cagccacatt tcaaaagctc agtagccatg tgtggcaact 102720
gggcatattg gcaacacaga tacgtcatcg cagaaagttc cactgggcac tgctagccta 102780
tgctcttgcc ttaacttttt caacactatg ccatgccatg cacctattga tttgtttatg 102840
ttccactaga atacatgctc tggatcacag agtttttttt ttttgttttc ccagaacata 102900
gctgaatcct cagtgcctaa agcagtgcct gacatagtac agtgctttgt aaatacttgc 102960
cgagtgaatg aacaacaaat gaatgaatga attttagtat tattttgcag tttcaaatca 103020
aaagtatttt gtctaatgtc cctgggtgac ctagtacacg ttctgccaca gtttttgaga 103080
tgaaagaacg aaaattctgt gatcaaagag aacattttaa agataaaatg atattaaata 103140
tactagtcaa aattttattt cttttatctt ttatattatg aagaataatg ggtacgaaat 103200
ttctgtttat caattaacgt atcatcctga atatgaacac agaaaatatc aattttcttt 103260
gcattaagaa gtcatgtaag tagaaggaga aaacaaagta cttattacat agctaactgg 103320
acttacagtc acatctaatt taaagcaaat ttgctccatg caatggaata tactaaaagt 103380
aatattgtgc aattatagct acagacatga taggaaatca taatacattc taaaagtata 103440
tagaaaaatg tcagtttact tcaacttatt ttaaacaaaa attacccatg aaatgattgc 103500
agtacctaaa aagaatttgc aatctgaaca aaatataact agaagcacga ctaccctata 103560
tctcctataa atacagattg aagctagttt tgtgatttca gccaaagatg cagcttcagt 103620
aaccttgaaa aacattgttt cctttctatt gggcctggct ttgtcaggag atactcagga 103680
ggtgatggtg aaaggaggta cctggtggag ccagacgagt cgggtaaatc agctttaaca 103740
agcagccaga tgatagatgt cagttgggtg tcatgcccaa ttctagttgc tgacaattag 103800
gaattagatt aaaataggag tgttttctcc ttcaccctcc ctttcttaaa agcagccatt 103860

-continued ttctgagtag tgttagttct tagttctcag tggatttgca aatgcagatc atgaggcacc 103920
tctagcttgg gcaggattgg tgttattttg ctatttcaag taaaaaacat gatggttagt 103980
gtccttggat aacctcatat actttcattg tttttcaaat caggtccagt gaagggccaa 104040
gttcttcata aatatcatgg ctaattttgg aaacccatat gttcagttaa ggtttctgaa 104100
actggaataa atatgaatgg aggatttatc aacatttgga tatttgcaat ttcaattctt 104160
gattcttttt tgaaaatcta ttctgggtct acatctgaaa tgtttatctc ctttggtgct 104220
agatccagag tacaattttt gaaaacttta aatcaagggt ggaacaataa attcacttgc 104280
tcttaagact ttaggggttg ttttagctgc caagagagca ttgcctgtgt gctgcgaaaa 104340
atacgagagc cacagaatgg ccaaattatt gcttttactc aggcagagtg aagaaaatgg 104400
ccctgtgaca gacatttcca gtttcctgta catagaaatg gggaaacagt tgtgaaaaaa 104460
aaaaaaaagc cagctggggt tcttgacaca cagttcatgc taattttaaa ttgtactaat 104520
acttgactat atagtgaggg atcctttgca ggatgatgat ctgttgaaga ctcagcaggc 104580
cactgtgggg agagggagag aggctgtcag aaccttcccc tccagaggcc ttttaatgga 104640
tactgaattc agaattgacc tcacagaatc tgatcattac tgatgcaaga gcaaagtcaa 104700
catcatctgc aaagataatt tctcatctat tcatgagtac ctgtgcttat caccacatct 104760
ggaaatctga ctactcaaat aagaatttct gtcgagagac tgaacaagcc aggcaccagg 104820
aatattttac tctgtatgta cagatggaca tcgatactgg aatatttctg tctcactgat 104880
gcttagggac catcttttga ttttgatccg tgtcaagatt ctaaggcagt ttaactaaga 104940
catgggtttt cagtgttttt ttgtttttgt ttttgtttta atttctgttt ctgtgagtgt 105000
aatttaggga ggagtaccag cttgtttttt ataagttgtt tcttacaatg attaacacat 105060
aatcttttct gccttaaggt ttataacaaa tgtgaaacta agtttcacag gttaattcca 105120
gcctaatctt ttcatagatg atagcgtagc ccagaagcaa tatgctgtga cattttattt 105180
tattttattt ttgagacaga gtcttgcttt gttgcccagg ctggagtgca gtggcatgat 105240
ctcggctcac tgcaacctcc atctcccaga ttcaagtgat tctcctgcct cagccaccca 105300
agtagctggg attacaggca tgcacaagca cgcccagcta atctttgtat tttaacagag 105360
acggggtttt gccacgttgg ccagactggt ttcgaacgcc tgacctcaag tgatccacca 105420
cctcagcctc ccaaagtgct gggattacag gcgtgagcca ccgtgtccag cctaccgtga 105480
cattttaaat ttcaaaatgt aataaaatca caagttatgc cagaaagcca ccgtacttct 105540
cattgaatat agtatctcct tggtgttcat gtccttatgt tcttatataa ctctgtgtgc 105600
cagtgtttca ccaaatctat caactctttt aaggcagaga ctacatttat ttattttta 105660 actttttgtt tgaaataaca aaactttctg ataacttcag acttagaaaa aagttgcccc 105720
aaaatactac actgattttc atgtaccctt gatacagctt ccccagatgt taccatctta 105780
cataatcata gtacagtgaa ggaaacagaa attgacgttg atacaatagc atcactaact 105840
aacctaaata acttatttca gtttgccgat tgtcctacta gtgtcctttt taaagtccag 105900
gatccaatct agaatcccat acaacactta cttgtcacgt cttgttagtc tcatctagtc 105960
cggaggagtc tttctataat tttcacgact taatactttt gaagagtccc gaccagtgat 106020
tttgtacaat gtccccagtt tgggtttgtc tgatgttttc ttaggataag aattagctta 106080
tgcatttttg acaacaatac cactgaagtg atgttgtgcc cttcccaatg ttttttgttg 106140
ttgttgtttt tgtttttgtt ttggagaagg ggtctccatc tgttgccctg cctggagtgc 106200
agtggcacaa tctcagctca ctgcaacctc cgtctctcgg gttcaagtga ttctcctgcc 106260
tcagcctccc gtgtagctgg gaccacaggc acacaccacc acgcctggct aatttttgta 106320
tttttagtac agacagggtt ttgccatgtt ggccaggctg gtcttgaact cctgacctca 106380
gatgatctgt ctcccacctc tgtctcccaa aaagctggga ttacagatgt gagccaccgc 106440
acccggcccc cagtgtatta tatgagaggg tacatgatgt cagtatgtct cattgctgtt 106500
gatctaagtt ttggtcactt agataatgtg gtgtctacca ggtttctcca ctgcaaagtt 106560
actgttcttc ccattagaat taataagtac tttgtgggga gatgctttaa gactctgcaa 106620
acatcctgtt tctcatcata cttttgccca ttaattttag atactattga tgattcttac 106680
ctgtaacagt tattagtgtt tgctaaatgc tgatatattt tatttccatc attccttcta 106740
tattattgta attctactgt aaggaagagc tgttctttct tctgctattt attgatttat 106800
tatgttaatg tggatatata attagttact ataatttttt tctcaaaata tctcagattt 106860
ggccattgga agccccttca gacaggctcc tgtctccttt tgacatatcc tcattatctt 106920
ttaaatgcat gttgtaactc tggcatcaca agatgtgtct ggcttatttt gctccagccc 106980
tagaatcagt aacttctcca aagaccctag ttctttttac tgtagactgg tatttagaaa 107040
caaaatctgg gtgctggata tgctcattgc tactggtata tcattgcttc taggccctct 107100
cagcttacag tgctaggaaa taatgtgtct gtatatccag acacatgttt ctctctccct 107160
ctctctccat atctatatgc ctatgactat ctacctatta aaaacaataa gtttatctac 107220
ttattaatac ttccacttac aattcaatac cactagtttc cttttagata tctctttcct 107280
tactcgtggc tttttctcca acagttagaa acctggcatt cattatctac aatatattta 107340
cttatttgct caaccctagt atatatgtaa agaagtttca gaactgtgat ttccataatc 107400
tctatgagaa acaagtttac caacaagact atatagcatc caggtgcagt cctttttgtc 107460
tttagtctta aggtatataa taaaagtact ggtttccaaa attaggttag atattttctt 107520
tcttacctct ttcatggtgg ctgttgtttt ttacttgtaa tacagctagg ttcttttgtt 107580
actgttcgtg ttccattttg ggttccccca acaccgagag gttggtttta attattcttt 107640
attaggggga tgtgaaacat gattattgtt ctcagagtca gaactctgtg aaaaggggcc 107700
ggtcgtggtg gctcatgcct gtaatcccag cactctggga ggccaaggtg gttgaatcac 107760
ttgaggtcag gagtttgaga ccagcctggc caacaaggtg aaaccccttc tctactaaaa 107820
ggacaaaaat tagctgggca tggtgatggg cgtctgtaat cccagctaca tgggaggctg 107880
aagtaggaga attgcttgaa cccaggaggc agaggttgca gtgagccgag atcataccac 107940
tgcattctat cctgggtggc aagctagact ccatctcaaa aagaaaaaag aaccatgtga 108000
aaaggcattt cagaaaagtg tcattccacc tcatcccttc tgtcacgttt cagtctccca 108060
ttcttcccat ctaccccgta agtgaccagt ttagtttcta ctttttttctt ctgtatttct 108120
ttttgcacaa ataaacaggc acatatatgt tttcttatac agagatgata ttcagtgtct 108180
ttttttgtgt ggtactgggc aatttaaatg ctgtttggta attttaactc ttaaggatac 108240
tgtttataat tgatctgtcc ttaatgccaa tgtattagaa agcacactaa atgattgttt 108300
tcttttttgt aaaatatttg tgagattttt taaaaaatga aggtgacatg aattttgatg 108360
ggcttattaa cactgaacta tttcttgata agagttgtct aaaaaaatga gaacatatgc 108420
caggcgcggt ggcttatgcc tgtaatccca gaactttggg aggctgagac gggcggatca 108480
caaggtcagg ggatcgaaac catcctggct aacaaggtga aaccccgtct ctactaaaaa 108540
tacaaaaaaa aaaattagcc gggcgtgttg gtgggcacct gtagtcccag ctactcggga 108600
ggctgaggca ggagaatggc gtgaacccgg gaggcggagc ttgcagtgat ccgagattgc 108660
accactgccc tccagcctgg gcgacagagc gagactccgt ctcaaaaaaa aaaaaaaaaa 108720
aaaaaggaga acataaagca agtaacaatg tttttcaagt tttctttaat gcattacatc 108780
tttttttcac aagatatttt aaaattttat ttttccttat taagcgaatt gaattatttc 108840
aagcatcagt gagagctgct agactgttat atttcggggg tcttgcaggg tagcttttct 108900
tacacatata agcagaagaa aacattttcc caagtcttaa aagagggtta tgatgcattt 108960
cattgtgtac tctttttctt cccatatact ctgcaggcat ttgggcagtc cttctccatc 109020
caccggaagg ttgctgaaga tggagagact cgggaggaaa cgcttctgca ggagtcagca 109080
tcgaaggagg cttactatct ggggaagatc ttggagatgc agaacgagct gaaacagagc 109140
cgggctgtgg tcactaatgt acaggcagaa aacgagaggc tcaccgcagt cgtgcaggat 109200
ctgaaggagg taaataaaca aattccctat gagagatttg tgagagggag aaataagaaa 109260
gttctctcca tagcagagag gaataacact tttgttttaa tcagaggagc tgtattaagc 109320
acgaaactac taatactgag ctagcaactt ttcttttta gtgaaatgat agctagcttg 109380
ttctgagatg agcttttctc tcttttattg tttcttgaaa attaagtttt gtatgtattg 109440
cggacttcgg aattggcctt actatttctg caaaggtatt ttaaaaatac agtgacctta 109500
gcacttcctc cctgcattag ctggtttaat acaatgtgga gaagaacggt tggctgtaat 109560
gctctgtatc tgcctgattt ccagctgaca gtggtgttgg ctcaggacac tgctcatagg 109620
gaatgacagc ctaggcgagt gtcctgagaa gtctttgagt ctggtgatgc agatccccaa 109680
aggatttttc tggttataga gaaggcagca aattatggct ggtatgaatt aggtcaggga 109740
gtctctcttg ctctgtgagt gttgagcatc caccaaactc agtattcctt gttagctttt 109800
ccaaggcagc atcacctgcc atatcatttt caaactggca gagtcatcct ttagtggagg 109860
ggtgatgttg gaaacagaga tagccaaaag tagcttcatc catcaaaccc ctgtaagaac 109920
atttttggaa gctatattca atcattcact ccgtattttg atatgaaagc tatagaagag 109980
acgcagacgt cctctaactc ctacaccaat gcagtgatca ttgacaggtc cacaaccaag 110040
tgggctcact agttgagcat tttagtgata gaaatatgta ggatgaaaat attcttcaat 110100
attgtaaagt ataagacaag caatccacat ttgaaataag tgacatatta caaatagggc 110160
ttcactatta taagatataa gttgtccaga atttattgga attttctaga taatttacgt 110220
ttacacatgt ccatattaca atgaactaaa tgaatactga cagcaaggtc acttatgaga 110280
taaggtttac ttatctcgtt atctttggat atgcccaaat atagcaatat gacttgtgaa 110340
gacagagaaa ggatctaatg aagtggaagt tagtgttgag tactaagaag aagatgagac 110400
agttttcagg ataccaggac ctcctcattt ccctccaacg tgaacaactg ttaaaaacag 110460
agctactctc tggttccttc tttctgagac agggtgtcac tctattgccc aatctggagt 110520
gcagtggcac aatccagcat ccattgcaga agtggacaga gggtcatgtg gagccaaagc 110580
ccaccattct ggattaagga agtcaccaaa catttgcagg gagcaacctc agcagccgtg 110640
agcagcaggg tcatgtgcaa gttggcagag aggatgtggc atgggcaacg tgaggaccgt 110700
gtgcacacgc atgcaggtgg tttatggaga agaatgtgac caatgagtcg agtattcttg 110760
atggccagtt ggatggatcc tctgaaagct gcaatcccca ttgtgtgtag cagctgcagc 110820
tgagccaaga acagccaagg ttgaggatgg ggcagggaat ccacagatgc ttttctgtgt 110880
gagtcaacgt ggtgatgatt aatggagcat cctcacttac acagccacgc ttgaaggcag 110940
ttccaatgag tagatttatg atgcatggca gaagttaatt aattaagcat gaagttacaa 111000
gttaggaatg aatggaggca gcaaaagaaa aaaaatttga ggggcctttc attcagatca 111060

```
gttctcaaac ttgaaggagc atctgaatca cctggagaac tcatcagacc atgaacacgg 111120
ggccccctcg cagagattct gattcagtag atcgaggtag gacccaataa tttgcatttc 111180
taacaagttc ccaggtgatg tgggggctgc tgctctggaa accacatatt aagaaccact 111240
aatttagatt ttttggcctg cccaaagctg aggaaggctc acaattggga cattgctata 111300
agcaccatga tctcctgaat aaatcaattg gttgtgattc ttcaattttt atgcatttta 111360
catagtagat ttgcagtaag agaataactt gttatatcca catttaggta tttttgatct 111420
aaaacagctt gaggcacttt agcctatgaa tgtgtttatt cagatttgtc aggtaactaa 111480
aagaaaaaaa agatcttgtg tttctttgtc ttctatgtgt gccaataatg tatttgttaa 111540
tgttctttct gatgagtgag agctggtgat attactataa ccctgagttt ttgtttttgt 111600
ttttaatcca gcagatacat tttattttgc tgtacctaag agaattatta ttaacattta 111660
gagctaacat aaaaggagaa taggaataaa ttctattttt tggtgtattg atacacactt 111720
ttaatggttg gtattaagtt gaaatctcag atttgatttc cttttaggct cagttttatt 111780
ttttgtacta taagcattaa ctgatgtaca gtgattggaa gagagatcat gtaacttaga 111840
acagttatga catgatggac catgagaaat atacaaggat aaccaaccca aaatatagta 111900
aatgatcagt ttgacagatg ctgtgtctct aagaacttaa ttaatgggat aatttttctt 111960
tactgaaagg actcatttcc tgttttagta ggattgttgg tcctggcaaa ggtgtgtgtg 112020
cgtgcatata tgttgggtgc atcgtgaaag atttacccat gtgtgtgtga ttacaatgtc 112080
aaattctctt ccataaatag tagttacagg atagtatggt ggaaaatgga aaaattgctg 112140
aattaggtat tagaaaatca atattctagt cagctctgct gaaagtttta gtattaaatt 112200
catgatattt gtaaaattta tgttaagatt atattgatat agagtacata cataaacata 112260
agcaattatc attaataatg ttctgcatac tccaaaaata tcattgacga tatgactcat 112320
tatgtagatc tatattctta gggtaaagaa acatgagata aatatctctg aatttatcac 112380
ctcaaaaatt ctttctcttg tgatatgaat caggcagtag aattacacat ttttatttct 112440
gccttgactg ttaagaagct ctgcggctat gcttaagtat aaaaaaacta acctagattt 112500
ttttcatcta attctcactt ttaaacgttt tgattagcct tattgtatat atgtttttaa 112560
tggtaaactg ctttaaataa ttttatatac tatactacaa ggctacagta accaaaacag 112620
catggtactg gtaccaaaac agagatatag atcaatggaa cagaacagag cccttagaaa 112680
taatgccaca tatctacaac tatctgatct ttgacaaacc tgagaaaaac aagcaatggg 112740
taaaggattc cctatttaat aaatggtgct gggaaaactg gctagccata tgtagaaagc 112800
tgaaactgga tcccttcctt acaccttata caaaaactaa ttcaagatgg attaaagact 112860
taaacgttag acctaaaacc ataaaaaccc tagaagaaaa cctagccatt accattcagg 112920
acataggcat gggcaaggac ttcatgtata aaacaccaaa agcaatggca acaaaagaca 112980
aaattgacaa atgggatcta attaaactaa agagcttctg cacagcaaaa gaaactacca 113040
tcagagtgaa caggcaatct acaaaatggg agaaaatttt cgcaacctac tcatctgaca 113100
aagggctgat atccagaatc tgcaatgaac tcaaacaaat ttacaagaaa aaaaccaaca 113160
accccgtcaa aaagtgggcg aaggacatga acagacactt ctcagaagaa gacatttatg 113220
cagccaaaaa acacatgaaa aaatgctcac catcactggc catcagagaa atgcaaatca 113280
aaaccacaat gagataccat ctcacaccaa ttagaatggc aatcattaaa aagtcaggaa 113340
acaacaggtg ctggagagga tgtggagaaa taggaacact tttacactgt tggtgggact 113400
gtaaactagt tcaacccttg tggaagtcag tgtggcgatt cctcagggat ctagaactag 113460
```

```
aaataccatt tgacccagcc atcccattac tgggtatata cccaaaggat tataaatcat 113520
gctgctataa agacacatgc acacgtatgt ttattgcggc attactcaca atagcaaaga 113580
cttggaacca acccaaatgt ccaacaatga tagactggat taagaaaatg tggcacatat 113640
acaccatgga atactatgca gccataaaaa atgatgagtt catgtccttt gtagggacat 113700
ggatgaaatt ggaaatcatc attctccgta aactattgca agaacaaaaa accaaacacc 113760
gcatattctc actcataggt gggaattgaa caatgagaac acatggacac aggaagggga 113820
acatcacact ctggggactg ttgtggggtg gggggagggg gagggatatc tttaggagat 113880
acacctaatg ctaaatgacg agttaatggg tgcagcacac cagcatggca catgtataca 113940
tatgtaacta acctgcacat tgtgcacatg tgccctaaaa ctttaagtat aataataata 114000
aaattaaaaa ttaaaaaatt taaaaaaaaa tgtaaaatgc ttccaacagt gcctgacatg 114060
tggcaaaaca aattaataaa cgttatctgt atcacaaaaa ataaaaaaat aaataaataa 114120
ataaataaaa ataaataaaa ataattttat aggccgggca tggtggctca tgcctgtaat 114180
cccagccctt tgggaggccg aggcggctgg atcacaaggt cgtgagttca agatcagcct 114240
ggccaagatg gtgaaatccc gtctctacta aaaatacaaa aaatttagct gggtgtggtg 114300
gtgggtgcct gtccctagat gcttgggagt ttgaggcaga gaattgcttg aacccgggag 114360
gcagaggttg cagtgagcca agattgcgcc actgtactcc agcctggcga cagagcgaga 114420
ctctgtctca aaaaataata atgataataa taataatttt ataaaataca gggagtataa 114480
acaaaaactg atcacccaaa ttggagaacc aaattaatag ttaatcttaa cctaattagg 114540
agttaatcct acagggccaa taataggcag agtgaagaaa tctctgagtt ctcttgaccc 114600
agcattattt ttggtaagag cataaagaaa gcagattgct ataggattta aatagatatt 114660
tagtaaacaa gtttgaattt cattttttct atcttcaacc tgtaggtata atatactaga 114720
agatagccta aaatttgggt aatatttact tttatactta tttatactaa actaaactaa 114780
aatccacatt aatgaaatca taaaatagga taatgaaact taatactact taattctccc 114840
aattactagc taatgtctca aatataagat atgttagaat taactgcaat atttacaaag 114900
tatacaaagc aattatgcag cattcctaac cagaattggt atatatggga taaaaagatg 114960
tcacataaga taggcccctt caggtggaat gcagaagatt ggagttatca aatgaattat 115020
cgaccttagt agagattaag cctataattt aaagtgaaaa taacaacatt tattgagtgc 115080
cagacactgt tctaaatacc ttacgtgcct taactgctga atctttctaa caaccctact 115140
gaggcagttc ctattatatt atacccctat tttactgatg gggcacgtgg atcaaagaga 115200
ggtcagatca tttgtccaga gcacatgggt accaagtgac aggccatgat ctgaactcag 115260
gaacactggc tctgatgtgc cattctttgc catgtcaccg tagctgccaa gagcataggt 115320
ttccctcttc cgaaccctgc ctcaagcaat gaaatttcta gaaaagtata tgaagtttta 115380
atacgatagc tgctatggtc tgaatgtgcc ccttttaaat tcatgcactg aaacttaatc 115440
atcaatgtga taatattaag aagtcgggcc cttaggaggt gaatgagatt agcgagttta 115500
tatgagggct ggagggagct agctaggcct tttggccctt ttgtcctttc cagcgtatga 115560
ggacaaggca ttcatcctct ccggaggaca cagcaacaag gtgccatctt ggacgcagag 115620
agcagctctc accagacact gaacctgcca gcaccttaat cttagatctt cagcctccag 115680
aactgtgatc aataaatttg tgtgttttta taaattctaa tgcaaggttt cttctataag 115740
gttattttgt ctatgttgaa aatctatgtt ttagtttagt ttacctttat caatgatctt 115800
agctagatct gctggatcac ttgctgcatt cagttaaaga catcagcact tgctacttca 115860
```

ccttgcactt tatgttatgg agatggcttc tttccttcga cctcataaac taacctctgc 115920
tggtttcaaa cttttctttt gcagcattct cacctctctc agccttcata gaattgaaga 115980
gaggcatccg ggtgtggtag ctcacgcctg taattccagc actttgggag gccaaggcaa 116040
gtggaccatc tgaggtcaag agttcgagac caggctggcc aacatggtga aaccccgtct 116100
ctactaaaaa tacaaaaatt agctgggcat ggtggcgaat gcccgtagtc ccagctactc 116160
gggaggctga ggcggagaat cgcttgaacg tgagaggcag gtgttgcagt gagccaagat 116220
cgcgccactg cactggagcc tgagtaacag aaagagactt tgtctcaaaa aaaaaaaaaa 116280
aaaaaagaat caaagagagc ccttgctctg gattaggctt tggctggttt gatcttctat 116340
ccagaccttt cttcatgtca gaaatgagac tgtttcgctt tcttatcatt catgtgtcaa 116400
tggagtagca cttttaattt tcttcaagaa cttttccttt gcattcacaa tttggctaac 116460
ttagctaact taacttggct aatttggcat atgcttaatc atttcttcct ttccttgaaa 116520
gtacgattct ttcacttgga cactttgagg ccactgtggg gttactaatt ggcctaattt 116580
caatattgtc ttatgtcagg gaataggaag gcccaaggag aaagagatgg ggaatggctg 116640
gtcagtggag tagtcagaac acacatgttt atgggttaag tttgctgtct tatatggatg 116700
tggttcatgt caatataaca gataaaataa taatgaaaaa gcttgaaata ttgcaagaat 116760
taccaaaatg tgacacagac acacaaagtg agcacattta atgtatccag taaaaaccaa 116820
agtgtttctt acagtctctg atgtttcctt ctgagtaatt ggtcattggg agctgtggtt 116880
acacatagct gagtgaagcg gacacttctg tgaaggcatg gcttggctct tgctgggaag 116940
ttttctgttt cctggcctgt tcctgtctct cttctcctct ccatacttgt tgggaatgga 117000
cctcatacct ctctggaatg atgcagtgca ccaaacagtg aagaactgtt gttgttttta 117060
actgatttac ataactgata ataatatcat agctaacatt tattgagctc accatatgcc 117120
aggtatgaag cttagcactt tactacgttc attattgcat ttaattctct caacaaactt 117180
gcagcgcata tgcgattcca caggagagag ctctatttct tttggttgaa aagttctttc 117240
taatacttgc tgagctacag taaacaaata tgtctattaa tgccattggg aatttggaag 117300
caaagtctta acaaaatata gacaattcat ttttgaataa ttgtgatttg attatgcttt 117360
tggggaatat cagattaaca aagtgggttt gtttgtaagg attagtttgc aattcaggct 117420
catagaattt ttgtgtgtgt gtatacagtt gtatcgattt tattttattg agatggagtc 117480
ttgctctgtc acccaggctg gagtgcagtg ttgcaatctc ggctcactgc aacatccacc 117540
tcccagattc aagcgattct cctgcctcag cctcctgagt agctaggatt acaggtgtgc 117600
accactacac ttggctaaat tttgtatttt taatagagac ggggtttcac tatgttggcc 117660
aggctgatct cgaactcctg acctcaagtg atccactcac taaagtgttg ggggttacaag 117720 tgtgagtcac tgcgcctggc cagttccatg aattttaact tgtaaataga ttcatatagc 117780
cacagccact atcaggaggt agaccagttt caccacttca gaaatctccc ttggtcagtg 117840
ctactctttg tagtcagagc cactcccacc tcagcctctg ataaccaatg atctattctc 117900
tattactata gttttgtttt atttttttct tttcaggaat gtcatataag tggaataaaa 117960
cagtatgtaa ccttttgaga ttgggtcctt cagcatgatg ccttggagat tcatataagt 118020
tgttacatgt gtcaatagtt tgttcctttt tattgctgag tattattcca ctgtatagat 118080
acattgtggt tgcattaatc agttcaccta ctgaagaaca tgagttattt tcagattttg 118140
gtgattataa ctagagcttc tataagcatt catgtacact tacgttttcg tgaagttttc 118200
atttttctag agtaaatact taagagagtg gggatactag gtcatatggt aagtgtatgg 118260
ttaagttttc cagagcagct gtaccatttt gctttcccac tagcaatgtg taaaagttcc 118320
tgttgcccct attctttcca gcccttggta tttgacagtt cttttttttct gttttttttt 118380 ttttttttt tagacggagt tttgctcttg tccaggctgg agttcaatgg catgatctca 118440
gctcactgca acctccacct tccgggttca agtgattttc ctgccttagc ctcccgagta 118500
gctgggatta caggcaccta caaccacacc cggctaattt tttgtatttt tagtagagac 118560
gaggtttcgc catgttgacc aggctggtct caaactcctg gcctcaggtg atccacccac 118620
ctcggcctcc caaaatgctg agatttcagg cgtgagccac cacgcctggc cttgacagta 118680
tttttaaaat tttagcaact ctaataggtg tgtagtgata tctcattatg gttttaattt 118740
gcatttcact attgactaag aatattgaac atcttttcat gtgcttgttt gccttccata 118800
tattctcttt ggcatagtgt cttttcaaga cttttgccca tttttaattg ggtgtttctt 118860
ttcctaggta agtttttttg ttttgttttg tttgtttgct ttgagacgga gtctcgctct 118920
gtcacccatg ctggaatgta gtggcatgat ctcggctcac tgcagcctcc acctcctggg 118980
ttcaagcgat tctcctgcct cagcctcctg agtagctggg actacaggca catgccacca 119040
tgcctggcta atttttgtat ttttagtaga gacagggttt caccatgttg gtcagctggt 119100
ctcaaactcc tgacctcagg tgatccacct gtctcggcct cccaaagtgc ttggattaca 119160
ggcgttagcc atcacacctg acctattttt aaattttata ttaatatatt aactggattt 119220
ttgtcaaata gagaattatc tttaaataac catctcctca cttcacactt agtctgggaa 119280
aaaatgagag caaatttctg tgcatccagg gagcatatca ccaaccaggc atgaagctta 119340
aagggagagt gcaggctgag tggccagcag gccatgggca tcccacaggg ccaggccagg 119400
acccaggctt cagcgaccct tctcccagcc cacctagtgg ccctcaaatc catgatggga 119460
cagacatgca ttctcctgtc ccagttgaga agccccttct agatggaagg gagaggagaa 119520
aagccatagg aaagaaatcc cagaaacact agcaggtaag tacaggggct tcctccccag 119580
ctgcggtgac cttgctcctg ataacaccca acccctggag ctcttcgcca gtgtgcctgg 119640
ggctggagcc tggcggggaa gggaatgtgg gctcacagtt tctggatgtt ggcctcccac 119700
agcttggcac agaccagggg aaggcatgtg aggagggcct ggggaggtcc tcggggaaga 119760
taacacagct caggaggttg agtgtaaagt ggctgccaga ccaagggagc tggatggact 119820
gtgaaggagg aggtggctgg agagcctcct ccatgtaaag ctactagagc aaaaatagaa 119880
caagggggga cacccgtgcc ccagaggaca gccctaaaga tggtaacggg gagcacggct 119940
gagcagcgcc ctggattctg agctagtgtg gaaagctggg ggccaggggc ctctctcttc 120000
cttcatcacc agttgctggt aactttacag tcagatttgg aggaggaaca aggccctcca 120060
tcgcctcccc tagcctctga tgctgcccca aggggagggg taagaatggg caaagagggt 120120
gggaaacagg gaggtgggag ggagtctact gggtcttctt attttcagag gagggggctg 120180
taatagtgta gtggcagagg ctggttccta ggtatgtagg tgttgtgtgg gttgcctggc 120240
actgacaact gcttctgtgg ctctggcttt ggctgccaga gcagaggggc caatggggcc 120300
actgaccaga ggttccatga gcccagatag ggcagtggca gggattgcag gcatcccata 120360
gctccatcca tcatgggagg tcctggatag aactcagatg gggactgtgg attggggtag 120420
ccaggagggc aaaggtacat tccattggca actggcagag gaaagacata ggctctgttg 120480
ggtatgtaag agtacccgta gcctccattg gggggcctcgc ccctggaggc ttgaaatgcc 120540
acctggagca ttcattgtcc aaactgctgt aaggttaact tgtatgaacc ccagccctcc 120600
cagccatctc ccgcttcacc cttcactgtt cttttgaagt agttggcagc aaacaggcta 120660
gttgatctca cagtccttca tcaggtgaaa aggcatcacg aaggcttcat ggagttcttc 120720
ttcttggaca gaaagatgat cggtaagggg taaggtagac gatgcctttc ttggtccctt 120780
tgaaggactc tggcacattc ttcttgtcat tgaatgtaag ttccacatgg acgtaggaca 120840
ttaggatgtt cttggtgttc ttgatcactc tgccaccctt tgagtgattc ttgttgagca 120900
cgatagtctc ttggaaaggg gtcctaagac tctcgatgca gggccttgag ttcgtttttg 120960
cataaaggag ttggtttaga ttgaggttcc tttttttggc atataaatgt ccaattgtcc 121020
atttgttgaa aagactactc tttctccatt gacttgcctt tgcacttttg tcaaaattta 121080
ttggccatgt ttgtgtaggt ctatttctgg aatctgtatt ctgctctatt gatctgtgtg 121140
tctatccttt caccaataca cactgtcatg aagtcagaga ggtaacagga agccagatca 121200
tgtagggcct tgtagaccat tgaaaggatt taggctttta tcttgagtga aatgaggagc 121260
tacaggaagg tgctgggcaa aggaggaacc tgactttatt gaggcaagga taggaatgtg 121320
aggttactgc agtcatccag atatgcaaaa atggtggatt ggaccaggat gatgggtaga 121380
agtggtgaaa agtagtcata ttctgaataa tttttgagag tagccccaat gggattttct 121440
aatgggttga atgtagagaa tgagagatag gcatgagaaa agaactctag tctgagggtt 121500
tagcttgacc aacgtgaaaa atggagttat caattgagat gggaaaacct tcaaatgaag 121560
cacattttag gaaggaaggt cagaagttca gtttcgaaca tgttaagttt taaatttcta 121620
ttagaggtcc acctgtggat gttgagtgaa tagtgggtga taagggctaa gagcttggga 121680
gagaggtctg ggaatggagg tatacatttt ggatcctggc ggggcacctg ggatcacgcc 121740
tgtaatccca gcactttggg aggctgaggc gagcggatta cttgaggcca ggagtttgag 121800
acgagcctgg ctaacatgac aaaaccccat ctgtactaaa aatacaaaaa attagccggg 121860
cgtggtggtg catgcctata atcccagcca ctcaggaggc tgaagcaaga gaattgcttg 121920
aacccgggag gtggaggttg cagtgagccg agattgtgcc actgcactcc agtcttggcg 121980
acagagcaag actctgtctc aaaacaaaaa caaaaacaaa aaatttttgg atccatcagt 122040
agatagatgc tatgtaaggc catggcattg gtgaaatcac caagggcaga tatgtagaga 122100
gaaaagggca agcactgagc cctgggtcac tgcagcattg agaggtgggg gacaaaaaaa 122160
gaaactggta aaggagacta aaaaatagta gtgaggtaga aagaaggtag acaatgcttt 122220
ctgagagcca aataagaaaa tgatatccag gaagtaaatg atcaacagtg cggatgctgc 122280
taataagtca aacaagacga ggacatatat tgaccattgg gtttacgaac aaggggtcat 122340
tggtcacctc agtgagagaa gtttccatag agtgttggga gaaaaaggct gaggatagta 122400
agtttaagag agaataaaag gagaggaatt gcaggcagag aatagaagcg tttttcatgg 122460
agtctgtttg caaataggac caaagaaatg aggaggtagc taggggacga gatgggctca 122520
cgtgcaagtt gttgggtttt attccttttt aagatggaag aaataacatt tgtgaatgct 122580
aatggccatg accccataaa gtgggaaatt ttaatgatgt aagaaggaaa gagaagaaag 122640
cctagagcaa ttgatttcct tgagtaaagg agaaaaggat ggaatctagt acaaaaatgg 122700
agggattgcc cttagaagga gctagaaaat ttaatatatg gtaacacttg gaaaagcaga 122760
atatgtggat gtggatgcca gcatatgggt agatagatgt gagtgaagca agtcctcttc 122820
agtctgcttc catctcctca ctgcggtgga agcaaggtca gcagctgaga gggaaggtag 122880
gggaggggct gagatttgaa gggacaaaag tgggcgataa tcacctggga gagtgaaccg 122940
taggagtcat gggagtgagt gcctgccata ggagagaaga tccctcaaaa agaggaattc 123000
agggctggat gcagtggctc ctgcctgtaa tcctagcacc ttaggaggct gagatggaag 123060
gattgcttga gcccaggagg tcaggactgc agtgagccaa ggtcacacca ctgcactcca 123120
gtctaggcaa cagaatgaga ccctgtctca aataaataaa taaataaata aataaataaa 123180
taaataaata aataagcaag caaataaata aataggaatt caagaattga gatcatctgt 123240
gtgggtattg agaatgccag gaattaagac cagaaattct agagatgatg gcaatggcaa 123300
tgagaaatga aggggaatga gttggtgttt gctacataac agtaacagtg ctggatagcg 123360
gatgatagaa tctgatgaca tgaggtttaa agcacagaat ttttagagag gagagaagga 123420
gaatgctctg aaagcagcca cgtggagcaa aagcggcgtc tgtctcacct cactttccag 123480
ccatgtggag caaaaggggc atctgtctca ggcccagtgg catgggagtg aaatagcact 123540
tcagagagtt gcaggggaaa cagtgtcccc aagggagagt caggtttctg ttaaaggaag 123600
gtgcattatg cacatctgtg aaattatcat gactgctgtc atcccatctg ctcatagaac 123660
cagtgaatat tgattggtca taaaatgcaa gcattatttt aaggagcatg gacatttaat 123720
ttctctttta aggactggaa ataatttttt ccatgatttg gaaagtgata ttatatttgt 123780
caatgagaaa taatgtaata gctttttaat agttcacaaa atgatgtcag ttgctcttta 123840
ttcaaaaata tctttagcct ttttgaggtt attttgggga gatgataagg acaggcatct 123900
ccataatccc aaatatttgg gagaaaactt caaaaattaa agcgtattta ggctgagcat 123960
ggtgactcat gcctgtaatc ccagcacttt gggaggtcaa ggtgagtgga tcacttaaac 124020
ccaagagttt gagaccatcc tgggcaacat ggcgaaactc tgtctctaca aaaaatacaa 124080
aaattagcag ggcatggtgg cgtgtgcctg tagtcccaga tactcgggag gttgaggctg 124140
cagtgagctg tgatcatacc actgcactcc agcctgggtg acagaacaag accctgcccc 124200
ctaccccctc ctccaaaaaa agcatattta aatattccca gaatccaaat gttgaacatc 124260
atttggacac agcttcaaaa tggtaccaat tcttttaatt tgtgactgct ttatttattt 124320
atttatttat ttatttattt atttatttat tattatactt taagttttag ggtacatgtg 124380
cacattgtgc agattagtta catatgtata catgtgccat gctggtgcgc tgcacccact 124440
aactcatcat ctagcattag gtatatcccc caatgctatc cttccccct cccccaccc 124500
cacaacagtc cccagagtgg ggttcccctt cctgtgtcca tgtgatctca ttgttcaatt 124560
cccacctatg agtgagaata tgcagtgttt gtttttttgt tcttgtgata gtttactgag 124620
aatgatggtt tccaatttca tccatgtccc tacaaaggac atgaactcat catttttat 124680
ggctgcatag tattccatgg tgtatgtgtg ccacattttc ttaatccagt ctatcattgt 124740
tggacatttg ggttggttcc aagtctttgc tattgtgaat aatgccgcaa taaacatacg 124800
tgtgcatgtg tctttatagc agcctgattt atagtccttt gggtatatac ccagtaatgg 124860
gatggctggg tcaaatggta tttctagttc tagatccctg aggaatcgcc acactgactt 124920
ccacaagggt tgaactagtt tacagtccca ccaacagtgt aaaagtgttc ctatttctcc 124980
acatcctctc cagcacctgt tgtttcctga ctttttaatg attgccattc taactggtgt 125040
gagatggtat ctcactgtgg ttttgatttg catttctctg atggccagtg atggtgagca 125100
tttttcatg tgttttttgg ctgcataaat gtcttcttct gagaagtgtc tgttcatgtc 125160
cttcacctac tttttgatgg ggttgtttgt ttttttcttg taaatttgtt tgagttcatt 125220
gcagattctg gatatcagcc ctttgtcaga tgagtaggtt gcgaaaattt tctcccattt 125280
tgtaggttgc ctgttcactc tgatggtagt ttcttttgct gtgcagaagc tctttagttt 125340
aattagatcc catttgtcaa ttttgtcttt tgttgccatt gcttttggtg ttttatacat 125400
gaagtccttg cccatgccta tgtcctgaat ggtaatggct aggttttctt ctagggtttt 125460
tatggtttta ggtcaaacgt ttaagtcttt aatccatctt gaattgattt ttgtataagg 125520
tgtaaggaag ggatccagtt tcagctttct acatatggct agccagtttt cccagcacca 125580
tttattaaat agggaatcct ttccccatga ctgctttatt tctgcattag acaataagaa 125640
ggggccgaaa cttctggcct gatatgacag tgacatcaac ctcttgtgta gtagcctgtc 125700
attaagccag cgccaaatgg aaaattaaat ggaaaatggc agagagcatt gcccaggaca 125760
taatgtagaa atggcaactc tggcactgac ataggtttaa aaaaattatg ttttaaaagt 125820
aatcttgctg ggaggccaag gcgggcatat cacttgaggt caagaattcg agaccagcct 125880
ggccaatatg gtgaaacccc atcgctacta aaaatacaaa agttatgttg gcatggtggc 125940
gggcacatgt aaccccggct actctggagg ctgagacaag agaatcgctt gaacccagga 126000
ggaggaggtt gcagtaagct gagattgtgc cattgcactc cagcctggat gacagagcaa 126060
gagtctgtct ttaaaaaaaa aaaaaaaaaa gtaggcttac acatattccc tttactgttt 126120
ttcaaggtca ttacattttt atctgttatt gttcaccatt taaaaataag cagtggaaag 126180
cagcctactt tttaaaatgc ggaactcgta tggtgtactt agcatatata taaggatttc 126240
tgtcctctct cttgcctccc tccctcccgt tcttccccct tcctcctcct tccttccttc 126300
cttccctccc tccctcccct ttcctatctt ctgagtaggg tcaaacacca gttctctact 126360
tctcggacca taagaataaa gatctgtgca caatccattt tgtacatatt gattcttgga 126420
ctaaaaatag ctcaatttgg tttcaaactt tttctcccac cctaagttca ggttttgttc 126480
cttgtgcagc ctggtaggcg ggcaagtaat gcatagtcag cattccatct gggatgctta 126540
ctggacaatt ttaatctttt ttttacgtct tgacctctat ttccaaagag catcccagtt 126600
ggcaggtcta gcctgattaa gattctgttc aggcatttaa ttctcctaag ggaatttaca 126660
gattaatcta aaaatcaagg ataccagaat ctactcagga cttaacttct tgaaggttat 126720
aggaaacata tacttgagca acctaatgaa tgagcttagt gatatcgtaa tgaattttta 126780
tatatacctc aaattacact ttttaatgca tatccaacaa aaatattttt aaaaacaaat 126840
actgtagacc taactggatt agctgtatta gtagatccaa atttaacttt caatttgaat 126900
taagttagaa cactatggat ctcataaggc aggctatata ttgattacct agttagccag 126960
cttccatatc accacttgtt caggaacatt aaaagtactt ttttagaaat agttttctga 127020 tatattttg gtttcactaa gacagctttt taaaaagcaa aattaggcag ggcgtggtgg 127080
ctcacgcctg taatcccagc actttgggag gccgaggcgg gcagatcacc ggaggtcggg 127140
ggttcaagac cagcctgatc aacatggaga aaccccatct ctactaaaaa tacaaaatta 127200
gccaggtgtg gtggctcatg cctgtaatcc cagctacttg ggaagctgag gcaggaaatc 127260
acttgaacct gggaggcgga ggttgtgggg agccaagatc gcaccactgc gctttagcct 127320
gggcaacaag agcaaaactc cgtctcaaaa aaaaaaaaag aaagaaagaa agaaagaaag 127380
aaaagcagaa ttataactaa acaccacttt ttttttcttt cttttttttt tttttttttct 127440 ggagttagag tctctcactc tgttgcccag gctggagtgc agtggcacaa ttttggcttg 127500
ctgcaacctc cacctcctga gtggaggtta ctcaggcaat cctcctgcct cagcttcctg 127560
agtagctggg actacagcca tgtgccatca cacctgaata atttttatat tttttgtaga 127620
gacaggatca ccccatgttg cccaggctgg tctcaaactc ttgggctcaa gcagtctgcc 127680
tgcctcagcc tcccaaagtg ctgggattac aggtgtgagc cactgttgcc agcctaaaca 127740
tctcgtctga ggctatcaca atatatacta ttctccagcc tacagtagat tatagacatc 127800
tagaatataa aaatttgttt cctgataggc ttggcacaca atattcctac agtcctttga 127860

```
aaacacacat attaacagag tgacaatatt tacaggcaga attactcatg tgtcttattg 127920
tagcttacag gagagtgtgt ctgtctaaga atggggtaga ggttggtttg taaaaacagg 127980
tgtcccacaa gctttcttgg atagttaact cagtagttag aatgaaggat gtaaaataac 128040
ctgtcaggat aacacctgct ctcttgccct caacaattaa tgataatgaa actaggcctg 128100
aagaggaata aaaatcttgt atcatctttg aattagtctt ttgttggtcg tgcgttccaa 128160
tgaaatgatg tttcacaacc ttttcttcat tatcatctct gaaaagatcc tttatggcta 128220
tttttttttc ctagttgcca caaaattaaa cacaggcata ctgtgtctta ctgtgctttg 128280
ctttcttgct cttggaagat attgtgggtt ttttttttta caaattgaag gtttgtggca 128340
cccctacatt gagcaagtct actgggacca ttttcttttc aacagcatat gctcctttta 128400
tgactgtgtc acattttggt aattcttaca gtatttcaaa ctttttcttt tcttttttttt 128460
ttttttttta gacagagtct cgatcagcca cccaggctgg agtgcagtgg tgcgatcttg 128520
gctcactgca acctccgcct cccaggttca agtgattctc ctgcctcagc ctcccaagta 128580
gctgggacta taggtgcatg ccaccacacc cagctaattt ttttgtattt ttagtagaga 128640
cagggtttca ccatgttggc cagactggtc tcgatctctt gacctcgtga tctgccctcg 128700
gcctcccaaa gtgctgggat tacaggcgtg agccactgcg cctggcccaa actttttcat 128760
tattgttata tctgttatgg tgatctgtga tcactgtctt tggtgttact attgtaattg 128820
tttggggatg gcctgaactg catccatata acacttaatt gaggccaggt gtggtagttc 128880
acgcctgtaa tcccagcact ttgggaggct gaggtgggca gatcgtgagg tcaggaattc 128940
gagatcagcc tggccaacat agtgaaaccc catctctact aaaaatacaa aaaaattagc 129000
tgggtgtggt gacgcacacc tgtagtccca gctacttggg aggctgaggc aggagaatcg 129060
cttgaactgg ggaggcggag gttgcagtga gccaagatca tgccactgca ctctagcctc 129120
agtgatagag caagactcca tctcaaataa taataataat aaagacttaa ttgatactta 129180
atccataaat gttgtatgtg ttctgagtgc tccacccacc agctatttcc catctttctc 129240
ctcctcctca gacctcccta ttccatgaga cacaacaata ttgaaattag gccaactaat 129300
agccctacaa tggcttctac atgttcaaga gaaaggagga gttgcacatc tctcacttta 129360
aatcaaaaca tagaaatgat tatgcttagt gaggaaggca tgttgaaagc ctagataggt 129420
caaaagctag gcctattgtg ccaaacagcc aaactgtgaa tgcaaaggaa aagttcttga 129480
aggaaatgag gagtgctatt ctgttgaaca cacaaatgat aagaaagtga aacagcctca 129540
ttgccgatat gcagaaaatt tgagtggttc tagatagaag atcaaaccag ccataacatt 129600
cctttaagcc aaagtctaat tctttttttt tttttttttt ttttttcaga gtcttgctct 129660
gttgcccagg ctggagtgca ttggcacaat ctcggctcac tgcaagctct gcctcctggg 129720
ttcacgccat tctcctgcct cagcctccca tgtagctggg actactggtg cccgccacca 129780
tacccggcta attttttttgt atttttaata gagacagggt ttcaccatgt tagccaggat 129840
ggtctcgatc tgatctcctg accttgtgat ctgcccgcct cggcctccca aagtgctggg 129900
attacaggtg tgagccactg tgcttggcca ccaaacccta attcagagca aggccctaac 129960
tcccttcaat tcactgaagg ctgagaaagg tgaggaactt gcagaaggaa agcttgaagc 130020
caatgggttg gttcatgagg tttaaggaaa gacaccatct tcataacata aaagggcaag 130080
taaacagcaa gtgctgatag agaagctgca gtaagttatc cagaagatct agctgagatc 130140
attggtaaag ctggcttcac caaataacaa atcttcaaat gtagatgaaa cgactttgta 130200
ttggaagaag atgccttcag gctaggactt tcatagctgg agaggagaag tcaatgcttc 130260
```

aaagtttcaa gggacaggct tttgtccctt gggctcttgt taggggctaa tacagcttgt 130320
gactttgagt tgaaggcaat gctcattgaa cattctaaaa atcctagggc ccttaagaat 130380
gatactaaat gtactctact tgtactctat taatgaaaca acaaagtctg aatgacagca 130440
cgtctgttta tagagtggtt tatcaaacgt ttaaagcctg ctgttgagac ctaccactca 130500
gaaaaaaagg ttcctttcaa aatattactg ctcattgaca gtgtacctgg tcacccaaga 130560
gctctgaaag tataaggaga tgactgttgt tttcatacct gctaacacaa catccactgg 130620
gcagccaatg gatccaggag tcattttgac tttcaagtct tattatataa gaaatacatt 130680
ttataaagat atagctgctg tagatagtga ttcctctgat ggatctgggc aaagtctatt 130740
gaaaaccttc tggaaaggat tcacaattct agatactgtt gggaggaggt caaattatca 130800
acatgaacag gagtttcgaa gaagttgatt ccaaacctca tggtgacttt gagggcttta 130860
agacttcagt agagcaggct gggcatggtg gcctataatt ccagcccttt ggaaggctga 130920
agcgggtgga tcacaagcat agagttcaag accagcctgg gcaacacagt gagaccccca 130980
tctcctaaaa aggatttttt tttaagactt cagtagagga agtactcgta aatatggtgg 131040
aaatagcaag agaactagca ttaagaatga agcttaaaga tgtgactgaa ttgctgtaat 131100
ctcatgataa aacttgaatg gatgaggagt tgcttcttat ggatgagcaa aggaaatgat 131160
ttcttgggag ggaatctatt cctggagaag acactgtgaa agttgtcgaa atgacaccat 131220
aggatttaga atatcccata aacttagctg ataaagcagg ggcaggcttt gagaggatcg 131280
actgcaattt tgaaagaagt tgtaccatga gtaaaatgcg atcaaacagc attgcatgct 131340
tcagagaaat ctttcttcac aaaaggaaca attggtgcag caaaattaat tttcttattt 131400
taagaaattg tcagccgggt gtggtggctc acgcctgtaa tcccagcact ttgggaggcc 131460
aaggtgggca gatcacctaa ggtcaggagt ttaagaccag cctggctaac atgctgaaac 131520
cccatttcta ctaaaaatac aaaaaattag ccgggcatgg tggcacgcct gtaatcccag 131580
ctacttggga ggctgaggca ggagaatcga ttgaacccgg gaggtggagg ttgcagtgag 131640
ccgagatcgc gccattgcac tccagcttgg gcaacaagag caaaactctg tctcaaaaaa 131700
aaaaaaaaaa aaaaggctgg gcgcagtggc tcacgcctgt aatcccagca ctttgggagg 131760
ccgaggcagg tggatcatga ggtcaggaga tcaagaccgt gctggctaac atggcgaaac 131820
cccgtctcta ctaaaaatac aaaaaaatta gctgggcgtg gtggcaggtg cctgtagtcc 131880
cagctacttg ggaggctgag gcaggagaat ggcgtgaacc tggcaggcgg aggttgcagt 131940
gagtcaagat tgcaccactg cactgtagcc tgggtgacag agtcagactc cgtctcaaaa 132000
aaaaaaaaaa aaaaagaaaa gaaaggaaat tgttggccgg gcgctgtggc ttacgcctgt 132060
aatcccagca ctttgggagg ccgaggcagg cggatcatct gaggtcagga gtttgagacc 132120
agcctgatca acatggagaa accctgtctc tactaaaaat acaaaatgag ccgggcgtgg 132180
tggcgcatgt ttgtaatccc agctactcga gaggctgagg caggagaatc acttgaaccc 132240
aggaggcaga ggttgcagtg agccgagagc gcaccattgc actccagtgc agtggagtgc 132300
agtggtgcga tctcggctca cgatcgttag cgttttttaa cactcaagtg tttttggttt 132360 tgtttttttga gttggagttt tgctcttgtt gcccagcctg gagtgcaaca agagctggca 132420
tgatctcagc tcactgcaac ctctacctcc tgggttcaag tgattctcct gcctcagcct 132480
cccaagcagc tgggattaca ggcatgcacc accacacccg gctaattttg tatttttagt 132540
agagatgggg tttcaccatg ttggtcaggc tggtctcaaa ctcccaacct caagtgatct 132600
gcccgcctca tcctcccaaa gtgctgggat tacaggcatg agccaccatg cctggcccac 132660
tcaagcattt tttaattaag gtatgtattt tttagatatg gtattgaaca cttaagagac 132720
tacagtatag tgtaaacata acttttgtat gcactagaaa ataaaaattt catgtgactc 132780 actttttga gatatttgct ttattgcagt ggtctgaaac caaacctgta atatctccaa 132840
gatatgcctg tactgaagag taagattttg tcagttagag tttaatcttg gaaagactac 132900
aaaccactgt aataacctaa gcattatttg attccccaag gaccaatttt caccccttg 132960 ggggccatat taatttttta tggctgctat accaaagtac tatgaatttt atggctgaaa 133020
acagcacgaa cttattccct tgtagttcta gaggccggaa atgcagttca ctgggggtaa 133080
tgtcaaggtg tagggccata cccccaggaa ggctctgggg aagcgtacat ttcctcttcc 133140
agcttccatc tttttctggc ttccagactt gcattctgtg tgttcactga ctcatgtctg 133200
cttcctccat ctttcaaagc cagcagccgt gtagcatctt gtttcaatgt cacgttgcct 133260
ttttcttctg tcaagtctcc ctctgcctgc ctctcatgag gacagtgtga ttacacttag 133320
ggtctacctt gctaattccg gataatctct gcatctcaaa atccttaatt taatcgtatc 133380
tgcaaagctt gtgttaccat ataaggtaag agtcacaggt tcccaggatt aggaactgga 133440
tatctttggg gaccaatact cagccacaga ggtgatacca ctccccaccc cttaaaaatg 133500
catgttctac accagtaagg aagaaagaaa ataagaaaga agagtaaaag ataataaata 133560
tgtaactttg gctacaaatg aattctttat tatatctcat tctatttggg gcacttgcta 133620
ttagaacaaa gagagaagat atatttaaaa ttaataggat tcagaagagt agagttgatg 133680
atgttcacct cattgcgatg tactcaccca ttcatttatt ttgcattacc cttcctgcct 133740
ggggccagtc agcagaggag ggcagtgagt cactccaagg tcagacagta ttattaccct 133800
cttattgtga tgggcaaatc caccattaag cttcagattg agagaaacac cattgagttg 133860
gcaaatgctt tcgatgtgta cgtgcagaaa gtcatatgta tctacaattt tccagacagc 133920
ggcaaagaga aatggaaact ctgtgctgta ttttaattgg ctgcaaaatg tttccttcag 133980
aaattaccat tccattaagc acctactctg tgcaaacgct ttgcaaacac tgctgggaat 134040
agctgcatgt ataagggcat gcctaccttt attagactgt tcaggggaat aaaatgaagt 134100
tacaatttat tctaatacta gaatgcagtt ctctccccat ggactgcacc tttcaggata 134160
gtggcctgaa tcagagcaga aaacacctgc tggatatcct ccaagtacac agtctgatta 134220
gtgccctctg ggaaacatgg aggcagatac tacttggctc tccagcctaa gggaagtatt 134280
attaattaaa aacttaaagc caggttcttc tctgtgtatg gttatgcatg tcctagatgg 134340
ccttgaaatt gatctgttct ccattagcaa tctgtgaatt gtactcctgt ctgaaattga 134400
gtagaggtca gagctatgaa ggttgaattc aacaagaatt tttatgaagt ataactagag 134460
ttagtgctct gctctaactg cttttggaga cagactttcc ccagtgtatc ccatcaaatc 134520
acagactaaa aacagtctat ttccccttat tcttggccag ataggaccta ggcacctgaa 134580
ttttttttta aactagattt ccaggaaatt ttattgaagg ctaacagcat agcatttcat 134640
gttggataaa gaagatgcac aagacgggac atggtaagac acacctgtaa tcctaccact 134700
ttggaaggat gaggcaggtg gatcacttga gctcaggagt tcaagaccag cctgggcaac 134760
atggtaagac cctgtctctc caaaacaaac aaacaaacaa acaaaaaaac aaaaattagc 134820
tgggcatgat ggtgtgcacc tttagtctca gctactcggg aggctgaagt gggatgatca 134880
cctgagccca gggaggtcaa ggctgcaatg agccatgatt ccatcactgc gctccagcct 134940
aggatacaga gtgagaccct gtctcaaaaa aaaaaaaaaa aaaaaaaaaa aaaggccata 135000
tgcagtggct catgtctgta atcccagcac tttgggaggc caaggcaggt ggatcgcttg 135060

-continued

```
aggtcaggag ttcgagacca gcctggtcaa cattgtgaaa ccagtctcta ctaaaataca 135120
aaacaaatta gctgggcatg gtggcaggca cctgtagtcc cagctactag ggaggccaag 135180
gcaggagaat tgcctgaccc caggaggcgg acgttgcagt gagctgagat cgtgccactg 135240
cactttagcc tggccgacag agcgagactc tgtcttaaaa gaaaaaaaaa aaattcacaa 135300
aagaaaaatt gtattaagta caatttaata taatttctta caagtttatt acctaaaact 135360
ttgcaaataa ttgaagttag aagctttgga ttttgttttt agagcttaat ccttttctgt 135420
aagtggaaat cctttccact ggtttatttt ccttttgatt ttattttact ttgacaccct 135480
aaaggtttag tgttcctgtt tttaaatcta ctgatcgttt cttatgagat tccttagagt 135540
gccctttaag tatgcacaga ttttgcaaat gcattcattt tcttatttgc cagggtttaa 135600
cactggctat gcacatgtta gctgaataac cttaggcaag taaattatcc tctctgggcc 135660
tcgatcttgt tagctattaa gtgggaataa tgacaattcc taactcaagg gtctgttgtg 135720
aggattaaat gagtccttac atgtgacata cttgaaatag tacctggtgc agagttaggg 135780
ctgggtgagt gttagctatt gtattattat ttcattgctg tttgcatata tttttaaaat 135840
gtatttagga ttttcttttt tttttgaga cagggtctca ctctttgccc aggccggagt 135900
gcagtggtac gatcttggct cactgcaacc tccacctccc aggctcaaga gatcctccca 135960
tctcagcctc ccaagtagct aggattacag gcacgcccca ccatgcctgg ctaatttttt 136020
ttttttttt tttttgtatt tttggtagag acagggtttt gccatgttgc ccaggcttgt 136080
cccaaactcc tgagctcaag cggtctgcct gctttggcct cccaaagtgc taggattaca 136140
ggcatgagca actgcgtctg gccagggtta tttcttaggg atagcattcc agaaatataa 136200
ttaaaattta ttgatccaga aatataatta aaaataattg atcaaatggt agaagacttt 136260
ttaaatttat atttcatcaa ttttacacat ttgttaggtt ttaatgtttc tactacttgt 136320
gtgtgccaaa aaattattga ttttcttaat cgttttctat gagtagaaat cctttccact 136380
ggtttgttat tttcctttg attttatttt acttttgaca ccctgaaggt ttagtgttcc 136440
tgtttttaaa tgtactgatt gtttcttagg agattcctta gagtgccctt taagcagaga 136500
atatctttcc ctctccttcc tcttcccttc actcttctca aaactataaa aatataatac 136560
tcatttctac ctgttttcgt ggcttttata ctttcaatgt gttcatctac atgagattta 136620
gtttgatgtg tggaacagca agagagttta aattaaaaat cttcccctaa atggctaaat 136680
gtcccagtgc catttacagt gtggtacccc tcctgtaata agaatattac attcttatcc 136740
gtattaatta tttcttattc aaacttacca gtggcattta agaaatcatt agttcagttg 136800
tttataggta agaagactca ttctttatct gctatttcaa aattaaaatc attgtctttc 136860
atagatattt tctgaaatga aatatggaaa acaattattt ttacaatgag acttggaaaa 136920
aaatcaatac taagtttctt ttgtatacaa gatagccaat aatacctagg cctaaaacgt 136980
tccaatctag tttttgtct gctaataggt gctcagtatg acggagcttt tcttgaggac 137040
catttgaccc tgtgtctctc tttgcctttc cccttatgaa aataagctga cccctacatc 137100
caatcaaatc atcatagcaa ggttttcatc attttttatg gaatgtcagc cttgccacct 137160
gcttgcctgg tacccaatac atataatctc tcttcaggct gcaacacaca gcacttgagg 137220
caggctgtca ttaattggag ttacctccaa ttgcctactt cttattctat tcctatcaaa 137280
aacccagctg acaggtacac aaggggcata gcccaaatta catgtaatcc ataaatctct 137340
ccattttttc ttaagtctta gttttctctt gatataggat tttttttttt tttttttgag 137400
atggagtctc actctgtcgc caggctggag tgcagtggca cgatctcggc tcactgcaac 137460
```

-continued ctccacctcc tgggttcaag cgattctcct gcctcagcct cctgagtagc tgggactaca 137520
ggcacgtgcc accatgccca gctaattttt gtatttttag tagaaatggg gtttcaccat 137580
gttggccagt atgatctcaa tttcttaatc tcgtgatctg cctgccttgg cctcccaaag 137640
tgctgggatt acaggtgtga gccaccatgc ccggccgaca taggctattt tttaaaatgc 137700
aagctcttct gaaccatata atatgatgtt ttaaaatata gactctgaag acaaagacct 137760
gggctcagaa tcaggcccca ccacttattt tcaatggaat cttgtctgaa tcttgtaatc 137820
tttccaagcc tcagtttttt catctgtata atagggataa aaataatagt aaacaaataa 137880
atgtatttct tttgaatatc tagtagtatt ttaaaaatca gataactaga attatataac 137940
tctatgtgct ttattttta cttgtttgct gggaatcaaa gagcttagtt ttgtttttttg 138000
ttttttttt ttttgagacg gagtctcgct ctgtccccca ggctggagtg cagtggcgcg 138060
atctcagctc actgcaagct ccccctccca ggttcacgcc attctcaaag agcttagttt 138120
aagctcaatt caagtgacta tttgaggcct ggtcaggata tctgctgtta tttggaacac 138180
aagctgtttg cccaggacta agatcaagtg attttcctaa agcaaacagt gtattgaatg 138240
taatccaaat catcagcagg aacaaaggag gccatatagc ttagcaatta aggcatggga 138300
tctgaagtca gagagacttg gatttgaatc atggccctga caagttacgt gcctctctct 138360
gcctgagttt cttcatctgt tagatgagca taatattgca atatagtgtt actttgagaa 138420
ttaaatgagg taatgcaaag ctcttagagt agttactagg ataagtgtcc aattaaccat 138480
agtttaagaa aaaggataag ctgggcacgg tggctcatgc ctgtaatccc acactttggg 138540
aggctgaggt gggcggattg tctgaggtca ggagttcgag accagtctgg ccaacatagt 138600
gaaacccctt ctctactaaa aatacaaaaa ttagccaggt gtggtggcgc acacctgtag 138660
tcccagctac ttgggaggct gagatgggag aatcgcttga acccaggagg cagaggttgc 138720
agtgagccga gatcgtgtca ctgcactaca gcctgggtga tagaatgata ctctgtctca 138780
aaaaaaaaaa aaaaaaaaaa aaaaggaaaa aggatgaaat cacaacttgg agcaaaaaaa 138840
cccaaaggca tatttaaaga tttgcgtatt gggttaaaac aagttttaac atctggaaag 138900
aaaaagcatc catcaacttt tcttatcaag aaatatgaat tatagccagg tccagtggtg 138960
tgtgcctgaa gtcccagctg cttgggaggc tgaggcggga ggatcacttg tgactgggag 139020
tttgagaaca gcctggggaa catagtgaga acccatcagg aaaaaaaaaa aaaaaaaggt 139080
tgattaaaaa aagaaaaaca aaagaggcca ggcacggtgg ctcacacttg taatcccagc 139140
attttgggtg gccaaggtgg gaggatcgct tgaggccagt gattaaagac cagcctggac 139200
aacatagtag gactccatct ctataaaaat tttaaaaatt agccagacat ggtgccgtgt 139260
gcctatagtc tcaactactt tggaggctaa ggcaggagga atgcttgagc ctggggggtt 139320
gaggctgcag tgagctgtga tggtgtcaat gaactctatc ctgcagtaca gagtgagacc 139380
ttgtctcaaa aaaaatcatc tttacagtta tttgattatt tgcagatttt cagtgtttat 139440
tgtttttact ttccttgccc cactattctg cattcatcaa atattcattg aacactgtct 139500
ttttgccaga gactgctgta ggcacaagag atacagcaaa aaacaagaca aaacccttgc 139560
tctcatgaaa cttacagtca agtgtgtgag atggacataa acatagtact gtgctgtcat 139620
gttgtaaaat gggacctctc attgagaagc tgggttggtt tgggggtggg gagtatgaca 139680
tcaagagttc tgttttgatc atgtttagtt caagatgcct gttatggtca ggcaccgtgg 139740
ctcacacctg taatctagaa ctttgggaga ctgaggtggg tggatccctt gagttcagga 139800
gtttgagacc agcctgggca acacagcaaa accttgtttc tacaaaaaat acaaaaatta 139860
gcccggtatg gtggtgtgtg cctgtagtcc cagctactag ggaggctgag gtgggaggat 139920
cacttgagtc atggtaacag actcgctctg ggtttcgctc tggatgacag agcgagaccc 139980
tgtatcaaaa aaaaaaaaaa aatgcctatt agaccttcaa gtggtgaaga caagtaggta 140040
attggataca caagtctggg ctcagggtag aggctgggct agagaaagaa atttgggagt 140100
catcagtgaa tagatgacat tttaagccat gggcttggag gagataacct aaggaatgac 140160
gagaatacat ctgaagatcc agcctcagac actctggtgt acagaagcag gtagagaaaa 140220
ggagaaacca ttaaagacct ctgttgggcc gggcatggtg gctcacacct gtaatcccag 140280
cactttggga ggccgaggtg ggcagatcac tcgaggtcag gagttcaaga ccagcctgga 140340
caatatggag aaaccctgtc tctgctaaaa atacaaaaat tagctgggtg tggtggtgca 140400
cactcacttc actctagcca gtagtcccag ctactcagga ggctgaggca ggaaaattgg 140460
ttgaactgtg aggcagaggt tgcagtgagc cgagattgca ccactgcaca ccagcctggg 140520
caacagagca agactgtctc aaaaaaaaag aagactgagt gtgatggctc acgcctgtaa 140580
tcccagcact ttgggaggcc aaggcaggcg gatcacctga ggtcaggagt tcaagaccag 140640
cctgaccaac atagtgaaac cccgtctcta ctaaaaatac aaaaattagc cacgtggtgg 140700
tgcgcacctg taatcccaac tattcgggag gctgaggcag gagaattgct tgaacctggg 140760
aggtggaggt tgcagtgagc cgagatcgca ccactgcact ccagcctgag tgacagagcg 140820
agactccatc aaacaaacaa acaaacaaaa aaaacaaaaa cccaagaaga cctctgtctc 140880
ctagagcagt cacctagaat cctagagaaa aatgtctttc caaaaggaag aaatgcagaa 140940
ctgtgtgagt aaaatgaagc taagaattaa ttactggatt tggcaagatg gaggttgctg 141000
atgacttggc aggagagttt ccctgaggtg ataggaacca aggtctgatg agagtaggct 141060
gaagagcaaa tgtggagaaa cagagatggc aagaatcaac agttcatatc aggattttgc 141120
tgtgaaaggc agcagaggga tggggtacca ttattttcat tttgttttgt tgttggtttc 141180
tgctgcagtg gtagtttatg ttgagatgta tattttaaac tgatgatcct taaagaagga 141240
gaaattgatg aaggagagag gtgggaggga taattgcaaa aatgaagtcc ttgagcagtg 141300
agatctgctt ccttattatg catatagatg aaacattaaa atgtaaaaca gactcttgtg 141360
ctgattttaa gaactctaag ttagaagagg gtggggagaa ctgggaagct ggggagccca 141420
agatgcagga ttttggctct ttagctcagc taggttcagg ttcttgtctc acaaccagga 141480
ggaattaggc acgtggacac cagagggtga gtagagtaga atttattaag caaaaggaaa 141540
gctctcagca aagagggggg tctggaaaag caggttgttg gctgccccct tcacagttga 141600
atactgtgct taaggcacaa attcctggcg gctccacccc atccttccag tgcgcatgtg 141660
ggcccttagg gtgagccact ccatattgat ttacttccct tactgcacat gtgttaagga 141720
atggaatttt ccactgcggg catgtttagg caagccccct gtgcaagttc ccacatctgc 141780
acaaaatatc tggtgtaagc atttgtgggg cgggttggag gttctccagg gacccttccc 141840
ttactgtctg cctaaagcaa gctggctaac ttcttacacc tgtgtattat acagcaccag 141900
tctttaggga aaggaacttc aggtgggtag ggtagagtat agcaatagct ggcaagaaaa 141960
aaaagatttg aagaaacaaa ctctgtggtg ccctagggag cagatgtggg atggaaaagt 142020
gaggctgggc cttaaatcac aagaagccca aggtgtacag ggatctcttt acaacagaac 142080
gtgttcttat atatgagtta tttgaaatag cttaattata ccactatact gtcattaata 142140
atggataaat gtacttcaaa gtaatttatt agtttgtctg tgaatatgtc tttccttgtc 142200
tcttttcccc cttacctaga atgtaaacaa gagagaagag aactccagat ctgattttca 142260

```
tggaggaagg tgatacagat cattatggct gtaaggggag gattcttgtg tttcccaggt 142320
gtcctgaaac cattcacatg gagcctaagt taaaatgctc tgggttcggg agtgtcttcc 142380
tggagatcac taagggcttc aggactcctt gagatggagt tttcttttct ctctctctct 142440
ttttttttt tagtatttta aaatgtattt cgttaattag cagcagtatg ccaaagttgt 142500
tccattatta tattttgttc attcttttgt acaagtgtct tccaatgtga tttgataatg 142560
ccaacaattt gcaagtgatt ttattgcagc atgactttgg ttcccaggaa tgctgaagca 142620
caggtcctag aacagaggct tgaaaaggaa ataaaaggga tttgatcata aatgcttctg 142680
gggttggcat accagatcat tttgagctca aataggagac aaaagaaagg atgttgggaa 142740
agctgtatgg tggagaggct gaactgttgg aatgaaaaga caagaagcat attattatgt 142800
taattccagc accctagatc tgcaatgctg aaaggactgc caaaactaaa gcttgtccta 142860
caccacgttc atcacaaaga aattctgttt agacgttgag ttaaactttc tcaactgtat 142920
tcagtacagg attaagtggt tgagatgggc cattctgcag ttacactgtt tccgttccag 142980
tctgggtctc ctcatgtatt agctgtgtgg accttgggca ggtaactcct ttgtgcctca 143040
aagaaatgga gatgacgata atacctacct cagtggggtt attgtgagga taaaatgcga 143100
ttaatagaaa ataattagaa tggtgcctgg gatacatact gctcattaaa cattgtatat 143160
ttttattatt agtgcactgt gctataatag gatggctatc tagaaaacat catgcaattt 143220
gtaatgcaca tttatcatcc agttaattga aagaggtagt gatgggacag tggtggcaga 143280
cattgaatgc tcagggatga aaaatgagac aggttttatc ttgttttgtt ttatttttgc 143340
ctctcattag gtatccacct acttttcaaa attgtgttat tttaatcttt attgcataca 143400
gacatattct cagtaaattg aggccaccat atggaagtgt aaggatgaag ccaggcgcag 143460
tggctcatgc ctgtaatcct agcactttgg gaggctgagg tgggcggatc atttgagcct 143520
acgagttcaa gaccagccta gacaacatgg ataaatcctg tctctacaaa aaaaatacaa 143580
aaattagcca gatgtggtgg catgtgccta tagtcccagc tacttgggag gctaaggtgg 143640
gaggattgcc tgagcccaag gaggtcgagg ctgcggtgag ctgtgatcat accactcact 143700
tcactctagc cagggtgaca cagtgagacc ctgtatcaaa aaaaagaaga agtataagga 143760
tgaaatcata agcttaggtc ctagttcttt tgagtgagtt agaacctata taaaattttc 143820
tccttttgga attttatttt tctaatgttt acctcattat tttctgacta taatagaaaa 143880
ttatccttaa agtttgccat tacaaaggga attgtacttc tttaaaatgc caattaaaaa 143940
tatcttcttg ttgttcttat atatattttt aagttatata tgcatatgtt aaaatattta 144000
agtgaaatag gaatgacata aaaataaaat cttcctcctc actacctcaa cctccagtcc 144060
catgctatag aagtaaatac ttaaattagt ttgctgtaac aaattaccac aaactttgtg 144120
gcttaaagca acacgaatcc atctcatagt tgtgtagctc agcattctga aatgcgtctc 144180
actgggtgaa aaattaaggc atcagcagga ctggtttctt cctggaggct ctagggaaga 144240
atcttttcct tgcccttctc acgttctaga ccccactatt aacactcata tattgtttca 144300
gaaatgttta atgctccttg atttttatca cctaattgta tattttctag aactctccat 144360
tcttttatat acagctacat actgttctac tatatggatg caccagatgt tatgtgtcca 144420
gctccctgtg ttaatggagt cttggtttat tttcaagttt ttattttcat aaattgcatc 144480
ataaataata tctttatact ttcatattta tgcattttga caaacagatc catgggataa 144540
gttgttcttg gtgtagtttc caggtaaagc aggatgtaca tttacacttt tgatacttct 144600
ttttaaattg ccttctcaaa agacatctat tatctttccc tccagtgatg agtaagagtt 144660
```

-continued catatttcca cacggttttg gggcgctcgg gagtttgttt tttttacaaa acttttaaaa 144720
ctttaccact atatatataa tatatttata atatatattt ataataaata tcatatattt 144780
ataatatata tttataataa atattatata ttatatattt ataatatata tttataaata 144840
tatatttata ataaatatta tatattatat atttataata aatattatat attatatatt 144900
acatattata tatttataat aaatattata taatatatac tatatatttt atatatatta 144960
tatatcttgt atatattata tatataactt ctctttttac ttcgtttcac ttgagttata 145020
aatttgccat gtttggaggt tttcgatggt cctagcaaac cagtttccct agaagcaact 145080
tcccttcagt ccgattcaca tcaaagatgt gacttcaata ccatctgatg ttcaagctat 145140
ttattttagc agtggtctta caagtcggat agtgggagca ggtgggtggc atgggccaga 145200
ttcaatcaga ggtcagatga ctgcctgtcc aggagggtct ccatctggag actattctca 145260
gagtttggga gattcttccc atttcttcta cctgcattta gttcagtcaa ttatcaggcg 145320
tttctttcat aagaggaggt taagctagtc ttataagggt aagctttgtt aaaggtttac 145380
gagatttgca tccgtgatga ggtggcctta tgtcctggaa atccctgggc cagcttggaa 145440
atccccaggc caggtggcct cacgctgcta agtggcacat agtgtcagtc ctgtgagagc 145500
ttgttaatgc cttatagcta tcattaatct tgtagtcatg atatgtctcc tataggatgc 145560
tacacagttg gttttagcat tttactatcg ttttgttgtt gattactttt gttttctttc 145620
gttttttgtt tctgtttttg agacagggtc ttactctgtc atcccggctg gagtgcagtg 145680
gcatgatcat ggctcattgc aacctctgcc tcccgggttc atatggaagg cagaggattc 145740
tcccacctca gcctcctgag tagctgggac tacaggtgca caccaccgca cccaggtaat 145800
ttttgcattt tttgtagaga ctgggttttg ccatgttgcc caggctggtc ttgaactcct 145860
gggctcaagc agtcggcccg ccttggcctc ccaaagtgtt gggattacag gtgtgagtca 145920
tcgtgcccag ccagcatctt actatgttta ttagccattt ggattccttt ttctttgaat 145980
tgctgcttgt taatatattg gccctttttt ctgttacatt attaataatg ccaggaatta 146040
tgctagttgc tatgcaagat gcagacttga ggaaaacctg gtcccagctt tcaaaatgct 146100
tactttccaa atctgactca tcgtttgact ttaatgcccc actggacttc tctaacagca 146160
ttttccattt tccctttcaa aaggactcaa aatatacaaa tttaatttga tgataagagc 146220
tcaagaaagg ccgtggattc tttttttttt tatttttata gtaaaagtga tcagactgtt 146280
tcctctttta agaagaaaaa gaaagcagag gtcaatatta agcttccaat taatgcttat 146340
tcatcacaaa tagtaagtaa ataatgacag aaataattcc ttagtcactc tctagcacac 146400 ttcttttta tttttaacat ttttcactat gtgagatttc ctagatttgt tttattttct 146460
gtttccctct aactgcaata caagctcttg tggactggaa ccacacctgt catattcatg 146520
ctgtatctca cctgtcatat tcactgccaa atcccacctg ccataatcac tgccgtatcc 146580
cacctgtcat aatcactgcc gtatcccacc tgccataatc actgccgtat cccacctgtc 146640
ataatcactg ccatatccca cctgccataa tcactgctgt atcccacctg tcatatttac 146700
tgctgtatcc cacctgtcat aatcactgcc gtatcccacc tgccacattc attgcggtat 146760
cccacctgcc ataatcactg cccatatccc acctgccgta ttcactgccg aatcccacct 146820
gccataatca ctgccatatt ccacgtcata ttcactgcca tatcccacct gccatattca 146880
ctgccgtatc ccacctgcca taatcactgc ccatatccca cctgccgtat tcactgccga 146940
atcccacctg ccataatcac tgccatattc cacatgtcat attcactgcc atatcccact 147000
tgccatattc actgccgtat cccacctgcc ataatcactg cccatattcc cacctgccat 147060
attcactggc agatcccacc tgccataatc actgccgtat cccacctgtc atattcactg 147120
ccatacccca cctaccatat tcactgctgt atcccaagct tccagagtag gctctagcat 147180
ttgtaggtgc tcagtgaata tttgctgaat tagcaaaata gaaaatttaa atctcttaac 147240
aggtaccacg ttttgacata atcacttgta acatctattt agaaatccat aggcagcaca 147300
agcacataaa taaaaacctg accttcccca agatctttcc tcctctgttc agcatgctgt 147360
gtcaagagca gcacattgtg tggtcactgt ctcattcaat tgggacagtc gcatcatctg 147420
ccccttgctg aatcgagcct ttgaattaga tgaaggaaat ttgggccaag tcttctggaa 147480
tttagtgact actattatct agtttccctc tggtgcaatt agaaatgagc aatgaaccaa 147540
tatataacct tgcttaaaaa gcaatttcct ttactattct ccttgtttaa ttagtctgtt 147600
ttgttctccc tgagctcgag aggcattttt tctcccaaag cagaagcatt aagtaagatg 147660
cattcagtgt tttcatgaga ttcattcatt cttcttggac aagatcttgg ccactgtatt 147720
agtctgcttg ggctgccata acaaaatatc acagaccagg tggcccaaac aacagaaatt 147780
gatttctcac agttctggag tctgagaggt ctaagatcga ggtgtctgct gatttggttc 147840
ctgctgaggg ccctcttcct gcttgtgaca gccaccttct tgctgcatcc tcacgtgact 147900
tttcctctgt gcttgcatgg agagaaagag acaacaagac agattcgctg atgtctcttc 147960
atataaaggc actgattcca tcaggccact gatcccatca tcccccagcc tcatagcctc 148020
atccaatccc atttaattcc caaaggccct atctccaatt accatcacat tgggaactgg 148080
ggcttcaaca taggagtttg ggggaactca aacattcagt tcataacagc caccatgtgc 148140
cagtcatctg gacagaggtt gaaaaagccc tatccatgcc aaaatcttac ctcttaaggt 148200
agtagaggca tactgctaat gtgaaccttt aaaaatgctc atttattcta cagatattcc 148260
ttgtttatgc catattactc actggcttaa aaatcttcta atgatgaggc atggaacttg 148320
gagaaaccac ccaaagtttc taccatgttc tgcaaggctg tgatcaggca cctgcttacc 148380
tctcacactg ctccagccac actggcctgc gtgctgctgc tttctccctt agggcctttg 148440
ctctggctgt tcattctcct tgtggtgctt tgccccagat agctggctca ttctcatcat 148500
tcaggtctca cttaagtgtc atctttcata ggacatccct gatacccaat cagaattact 148560
cccttggcca gctggcctgt gccagatgct ttgctggata tgaagacaca aagatcagta 148620
gtgcggccag gcgtattaaa atattaccct taatcaatgt tgactcgaca ttaataatag 148680
agcatattaa tgataatatt attaattaat tattattaat ttatcaatag agcagatatt 148740
gaacacttac tatttgcaag gcattatgct aagtctttgc cattattata attattgtta 148800
ttttattttt tattctttta gaggtagggt ctcactctgt ggcccaggct ggagtgcagt 148860
ggtacaatca tagctcactg caaccttgac cccctgggct caagcaatcc tcctgtctca 148920
gcctcctgag taggcaggac tacagccatg cactaccatg cccagctaat tttttaattt 148980
tttgagacgg gtttttgcta tgttgcccag gctgatctcg aacttctggc ttcaagcagt 149040
cctcctgctt tgaccttcaa aaatgctggg attacaggtg tgagccacta cgccctgccc 149100
tttgccatta tttatctaat ttaaccctca cagccatcct ctgatataca tatgattatc 149160
atccccactt tgggtcagat cataaaaccg aaccttaagg aggtcaactc acctgccaaa 149220
ggccacacac aggaaagtga tagagctgag atttacccag ttttgttgag cttcaggttt 149280
taaagccaga aagatttctc ttttagaaaa tgataaagaa aagttttttt attttgaaaa 149340
attgaacaaa taatagataa gaaggaaaat tgtaaaaaga gacagtgatg actaatgaag 149400
ataaagttgt tttgtaatca gacagaccct ggtttgtatt ctgacccagc caccaattgg 149460

-continued ctgtgtcact gtggattcaa cacttctctt atctttgttt tttatctgta aaaaggaagt 149520
tatgagcatt acacgaaata aacactgaca tgaacagatt ctcattcaat gttagtttga 149580
ttttattgaa taatattaac aaattacagt atctaattat gcagttcatc atcagacaca 149640
aataagcact taatttcttt ttaatgatat aaaatctttt ctggctgggt gtagtggctc 149700
acgcctgtaa taccagcact ttgagaggcc aaggcgggcg gatcacaagt tcaagagatc 149760
aagaccatcc tggctaacat ggtgaaaccc cgtctctgct aaaaatacaa aaattagctg 149820
ggcatggtgg caggtgcctg tagtcccagt tacttgggag gctgaggcag aagaattgcc 149880
tgaaccgggg aggcggaggt tgcagtgagc agagatggca ccactgcact ccagcctggt 149940
gacagaggga gactctgtct caaaaaaaaa aaaaaaaaaa aaaaatcttt ttaaagcatc 150000
actaggatca gaaatgcaaa tttttcagaa atttcaaaaa tgtggagaaa aggttggaca 150060
ttttgttagg gaagtaaaag catatacata taaaattata tttgttctgg aatataaaat 150120
atgttatttg tattgctcac tatagatcta gtgattgtaa gaacttatgt agcattttat 150180
caagcctcca tatctctttg gagacttcaa agactttaga aaggtataga taatatcaaa 150240
tgttggtcaa gatggtagtc aacaggaact ctcaaacatt gagagtaggc atgtaatttg 150300
gtacaaccat cttgaaaaac tgtttggcct tatctagtaa agctaaagat gtatagatcc 150360
taagatctag caattccagt tggaggtatg aaccctagaa aggcttgcac ttttgagtca 150420
gaagatgtag acaacaaaac tcacagcagc actgtttgta acagagaaaa ctaaaaacaa 150480
cggaaattac tatccacagt aaatagaatg aattacagta aatatggtta tacaatggaa 150540
ccttatgttt gtgcagttta ttcaagtggt tgcatgtggc cacagttcat tttgttctca 150600
atatatataa tatatagatg atacatgtat gtgtgtatac atatatttca ttgtgtgact 150660
atactacatt taatttttcc attctgttgt catttgacgt ttcagtttca gatagttagc 150720
tattatgaaa gagctactat gaacatcctt gttcatgtat tttggagcat gtatatgagc 150780
atttctgttt attatacgcc tagaggtaga attgcagcag agtatgcttg ttcagcttta 150840
gtagagactg ccaaacaatt ttccatagtg gttgtaccag tagacaggcc caatatgtga 150900
gggtttgctt actccacagc ttcaccaaca tttggtattt tttcatttca atacttactt 150960
tcattttcat tttatatttc atttcaaaac tttcatttca gtattttagt tcattttgat 151020
gcattttcat tgtagtcact ctagtgagtg tatagtgata ttgtactatg gtttcaactt 151080
gtattttcct tatgactaat gaaatcgaag accttttaat atgtgtgttg gtcatttgat 151140
atgctattat tttaaagtaa taaatatagg gtccagacct atggggctta gcgggtgttc 151200
tctccgtgtg tggaaacgag agatctaaga aataaagaca caagacaaag agataaagag 151260
aagacagctg ggcccggggg accactacca ccaagacgca gagaccagta atggccccga 151320
atggttgggc gtgctgatat ttatcgtata caagacaacg gggcagggta aggagggtga 151380
gtcatccaag tgattgataa ggtcaagcaa gtcacgtgat cataggacag gggggccttc 151440
ccttataggt agctgaagca gagagggaag acagcataca tcagcatttt cttctatgca 151500
cttatcagaa agatcaaaga ctttaagact ttcactattt cttctaccac tatcttctaa 151560
caacttcaaa gaggaaccag gagtacggga ggaacatgaa agtggacaag gagcgtgacc 151620
actgaagcac agcaccacag ggaggggttt aagcctccgg atgactgcgg gcaggaatgg 151680
ataatatcca acctcccaca agaagctggt ggagcagagt gttccctgag tcctccaagg 151740
aaaggaagac tccctttcac agtctgctaa gtaacaggtg ctttcccagg cactggcatt 151800
accgcttgac cagggagccc tcaagtggcc cttatgtggg cgtaagagag ggctcacctc 151860
ttgccttctt ggtcacttct cacaatgtcc cttcagcacc tgaccctata cccgccgtta 151920
ttccttggtt atattagtaa cacaacaaag agtaatatta aaagttaatg attaataatg 151980
tccacgatca tctctatatc taatttgtat tataactatt ctaactgttt tctttattac 152040
actgaaacag tttgtgcctt cagtttcttg ccttggcacc tgggtaatcc tccacccaca 152100
aataaataaa ggattattgg aaaaattact taataagatt gattacgatc tatgtaaagc 152160
aatgtatcag tggactgagg cttggttatc ctaacagtga cacatgactt gagaatctca 152220
gtagcttaag gcaaggttta actcttgttc ttgctgcatg tctatttcca acagtcagtg 152280
ggtctgctcc acatcagcat cattctggca gcttctgtga agggacagcc tcaatatggg 152340
gcattgctgg tctccaggca gagagaaagg agagatggca acacaatggg ccacacacaa 152400
gttcttagaa ctttggctca gaagtggcac acacttcact tacactcaca tttcattggc 152460
caaaggagat cagatgtcca agactgatgt tagtgagtgg attatataat ctaaaggcaa 152520
gggcttgtag gaagaggcag tcaatatttg tgaacaagag aatgatcagt aacatctttc 152580
tgcagagtag gcttataaga gtattactgt aggatagaga aaacaagctg tgtgtctgtg 152640
ggctgttgtc aacacatata tatacactac acactttttt tttttttttt tgagatggag 152700
ttttgctctt attgcccagg ctggaatgca gtggcttgat cttggctcac cacaacctct 152760
gcctcccggg ttcaagtgat tctcctgcct cagcctccca agtagctggg attacaggca 152820
tgcaccacca cgcccagcta atttttgtat ttttagtaga gacaggattt cttcatgttg 152880
atcaggctgg tctcgaactc cccacctcag atgatccacc cgcctccgcc tcccaaagtg 152940
ttgggattgc aggcatgagc caccacgccc agcctcactt tttttctttt gttttgttga 153000
actggttgcc aacgtttaaa aattatgaca tttaacaaag atgcagattt ctggcttctt 153060
ttggaaatcc taagctatag caagaatcat ttggaactga gttgtagctg cccttctggt 153120
gggatgtgca ctctctggtt ttccatgact gtatctgcct gtcttctctg cagcagtgcc 153180
tttcaaacat tttttacgta gctcacaata aacaatacat tttacattgc taccaaggac 153240
tcgcatgcat gtgtgtgtgt ctgcattcat atataggtat agatatgcat atacatatac 153300
attccaaagt aaaatacatc aaggaaacag tgcttaccat tactcattga aattgtctgt 153360
tctattctat cctattgtat tctagtactt tttttttttt tttaatgctg gaatcaactc 153420
cctaaattga tttcacaaac cacttctggg tcatagccca taggttgaaa acatggttgt 153480
ctatcatgtt acttgtctgt ttctcctcta aatgctattg gttagttttc tagcctggat 153540
tcctgtctaa gccctttagg gtttcaggac aattcactgt gtgggtgagc agcatctgct 153600
tcccttcact taaacctggg caattactgg ttttgcccaa gggtcttaaa acttaaactg 153660
cttgaatatc tggcagtttc cccgctgact tttcccttgt ctgatttcct atttcaataa 153720
aaatagcctt gtaggcgaat atgccactga ttcggagaat ctcagtttcc tgactgggct 153780
aggcaatcaa gggcaaatga aagtgagtcc tgttgtacag gaaggagagt tctcagatga 153840
tgaggatggt catggggact ttgttaccga aggaggccca agctcatgat ttcacaggat 153900
tgattcctcc atctcactga tcatttaaca aatacttatg gatgacccat gtgccagacc 153960
ctgtgctagg gaactcatcc aaaacttaca aaaatttctc ctagatgcac agacgatgaa 154020
tagtaattac ctcttcctgt gttttaccct tcctatttct tcttttcttc ccttgaccca 154080
gaaattcatc aattgcccta gggctgttcc ggcttagtgc ttgttggtca gttggatgtg 154140
cccttctgct caggtctttg tgggctctca ctggtgttcg tatgcatata gaatggatgt 154200
ctgcatcaca ttgtagggac agtgtatggg gatgtgaaga caataagtga aagtctgccg 154260
cccactaaga cacaagcagc attgctataa actccagtgg aaaaaggtga tattataggg 154320
aaggaaaacc gtattgtcat attttcatgg aattcagtga attgcatttt gaggaccagt 154380
gccattttga tgctggagga ttccaccacc tttgtggtgt tgtttcctgg aagagattct 154440
actactgaag tggtgttggc agcaggtgta cccagcaaaa tcaggtagca aggcctggtg 154500
gaacttggca gaaaggagct cactggggcc atcagagaca gtagtgaggc cccctttgtgc 154560 cagttagggg gcagcagaga cccaaaagtg gattttacca gaaagggttg aagcaggaga 154620
ggaaggaaat ggcgaatgcc ttgacaggcc atgtttgtga gtccaggaag acaactcatg 154680
ggagctctca gaaataattg tggggtgagg tgagtgcata cttggataga gatgttacag 154740
tacctgacag gggcaagacc cagtaatata tgggttgtta ctattaaacg tgaccccatt 154800
ttaagtcgtg ggtttatata acaaggttat ttatgcttgt tatatgcttt atgtgcatta 154860
cctataaatg tccttaaact tttatcacag tgcaaatgca gctcattacc agaatccgtg 154920
agcactgtct tcaaaccctc cccattgcct tgacattggc tttttcttaa ttctgtctct 154980
ttttttggcc actctgctct tgatcttgtg tctacatctg agcctgaaat tggagagtcc 155040
ttggctactc tataatctga gtcttctact tcctgctttc cctattcagt ctcccatttc 155100
cttctccagc cccatccctg gtactagcaa gtccctccct gatgtcttca ccatccgttc 155160
ctttcagaca cctgccaccc ttcacattag caaaatgaca aaaaataaga ataaataagg 155220
tgagtatagt agattgcata gtggccccca aaagatacac cacagagctc cacacatact 155280
aacccttggt ccctcagaat gtgacttatt tggaataagg gtctttgcca atgtaattaa 155340
gataaggatc tagagatgag tccatctcct gggttacagt gagccttaaa gccaatgaca 155400
agtatcctta taagagacag caaaggagaa ggtggccatg tgaagacaga gacagagatt 155460
ggaattctgc tgccataaga caaggaatgc caggggcacc agaagcagga gctttctgaa 155520
ggtgcatggc ccctgccagc accttaattt caagtgtctg gcctccagaa ctgtgagaga 155580
acaaactctg ctgtttaaac caccaaattt aggctgtgag tggtggctca cgcctgtaat 155640
cccagcactt tgaaaggcca aggtgggcgg atcgcttgag ctcaggagtt tgagaccagc 155700
ctggccaaca tggtgaaatc tcgtctctat tgaaaaaaaa aaaattagcc aggtgtggtg 155760
gtgcacgcct gtagtcccag ctacttcgga gagaggatca cctgagcccg ggcagccaag 155820
gctgtagtga gctatgatct ggccactgca ctccagcctg ggcaacagag tgagagccgg 155880
tctcaaaatc aaacaaaaaa gccactaagt ttgtggtaat ttataacagc agccctagga 155940
aactgagaca atgggtgacc atacagcacc aaaggacttc tatttcatga ttggtgaaca 156000
ttttaaaata agaaaaggcc aggcatggtg gctcacgcct ataatcccag cactttggga 156060
ggccgaggcg ggtggatcac gaggtcagga gttcaagacc actctcgcca agatggtgaa 156120
accctgcctg tactaaaaat acaaaaattg gccaggtgtg gtggtgggca cctgtaatcc 156180
cagctactcg ggaggctgag gcagagaact ggttgagccc gggaggcaga ggttgcagtg 156240
agccaagatc acgccactgc actccagcct gggtgacagt gagactccat cccaaaaaga 156300
aaaaaaaaaa aaaagtatta cagaaaagaa tgtgagaaca tgtttcaagt attaacaaat 156360
aaaagaatgc atgctaaata attatttgca acacatcata gagccagttc tcacctggca 156420
ataaggtact ccaaaagttc attcataagt aaattgagac tcagaatgca tatttttcct 156480
gcaggagtca tgtgatatat tatggatgtt ttcaaatatt aatccataat aatcatttta 156540
agttaatcat atgcggacta tagttttctt gaagcgaggg attgttctac acgtatttaa 156600
gtcttgctgt ctagcagagt gctttgcatg ggtagggcct ccaataaatg cttgatgagt 156660

```
agtagttcat taaaaaattc tttaaaattt tttttaccac aaaacatctg caagtagagt 156720

agttcatttt ttaaagcacc atacactaat atttaatagc agctgtttta gagtcagatt 156780

gcaaggcttc agatcctggc tctgccactt acagaatgca aatcattaag caaatttaca 156840

taatctctgt gtgcttcaat ttatttgtct ataaaattgt gatattaata cctatctcac 156900

aatgctgttg tgaggagtaa atgaattatt atgtactaaa tacttagaac attacttgca 156960

tgtacggatt caataaatct taaatattgt tattagctct taagtatatc tcctcaacta 157020

aattataaac tctgaggaag aggcaagatc ctatcctttt taaaatcccg gcatctacac 157080

aatttcttgc atattgtgtg cactcagtga gtatttgttg aactactaaa aggaatgaat 157140

gattggctat atgtttacaa taccttctcc ataaaaaata catatagaat tgataacatt 157200

ctaacatttg ttacagtaaa aaatgttttt agaaattaaa tagaattttt tttttaagac 157260

agtgtcttgc tgtgtcgccc aggctggagt gcagtggcat gatgtcagct cactgcaacc 157320

tctgcctcct gggtccaagc aattctcctg cctcagcctc ccaagtagct gggactacag 157380

gcacgtgcca ccacaccctc ctaatttttg tatttttagt agagatgggg tttcaccatt 157440

gttggccagg ctggtctcaa actcctaacc tcaagtgatc cacctacctt ggcctcccaa 157500

aatgctggga ttacaggtgt gagccaccat gcccagccta aatagaattt ttaagatgtc 157560

agagcaaaaa ggaaattatt accagtgtga aattcttcac tatattttag cccctaagag 157620

gcagagacct tgtcctgttt ctttgtaact gctgcatttt gcgtgatgtt ttgcagaata 157680

ggcatgtgcg accttgtaca cagaaagggc ttaagcaaat ccttatgcag attcctggag 157740

ttatttttct gtgctggtcg ctcctttcca gaattctact ctgcaacttc cagctgcctt 157800

agccttctga actcagagcc ccctctcctt acctccacga ggcctctggg gtctctgggt 157860

ttccccttct tgcacttgca gtttatacat tgcctccaag cagaaggccc aggtgtttct 157920

catgctcatc ccatctgttt cccctctaac agagattagt cttacaaggc ctcgtgttca 157980

gtctgaaaac agctgcttcc tgtacttcgt tcagttctct aattgctcac aataaaaagc 158040

taagtccttt cttacttcat catggctaga agcagttccc atgcgaatgt cttggttaaa 158100

ggagaaaaat gtataaggta actataaact aagactttca catcaattca gttggttctt 158160

ttgttaagaa ttacagggtt gggcacgatg gctcacacct gtaatcccag aactttggga 158220

ggctgaggcg ggaggatccc ttgaggccaa gattttaaga tcagcctggg aaacatagtg 158280

agaccccgtt tctacagaaa aaaaaaaaaa aaaagtaaaa attaggcaca gtgtcgcatg 158340

cctctagtct cagctacttg ggaagctgag gcaggatgat caatcccttg agcccaagag 158400

ttcgcggtta cagtgagcta taattgtgcc actgcattca gcctaggtga cacagcgaga 158460

tcctatttaa aaaaaaaaaa aaagacaaaa agaaaagaaa attacagtat aatttttctg 158520

tgttgaagag cttctgctgg acaaattttc agtcttggtc ggcagtttaa ctcaagaaca 158580

gactcttcta tcttcacttc cagcttacat aaattagaat ggagaagaga attctaaagt 158640

ataaagaatg tacactgttc tctgccccaa ttacacatct gtctcacggc ttgttaggca 158700

gcatgatgaa taagcgtgtc atctctctcc atttatttgt gcatccattt ttatatccat 158760

agtctataga gactttcatt gcttctcaca aatttgttta aacttttaat agtgatatat 158820

acagacttcc tcatctaagc acagacacga tttctattta ggtcatttct gtgcagtcac 158880

ttcctcttcc taggtcatag ccctgtagtt ctatcataca tagactgtct attttaatag 158940

aaacctgcag caatggtgga aggaggggaa cgggagtcat ttcatcagaa agatgcattg 159000

tatctactgg agaattttct tgtcttagaa acactagaaa ttatattttc tggaaatttc 159060
```

aaattttact aaaatgtggt cattgtcaat tatgtaacag gggctttcct tttcaatata 159120
gcgactatca gtaatagtgc tggaaatatg ataacaggcc acattctaaa aattcatttc 159180
ctctttaatt aggacctaac tcttggaaac tccttcatgt gagctgccac aacatcatct 159240
aaaagcaaac tgccaaaaaa tcatcttaaa ccgcatcatc taaaagttat tttggcaaaa 159300
tgcatggtct caaatggaag ataatgacag ctaagataga atttagaatg agccccagca 159360
ctttgggagg ccaaggcggg tggatcactt gaggtcagga gttcgagacc agcctggcca 159420
acatggtgaa accctgtctc taccaaaaat ataaaaaaat agccaggcgt ggtggtgcat 159480
gcctataatc ccagctactc gggaggctga ggcagaagaa tcacttgaac ccaggagatg 159540
gaggttgcag tgagccaaga tcacgtcacc gcactctagc ctgggcaata gaatgagact 159600
ctgtctcaaa aaaaaaaaaa aaatttagaa tgagcacgaa gttaatgaat aatacctcag 159660
tcacattcta gtaagaaacc attcctcctt gtgggaatta gagccctgcc cccagaaccc 159720
tggctctgag gtttgacttc tgttatgtac tgacagtccc cattacgctc atggttccat 159780
ggtgccagca caggagtggc tgatgacaga ggctgacatg tcatgcacat cattctgtct 159840
atctcattgt ttagtgtctc ttccttggta aatgctctct gataggtgtt accatgcaat 159900
cgaaagatca cacacctgat actactatgt gtctatccat ttgcctcttt cctagacatc 159960
ttatccctag cctttcaaac tttctccttc tggatccctg catatgtaca cagtgtatac 160020
aatgaactgt aattaaataa actacataat ttacttattg attaggtctc ttttaaacta 160080
tttcttgtga gttcaagaaa gcagagatct ttgtagtttt tttgttttgt attttaatta 160140
ctactgtatc cctagcactt ataatagtgt gtggcagaga acaagtactc agtaaatagt 160200
tgctgggtga atccatacta aatataaatc tttgtcaatt agtatatgtg tgagaaatat 160260
ctattcctag ttagaggctg gtcttttcat ttactttatt gtaaatgatg tttgaatgaa 160320
cagaagtatg gaattttaat gtagttaaat ttatcaatcc ttattaagct atttttttgt 160380
ttcttattta agaaattctc tgctgcaaag tgataaatat gttctggtat attttcttct 160440
aacccatctt tcccccactg atctgcaatg acatttttgt tgttaattaa cttttattac 160500
cagtgaatct gtttctaggc tctctatttt gtttcattgt ctgactatcc tttttaaaat 160560
aagttttttt agagacaggg tctaactctg ttgcccaggc tggagtgcag tggcacaatc 160620
atggctcact acaccctcta actcctgggc tcaagtgatc cgccgcagcc tcctgagtca 160680
ctgggactac aggcatgggc catcacttct ggctaattta aaaagtgttt tttttgaaga 160740
aatggtgtct tactgtgtag cccagactgg cctcaaactc ctggccttcc tcccacctca 160800
gtgtcccaaa gcactgggat tacaggtgtg agccactgca cccagcctat cctatttatt 160860
tttatttacc attatttatt tttaattgct ggacagtttg acaagtccag tttgagctag 160920
ttatgtatca catcccattt gcaagggttg tttgtcttgt tcaaaggaca atgagtacaa 160980
ccaatgtcaa cagaagttgt ttttcttcct tcgaagagaa gggatgcgcc aggatggaga 161040
gtgcctgcat tcctgcccat cagggtacta tggacactga gccccagata tgaacagatg 161100
tgcaacttct ctcggagaaa acaaaataaa aaatacgtca ttggtccatg ttcaactgcc 161160
catcgtaaaa aagaaataca tcattggata agcaacttca ttcaaaagtc agtgccacag 161220
caagcaagaa attagaagct tgtaaaaata agatggaatt ttgagctggg cacggtcgct 161280
catgcctgta atcttagcgc tttgggaggc caaggcaggt ggatcacttg aggtcaggaa 161340
ttcaagacca gcttagccaa catggcgaaa ccccgtctct actaaaaata caaaaattag 161400
ccaggtgagg tggtgagtgc ctgtaatccc agctacttgg gaggctgagg cagaagaatc 161460
acttgaaccc aggaggcgga ggttgcagtg agccaagatc gcgccactgc actccagcct 161520
gggtgacaat aaaaataaat aaatgaaatg aaaataaaat aaggtggaat tttcacccat 161580
tgacaaaaag ttaataatta ttattgtatc taatttctgg acattgaata gctcataagc 161640
caacctactt atgagcatct gttttctgga tgagcttcaa ccgttgcaag tggatttttc 161700
ttctttggac tacttgtcaa actgtagtgt gaatcagagg agtttaatac agattgctga 161760
agtttttgat ttgtaggtct gggatgggac ttgagaattt gctttttttcc aagttcccat 161820 gtgatgttga tactgctggt tctgggacca cattttgaga aactttgttg tcaataatgt 161880
gcccacagct gcattatttt ttttttattt tcccaagaat taatgtcatc agatttaaat 161940
agtagtatat attaatactg aatgacaagt tagaaagata gatttgttta aaagataata 162000
ttggaaatag gcacatgaat attttgaact taaaataaat gtttcagtga tttttattaa 162060
agtaatatga atattgtcct ccaaaacttt gatgatagag ttttgtttct ttaatgtgaa 162120
ttactttctt acattgtgaa aacttagagc atattcttcc tcaggcctaa gtactgtata 162180
ggaactatta agtgagaact ttaacagtaa ttctccatat gcaaaaaagc atttttacta 162240
gtctgtactt aacaacttgc aaatttgctt ttatccaaaa ggaagagaat tagagaaatg 162300
attttagtaa gaaatgctaa aatcaaaaag ataggtaaat atttaaggaa tcattgtagt 162360
attcccaaca gttttataga tgaaatttta agttctctgg gttataactt gctttctgat 162420
gccattataa acctgatggc tgagacactg gtcgatcacc cattaggaat atatgctaaa 162480
attgttgctt tcagttttta aaatatggct taattttatg tttgcttaaa attggtttgt 162540
tttggcctgg taatatctcg ggtcccacac atatgatcat tcacaattat catatcgggc 162600
tgagcagggt ggctcacgct tgtaatccca gcactttgga aggccgaggt agacagatca 162660
catgagtttg ggcccagcct ggccaacgta gcaaaacccc atctctacta acaataaaaa 162720
aattagccag gcgtggtggc acgtacctat agtcccagct actcgggagg ccgaggcagg 162780
agaattgctg aacccaggag gcggatgttg cagtgagcca agatggcacc actgctctcc 162840
agcctgagcg acaaagccag actccctcta aaaaaaaaaa aaaaaattat tattatttag 162900
ttttatcttc tctatctgtt aatgagagag actaaaataa tgatgaagaa aacattttaa 162960
tatggtatat gaatagtaat aaaataatat aataagatgt atctccaaaa tctgaatcta 163020
atggtactat attcgtatta tagctgattc tttacaaaaa gcagtcttgg cttactggaa 163080
aattcacatt ttaaaagtcg atcagtttca tttttctgg agaatgttag ctttactgaa 163140
agtataaaag tttcgttgtt gtagacacca ggtcctaata aaaacaagta aaagaagaaa 163200
aagtttgtta tgggtggaac tgattaagtg aggtaccact gaagaattaa agatatctca 163260
cacatacttt gattaattaa atggtgaata agaacttgtt ttaatctcat tattcaagtc 163320
actaaaatgt taaacaggta agacaaaaag gcaattatta caagttttta cgtaaaacta 163380
tgataagatt ttttaaaaag tgaaacacca cccatacaca ctgaattcat ttggctggta 163440
ttgattctga atatgtattt tataatattt cattggcctt gacccacaaa ctaaacacag 163500
acattttctc aattagtcat tttcaggttt attgcctaag atgctaattg aaattcaggg 163560
caggcaaaaa tacatcattg gcctttgtat atctttgaaa ggccttctga tgggaccttg 163620
ctccgtataa aggcttctct tctctgcaaa ctgaaaggga ccctgtgtgt gaagtgtgtt 163680
cagtggggtc ttcaaggaac aacatagaga gcagccgctg gccagccgga agccaccatg 163740
cgctgtcctc aacagagcag ctccaggctg tatgaccccc aggcaattag gcaccaaaag 163800
aagatgctca cactttccaa aattctttcc cagggctggg ggaagggagc cagacttgga 163860

```
gcccctatgt ggaacttagt ctccaaggaa agaaagcatg ttctcatcct acaaacactc 163920
cattttctcc ctgaattagt gtcctttctt tgaaccagat gagacttcgc tcagagctgg 163980
aggctatggc cccttagttc tgtttccaca gtgcttccag ccctctcccc agtttggagg 164040
cccccaaaat gaggcgctta tctctttgat tttgtgaaag aaaatgcaca gttcgtctat 164100
ttggggcttc tgaaagatgt taggccctga agaaggttga ctgggagact gagtggggag 164160
tgacagacca tgaccttaat tactgacctt ttgttataga ttaacttcct tcctatttta 164220
ttgttcctgg cccagaccag atagcacttg agataaaaga tcccttgatt attacatcct 164280
taatgtggaa tgttaaatac tcccttcccc caaggaatca ctgcctaaaa ccagtcagat 164340
tgctgcgact gtgcactaac cttgtgtgga aaatgctgtc atcctgttaa gcttccccat 164400
accgtgcctg tataaacaat cctcaaacct cgctgcttca gagcactaac cccatctttt 164460
tggagtcctc ctgggtgacc ctcctcaaac tttgtgctca gtattttaat cctattgcct 164520
ggatctcgat ttaaagttga taattttcag agaattcttc attttctctt tgcatatttt 164580
attgtttcct ttccatctgt ttttctttta cttactgcct gaagccaaga gacaatgtca 164640
aggtgtctta gtgaaaggag ctcatactta agggttcctg ggtcaaaacc tacatctctc 164700
atttcttagc tctatgatct acctgtttcc ttaatctctc tgggcctcag tttacccatt 164760
attgtagtaa aacatgtact acaagttact ttttatttaa ctacttatgc catatttaat 164820
tcccaaccac taatattaca tattagttat atattgttaa atcataatgt tctttcacta 164880
tttcttttat gactgagaaa tttcttttca atgtataaat catatacatg ttgctcctgg 164940
acaaaactga gggtcaggct gctacttctc ctggcccaat aatgagatgc agacaaactg 165000
gggaagagag gttttatttt tgcatttggt tacagggaga aggcctagaa attgtcacca 165060
caccaactca aaattacaaa gttttccaga gcttataaac cttccaagct gtatgtctac 165120
atataagtgt gcattcatct aaagacataa gtgattaact tcttttaatc tataactaag 165180
atctgagtcc tgaagacctt tctctggagc ctcagtaaat ttacttaatc taaatgggtc 165240
caggtgctag ggtgattacc cttatcttgt ctcctgctaa atcacagagg tttggggagt 165300
tccttcagac ctccaataaa cttgtgtgtg gaggcctggg gaatttcttc agactgacaa 165360
taaaacttgt ttattccagt ctggccaaca tggtgaaacc ctgtctctac taaaaatacc 165420
aaaaagttag ctgggcgtgg tgacgtgcac ctgtaatctc agctactagt gagacctggc 165480
ctgccacaat gtggttaagg aaacatatta aaacattttt aaaaatcaag attttccatt 165540
tcaatggcct tgtaattgat tgaaaagttt attttgagtc acatggtgtt ctagactctt 165600
gtggagggtt tagattggaa aataagtaat gacagtgaag cagttgttat gttcgtataa 165660
aagaaagaaa agaaaaaccc acaggacttt atttggtttt aaaagtctat ctgcaaagat 165720
atagtttata ggaaaattca attccaaatg tttctcattg ctctggagtg tgtgaagaag 165780
aggcctaaga atattcttag gaaggcaaaa actttcagat gcagttcata tgcttgacac 165840
ctctgtttca cttttggctg acttgtgtag tctgattttt ggtcactgac aggctcagca 165900
tcatgagtgt gcaagacgta agggaggcag gaccttgtct tttcaatggt gtcttcctgg 165960
gtggctgcca gaattcatca ttattgcact ctactctcat agcctcgatt tctgtttttg 166020
tttgctttta ctgaaattgg agtagtgaca cagagtcaga tcattgaaaa gactcacaag 166080
attccaaagg gtatactggt agagtataaa ctggaggata aggtacagcg ggagaaagca 166140
agtaccagca gacacagagg gggctgagac tcctgcaagc agcgcctttc ctcaggctca 166200
ctggatgtgc tctgtgtttg ggtgtgaacc accaagatgc atgcatgata tctgttttca 166260
```

gggaagccaa gatacaagtg tacagaaaag ccattatacc cccgtcacat tgctgaaact 166320
ggatgattaa accacgtacc aagcggtgtc taaatttcag taataatgat cagctagtag 166380
agggtgcctc aaggcagttt cagactttaa ataacatagt agaaatcact agctagtcca 166440
tttcatcctt atcattgttg cagaactttc tccttagttc agctaaaacc gggttcttgt 166500
cacacaaccg gaaaagatta ggctcaggga cacatagaag ggtgaggggc agaatttatt 166560
gggtgaaaag gaaaaaggaa aaagaactct cagcaaagcg agagggagtc ttgccaacag 166620
gccctccacc tcacagactg aacaccaggc caccacacag gaactgaaga ggccaggctc 166680
ctccccgctg aacaagcgta aacttctctt ggctccaccc tcttccccca gtgtgcaggt 166740
gggcattatt cagagagaat cagctgagaa agggcaggct ttatccggga ccagcagtcc 166800
agttcttcag ccttcaggct cttttaggct tgaaggcagg gtttcgtggg ggaccttggt 166860
aagaagagtt cttttcgaca ctttaatgta gattgtaaga ggtagaaaaa aattgatcac 166920
atttaacata tagttactta aaaacacatc tttgagtttt ctagacttct aatatgattg 166980
tagaaaatca gcgtggcagc caacttaaga cagatcaata cctcgaagtc tgtaacttta 167040
ataagaacat cagaactgaa attctatatt agttacccta ttgtactcac agtcatggaa 167100
tacagaacag gaaagattct ggaaacacat tttgatagtc agggtcacag atattgctct 167160
gtttcagtaa ccaggttttc tacttatgaa agttatttaa aaggcaatga atattcaaaa 167220
tgtgagcagc tattgctacc attagctcca gaatcagttc tgaagaattt gtaggaagtc 167280
atcttgaaaa taataaagca atatattttt cagaaatagt atccactaaa tcataatctg 167340
aggccacttt actgaggcgt ttatatttat atttatatta atttgttatt ttacacagaa 167400
agggaaacta tgacctaaag acagagataa caataatctg attagcatta gccaccccat 167460
tccaacaaca aatcacgtta ataaggcatt tttagaagta gcaaagcata gtggttaaga 167520
acatatgttc tagaactaga cagtctgagt ttgactcctg ataccactta ttttattcta 167580
aaacttttgg caaattatta cataacctcc cttgcctcag ttggccaagc tgtaaaatgg 167640
gactaataat ggtgtccaac tcacaggatt gctatgtagg ctaaaaggtt aaaagagttt 167700
tatatttcta aaacaatgtg cttgtaatag tcttggcaca ttgtaaacat tgtgtaagtg 167760
cttattaaaa ataaattcat gcttgtaatt gaagatcgcc atatgagata cacattctag 167820
tgatctatat gtttatcatt agatatatga tatatacaca cactcatatt tcagtcccct 167880
gagggattaa cttttaatcc cttgatttgc aaatcaagtt gtaaattaca cgtataaata 167940
aaataccttt gtagtgattc gttcattata aaattatgct aactatgttg gttttcatgt 168000
aggcataagc tggctctata aataaagttt gaaaataagt aaggtataaa ggaaccctgg 168060
cgggatagat aagatactag gaacagtggt ttgggagtga ggatgggaag tagactgatg 168120
tggaacaaga tgggagtgag actttttta gtcaccgtct atatttttat aatttctggg 168180
tctggaatca gtatctcctc atcctaactt gttcatatga tgagttagag tcatatctgc 168240
ctgctgttag ttttttcaaa gaatcttcaa atggggcaac cccctttggg tcccctccct 168300
ttgtatggga gctctgtttt cactctatta aatcttgcta ctgcactctt ctggtccatg 168360
tttgttacgg ctggagctga gctttcgctt gccgtccacc actgctgttt gccactgtcg 168420
cagacccgcc gctgattccc atcgccgctg actcccatcc ctccagatcc ggcagggtgt 168480
ccgctgtgct cctgatccag cgagactccc attgccactc ccgattgtgc taaaagcttg 168540
ccattgttcc tgcacggcta agtgcctggg ttcgtcctaa tcgagctgaa cactagtcac 168600
tgggttccac ggttctcttc catgacccac agcttctaat agctcatcgc atggcccaag 168660
attccattcc ttggaatccg tgaggccaag aaccccaggt cagagaacac gaggcttgcc 168720
accatcttgg aagccgccca ccaccatctt ggaagcggct tgccaccatt ttgggagctc 168780
tgtgagcaag gatccccggt aacattttgg cgaccatgaa gggacctccg aagcgtttgt 168840
ctcttccaga attgaaactg taaaactaca aatggttctt caaatggagc cccagatgca 168900
gtccatgact aagatccacc gcagacccct ggaccggcct gctagcccat gctccaatgt 168960
taatgacatg gaaggcaccc ttccggagga aatctcaact acacaacacc tactatgccc 169020
caattcagca ggaagctgtt agagcagtca ttggccaacc tccccaacag cacttgggtt 169080
ttcctgttga gagaggggac tgagagacag gactagctgg atttcctagg ccgactaaga 169140
atccctaagc ctagctggga aggtgaccgc atccaccttt aaacacgggg cttgcaactt 169200
agctcacacc caaccagaga gttcactaaa atgctaatta ggcaaaaata ggaggtacag 169260
aaatagccaa tcatctattg cctgagagca cagcgggagg gacaaggatc aggatataaa 169320
cccaggcatt cgagctggca acggcaaccc cctttgggtc ccctcccttt gtatgggagc 169380
tctgttttca ctgtttcact ctattaaatc ttgcaactgc aaaaaagaaa aaaaaaagaa 169440
tcttcaaatg gctattgatg ctaaagaaag ttctgaagga gcattctcca atgcagttat 169500
ttcctacaga agattttaag tgattttta aaaaactgcc tcttttctaa aaatatttca 169560
gcttttattt tagatatggg ggtacatatg taggattgtt acatgggtat attggatcca 169620
ggtagtgagc atagtaagca ataggtaaaa aaatgacctc ttattcaaga gggtacctca 169680
ttactattta caaagtgctt tcaaacattc tttctcattt tttctgacaa ctctggacgt 169740
cccccctac ttttagaaga aaactaacag tcccaaaaat gttttggtgt aagtcaatat 169800
atgaacccag gtccatgtcc agaactgttt accactcacc tctttataaa acggtaactg 169860
tggccaggca cggtggctca ctcctgtaat cccagcactt tgggaggccg agggaggtgg 169920
atcacttgag gccaggagtt caagaccagc ctggccaatc tgttgaaacc ccatgtctac 169980
taaaaataga aaaattagtt gggcatggtg gcacgcacct gtaatcccag ctactcggga 170040
ggctgagaca ggaaaattgc ttgaaccggg gaggtggggg ttgcagtgag ctgagatcat 170100
gccactgcac tccagcctgg gcaacagagc aagactctgt cttaaaaaac aaaaacaaac 170160
agtaacagtt acttctctga agctattatt ttttatcctg ttacatatat caaagacttc 170220
atttgggtaa ctatattcac gattatttta agctttcttt ttcattacca atagttgggc 170280
taacctttat tttctggatg gtaaaggtgt tttatagcaa caaaaacaaa cagctaagtc 170340
aatccgtcca ggtaccctgt taaagcttca aagactctgg atcagaatga tctctgctat 170400
acacacatac ccaaagaata aacaaaaatg ctattgctaa tatctctcag tcccttgagg 170460
gattaacttt tagtcccttg atttgcaaat caagctgtaa actatattaa ttcccccctt 170520
tctgtacctt tcctttcgga tgatgctcat ctagcatttt gctgtcttga ataccttctc 170580
ctttctcatc cctatatatt ttcattcttt atttgagtat aattccactt taacacatta 170640
ccttaatgca aaccattatc tccatttttg ctcacttctt tccctttcac agcacctctt 170700
ctcaataaaa gtctatatgt agtgtgttcc catggtgatg ggaactaaaa ttacttataa 170760
tcaatggttt ttatattgtc gctgctgctt atctcttggg ttaggcctct ctttgcagcc 170820
aggtcacagg taagtctatg aaggtgagat gaaacaatat ttaccagaga ttgaactact 170880
tctggaatat ttgtgaatcc agccttcacc attattgcac catctagatt tcacatctgt 170940
ttagtgtatt accaatattt cctttttcca tataatgaat tcttttattg tagtaattgt 171000
ggtatcaggg caccatggat attcatagtt ataagaagat attatcatag aagaaaattg 171060
tcatgccatc attcattatg gtgttttgca tctttgaatt ttaaacagag aaagagaaag 171120
aacagtcaag ctagtaagca agagataacc aatctacttt gggaaatgac caatggttct 171180
tgatttcagg gtagattata gaaaagagaa aagattatag tattttatat ctgcaaaact 171240
tattccaaaa caaatcagta aatccaggtt aaaataccca ggtcagacag tcacattttt 171300
actaataaaa attaactagc agcccgggcg aggtggctca tgcctgtaat cccagcactt 171360
tcggaggccg cggccggcgg atcacgaggt caggagatcg agaccatcct ggctaacaca 171420
gtgaaaccct gtctctacta aaaatacaaa aaaaaattag ccgggcgtgt tggcgggcgc 171480
ctgtagtccc agctactcag gaggctgagg caggagaatg gcatgaaccc ggagggcgga 171540
gcttgcagtg agccgagatt gcgccactgc acgccagcct gggcgacaga gcgagaccct 171600
gtctcaaaga aataaaataa ataaataaat aaataaataa ataaattgca gcccattgag 171660
tgaactttaa atgatcatgc tactttgtga aatagaatat cacattacta gatctgttgt 171720
gtgctggaca aatgccagca caatgcagta ctttgctgat atagtgtgga atagattttg 171780
tgctgcagca aagctgtcta tagacttcaa aaaacaaagg ttatatgagc attaaccaaa 171840
ctgtttaaaa tcttacagtt tcaaaggacc acatattcta tgattccatt tatatgaaat 171900
gtccaaaata ggcaaatcta taaagataga aaatagatta gtggttacct gggacttgcg 171960
gggatagaag cattacaggg tcagggcagt gaccttccct aaaagataca gaatttattt 172020
tctaggtgat agaaatgttc taaattgatt gcggtggtgg tcacaactat gtgacaatat 172080
taaaaatcat tcaattgtat actttaaatg agagaattgt aaatatatga gttatagctc 172140
gataaagtga taccaaaaga aagatcttcc ccaaaaagct ttcccgtaaa aatacatgtt 172200
ccacccaatt aaaatgcaat gtcaatacgt attcgtttat tttattgctt aaaataatgt 172260
gttcttttgc acaaagaaga aaaaatagaa atcagaatgt aagaagacaa gtcatttatg 172320
atttattttg caccatttat ttcaactgtt taaaataaaa gggccgattt tatgctgctg 172380
tcaaggtttt gcttatgata aatgtttgaa gtgacactga aatgtgaact ggttgtgaga 172440
caggctctcc ttggcttcta atggaggcag gtatcccatg ggacagatgc ttgtattgct 172500
tcaaattcat tgtaggagaa ttaacccttc gtggtgccac tttcttcata tgaattaaag 172560
tgaaaattgc cagggtcagt ggcttacgcc tgtaatccca gcactttggg aggctgaggc 172620
gggtggatca ccggggtcgg gagttcgaga ccagcctgac taacatggtg aaaccccaac 172680
tctactaaaa atacaaaatt agccaggcat ggtggcacat gcctgtaatc ccagctactt 172740
gggaggctga agcaggagaa tcacttgaac ctgggaggcg gaggttgcag tgagccaaga 172800
tcatgccatt gcacgccagc ctgggcaaca agagtgaaac tgcatctcta aataaataaa 172860
taaataaaaa taaagtgaaa attatgcagt atgggtttca ctgtagtttt actactcttg 172920
tatagaggag gaaaaatttc tcctctacct tcttacaatc tctggctagg cctaagaatt 172980
aaacttatat aatacagatt aatagaagag aagcatacaa attttattat aattttactt 173040
gcacatgaaa gtcctcacaa gacaatgaag acccaaagaa gtgaccagaa gtagtaaact 173100
tatatatctt ttagatgaag aaatgataaa tttgtgaaga agtgataaga caaagcagtt 173160
tggattatag gcagtaaatt gtgaggaagt cactaaaaat atagaggggg aaactaatgg 173220
aagataaggg atattttagt aagtttgtac agatctattt cagagtcaat tccaagtctc 173280
aggtgataaa gatgttcttt tcttcctggt acagggaggg caccttctc ctggaaattt 173340 taatggtgtg tttttaagta gaaaggggga ggtcaaaagg ctttcctgca tctgctattt 173400
ctccattgct ttcagctcta aataatcagt atgccaaagt ggcatatttt ggggtggcac 173460

```
gtcctgaagt ccttcacttg tttactcact cgttgctaat caggacttga tcatctttgt 173520
ctcacccctt tttacagccg tccagcccta tgctttttat tttatgccat tatttaaatc 173580
tgatgttcca ttcagttctc tacagttgga agggtctagc ttgggctacc tttgtattgt 173640
tcaaaatgct tttttaaaag gacaaaggtc ttgtggtcaa atcagtttag cgaatggtgc 173700
ataccatatc ttgctcttac agagtctcag tgcacactaa catattaaag gttctgagaa 173760
atccagaaga aaaaacaagt atgtaacttt atttaaccta atatttccca aacttttttt 173820
tagtgactca cagaaacact ccgtagaact agcctctgca gaacacccta tgggaaatgg 173880
tgttctggag tcataattat ctccccccttt attaccttat tactctttcc cagctatgac 173940
agatcttttt atatttcttt ttttcttccc gaacatgttt gttttaagcc acaattcaaa 174000
cttgctacat ttacttttttc ctggttattg cccagttgtt aagtctggat tgccctggga 174060
agatgctgat tacatggtgc tctgaatacc ttgcgttctt tgccagtagc tctcctaaag 174120
atttgtgatg catacattac tgcccaacag agaattgggc ttgcctcatt gcaatttcag 174180
aagacaatcc tcctgcgtcc atcagcttgt tattggctgg caccacagag atgtgtttct 174240
ctggccctca ttaattgtaa ccaaccctaa gagagttaag ttgtatcagg catgtgtata 174300
ccttacagtg gataagtttg tcagatactt tccttagtgc atattttttta aagagataga 174360
ataaagtata aatacacatg gaatggatgt caccaataag ggtttttaaa cactggagaa 174420
ttttatatgg gcctgctttg tagatatcct ttttttttc aatctatgaa ctcaaatata 174480
tgaaatatgt ctgtaccctc cttcttttgg ctgcccagct aagctcatcc caacaacgct 174540
tcccagcttt cttcaggtca ccaccaatcc aatccaggct ggaagtgatg agactgagct 174600
gtggaataca aggagcgtgc atggggtgct cttctggatc ctggggatat agtggttaaa 174660
ccgttactga caacatgctc tcatggctct tagatctagt gggggaaaga tagccaataa 174720
acacacaaag aaatcaaatc ttgataaaca cttttcagat cactaaaatc agattatgtg 174780
agtgtgacca agtggctgct gtagaaggaa tggtcttaga aagctgcttt tggagatgac 174840
agttaggttg aggatcctag tgaaaagagt gtgaacaagg agaaagaaat ccaggcagag 174900
gagacagctg ctgcaaaaac tctaaagcaa gacccagctt caggtcttct tctttttttt 174960
tttttttttt tttttttttt tttttttga cacagggtct cactctgttg cccaggctgg 175020
agtgcagtga catggtctcg gcccactata gcctccacct cctggactca agtgatcctc 175080
ccacttcagc ctcccgagta gctggaacta taggcacatg ccaccacacc cagctaattt 175140
ttgtattttt tgtagagtca gggttttgcc acgttgccca ggctgcacct tgaagtcttt 175200
caagaaccaa cagaaggcca gggaggggag caaagtggat gagtgggaga aggatacttc 175260
ctgagctctt tcaaggaggt cagggcaagt cgcatagggt tttgttaacc ctgacgtgga 175320
tttgagaatc atcagcacgc aaggaggtat ctaaagctgg aggcctggat gaggttgcct 175380
ttgggaagtg aggaaacagc aaaaggaggg gcttggtaca gacctggatg gctcaacctt 175440
tagaggttga gcagagacga ggggactgca aagaagcagc caggcaggta agagttcaga 175500
tgtctgggaa gccacacgag aaagtgtttc caaaagcaac acatgctgtt gaagaagccc 175560
agaaagagga agatacagag gtggccaccg atccaatgac aacgtgcaag ttgttgatga 175620
ctttgacgag accaggttca gtgttctttg ggaggattga ggaggaatgt gatttaagaa 175680
tagatgttca tgaccgtaga agtggaaata tgaatataaa ggttaaggtt tgtttgtttt 175740
aagatgggac ttactgtctt taaactgtct gcagtagaat ggaagcaact aatgaaaatg 175800
aaggtgggga tagaagccat atctccttgg ggttttttttc ccccttaagg aaatatgagg 175860
```

caaggttttc agggagggaa gatggactga ctgtaggaag aggaagagag agaagtaaat 175920
aacttgctat actgtgaaca tgtagtatga ccactggaca gtatttacag cctattagaa 175980
tttgagagat tcaggactat ttgttttttt taagtccatc actcttatca gtgattttga 176040
ccaaatttag ttaataccga agtcaggatc tgaacccggg gacgtcttgc tcagagtctg 176100
ggcatttgac cactccactc cactccactc cactccactc cactgcctct ccacgagtta 176160
cagctgaaac tagtccccag tcagcacaga tctgtcattt ctccagttct cctcagctat 176220
gagcatgcat agagaaggca gagagttagg ttttatgacc aaaagagaga gatgagacag 176280
aattaaatgt gtttgcaagt cagtaagtat gcgatgatgg tgaaatcaaa gaagtgaaga 176340
accaccgttg tagataatga gcaaattggg gatcaaagga taggaaacgt tgatgaggtg 176400
gaagagcgag tggtttgatt ggaagaagtg cagagcctga tttggaagaa tcagaggtgc 176460
agttattggt gataacatga caaatgatat gggtgtgagt ggctcatgtg ggtacaggag 176520
cagatcacct gtgttgagaa ggttgaggat tgagaagtct gggcctgtcc catggatctg 176580
acatccaggg gtcccagcct tcttgttttc tacaaaagag aaactcagag cctgtgcccc 176640 tggaatttc aaataaagca tgtgcttgtc ccaaggtatg gagaatagcg gccgtgcagc 176700
caataatgtc actgggctca cttgggctaa agtgggtctc ccctttcctt ccctgccctc 176760
cctctacccc gaaactttcc ttaactactg aagatcaggc cttcttggcc ccaacacaga 176820
aatccctgtg gggtgggggg caaggagaac tgttgtccac tcctgtctgc aacaaaagaa 176880
gagttcattt ttggccaaat gaatgacaat gaatattagg gtcttggact gccagaactc 176940
cctgccagtg gcactccctg ggagagaagg cctgttccca caccccctctc tccagctttc 177000 tccacctgga ccagatcagt tgttctccct tactcccctc taggatccag aattcctggt 177060
ttgactatca aaagtaacac tacttataag tatttatagg atacatcatt gactctcaca 177120
ttcactttat tataaaattt ctttttctct aacaactcta ggtactttta ttgttattag 177180
gccattgttc cttactcttt gttttcttgt attatcacat cagtcagcga ccaaatcctg 177240
ttcattctaa ctgagatgtt ccccgatctg tcccctccgt attcttcatg tcttctctca 177300
tgttgggcat tggagcagct gcttaatttg ttctctttga cctttcttgc taaagtccac 177360
cctcgcaact ctcaacagag tcacttggca aaacgtaggt ctgatcgtgt ggctgttttg 177420
cttaaaagtc tttgatggtt ccccagattg ctttgttaaa caaaggaatt tctactttaa 177480
aagtagaatt tcctgcggaa tctttctcaa gttactttgc tccaaccaca ctaaaccgca 177540
ccgttcccta aaccacagcc tagttaagaa ctttaaagat tccaagcact gactatattt 177600
tggttcctcc cactacttca gaggttcgcg acactagact aatttaacat tttattctac 177660
aaaatagcac cgaacttagg catatgtgga aaataactag ctgttttcca gatttttctg 177720
tttctgtctt ctcttttctt ttgatcactg ctccaggctt gctggggctg taaggaaatg 177780
ctcagtctaa ctggagaatt ttagcattgc cttcaacaca aatataaggc tacttctgtt 177840
tgaaggttta tctctggctg gaaaatctgc cctcctctat ctccatttag ttaaccttta 177900
cttttccttc aaggttctac ccaatgataa cttcctttat aaagtgttcc ctggctcacc 177960
caggggtaat caattgctta ggcttttgcg tgtgaacttc tgctcgtgtt accataaatt 178020
atctgtatgt ctagcatcct tgctcatttt accatgttat atcattaaat cctcataatt 178080
atcatgtaat cttaagtatt aggattcctg ttttgcagat agtaaacagg ggtttgttac 178140
ccacctaacc aagctattat taatatctaa tgtgacaatg ggtataatta atttataaaa 178200
gactaagagc attaaaactg gaaggcagta ttatttttaa tatattgact ctgtgtggtg 178260
acaagcgttc atctgtattt tttcttcttg ccaatagtga agggaattta tgattcctac 178320
ataaagaaat ctttttaatg ttaattaaac taaactgtaa gaatgctgct atgctcaggt 178380
gcaatgcaaa taatgaggtg actctatccc tgccatctca ggctaatccc ctctcccctg 178440
aggagctgag actcagctcc ctggaggtga aaagctaaag cattcccctg ttgtgccatt 178500
ttcttccctt tctctcatgc attatttttc ttactctggt tattcttgat gggaattttt 178560
agcagagctc agcgccatct tatcccagga agaaaaaaaa attgtaggag ataaatgtat 178620
gatgaatggt gcaaaacaca acagttgcaa tcttttaaat ttattgtgaa attaaagaac 178680
atgcccctag aatataatcg ctggcaattc aaaaagcaag gatttttagc aaaataaata 178740
agaccagttt tcttcctctg ggccttgtgt ctgttcatct cagtgagtct ttcagcttaa 178800
ccagtgttgc agcccaagct cttccttgtc cttaattagc atcaggagtt ttcattagtt 178860
attttacgag ttgttagtga tcctcattag ctttgctgtg gtcttaaatt ttcttgacat 178920
ttactgtttc actgcataag attttatggt taattcccag agtatataag ccagattatt 178980
agccgttata ttttttacaa tgtatatatt cccatttcag aatctcttgt atcttaacat 179040
ttttctttac aattttatat aaatgactgt catccagttc gttgggcttc ctgatatctt 179100
ttttatacat attaaataag gaaaaataag taaatatata tatcattcac tcagttgata 179160
gatttttcaa gaaagaaaaa aattaagata atatgtttct acaaaaaaag aatgtaatga 179220
aatactgtaa tttgacttta tagccaaatt aggggaacac tactattttt cattctacaa 179280
ttattccaca ctatgctgca agtattgccc aaggaacaga aggcagaaac caagtaactt 179340
gacaatatat tagagaagaa taacaagtca agttattttg aagatttagg tgtattttat 179400
ttcaaagtgc attgttctcc ctttgtgcct ccttctcaaa taacacaaca caggaagctg 179460
tcatccatgt aatatatatt ttttggggga ttaatcactt gtatacctgt tttattattc 179520
attccatggt cattagggcc taaaatgtac caggtattag ggacacagga taacaaggca 179580
gcaaaggatc attatattca gatgcaaaag gaaatgtaat aaatataaaa tgtataaaaa 179640
gtaagtagcc agtttcaaat aataatcagt gtcattctgt caacacttat tttctaagta 179700
tgtactccat gctaaatact aatctataaa gtaactctga tgggtgagtg gagggcgagg 179760
ggagctattt tatattagtt gctcagggaa ggtttccctg aggagatgac atctgaaatg 179820
agacttaaat aacaagtaaa cacagaagag tttttcagct gagtttctgg gagtctgtgg 179880
atagatttca ggaggtctat agacttggat cagaaaaata attacatctg tattttcact 179940
caactcagac tgaaatttag cattttcttc tatttgaatg tagacaacaa atctcagtag 180000
tactagtagc acttgttact ttgttaccag tagaaagtat agttttttta aattatatct 180060
cagttttcac aggtgtcttg aaatgttatc attgctttga aattatgaga tttcttggat 180120
gtgatactag atctgattct aattgtgtta ataaagaagc acatgtatta ctgtattgat 180180
tatgtattac tgggtaatga atgacccaca atttgggagc tttaaacaat aacccatgat 180240
tctgttggtc agcaatttgg gctgtgctca gctgggtggt gttttttttt ttgttttttt 180300
ttttgagatg gagtctgtct ctgtcgccca ggctggagtg cagtggcacg atcttggctc 180360
actgcaagct ctgcctcctg ggttcacgcc attctcctgc ctcagcctcc caagtagctg 180420
ggactacagg tgcccgccac cacacctggt tacttttta tattttttag tagaaacgag 180480
gtttcaccgt gttagccagg atgatctcga tctcttgacc ttgtgatccg cccgcctcgg 180540
cctcccaaag tgctgggatt gcaggcatga gccactgtgc ccggcctcgg ctgggtggtt 180600
cttaaggact tgccaggatt gctcatgtgg ttgcagtcat ctgacagccc cactgggcca 180660

```
aatagtccaa gatggccttc ctcccatgcc cagcagctgg tgctgactgc aggctgggcc 180720
acatggctcc aacaggctac cctggggctc ttcacatagt cacagtgtta caagacagca 180780
agagcatgag ccacaaagcc ccgtgaggct caggctcaga actccccagc acttccactg 180840
tcttctgtgg gtcataacaa atccaaaggc cagctcagtc agtttgagag ggaattccat 180900
gggttgtgac ttcagggaag tgtgattaat tgggggccat taatatactt acctgtcacc 180960
taccaagtcc taattttttt ttttttttt tttttttctg agacagggtc tcactctgta 181020
gcccaggctg gagtgtagtg gcatgatcat ggctcactgc aggcttgacc tttggggctc 181080
aagcaatcct cccacttcag ccccctgact agctgggact aaaagtgtgc accaccatac 181140
ctggctaatt ttggcatgtt cttttttttgt acaaaataat cttctggatg gggctcacca 181200
tgttgcccag gctggtctca aactcctgga ctcaagtgat cctcccatct cagcctccca 181260
aggtgtgggg tttacaggca tgaaccactg tgcccagcct atgtcataat tttaaaaatt 181320
attataataa gttggccggg cttggtgact cacacttgta atcccagcac tttgggaggc 181380
caacgcaggt ggatcacttg aggtcagaag ttcaagacca gcctggccaa cacaacgaaa 181440
tcctgtctct agtaaaaata caaaaattag ccaggtgtgg tagcaggcac ctgtaatccc 181500
agctacttgg gagactgagg cacaagaatc acttgaacct gggaggcgga ggttgcagtg 181560
agccaagatc atgccactgt actccagcct gggtgacaga gcaagactct ttcaaaaaaa 181620
aaaaaaatta tagtaatttt aacatgttcg gtgttttctg taattttgtc ttttacactt 181680
tttaaaatat tattctgaga agaggtacat aggcttcagc acattgtcaa agagggtcaa 181740
gcacattatg agattaggag cccttgatct aaaggcaggg agttctggaa agaggagtat 181800
agaagcctca aggcagaagc aagctggcat gtccaatggg atagaggagc agaaggaaag 181860
ctcctgcggc cagagccaaa gattgagggg cagagtggtt ggagacagag gtagggccag 181920
atcatgtgac ttctttgaaa gcttctgaaa cttgcaaagg gacctccact tccccactgc 181980
accatacccca cagagtgtga aagtaggtat tgtatgtaaa ttgtatttta tgattttttg 182040
gggtcattgc taactttttt cagttatctt ggcagaaata agaaaattct tttttgctat 182100
tccatatatc tattgtgata tcagagtctg ttgtttgttt gtgtgtttgt ttgtttaaga 182160
cagtcttgct ctgttgccag gctgaagtgc agtggtgcga tctcagctca ctgcaacttc 182220
tgcttcccag gttcaagtga ttctcctgct tcagcctccc aagtagctag gactacaggc 182280
gcgtgccacc acacccagct aatttttgta ttcttagtag agacagggtt tcaccatgtt 182340
ggccaggatg gtttgatctc tcgaacttgt gatccgccca ccttggcctc ccaaagtgct 182400
gggattacag gcgtaagcca ccgcacccag ccccagagtc tgttgtttat agaggatgat 182460
tgggcgtagc tttctagagc tgggaaaacc acctttaaac agtattatat accaatattt 182520
actatttcat aaattcaggc atatttgctt aaaataatct cctgtagaga ggcaagaaac 182580
agaagcccat ttttttgttt ttaggaaatt catagaagcc tttggtaagg ttcttttaag 182640
ttggcaaact ctattttcag aagacttcta tgttgacact tgtgacctac agaattgctt 182700
taagaggtca gcactgataa aaacagaggg aagctgtaaa gggaggatta ggctaaagtc 182760
aactggtgga gtaggcatag gtgaattact aaagtgttga tgaaatgact ctgttggagt 182820
taccagttta ttataatgag agctaaagtg aaaaacgcca gacagcctag aagcattctg 182880
aataacaagg agctccaacc ccttatatat aaatgaggtt acatatagta ggttgaaagc 182940
aggtttccaa aacaaccaat tagtttgtat agcttcagct tcaggattga tgattacatt 183000
ccataggata ttacattaaa ttgatgaaat ctgcacgtct ctggggaact ccttacaagc 183060
```

tagccagtga gcttttatga tgataagata cagaatggat aaaaatcttc tgatgccaaa 183120
aaagctttgg ccctgcccaa gttaggatct atattcatat tatcaccagg taaagtgtct 183180
tgcaaacttt cttagctttc attcctatca gactgcagtt catgactgtg aggtgtcaaa 183240
gactctctcc ttaaccaagc ttcagtcatg ctctgctaat gtctcttttg gaccaggctt 183300
caagcttgct ccaccccag ctttggcttg cccagcccag ccttagcaag gaattctgct 183360
aagtcatctc ccaaccctag atatctaatt acccttgata tctgatcaag ttcttcatcc 183420
tccacctttt tgatgtctaa gtccttggac tgcctttagc aagagtcctg ttaggccagc 183480
ttagcaagaa ttcccctgcc cttgatgtgt tcttttagca atttcccatc ctttgacatc 183540
ctcatgctgt tcttggctat aaatcttcac ttgctcttgc tgtttcagag ttgagcccct 183600
tcttttcccc cctccaattg caatggtttt gaatgaagtc ttccttacca ttttaacaag 183660
tgtcagaata attttttaa catctgtctt tacaccacag tcaacaaccc cttatcctcc 183720
ccaaaactct gagctaacgc cactacttag agattacagt gtctgcctat tttattagct 183780
ggaactgcat cagtgatttt ggagttgaat ttttcatttt ttacatgaaa gattatgtgt 183840
ttataatttg ttgttttcac atatgcataa acagaactag gaagagctgt actcaggagt 183900
caagtcagaa gaaaaaacat caccatgttc aaatagacaa ctgaacatgc ctctgaaaac 183960
cagagacaaa gggagttatt tacagttaac atctatagaa tatgggccgg gtgtagtggc 184020
tcacgcttat aatcccagca ctttgggagg ccaaagcagg aggattgctt gagcccaggc 184080
attcgagacc agcttaggca acatggcgag accccacctc tataaaaaat ttaaaaatta 184140
gctgggcgtg atggtgtgca tctgtaggcc cagctactca ggaggctgag gtgggaggat 184200
cacttaagcc tgggaggtca aggctacaat aagctgtgat taaggcacct gggcaacaga 184260
gcaagaccct gcttctacca aaaaaaaaaa tatatattaa atttgtagaa gtctgggcac 184320
agtggctcac acctgtaatc ccagcacttt gggggctgag gcagaaggat tgccttcacg 184380
agtttgagac cagcctgggc aacatagtga aataccatct ctacaaaaaa tacaaaaatg 184440
agccagttgt gctggtgtac acctgtagtc ccagctactt aggaggctga ggtgggagaa 184500
tcacttgagc ctgggaggtc aagactgcag taagccgtga tcatgccact gcactgtagc 184560
atgggtgaca gagtgagaac atgtctttaa aaaaaaaaaa tctgtggact atgaagcaag 184620
atgagagaca tttgaaagca tatgtcggaa agtcaggtat acttctagag ctggctctct 184680
gttaggatag agacctttaa aatgtttcta gtgcttgcag atgtcaccct accctcctgc 184740
aaagataaca gtgcatttac ttctgtcact gtagattagt tttgcccagg tattcttttc 184800
ttagggctgc cgtaacaaag tctgggtggc tttaaaacaa cagaaattta tcgtctcaca 184860
gttctggagg ccaaaagtca gaaatcatgg tgtcggcagg gccatgctcc ctctggcagc 184920
tctagggaaa ggcctttcct tgccccttcc tggcttctgg tgtttgctgg caatccttga 184980
tgttccttgg cgtgtagatg ggtcacttcg gtctttgcct ccatggtcac gtggccatct 185040
tttccctgtg tttcttcaca tagtcttccc atcccacatg cagaagtatg tgtcagtttc 185100
tgtgtggctg aatttcccct ttttataaag acagcagccc tatcggattg ggcctcctct 185160
aatgatctca ttttaatttt tgcctttgta aagaccctgg gagttaggac ttcaacatgt 185220
ctttttgggg agacaattga acctacatag catgtttttg aactttacat gcagaatcat 185280
attgtatgta gtcttttgca tctggcttat ttcagtcaat atattagtga gattcatctg 185340
tgttgcaata gcagtttcta ttcattgtca gtcctaccta ccactatatc aaggctctgc 185400
aaattatggt gtgaaggcca aatgcatcat gacttatttt tttcgcatat ggatatctag 185460
gtattacata agaaaatgtg gtttttggtt tctatgatac ttcttcccat atttctcttt 185520
gtttgaatag gaaacaaatc taattaatcc ttaattaaaa gaaaactttt atatcccatc 185580
tttccatgac tatgaatatg ttacatgtat aaatgtttat atctgttatg tggtcattat 185640
acattttgaa ctaaaacata gcttatactt gccatataag tttatggaaa aagttaaata 185700
ttttacttaa ttgattgatt tatatcctgt aactttacac ataagtcctg gtaatacaag 185760
cttgttgtta aaaaaaaaat tgaaatgatc cagaaggaca taaaatcaaa cgaataggct 185820
cctctcctta tccctgtggc ttgcccagtc taattcttta taagtcaccg ctattgacag 185880
ttttctggat attcttacaa atattttttc tgacatggaa gtgtgcatgt atctgtgtat 185940
gtgtgtgttc cctgtatttc taacatacct gggatcctaa tatgcatact aatctatgac 186000
ttgcttttca catttaataa tatattgtga ctacatttcc attttagtac aataaagttt 186060
ctcctcattc tttttttctg tttttgagat agagtcttgc tctgttgccc aggctggagt 186120
gaagtggcct gatctcggct cactgcaacc tccgcatccc aggttcaagt gactctcctg 186180
cctcagcctc ccaagtagct aggattacag gcgcccacca ccacgcctgg ctaatttttt 186240
tttttttttt ggtattttta gtagagacgg ggtttcacca tgttggccag gttggtctca 186300
aactcctgac ctcaggtgat ccacctacct tgacctccca aagtgctggg attacaggtg 186360
tgagccacag cgcccggcct ttctcgtttc ttaaaataat tttataatgt tccgttcaat 186420
ggatgcatga taatgtgttc cccaaatagc aaacgtttag actgtttcca attttttgtg 186480
taagtataca tggatttgtt tctgtttcta tttacttcta tgaaaacata cttaagaatg 186540
atttttagat gttgaattgc tgggtaatat atatgtgctt ttaagttttt gacagatacc 186600
actaaattgc cattcgaaaa aatgcagtaa caatttacac cccatgaggt gtttttatta 186660
ttatttttaa ctaccaggac tttacacctt gtaaaatcta caataagaga gttatatatt 186720
gactgtttac tctgttgttt cagaacaatg agatggtgga gctacagaga atacggatga 186780
aggatgaaat ccgagaatat aagttccggg aggcacggct ccttcaggac tatactgaat 186840
tggaagaaga aaatatcaca ttgcagaaac tagtgtccac gttgaagcag aaccaggtaa 186900
ggtttaagaa attttttgtt atactgaaga tggatctaca tcttctgacc actagggtta 186960
aatctccaaa cttgtcagaa tttattgtta ctcttttatc ttctctctat aacatttatg 187020
tactgcaatg tcccaaccct cctatttcag ctaaaatata gaaggaaaaa atacacctgt 187080
aagtagtata gtgtacacta aagttttatt gaataagaaa aagaatttta gtttttattt 187140
tagctctgtg ttcatttatt tcataagtca aatgtatcgt aacaaattta acctgacaac 187200
ttctcattaa aagcctgagt cttagccggg catggtggtg tgttcctgta atcccagcta 187260
cttgggaggc tgaggcagga gaatcacttg aacccaagac gtcaaggtag cagtgagccc 187320
agattgtgcc actgcactcc agccttggtg acagagtgag actccgtctt aaaaaaaaaa 187380
aaaaaaaaaa aaaaagcctg ggtctgtaag cttgtctatg agcttagggt ctccctacaa 187440
tcactggtct ctcactccct taaaattttt tctgtaaatt gctttcaaat cgtagagggg 187500
aatggattat gaagtataaa tcaagaagag caaaattata agaaaaagag gccgggcgtg 187560
gtggttcatg cccgtaatcc cagcactttg ggaggccgag gcgggtggat cacctgaggt 187620
caggagtttg agaccagtct ggccaacatg atgaaacccc gtctctacta aaaatacaaa 187680
aattagccag gcatgttggt gggtacctgt aatctcagct actcaggagg ctaaggcagg 187740
agaattgctt gaacccagga tgcggaggtt gcagtgagcc gagattacac cactgcactc 187800
cagcctgggt gacagagtga gattccgtct cgaaaaaaaa aaaaaaaaag aaaaagaaaa 187860
tgcctgtttt ctttttcagc tgtaacctga ctacaaagat tacattcgta catttaaatg 187920
atttttttgc tgtaatgggg gtttgatagc ttaattttcc tgattggttt gcattgtgga 187980
ttttcagaac tattaataat tattgaatct gtaattttag aagaatttat ttatgaatac 188040
agttgaatcg agtagttaat taagcaaagg tgaattggat gttcgagttc ttttcaaggt 188100
gcttcctcag cgacacctct attctggtct aaacgctgtt gccacctctc agttcagatc 188160
aacagcctat gtgccaggtg ctgtgctagg ttggacagac acaagaatcc atagggcatg 188220
attcttgtcc tctgtaaact tagaagccag cccagatgta tgcttttacc tcactccctt 188280
cctgagttgg tatctacatg atacactgat tgattgattg attgatagat ataagggtta 188340
agagggaaaa gaaaaaaaat ccagaagaga aaaatccatg tagtggcaca attaaaattt 188400
gatttctttt tttttttttt tgcgacagag tcttgctgtg ttgcccaggc tggagtgcag 188460
tggcatgatc tcagctcact gcaacctcca cctcctggtt caagcaattc tcctgcctca 188520
gcctcccgag tagctgggat tacaggcatg agccaccaca cccagctaat ttttgtattt 188580
tcagtaaaga cagggttgta ccatgttggc caagctggtc ttgaactcct gagctcaagt 188640
gatccgtcca cctcagcctc ccaaagtgct gggattacaa gcacgagcca cagcgtctgg 188700
ccaaaatttg atttctgatc attgccactt cccccagatt tggagtgctg gggggaaggc 188760
atgtaagggg acagtttcag tccatcaaaa aagggctact ggagtatccc catgtgtttc 188820
tgcctcattc cttccgtaag cactgaatcc ccatatgtgt gctgagggct ggccattcca 188880
gaggctcccc aggtcttgat ttggctggga taagtgagct cacagtggag aaatgtagac 188940
ttagaaaaat acatttgtaa agatgcttct cgaatacttt ttaaaataag aaggggtttt 189000
tttttgtttt tttttttttt ttttgagaga cggagtctcg ctccgtcacc aggctggagt 189060
gcagtggcgc gatcttggct cactgcaacc tctgcctcct gggttcaagc gattctcctg 189120
cctcagcctc ccgagtagct gggactacat gcatgtatca ccacgcctgg ctaatttttt 189180
atatttttag tagagatggg gtttcaacgt gttagccagg atggtctcga tctcctgacc 189240
tcatgatctg cccgcctcag cctcccaaag tgctgagatt ataggtgtga gccaccacgc 189300
ctgacctaag aagggtattt tcttgtggtc ctttttttgg ttattgatga aacacataga 189360
ggatttgaaa caaatttact tgaagtgcaa ctatttaaag tggcccttcc ttcccgattc 189420
ctacactcct cactgctctc tagagcatgg tgagagcacg atcagcagcc tccctggaga 189480
gccttccctg accgcatgtg gagactgatg gactcaggag gttaatgaag gccagtatta 189540
gatattcttg aaagactgcc aaggtatccc ttgagtattc attaacccag atgccggttc 189600
tgggagaatt tgtactgtca ttcctgttgt gagtttcccc atgcccttct cccagtaatt 189660
gaaacatgga atccaatggt taactcagaa gttttttaaa aaggaggggg gacttacaca 189720
ttttttattt ccaacatgcc atatgctaat tttcccaatt aagtatctaa ttaattcatt 189780
caaaatcatt ttctgcacag agcaccattc tggtttattc cctgaaattg ggggaactga 189840
aatgccacaa gtctctccca gctaagaaaa tgctgtgttt gtttccagta gtaactgatc 189900
tttctttata gatgctagca tctatcataa actctctcta atcaataaag ttttttggtt 189960
ttttggggtt ttcttgagac agggtcttgc tctgtcaccc aggctggaat gcagtggctt 190020
aatctcggct cactgcaacc tccgcctcct ggtcttgtga ctcggcctcc tgagtagctg 190080
ggattacagg cgtgtgccac catgtccagc taatttttgt atttttagtt gagacagggt 190140
tttgccatgt tgccctccct atgttgccca ggctggactc aagtgatcgc ccacctctgc 190200
ctcccaaagt gctgggatta caggcatgag ccaccatgcc cggccctaat taatgaagtg 190260

```
ttaagtacaa tattgtatgt acaaatgcca cagagttttt taaagagatg acaatgagta 190320
gcattcggtc acaaaattgg actgtgttac tttgtactga agttcccaat acgttgtata 190380
gtccttcagc ctggtttgat gtttctctaa acagcaaagc tactaccatt ttaaaatgct 190440
tagttcaaag aattttccct tctgaagtat tatttttctt ttagttattt attattttct 190500
aagtacagtg taattattgt ttaaaaaaca cctcttactt tctataaaga gtctatttac 190560
attccatttc cttccattaa catatagcac ctacgataga gcctgatcca cagtagatat 190620
taaataaata cttgttgaaa gaataagaaa actggccagg cacggtggct catgcctgta 190680
atctcagcac tttgggaggc tgaggaggat cacttgagtc caaaagtttg agaccagcct 190740
gggcaacata gggagacctc atctctacca acaacaaaaa aaattaacca agtgtgatga 190800
tgcacacctg tggttccagc tacttgggag gctgagatgg aaggattact tgagcctggg 190860
aggctgaggc tgcagtgagc tgtgatcaca cctctgtact ccagcctgag cgatagagtg 190920
agaccctgtc tcaaaaaaaa aaaatgggaa aaaaaaaagc aacaattcag tcacacttct 190980
aatatgaaac atttcctcca atgtcaggta ataatatata agaatatcac cctgggtgca 191040
atggctgatg cctggaatcc cagcactttg ggaggccgag gtgggcggat cgcgaggtca 191100
ggagttcgag atcagtctgg ccaacatagt gaaaccctgt ctctactaaa aatataaaaa 191160
agaaattagc cgggcgtggt gacaggtgcc tgtagtccta gctactcagg aggctgaggc 191220
aggagaatcg cttgaaccca ggaggcggag gttgcagtga gccgagatca cgccactgca 191280
ctgcagcctg ggtgacacag tgagactccg atccacctca aaaaaaaaaa aaaaaagagg 191340
ctgggcatgg tggctcatgc ctgtaatccc agcacttggg gaggccgagg cgggcagatc 191400
acctgaggtc tggagttcga gaccagcctg accaacatag agaaaccccg tctctactaa 191460
aaatacaaaa ttagccgggc gtggtggcac atgcctgtaa tcccagctac tagggaggct 191520
gaggcaggag aatcgcttga acctgggagg cagagattgc agtgagccga gatcatgcca 191580
ttgcactcca gcctgggcaa caagagtgaa actccatctc aaaaaaaaaa aaaaaaaaag 191640
aatatcataa ggtaatatca taaaagacct aggaaatgta ttcagttgtt ttatttcatt 191700
taaccggtat ttcaggggta tctctctatg agatcatgta ctttttagag acaaaagata 191760
cagtcactgg ctcaaagagc ttgtagtccc aatagggact cctagcaatt tgtgtaaatg 191820
aatattaaag ccacatgtta ggtttggcaa cacagggata gattaagatc tttagagttc 191880
ctaagctctg aaaggattat gatatctaac cttgaccgtc atgtagttaa aaataaagtt 191940
attaaactat gaagttgcca taaggaatcc taataaagca cttatttttc ctatggtgac 192000
tgctttgatg ttgtctttaa aatatcaaac accagttttt aagcaccttc ttgttccgtt 192060
tcttgcttcc tctgctttgc tggggctcta atcacatggt gcagccttac aacaacggca 192120
cagaaaggag tgatgagttt gcctcagtgg gcaccaaaga cttcagttag gatgagattc 192180
ttaacttagg tgttaaaaga ggaataagag ttttccagat gacagccttt tcccaggcgg 192240
agaaacatga aacagctggg tgaatagtag gagcttgtac cacatttgag tgagtggtgt 192300
gagtgaagct gcccagacag aaagagatca gggccaggca cggtggctca cacctgtaat 192360
cccaacactt taggaggcca agtcacgagg atcacttgag tttgaaacca gcttgggcaa 192420
catagtgaga cctcgtctct acaaaaaaac aatttaaaaa atgaggcgag aggatgactt 192480
gagtccagga ggttgaggct ccaatgagcc atgattgtgc cactggactc ctgcctgggt 192540
gacatagcaa gagatcgggt cttacaggaa gtctaggcca tcaattgaat aaatactact 192600
gaattttaaa ctctgcagtg caaactaaat taatgtcttc aagtcaagac cagagttagc 192660
```

```
aaactttttc tgtgaagggc cagatagtaa gtatcttagg tttcataggt cacatgatct 192720
ctcttgcgac tacccagctc tgctctggta gaagcagcca tagacaacat gtaaacaaat 192780
acatgggagt gtgttccaat agaactgtct acacgaaaat aggtggtggg ctggatttgc 192840
tccggaggac atactatttt tttttttttg agacagaggc tcgctctgtc gcccaggctg 192900
gagtgcaatg gtgcgatctc agctcactgc aagctctgcc tcccgggttc acgccattct 192960
cctgcctcag cctcccaagt agctgggact acaggcaccc gccaccatgc ctggctaatt 193020
ttcttgtatt ttttagtaga gacggtgttt caccgtgtta gtcaggatga tctcgatctc 193080
ctgacctcat gatcctcctg cctcggcctc ccaaagtgct gggattacag gcatgagcca 193140
ccgtgcccag ccaggacata ctattattgg acaacctctg gtctaggcca tcagtttaac 193200
aaagattgca gcaaaacagg tctacaatgc aaactaaagt aatgtctgca aatataagct 193260
tatcacataa tctggggcag tcagagggtt ggttgaaata ctaggaaagg ttggcaagag 193320
gtgtcctatg ttgtccaggg aaagaaaagg aaagggttga gaggaagatg actttacagt 193380
attttttttt tttttttttt tttttttttt ggagacagag tccagctctt ttgcccaggc 193440
tggagtgcag tggaagcaat cctggctcac tgcaagctct gcctcccggg ttcacgccat 193500
tctcctgcct cagcctcctg agtagctggg actacaggca cccaccacca tgcccagcta 193560
aatttttttt ttttgtattt ttagtagaga cagggtttca ctgtgttagc cagtatggtc 193620
ttgatctcct gacctcatga tccacccacc ccagcctccc aaagtgctgg gattacaggc 193680
gcgagtcact gcgcccggcc caactttaca gtatttaagc aggcctgaaa gaaaccatga 193740
cacaaggaaa cacactgctg tctgaagcaa tttccaagtt gcctttctta taaccacact 193800
gagggcaatc cttgcttctc ctttcataag gaggtaaagg cccttctgat ttccatactc 193860
cttcatccca agtcacctgc aaagcagtaa atcatgttga gcatgcgttt ctggattcct 193920
ctcttcctcc acacttcatc ctcagtttcc ccctgcttcc tggctaacaa attgagattc 193980
ctataatcag agaatgaacc tttcatttca ctaccagaga taaagtaaaa aatgcatgtt 194040
tttgcttgaa gtaacaacct agttgaaatg cagtcagtca gcaagtataa aggaaaggtg 194100
actggatgct ttagtgtggg aaaggttgtt tgctcggtgg aaaaggttgg agagagtcag 194160
tcacagggca ggagcagtga actcaaatga ccacaagcag cttataaata gcattaagta 194220
caagatgtaa acaaaaagta gaggccgagt gcagtggctc acgcctgtaa tcccagcact 194280
tcgggaggct gaggtggaag gattgcttcg gtccaggagt ttgagaccag cctgggcaac 194340
atggtacaaa accttgtctc tacaaaaaga aaaaaaaagc caagcatgga ggtatgcgcc 194400
tgcaatccca gctacccagg aggctgaggt gggaggattg attgagactg ggagatcaag 194460
gctgtagtga gctgtgatca agccactgta ctctagcctg ggcaacagag caagaccctg 194520
tcacaaacaa acaaacaaaa gaaaaagtag atggaaaagg aacagccagt gctcacttac 194580
aggtgatttt tgtgctctgt gaaggtgggc ccagtgttgc ctgaattatt tatttatttt 194640
tatttactta tttttagacg gagtcttgct ctgtcgccca ggctggagtg cagtggcgcg 194700
atctcggctc actgcaacct ctgcttcctg ggttcacgcc attctcctgc ctcagccttc 194760
tgagtagctg ggactacatg cacctgccac cacgccccac taattttttg tatttttagt 194820
agagacgggg tttcactgtg ttagctagga tggtcttgat ctcctgacct cgtgatccgc 194880
ccgcctcagc ctcccaaagt gctgggatta caggcgtgag ccactgagcc cagcccgaac 194940
ttttgatttt tttaaaaaag aaatcagaag ttttcaaatg tttgtgaaat catcagtttt 195000
ctaaatattg gcaatcaatt ccaaaagttt tataacgtgt tacaagccaa ataaagcaca 195060
```

-continued

```
tctataggct cgatggtcta tgggcacccc ttgtgatctc tgctttaaat catttgatgt 195120
ctgaattggt ggaagggaca cgggagcaca caccagcctg gggagcccac tagagtacag 195180
aatgcaaact acagggacac atgcctttga gcaggtagta gatagccagg gcctgtcaag 195240
ttattaggtg tcccaggcca ggtaataact ccttggagtt gtgaaaagta tatttcattt 195300
ccatgccatc atgtttgtaa catgctattt atagtgccca gttatcattt ttcccaaagt 195360
gcaatttttc tcccatgaag tactcataat cttaagtaat gtagttgata tgtaacccag 195420
aaactcctac ttgattagaa gacagttatt ggtagtatgc cattgataga tttgttaatt 195480
ttttgttata tttattcaaa tgcatattca tggtagaaca attagcactt tctagttttc 195540
attctaaata atggatatta taaataatgg tctccaatat tgactctttt gagtaattct 195600
atcagggaca tgttgaaatt ccaatgacca tttttttttt tttttttgcc ttagaggcat 195660
cttttgtaca taatgtattt cttttttttt tttttccct caagacaggg cctcactctg 195720
ccacccagat tggagtgcag tgacaccatc agggctcact gcagccttga cctccctggg 195780
cccgagtgat cctcccacct catcctcccg aatagctggg actataggtg cacgccacca 195840
cacctggcta attttcttat tttttgtaga gagagggttt cattatgttg cccaggctgg 195900
tctcaaactc ctgtgctcaa gcaattcacc gagattacag gcctgagatt acaggtgctg 195960
agattacagg cctgagccac cgtgcccagt cctcataatg catttcacac accatagtgt 196020
ggtgagcaca ttctttcact gaaataacac tatccatatt cacatataca actggcattg 196080
ttagaaacat ctgctataca tatgtcttta tgagttgcat cctattagag caccacagtg 196140
tttcggtgac cagtgagtgc tggtttacca tcagctttca ttgttccctt ctgacggtgt 196200
atttctcagt tttttcctgg gcccagtgct gcccagagta aaggctacat tcttcactcc 196260
tcctcgcagc caaatggcat aagactagta ccagccaatg atatataaca agtgatgtgg 196320
gtaactttta atgtccttaa agggagacag tgtgctcctt attttgtgcc accgcttaga 196380
acatgatcaa atggcaagcc acctgagata gtatggtcta gactagaagg ctgtacaaca 196440
acagaggaag agcctggctc ctggatgacc tcatggagca gagattccat gaggaatctc 196500
ctcctgtcta cctccatact gttacataag agaaaaacct ctggctgggc gtggtggctc 196560
acgcctgtaa tcccagcact ttgggaggct gaggtgggtg gatcacaagg tcaggagatt 196620
gaaatcatcc tagctaacat ggtgaaaccc tgtctctact aaaaatacaa aaaaattagc 196680
caggcgtggt gacgggcact tgtagtccca gctactcagg aggctgaggc aggagaatgg 196740
cgtcaaccag gaggtagagc ttgcagtgag ccgagatcac gccactgcac tccagcctgg 196800
gcgacagagc gagactccgt ctcaaaaaaa aaaaaataga aaaagttcca tcttgactaa 196860
gtcactcttg cttaggtgtc tgttacatca gccaggctac atcccaacta aatctctacc 196920
ctaacctttg cgagacaaac cattgcattg agattatata aagggaagtt gggggagaaa 196980
gagaaatata tgatgatgat actggtcaat gttccctatt cttcagtttt taaaatattt 197040
tttaaaattc aagttcaaac taatatatat gctaaaataa atatgaaact aagcacatag 197100
tttgtattag catctaatat catgatgact ttattttact ttttctactt tattttttca 197160
ttctccatag ttctttattc agcaaatgca cattgaacag cagaattctg ttttaaacac 197220
catgaaggaa cactgaagca ctatgaggag caatgaggtg gataaaaaag tacttacttt 197280
ctctaaggag attacagtgt acttgtggag ataaaatgtt tcttaaaagg tggcatgtga 197340
taagtgccat ggaaaggatc ccaaggaggc atgtcggctc agaggagaca tccctgtcac 197400
ccgtgggcct tcatgaccaa gagattgttt gaggaggttt atttttattg catttcaaaa 197460
```

gaatattacc tcaataacaa catatggcca ggtgcagtgg ctcacacata taatcctagc 197520
actttgggag gccaaggcca gaggattgct tgagcccagg agttcaagag cagcctgggc 197580
aatacagtga gaccgtctct acaagaaata aaaataaaaa ataaaaaaaa tagccaggta 197640
tggtggcaca tgcctgtgat acttgaggag ctgaaatggg aagatcactt gagcccggga 197700
ggttgaggct gcagtgagcc atgatcatac cattgcaccc cagtctgggc aacagagcga 197760
gaccctctct caaaacaaac caaccaacaa acaaacaaac aaaagcaatg taggtatttt 197820
ttgttactgg atagtttatg taactgttct ttcagattct gtctatcctt taagcacata 197880
acaatgatct ttgcattttc atcttactct caaacatttt actgagatta tgttattata 197940
atcgttaaca aatttatctc tgggtataaa aatttcctca ttattaataa ggaaataaaa 198000
caaagtaatg gtgatgatac aatcttttct tagattgcaa atattctcat aagttattac 198060
aaaaaatatt ccctatttat tgggcaaaca gtgccccctt ttgaccactg gatcctatga 198120
aagaaatcct aagacaatag actcttcatc tctgctaaaa attgaattat atagagagtt 198180
atatagatgt atattattag atctaattat atataacatt tatgttatat cactataata 198240
cctaattata tattttatat atggtatata atttctaaag aaactatcct atataacttt 198300
aaggatatat tgtgtgcttt ttattattta ttttttagac tcatgttgta ttttgttaag 198360
tgattaggtc cactagagtg tttaatggca gttttgtaag atccacattt tagttttatg 198420
aatcttcttt atcctgtctg attcaggttg aatacgaagg cttaaagcat gagattaagc 198480
gatttgagga ggagacggta ctgctgaaca gccagctgga agatgccatc cgattgaaag 198540
agattgctga gcaccaactg gaagaagccc tcgagacttt aaaaaatgaa agagagcaaa 198600
agaacaacct gcggaaggag ctctcccagt atatcagcct caatgataac catatcagca 198660
tctcagtaga tggactcaaa tttgccgagg atgggagtga accaaacaat gatgacaaaa 198720
tgaacggtca tatccatggg cctcttgtga aactgaatgg agactatcgg actcccacct 198780
taaggaaagg agagtctctg aaccctgtct ctgacttatt cagtgagctg aacatttcag 198840
aaatacagaa gttgaagcag cagcttatgc aggtaagaac tttgtttagg gccgctagag 198900
tgaatttctt gtagattgca ggtagcatgt tgtgggactt ctgattctcg catttcactt 198960
ctagatttct tttcttttt cttttcttct cttttctttt ctgttctttt cgagacagag 199020
tcttgctcca tcgcccaggc tggagtacag tggtgcaatt tcggctcact gcaacctccg 199080
cctcccaggt tcaagtgatt ctcctgcctc agcctcccga gtagctggga ctacaggtgc 199140
ccgccaccat gcccggctaa tttttttgta tttttagtag agacggggtt tcaccgtatt 199200
agccaggatg gtctcgatct cctgacttcg tgatccgccc gccttggcct ccaaagtgct 199260
gggattacag gcgtgagcca ccgcgcccag ccccagcttt cttttctaaa tattgcttct 199320
tcagctagaa acttcgaaag tgcagtattt tagaaagaca tgacagaagg agcgttaaag 199380
agaaatgcag tctctcattt gcatcacttc aagaaatgaa cttctgagag ccacaaattg 199440
agctccaatg aagtctgaga aaagacagaa aaaagttcct tgggccgggc gcggtggctt 199500
acacctgtaa tcccagcact ttgagaggct gaagcgggcg gatcacctga agtcaggagt 199560
tcaagaccaa cctggccaac atggtaaaac cccatcgcta ctaaaaatac aaaaaattag 199620
ctggacgtgg tggtgggtgc ctgtaatccc acctaactca ggaggctgag tcaggagaat 199680
cacttgaacc cgggaggtgg agattgcagt gagccgagat cgccattgca ctccagcctg 199740
ggcaacaaga gtgaaacgtc atctcaaaaa aaaaagaaaa agaaaaaaga aaagacagag 199800
ccttaatgca tttctgatta acaaaagaat tcaaaagctt tatatacaag taaaatgatg 199860
gaaaccatgc agtttttcat cacaagcaac tgtgtttata gcttccagat ttatggttac 199920
atttcacagg aatacttgaa gccttaaaag acgtaaagga cttcctatgt acaaattatc 199980
caggataccg tatgattaaa aatacagaac aggtataatc taagaccaaa ggattcttat 200040
tgcaacatga gttaaacctt aaatttttag cgtcttcaaa acaaatgtct tgtgaagatc 200100
ccagccttga aaaaatcgct ttctagttta gagtcttgcc ttcctgccac atgtaatgga 200160
aatgttgttt aagaaacagc agcattacca tcacctgggg gcttatttat acaaattgtg 200220
gagctccgtg tagatctact gaactagaaa ctgaactaga aatctggtat aacaagcttg 200280
ttaagtgatt aaatttgagg cttaatcttc aatctcaatc ttatctctcc aaggttcttc 200340
atgtatagct gataattaga ggctgttaag cctctggcag tcatctgcct ccacggaaat 200400
gatgactgga aaagtgaaat tagcagaaat aagtaagaga acagagagcc aatgatgttg 200460
atttgttaac aggtttattt tctatgtctt tttgctcagt ttacactaat atgactagat 200520
tgattgaaac agaaaacata tttccttgtg aaaaagtttt acatgacaga tgtattcata 200580
agaatttgtg ccccccagat tgaataccat taaatagaag ttttatgagt tttgtttaac 200640
tctcatattg gtggctttga gataaaaagt tagtgggttc aggctttttg tttattcctt 200700
ttgttttggt ggcagtgcag aagataatag gaaaagaggc ttctatgcat gaaacagcac 200760
aacaattttc aagcaggtca tctattggct gaaagctcag agctgtgctc agatttaatt 200820
ctaaatgtga tctgaattgg gtaatacaaa agtctaaaaa agatgaaaag ttcaattaaa 200880
agaatggtgg aaaacaagta agtactcagc tggagactgg ctctcctgag ttctcaatag 200940
actgtcgttt tcgtttggtt taggcggttc ctcattgcca gagaatgttt tcttccttga 201000
gaaggtttag cgtctctgat cccaactcat gagatgctgg ttacatttcc tcagttgaag 201060
tgatgaccag aaactcccca tgtatttcaa atgctctgag agtcagccac tagttgacag 201120
tcattcttag aggacagcac tttactttcc catggaatgg gatacataat accttcctcg 201180
ttagagtgtc atgaaggttt atgagttata tgcagagtgc tgagaacagg gactagtgca 201240
cagtaaatgc tcattaatta tgaactgtta tcattatttc aactccattg gtcctttaat 201300
ttattaggca ctcactttat aataatttag ataattatta ttaactatta tttttgggct 201360
attagctcaa ggccaatcac cccaaaaggg actgatgtgg atactggtag gaatatagaa 201420
aaataacagt taagtctcat ggtgcaagaa ggtctgaaaa aggatattca tttagcaaaa 201480
tgttagggtg agaaaaactt tgctggataa accctccatc agtctattga gaaagctgtg 201540
tcccttcaaa tctttcttca acccttaact gatgttgaca gtttgcaaag atgtagaggg 201600
gcgcaggtag gtccttatat cccaaagttt gctccagatt tagttgtgaa aaccaggttc 201660
aacacaggaa gggctttgca gcttccaatc tcatactaac aacactaact gtaaattttt 201720
ttttaggtag aatatccatt tatcttcttg taatcagcgt ttttaaaaag catgtcagct 201780
tttcctaaga atatatttta ttcaaacaag tatattcatg agaagtatac cttctcatga 201840
actatttttt tgcaatacag ttttttcctt agccacacat ctttttgggt taaatttatg 201900
taaataaaca cattacaaaa acattacagg atacattgcc tagaatttat tgtaattggc 201960
tttgatgtta ataaggatta aaaataatat ggcaagtctg atcaatgaga gtactgtgca 202020
cctgaagcat atatgtgtca gtaccattgt tctggaaatt atgaagagga accaatcaaa 202080
tgtactttaa gtatagctat ctggaatgct tgggaccagg tgtgttttaa aaattcaggt 202140
ttcagattgt agaaaggtaa tatgcagcat ataccacata gattgtgata tctccactgg 202200
gatcagatgc agcatccggt gatcaaataa tattaacatt tctgcagtga aacatgagta 202260

```
ttcacactaa gaataagatg aggaccatta aaggccttac accagtcagg tgcagtttgg 202320
ctgccctggg agtttaggac tgtctgaata ctgccaagtg agttttatca taatcaagtg 202380
aattatgata aaacttgatt tcgagctttt tggattttgc agttgcaggc gttgtaggaa 202440
tagcactgtc ctgttgggcg gctgtcagtt ttgcgcacct cagcttacag tgtcaacata 202500
cttggaacgt gacagtttgt attttcattt tttttatta ttattatact ttaagttcta 202560
gggtacatgt gcacaatgtg caggtttgtt acatatgtat acatgtgcca tgttggtgtg 202620
ctgcacccat taactcgtta tttacattag gtatatctcc taatgctatc cctgacagtt 202680
tgtattttca tagttccttt atctcttagg atttctcctg gcctggatcc aaaacactgc 202740
atgggagagg ccgccttgtg cctctaatcc aacagctgtg cttagctaac agctcatgac 202800
agtgtagagg ggcacaggca aggctgtaac tccctgaacc aggtgatatg cagcagttca 202860
ggttttcttc cttctgatca agtacccctt tgatggagta agttcaagag atctatagta 202920
caacacagtg actgtagtta ataacaatgt attgtattga aaataaaaga gtagatttta 202980
agtgttctca gtgttgtaga acccctaaat gtaggtccac gtgttggatg ggcagtaagc 203040
caaatactga cacatcagtg cttagcagca gagaaaggtg tattcatttt tccaaaaatg 203100
acattgtggg agaggcaatc ggtcaaatcc tacctgcctt tgaacgtaac tgggggtttt 203160
tgtgagtaag gcagctgtgc aggagaatga aatcccccaa tgatcaaagt tgtttgtgtc 203220
ccgcagctca atcagacttc tggatgccat caaggaggtc tgcatgacct aaggatcatt 203280
gttctttgaa aggaaaacaa gttcattaat cttactggct gccagggtta ggatgcaaag 203340
ttaatcaatt attagtgact accgtctacc gaatgactac gtgcaagcag tcatgcatgg 203400
aggaagaaaa ggacaaagag aaaggaaaat aagtaaaaaa caaacgttta atgattttga 203460
taatataggc tcagttacat caccacaaac atgataagta tgtcaggtca tgcatgtcat 203520
aattagctca atttccactt tgcctacata tttcaaaaca tcatgttgta catgataaat 203580
atgtacaatt tttgtcagtt aaaataaata cattaatttg tttttaaaga actcctttga 203640
aaacagtata cctagtccat atacccttc ggccttttct tctcctacaa ggctcaatgt 203700
atgcccatga tttatgtttt cccatccata ggtatttatt taacctggtt ccaggaaaaa 203760
aaaatgcctc tgtcgacgaa gcaagtcaaa ctctgtaaaa tattttaaga gatttattct 203820
gagccaagta tgagtgacca tggcctgtga catagccctc aggaggtcct gagaacatat 203880
gcccaaggtg gtcggggtac agcttggttt tatatatttt agggaggcat gagacatcaa 203940
ttaaatacat ttaagaaata cattgggccg ggtgcggtgg ctcacgcctg taatcccaac 204000
actttgggag gccaaggtgg gtggatcatg aagtcaagag attgagacca tcctggccaa 204060
catggtgaaa ccccatctct actaaaaaaa atacaaaaat tagctgggca tggtgatgca 204120
tgcctgtagt cccagctact tgggaggctg aggcaggaga atcacttgaa cccaggaggc 204180
ggaggttgca gtgagccgag atcgcgccac tgcactccag cctgcgacag atcaagactc 204240
tgtctcaaaa aaaagaaaaa agaaagaaat acattggttt ggttcagaaa ggtgggacag 204300
ctcacagcgg gggcttccag gctataggta aatttaaaca ttttctggtt gacaattggt 204360
tgagtttgtc tgaaggcgtg ggatcaatgg aaagaaaatg ttcaggttaa gataaaggat 204420
tgtggagacc aagttttatt gtgcagagga agctctcaga tagctgactt cagagagagc 204480
aggttgtaaa atgtttctta ttgcacttag aagggtgcct ggctcttagc tgattatctc 204540
ctggatctgg aaaggaagga aggaaaacaa agcggggaaa ggggattctc tacagaatgt 204600
ggatttttcc cacaagagac tttgcagggc aatttcaagg tatggcaagg aaatatattt 204660
```

tggttttctt tctttgccag tatcagattg gaaagtaact cttgatatac agggttaaat 204720
aaaacgcatc cgatgagaat ttatggtttg tagggcatga actccccaga ccccttagat 204780
aggaatttgg gcaagataaa aaaaaatcag atcttagtcc tcacctctgc cttaattatc 204840
aggaatgttg agtgaattgt tttgcttctc tgaggctcat tcaaaagggg aaggtaataa 204900
attagcccca ccatttgtct ctgccatgcc tttgttggaa ctatggaaaa aacaaaacaa 204960
aacaaaaatc aggtctcctt cttgaagcca tcatactgcc atctgctggg aaatggtaat 205020
aacaagtata aacatttata gctactacaa tttaaatagc acctcctgga gttgtttgca 205080
tacaacctgc agacttctgc attgaagccc tggtgataat gccatgcctc ctctgtagaa 205140
ttgtgaggac caaatgggat ggtaaatatg aaactgtgta taagtcataa cattttataa 205200
attattattg tcctggaaac tgccatcagg tttcgagatg ccaagaaggt ccccactatc 205260
cctgtgtata aacggtcaat acataaatta taaaaagtat gggaaaggca agtggtggta 205320
agcctgtatc taaattaggg agagcttttt ctcagaataa attagagtga atattttact 205380
gaattgtatg ccttcctagg ttatggaata aaatacagga atattttaaa cttagctaat 205440
catgctaagt ttcacataat acagaaacat atacacaaaa aatacagtaa gaaaacattt 205500
tgattcacct cagtctctat aaacttgaca atagtccttg atagtgaata gttcaatgag 205560
tgtcatcctt tattcatgag agaagttttt cagagtatta tcggataaat tattttggtt 205620
ttttggtgcc ctcaagacct cattatttca aataggttgt aattgacatt ttccagtggc 205680
agtcaaatac cttaattagt tttattagaa tgaaaataag tagattctgt ctggaaatac 205740
taactaaatt acttaatcaa tttaaaggtg tcctgtatgc ttgtgctgaa atttctgtct 205800
ttgataaata gcctctaact ttacatctgc atagagtcaa actaagcagg ggaaaactct 205860
ttggattttt tttttcagta ttatgctggg tatataattt cacatgtagt atgagaaaac 205920
agtaatgttt ctgtaaaact aaaattaata tattctgttg catcctcatg gatgtggaag 205980
aaatatattc atattatgtt ttgatccact ctattaaagg caattttagt tttttctata 206040
atgattgatg ttaagtggtg atggtaattt gctatatgtc ccataagagt tcaaagcaat 206100
ttttatatat ttgcttaatt ggttgctgct tataacaact gtatggggta gagagtatta 206160
ttatcttcat attatagata gggaaactga ggcatgactg tgttatgtca ttagttcaag 206220
gtcaaaaatc tagtaagtgg agttgctaca cagagacagt cgaacaagtg aaatattatc 206280
tctgcttaaa cactcacaga atatttatag gatgacatta atgaaaacaa gattggttag 206340
ttcttgggtt ctgaaactta aagtgacaag tataattatt tcctagtaca aagctgacaa 206400
atggctaaac tattacagat tttatagtta gagattacaa actagctggg cgcagtggct 206460
catacctgta atcccagcac ttcggaaggc tgaggcagga ggatagcttg aggccagggg 206520
tttgagacca gcctgggcca catggcaaaa ccccatctct accaaaaata cccagaaaaa 206580
attagctggg cacggtggtg cgtgcctata gtcccagcta ctagggtcgc tgaggtggga 206640
ggattgcttg agtctgggag gaggtcaagg ctgcagtgag ccatgaccat gccactgcac 206700
tccagcctag gtgaaagagc gtgaccctat caataaataa ataaaataaa aataaatgga 206760
atcatacaat gtgtggtctt ttgtgactgg cttctttcac ttagcataac attttaaagg 206820
ttcgtccatg ctgtaatata tcagcacttc attttcattt ctttctgttg tcaaataata 206880
ctccatggta tgcagatacc acatttcatg taaccattca tcagttgatg gacactttag 206940
ttgtttgttt ttttagctat tatcaataaa gctgctatga acatttgtgt acaagttttc 207000
gtgtgcacgt atgttttaat tcccggggga gttaatacta gaggtggaaa tgctgggtca 207060

```
tatggtaatt ctatgtttta ccttctgagg aactgctagt tttgaaaaca aatcgagtgt 207120
accatttttt tatccccacc agcagtgtat gagtgttccg atttctccac attctcacta 207180
acacttgtta ttatgtgcct tttcaatcat agccatcctg gtggatgtga agtggtattt 207240
cattatcatc ttgacttgta tttccttgat ggctatgatg ttgagcatct tttcatgtgc 207300
ttatctgctc ttttatatct tctgtggaaa aatgtgtatt cagattattt tttgactggg 207360
ttgtcttttt atttctgagt tgaaagtgtt ctttactgat ttggatacaa atccctcatc 207420
ataaaagtga tttatgattt gcaaatattt tctcccattc tgtgggttgt cttttcactt 207480
tcttgatggt gtcctttgat gtacaaagga gttttttttt ttttaaaaga gatgggtctc 207540
actatgttgc ccaggctgga gtgcagtggc tattcatagg cacaatcata gcacactgca 207600
gcctcaaacc cctggactct cctggcctca agcaatcctc ccaccttagc cttctgagta 207660
gctgggacta caggcgcatg ccactatgcc cagctaaaaa aactttttaa tcttgatgtg 207720
tctagtgtat tttttttctt tgttgtttgt gcttttggtg tcatacaaaa ctgttgtcta 207780
atctaaggtc atgaacattc atggctaggt tttcctctaa gagttttata gtttatctct 207840
tacatttagg tctttgatcc attttgactt aatttttgaa tatgatatga ggaagagatc 207900
aacattacta ttttacacgt gggcatccag ttgtcccagc accatttgtt gaaaagacta 207960
ttctattctt tctttcccct attgaattat ctttgtaccc ttgtccaaaa tcaactggtc 208020
atagatgtat atatgggctt atttctagac tttcaattct attccattaa tttatatgtc 208080
tgtttttatg ccaatactat agtatcttga ttatagtttt tttgtagcaa tttttgaaat 208140
aggaaagttt gctagttctt tttcaagaag tttcttcagg actgttttgg ctattctagg 208200
tcctttgcct ttccatataa attttatgac catcttgtca atttctgcaa agaatccagc 208260
tgaaattctg ttggagtttg cattgaatat gtaaataaat ttgggtagta ttgccatctt 208320
aacattcagt tttttgaccc agaaacaggg gctgtttatc cctttattta ggtcttcttt 208380
catttctttc aacaatgctt tataattttc agagtacaga tggtccttga cttgtgaatg 208440
ttcgtctaga ctttttttatt taacaatggt gttaaagcaa taccatttag tggaaaccat 208500
actttgagta cctatacaac tgttctgttt ttcattttca gtacagtagt caataaatta 208560
catgagatag taaacatttt attataaaat aggctttgag tggggctggg cgtggtggct 208620
catgcttgta atcctagcac tttgggaggc tgagatgcgt ggatcatctg aggtcgggag 208680
ttcgagacca gcctgaccaa caaggtgaaa ccccgtctct actaaaaata caaaaattag 208740
ccgagtgtgg tggtgtgcgc ctgtaatccc agctacttgg gaggctgagg caggagaatt 208800
gcttgaaccc aggagccaga ggttgcagtg atctgagatt gtgccactgc actccagcct 208860
gggcaacaga gtgagaccct gtctcaaaaa aaaaaaaaaa aaaggctttg agttagatga 208920
tttttgccca actgtaggct aacgtaagtg ttctggacac ttttaaggta ggctagacta 208980
agctagaatg tttggtaggt tatgtgtatt aaatgcattt tggacatgat attttctttt 209040
tttttttctt ttttgtttga gatggagtct cactctgttg ctcaggctgg agtacagtgg 209100
catgatcttg gctccctgca acctccacct cctgggttca agcgattctt gtgcctcagc 209160
ctcctgagta gctgggaata caggcacgtg ccaccacgcc cagctaattt ttttttattt 209220
tttatttttt agtagagacg gagtttcacc atgtcggcct ggctggtctc aaactcctga 209280
cctcaggcaa tccacccgcc tcagcctccc aaagtgctgg aattacaggc atgagccaat 209340
gcgcctggcc atacttagga tattttcaat ttacaatggt tttattgaga tgtaacccca 209400
tcacaagttg aggagcatct gtatacattt tgcacttctt ttttttttct ttttttaaaa 209460
```

```
ttttattatt atactttaag ttttagggta catatgcaca acgtgcaggt ttgttacata 209520
tgtatacatg tgccatgttg gtgtgctgca cccattaact tgtcatttag cattaggtat 209580
atctcctaat gctatccctc ccactctcc ccaccccaca acagtccccg gtgtgtgatg 209640
ttccccttcc tgtgtccatg tgttctcatt gttcaattcc cacctatgag tgagaacatg 209700
ctgtgtttgg ttttttgtc cttgcggtag tttgctgaga atgatggttt ccagtttcat 209760
ccatgttcct acaaaggaca tgaactcatc atttttatg gctgcatagt attccatggt 209820
gtatatgtgc cacattttct taatccagtc tatcattgtt ggacatttgg gttggttcca 209880
agtctttgct gttgtgaata gtgccacaat aaacatacgt gtgcatgtgt ctttatagca 209940
gcatgattta taatcctttg ggtatatacc cagtaatggg atggctgggt caaatggtat 210000
ttctagttct agatccctga ggaatcgtca cactgacttc cacaatggtc gaactagttt 210060
acagtcctac caacagtgta aaagtgttcc tatttctcca catcctctcc agcacctgtt 210120
gtttcctgac tttttaatga tcgccattct aactggtgtg agatggtatc tcattgcggt 210180
tttgatttgc atttctctga cggccagtga tgatgagcat tttttcatgt gttttttggc 210240
tgcataaatg tcttcttttg agaagtgtct gttcatatcc tgcacccact tttgatggg 210300
gttgtttgtt tttttcttgt aaatttgtat gagttcattg tagatcctgg atattagatc 210360
cagatttgtc agatgagtag gttgcaaaaa ttttctctca ttctgtaggt tgcctgttca 210420
ctctgatagt agtttctttt gctgtgcaga agcgctttag tttaattaga tcccatttgt 210480
caattttggc ttttgttgcc attgcttttg gtgttttaga catgaagtcc ttgcccgtgc 210540
ctatgtcctg aatggtattg cctaggtttt cttctagggt ttttatggtt ttaggtctaa 210600
catttaagtc tttaatccat cttgaattaa tttttgtata aggtgtaagg aagggatcca 210660
gtttcagctt tctacttatg gctagccagt tttcccagca ccatttatta aatagggaat 210720
cctttcccca ttgcttgttt ttctcaggtt tgtcaaagat cagatagttg tagatatgca 210780
gcattatttc tgagggctct gttctgttcc attggtctat atctctgttt tggtaccagt 210840
accatgctgt tttggttact gtagccttgt agtatagttt gaagtcaggt agcctgatgc 210900
ctccagcttt gttcttttgg cttaggattg acttggcgat gcaggctctt ttttggttcc 210960
atatgaactt taaagtagtt ttttccaatt ctgtgaagaa agtcattggt agcttgatgg 211020
ggatggcatt gaatctataa attaccttgg gcagtatggc cattttaacg atattgattc 211080
ttcctaccca tgagcatgga atgttcttcc atttgtttgt atcctctttt atttcattga 211140
gcagtggttt gtagttctcc ttgaagaggt ccttcacatc ccttgtaagt tggattccta 211200
ggtattttat tctctttgaa gcaattgtga atgggagttc actcatgctt tggctctctg 211260
tttgtctgtt attggtgtat aagaatggtt gcattttgca cttcttttgt taaatttatt 211320
cctgccgggt gcggtggctc acacctgtaa tcccagcact ttgggaggcc taggcaggtg 211380
gatcacctga ggtcgggagt ttgagaccag cctgaccaac atggagaaac cccatctctg 211440
ctaaaaatac aaaattaacc aggcgtagtg gcgcatgcct gtaatcccag ctacttggga 211500
ggctaaggca ggagaatcgc ttgatcctgg gaggcggagg ttgcagtgag ctgagatcgt 211560
gccatcgcac tccagcctgg gcaacaagag tgaaactcca tctgaaaaaa aaattttatt 211620
ctgaagtata ttatttttg atagtgctat aaaagcaatt gttttattaa ttttattttt 211680
catttttcac tgctagtata tagaaataca actgatgttc gtatattgat tttgtatcct 211740
gccaccttgc tatacttgct tattagtcct aatagttgtt tcttagtgaa ttccttaaga 211800
atttctatta atatttacaa gagcacgtca tctgcaaata aagatcattt tacttttttc 211860
```

tttccaatct caataccttt tatttgattt tctcacctaa gttccctggc tagaactcta 211920
gtacaatgat gaataaaaat ggcaagagca gccatccttg ttttgctctg ggtgtttcat 211980
agatgccctt tatccgggtg agggagtttt cttctatgac tagattgttg actttttttt 212040
attatcacaa atggatatta aattttgtca aatgcttttt cttcatatat tgagatgatc 212100
atgtggtttt tgtcatgtat tctattagta tggtatatta tatttattga ctcttgaatg 212160
ttaaatcaac attgtgtttc tatgattgca tttggttatg ttgctggatt cagtttgcta 212220
gtattttgtt gaggattttg tgtctatatt cataagaggt cttggtcttt agttttcttt 212280
tcttataata tgtttctctg ggagggagag gtcgtttgtt ttttagtttc gttttttttt 212340 ctttttgaa acagtcttgg tctgttgccc aggctggagt gcagtgacgt gatcttggat 212400
cgctgcaacc tctgcttccc aggttcaagc aattctcctg cctcagcctt ccaagtagct 212460
aggattacag gtgcccacta ccacatcagg ctaattttg tatttttagt agagatgggg 212520
tttcaccatg ttcaggctgg tctcaaactc ctgacctcaa gtgatcctcc cgccttggtc 212580
tcccaaagtg ctgtttctct agttttggta tcagagtaat actggtctca taagagttgg 212640
gaagggcccc tctccctcca tctttttag tcttcgtcca gttgactgac ttttgtgtgt 212700
tagtgtgcat gaattttctt ttcaccacac actctaaagt agacactttt aacaactgat 212760
gaattccctc atatagagtt tctttgttct atcttgatct tttttcatag aattatcttt 212820
tgttggggca cagatatgca ttatcagagt tgtttctctt caagcagaga agaacaaatt 212880
atttaggagt tccgtttgtg catatcgatg ctatgtatac tgttagaaga atcacatgat 212940
catttaagtg tcaaactgag agtcaaaaga cttggctggg cagggtggct ctcacctgta 213000
atcccagcac ttgggaaagc caagttggca ggattgcatg aggccaggaa ctcaagatca 213060
gtctgggctg catagagaga ccccatctct atttataaaa aggttttgag gctgggcacg 213120
gtggctcaca cctgtaatcc caacactttg ggaggccgag gcgggcagat cacatgaggt 213180
caggagttca agaccagcct ggccaacatg gtgaaacccc atctctacta aaaatacaaa 213240
aattagccag gtgtgttggc acgtgcctgt aatcccagct actcgggagg ctgaggcagg 213300
agaattgctt gaactgggag gcagaggttg cagtgatcca agatcacgcc actgcactcc 213360
agtctgggcg acagagtgag actccgtctc aaaataagta aataaataaa aaataaaagg 213420
taaacactca gtgaaataaa aaaaaattct atgggatata ggaacaacaa tgacaatagt 213480
aaacatatgt tgtatactta cactagacta aacagttcac aaatactgaa gtcaggtttt 213540
ctggcaaaac aaccagctct gctgtgaaaa aataaaatct ccagttccag acagaaactg 213600
aagattgtag gaagagaaat aagacaacta ttctcagtca ctacagaaga tcataataaa 213660
ctcctcaact ctctgttgga taaattcttt acaaatggaa attaaaatag taacacttaa 213720
aatgtatagt aattttaagc tttaaagtgc tttgcatgtt attcattcag agcactaaat 213780
ctaaaacaat ttaggccagg tacagtggct cacgcctgta atcccagcac tttgggaggc 213840
caaggtgggc agatcacctg aggtcagggg tttgagatga gcctggtcaa catggtgaaa 213900
ccccgtctct gtgaaaaata caaaaattag ccgggcgtgg tggcacgtcc ctgtaagccc 213960
aactactcgg gaggctgagg caggagaatc gcttgaaccc cggaggcaga ggttgcagtg 214020
atccaagatc acaccactgc actccagcct gggcgacaga gtgagactct gtctcaaaat 214080
aaataaaaaa taaaaggtaa acactcagtg aagtaaaaaa taatttctat gggatatagg 214140
aacaacaata atcatagtaa acatatgttg tatacttaca ctaaacagtt tacaaatact 214200
gaagtcaggt tttctggcag aacaaccagc tcttctgtga aaaaataaaa tctccagttc 214260
cagacagaaa atgaagattg taggaagaga aataagacaa ctattctcag tcactacaga 214320
agattataat aaacccctca actctctctt ggataaattc tttacaaatg gaaattaaaa 214380
tagtaacact tcaaatgtat agtaatttta agctttaaag tgctttgcat tttattcatt 214440
cagagcacta aatctaaaac aatttaggcc aggcccggtg gctcacgcct gtaatcccag 214500
cacttttgga ggccaaggcg ggtggatcac ctgaggtcaa gagttcgaga ccagcctgac 214560
caacatggtg aaactctgtc tctgctaaaa atacaaaaat tagccaggcg cagtggcaga 214620
cgcctgtaat cccagctact tgggagactg aggcaggaga atcacttgaa cctagaaggc 214680
ggaggttgca gtgagccgag atcacaccat tgcactccag cctgggcgac agagtgagac 214740
tccgtctcaa aaaaataaaa taaataaata aataaataaa acagtttaag catctgctct 214800
ttgaaatcca aataccattt aaggtactct aagccttaat agctgagtga aaatacagtg 214860
ttggagtttt acaaaattac ctgtatttta gtaatttttt tgtcaggcca aacttaatta 214920
tctgggagaa atatatatag atagatagat atgatatatt tatatgtgta taatatatat 214980
ttacatatgt gtgtaatata tatgtaattt ggatacaatt tcctattcaa ttgatttcag 215040
cagaaacgta ttaaatatag aaagtagtac tgtatagcag cagtccccaa cttttttttgg 215100 accagtgatc tgtttcatgg aagacaattt ttccacagat agggtgcggg tggtctgggg 215160
ccattagatc tcataaggag cttgcaacct agatccctcg catgcgcagt tcacaatagg 215220
gttcgcactc ctatggcaat ctgatgctgc cactcatctg acaggaggca gagctcaggc 215280
ggtaatgttt gctcgcctgc cactcacctc ctgctgtgtg gcctggttcc taataggcca 215340
caaactggta ctggtcagag gcctgggagt tggggactcc tgttgtgtag ggaggaaaca 215400
cacatgcaag agacagtgtt ctatttgatg ttttctggag atgctatcgt gaagacactg 215460
tagacttacc tttttaggct tagaaaatgt ttatattaaa tctcaactgt cagagtccag 215520
attgaaggct gttctaaagg catgacctta ttcatcataa cacttttgct gctaaaacaa 215580
gcttcagaca cattcagtac attttgtttt gatccaatat ttatttgatc cagaggcctt 215640
tccttttgaa gggcgttttg gaaacagcct tatctgtaat catgtgtact aattgaataa 215700
cgtttacact ttccagtgca aatttgctta attttcaaag gaaaaaagga aaacaaaaac 215760
acttctgaca taatcagttt tcactgagat tgtatagaat agagattttc catctccttt 215820
atgaaaaatt caaatgacat ggctattcat gaaataccat attacataat taccaggttt 215880
ttcactgaaa actattgccc aaatagtctg ggtaagcaaa ttcatcatca cctctggaga 215940
tacagtctgt tataactaat gaaatccagc taagatttgt attcaaatat ttcctgactc 216000
taaaatgaaa gagttgcttt tataaaattt tcaaaattgt gagaacagat gtgtttgcca 216060
tgtaaaaaca ttttggttgt gggaggtgga ccacagctaa ccaattgttc acaatagcta 216120
acattgtaga accttcagta ttaaattcac taactcactt catcatcaaa attccctatg 216180
aggcgttact gtgctccttg cataggttac caaactgaag ctttctcaga gtcacatagc 216240
taagtaaatg ttggtcccga gatttgactc cagtgttctc tgatgccaca ggcccagttc 216300
tttacctgca gtactatcat ttgggaataa tttggtttct gcagccataa tatataattt 216360
gtgggttgct ttcctttcat aggtatggac aaacactatg tcataaaatc agagctacaa 216420
cttaaaagcc tctaaataac accttgagat aacaaaactg tatcttaggt tctaatatat 216480
gtgatcatac tatacaggca gtccttggtt tgcatagtag tctgggacag taaaaaatgg 216540
tcatgcaaac tgaaaccatg caaaacaaac ttaataatta atggggaaat ttacaattgt 216600
tttgtgatct ttaaatattt ttgtgaaaca ttaaaaagtc tcttactgtt ggttataaat 216660

```
atatatagaa atgaaaatat agtaaaacta cttagtactt cataatttaa aacattagga 216720
atattgagag ttaacctttt atttctttgt aaacagctta tcaagagtat tttgatcttg 216780
ccttcccata aagcttaggg ccgggcgcgg tggctcacgc ctgtaatccc agcactttgg 216840
gaggccgagg tgggcagatc acgaggtcag gagttcgaga ccagccgcca ggctgaaacc 216900
ccatttctac taaaaacccc atggtgaaac cccatttcta ctaaaaatac aaaaattagc 216960
caggtgtggt ggcgtgtgcc tgtagtccca gctgcttagg aggctgaggc agaagaatcg 217020
cttgaacccg ggaggcggag gttgcagtga gcgtaaatca caccactgca cttcagcctg 217080
gtgacagagc tagactccat ctcaaaaaaa aaacaaaaaa aaaaacttag gacactgagc 217140
aagaatcttt tctatgcttt ggcaaattgt catcctcatt tctaagtttg gatcaccttc 217200
caacatttta tcctctgcac tttaaacatc tggaaatatc tttgtgagta cctttaatgt 217260
gccagcatca cttcctcttc gacattttca tcctttttgc aactactgta ctgtactttt 217320
ctttttcttt ttcttttgag atgaagatgg agtctcactc tgtcgcccag gctggagtgc 217380
agtggcacaa tctcggctcg ttgcaacctc catcccccgg gttcaggcaa ttctcctgcc 217440
tcagcctccc cagtagctgg gattacaggt gcgtgccacc ttgcccggct aattttttaa 217500
aatattttta gtagagacgg ggtttcacca tcttggccag gctggtcttg aactcctgac 217560
ctcgtgatcc acccacctcg gcctcccaaa gtgctgggat tacaggcatg agccaccaca 217620
cccggccata ctgtactttt tcatttaata gattgaaaaa tttgcctcca ctaaatttct 217680
ttgggtgaac atctaaagtc cctcaaacag cattagtgtc aacatttcca tattcagtta 217740
tttcttctat aactccattt aggtagtttt ggggattttt ttagaggcag ggtttcacta 217800
tgttgcctca gctcctgggc ccaagcaatg cttctgcctc agcccctgga gtagctagga 217860
ctacaggcac accccactgc acctggctcc atttatgttt tttttttttc agatttcatt 217920
tccaacattg tcactctttg ttgctgtcct ttctttcttg taattcattt ttgtaaaaca 217980
tcacatggat ttatcactag gagacaagac aaggcaacta catccttagc tgtctatgag 218040
tgaactgaat aacagatacg tagtaaccaa tcactggccg actttgaatg aagtggtgtc 218100
attggccgtt ggtcatgatg ttatgtagtg attttataga ctgaagtgct ggcagcaaag 218160
attgtgcgtt atgcattgct cacaatcaat atatttggtc attgaaattt ggaccatggt 218220
ttgaggagta gctggtgttt taactaaagc atagtaactg aaacttaccc atatcagaac 218280
ctcgccaaga gaggactacc atgaaagtta aatgaggggc attaggttcc ataaaggatc 218340
ataaaaatac tactctactc tattatacat ttacatatac acatgtgtat cctaaagtaa 218400
taagctagtt ttaaaatatt aaccatactt aatgattaat atttattata tctaattata 218460
ataattttac ttgccaccta gggatttaga agagttcaga gggatttaat gtatgatcca 218520
ggaagtttga aagtttgaat tgggccaggc gcggtggctc acgcctataa tctttgggag 218580
tgtaatcttt gggaggccga ggtgggcgga tcacgaggtc aggagatcga gactatcctg 218640
gctaacacgg tgaaacccca gctctactaa aaatacaaaa aaattagctg ggcgtggtcg 218700
tgggcgcctg tagtcccagc tactggggag gctgaggtgg gagaatggcg tgaacctggg 218760
aggcagagct tgcagtgagc cgagatcgcg ccactgcact ccagcctggg agagagtgag 218820
actccatctc aaaaaaaaaa aaaaaaaaaa agaaagtttg aatagatact ttcctttaga 218880
tatgaagaca ttcagcatca attcattgct cttaaagcag atctcatgat ggtttatttt 218940
ttaaaaagaa gaagaaagaa aagaaaacac aagtgcagaa ggatatgaac accatgatac 219000
ttcttataga acaataatgt aaacaatatt atttggttat tgagaaacat ttacattata 219060
```

```
aatgtaaaaa ctcataattc ataatattca cccatatgga aggagagaaa atggtttaaa 219120
atttttccac attgcaattt cttatatacc tatgtttaat gagacagtat tttatatgga 219180
cacctgagtg tttttcatca cacggtaata cttacatatc acattattca aattaattac 219240
taatatttaa aattcctatt ttggactgaa ggaattgaat tgacttataa gttgttcttt 219300
tagccctaaa attctgtatg tattctttga cttttatatt agaaaccatc aaagctgggc 219360
gtggtggctc ctgcctataa tcctagtact ttgggaggca gaggcagggg gctgacatgc 219420
gcctaggcat tcaacaccag cctggacaac atagcaagac tctgtctcta cacacacaca 219480
aaattagcca ggtgtggtgg tgcatacctg tagtcccagc tactcaggac actgaggtgg 219540
aaggatcact tgagcctgag aggcagagcc tgcagtaagc cctgattgtg ccactgcact 219600
ccagtgtggg tgacagagcg agaccctgtc ttaaaaaaag ataaaaacta tcaaatgtag 219660
tgcgtgttta ttttggggac taaatgctta tttttaaggg gatggttaaa gtactcagca 219720
ttatttaggg agttaaagcc ttaggtttta aacctgattt ggggttgagc tctgggaagg 219780
aaaagatgat tgattcatag gcaccctgat acagtcactt atgatctgaa aagcagatgt 219840
actctaaggc actcaaaata aaaataacac cagtcctatg cttatctctt aaagtcatgt 219900
tgttttctgc aaggtgttaa aaatcaaaat aagattgttc taataacatt gaagtttcgt 219960
cagtatatgt gtatgataca agcgaaattg atgggtaact acttgcagta taattctttt 220020
agaattatgt acttttagat tgacttacca gaactgctga aataaaaaac actccaattt 220080
aatttgaaat agtgggaaca ttggctctgc tgcagtgatt ttaagtgtat acatgcccga 220140
ctgtgaatgg attaagttca tcattggtgc tgccttgagg tgattcagaa actttctttt 220200
gccattgcag gtagagcggg aaaaggccat tcttttggcc aacctacagg agtcacagac 220260
acagctggaa cacaccaagg gggcactgac ggagcagcat gagcgggtgc accggctcac 220320
agagcacgtc aatgccatga ggggcctgca aagcagcaag gagctcaagg ctgagctgga 220380
cggggagaag ggccgggact caggggagga ggcccatgac tatgaggtgg acatcaatgg 220440
tttagagatc cttgaatgca aatacagggt ggcagtaact gaggtgattg atctgaaagc 220500
tgaaattaag gccttaaagg agaaatataa taaatctgta gaaaactaca ctgatgagaa 220560
ggccaagtat gagagtaaaa tccagatgta tgatgagcag gtgacaagcc ttgagaagac 220620
caccaaggag agtggtgaga agatggccca catggagaag gagttgcaaa agatgaccag 220680
catagccaac gaaaatcaca gtacccttaa tacggcccag gatgagttag tgacattcag 220740
tgaggagtta gctcagcttt accaccatgt gtgtctatgt aataatgaaa ctcccaacag 220800
ggtcatgctg gattactata ggcagagcag agtcacccgc agtggcagcc tgaaagggcc 220860
cgatgatccc agaggacttt tgtccccacg attagccagg cggggtgtgt catccccggt 220920
agaaacaagg acctcatctg aaccagttgc aaaagaaagc acagaggcca gcaaagaacc 220980
aagtccaact aagaccccca caatctctcc tgttattact gccccaccgt catctccagt 221040
attggataca agtgacatcc gcaaagagcc aatgaatatc tacaacctta atgccataat 221100
ccgggaccaa atcaagcatc tgcagaaagc tgtggaccgg tccttgcaac tgtctcgtca 221160
aagagcagcg gctcgggagc tagcccccat gattgataaa gacaaggaag ccttaatgga 221220
agagatcctc aagctaaagt ccctgctgag caccaaacgg gagcagatcg ccacattgag 221280
ggcggtgttg aaagccaaca agcaggtaat ctcattctac tggtgaaagc atgccagtca 221340
aagctttctt aactaattta ttccctaatt ttattgagta tcgagtatcg tcaagatgag 221400
agttcagatt cttggtaagt ggataaataa aactgtccca gtgccagatc agaatgtcat 221460
```

aataattatt gtttttaaat gatgaaatac ctgtgcccag ttaggtggag gcagaggtga 221520
ggaacttaaa gcaggaacac aggagaagat ctagatgcct ttctgcagat gtagaaaggc 221580
agctcaggcg gtgctgggct gaagcctggc agtgagtggc tgtggaaaca ggagatggag 221640
ggtggcagaa taggctggca aggcaggtta caccaaccag ggcgatacag caagaaagac 221700
aaacacccag caggcagcta gagcaaacag agggaaatct gggtacatat ggtgaagaag 221760
gtctgatggc caataactgg accccagctt tggagctgga ggttcagatt caagactcaa 221820
tttctaggag tatagcaaaa ttattattat tattattttt tatttttgtt ttgagacaga 221880
gtctcgctct gttgtccagg ctggagtgca ctggcgccat ctctgctcac tgcaacctcc 221940
gcctcctggg ttcaagcgat tctcatgcct cagcctccga agcagctgag attacaggca 222000
tgtgccacca tgcctggcta actttttgtg gagacagaat ttcaccatat tgtctaggct 222060
ggtctcgaac tcctgacctc aagtgatccg cccacctcgg cctcccaaag tgctgggatt 222120
acaggcatga accaccgcgc ccagccaagt atagcaagat taaaaggagt gttttgtcct 222180
tcatcccaaa cttagagaaa caagagcgct aaataaatga ataagtcagg gatgaaaggc 222240
aagacaactg tgaggacctg agtgagtaac agaaacaaag ccagacagat tgttaccaac 222300
aaattaaata gtttggggcc actttagcaa ggaaataata gagagtgtgt gtgagagagt 222360
ataagaatga gctctacctg tgctactgac cacgtatctg aaatttaggt tcatttggga 222420
tgttaaccca cctgggtcag aggttaagta atagggagct tttcctagct attgatcttg 222480
tccttctgga caagtagtaa tgttacaaca tgaacctgtc taattcccag ccctccttaa 222540
tgactgaaat tgttttcacc ctgagtttta ccttggtggg agtgctgcga aatataggca 222600
ggaaaattat tttcaccttt atttagttta tctgaaaaga tattcttgaa agacacatat 222660
ttgagaaagg tgctgaataa atgttggtgt tgataaagag aagcaacaaa gcaccaaata 222720
ccctcctgca aacgcaagca gtgccagtga atagtaggtc aagggagctc ttggtctttg 222780
gagaatgagg attaatttca gattcagagt gtcttctcca tttgccatca tctggggaaa 222840
accacgccct tattatctca tctacagtgc agctttcaag tcctcatctc tagttcccat 222900
aaatctattt atataattga catctatacc ataagccata atattgtttg cactattaac 222960
atgttttata taaacctaag ggcaaaatat gactttattt tatgttgtca ctttagagaa 223020
atagaaaaga ttagagtgaa tgaaaccatc attctcagca aactatcgca aggacaaaaa 223080
accgaacacc acaagttctc gctcataggt gggaatcgaa caatgagaac acatggacac 223140
aggaagggga acatcacaca ccggggcctg ttgtggggtg gggggagggg agagggatag 223200
cattaggaga tttacctaat gtaaatgacg agttaatggg tgcagcacac caacatggca 223260
catgtataca tatgtaacaa acctgtacgt tgtgcacatg taccctagaa cttaaagtaa 223320
attaaaatat atatatataa aataaataaa ataaaaaaag aaaagattag agtgaatgaa 223380
gaatttgtga gagatctgac tctaatttta ggtcggaata aaggaattta ttattgtaac 223440
tctgctataa tttaaagacc caatgattca gagtggtcat aaataaccaa taccatatta 223500
gataaggctt acacaaggac atgctatcct ggggcattct tgatcaagcc atccagataa 223560
cttctctgac ttcttcctaa aggttgaata ttaacaattt aggtctgggc gcaatggctc 223620
acgcctgtaa tgccagcact ttgggaggcc aaggccagtg gatcacttga ggtcaggagt 223680
ttgagaccag cctgaccaac atggagaaac accgtcccta ctaaaaatac aaaattaacc 223740
aggcgtggtg gcgggtgcct gtaatcccag ctactcggga ggctgaggca ggagaatcac 223800
ttgaaccccg gggggcggag gttgcggtga gcctagattg catgattgca ctccagcctg 223860

```
ggcaacaaga gcgaaaatct gtcttaaaaa aaaaaaaatc aagatgctta actgaaacag 223920
aggtatagat aaggacactt ggccaaccaa cagagactaa tttgtgaaca agcattcatt 223980
gattacatat tttctgggag gcagtaagta gggatgcaaa aataaatgac ataatctagt 224040
aggaattccg caattgcctg tagctgttta caagacagga cttatcaagc actttagagt 224100
gatgtaaaca gtaccacagg aaatcagaac agaacaaagc attcctagct gaagttttat 224160
tttcactgtg ctttgtggta caggttgagt atcccttttc cgaaatgttt tgggggacaa 224220
gaaatgtttc agattttgga ttttggacat ttgcatatat acataatgag ttatcttggg 224280
gatgggatcc aggtccaaac atgaaattta cttatgtttc atgtattcct atatacatag 224340
cctgaaggta attttataca attttttaa tgattccgtg gctgaaacaa agttttgact 224400
gccactcatg acatgaggtc aggtgtagaa ttttgtggct catgtcagca ctcaaaaggt 224460
ttcagatttt gaagcatttt ggattttgga ttaaggatgc tcaacctgta ccatttgcat 224520
tacattagag ttacagtcta tatgggctca gtaaattaaa tgaaaacaca tttctagcaa 224580
tgcatttggt ctgcacgttc atgatgttgg ggctgttgct gtgatgctta ttgccgtaaa 224640
tagcttcaag tattaacaga tgacattcac tatatttatt tagacattgt gaaatgtttg 224700
tttttaaggt taaggtgaga attctggggt acaggggaaa aaaggaaatc tccctgtttt 224760
aaaataggca ttctactata cagccataag aaagaaaaga atgagatcat gtcatttaca 224820
gggacatggt tggagctgga gaccattatc cttagcaaac taacacagga acagaaaacc 224880
agataccgca tgttctcact tataagtggg agctaaatga tgagagcaaa tagacacata 224940
gaggggaaca acacacactg gttcctgttg gaggctgaag gatgagagga aggagatgat 225000
caggaaaaat aacaaatgga tactaggctt acatacctgg tgaagaaata attggtacaa 225060
caaaccccca tgacacacat ttacctatgt aacaaacctg cacatcctgc agctgtaccc 225120
ctgaacttaa aagttaaaaa taaataaata ggcattctgt agtctctatg aatcttctca 225180
tttacttaag gattttttca taggcacagt gccttctgat gaagtcagta aatgcttatg 225240
aagcaccgtc catctagcac tgtgctagat gctgaagatt caaagaagac taacacatgg 225300
tccctgcctt ccagaagact cagcctcctg gggatgtcag gatagaaaca caattacagt 225360
tcaacgttac acatgctgta atccaagtta tgagaacaat gcagaggaag caactaaggt 225420
ttcctagagg agcggaaaag acttcacaga agcaattata ccttagtttg ttattaaagg 225480
ataagaagtt gttttccaga ggaggaggaa gtaattccag acagaacagt aggtagagag 225540
gctttggagt gacaaaatag aataatatat tcagggaatg ctcacaaagg cctatgtggc 225600
tggaaataag actttttta tttagaaagt caactttgga atgtgtggag aaagtggtga 225660
aagcagaaat cagcaaatcc agtgagttat ggatacttaa aattacttaa ttctggaaaa 225720
actttgcaca gtcaatggac aaacaaatct acaaacaaaa ctgaggcttt ggggtatttg 225780
tcacaaacaa taaatgattt tgtatttctg tttcagatct agctcttctg ttatccccca 225840
ttttattccc cttagatact gaccatggga ttctatgtgc ttacaaattt gttacatcta 225900
catttcacaa cttaaacata cttttctgtt ttaaatgaat atgtgtctaa gctttttaaa 225960
cactaaacaa ctgccgtttt tccccaggtc aatttctgcc ttgtggataa ttttctgaat 226020
ctgtaatatt tctgaagatt cctccaagta tttacagaac atacagaagt attttatgag 226080
taaagtctca ttttaatctg aatttaaatc caatcaaaac tcacaagaaa ctacttcgga 226140
atcaaaacag taacaaagta ccctatccca acattgattt aattaagaaa gaatttattt 226200
ctatagatgt tggcactttg catatgaagg tttgaagctg cccatttcaa gcaacaaaaa 226260
```

```
gaaatgttaa aaaccaaggt agtcttcctg ggaaatcccg ttagtaatgg atttctctgc 226320
tagtaatggg gttgttcatt agtatggggt atttgtatac actttgaaaa gttatagttt 226380
ccagtttgta aaaatcatgt gttcccagtt tggcttcaac atgcaaactg tgtgctatgc 226440
atcaaacagg caatccctaa gtatacactg attttatgca ttgattcagt cagtgtgttt 226500
ttttacttgt gtgtgtgcca gggtagctct tgatttgaaa cactattaat tccaagaact 226560
tcggacatgc ccaaatccca gattcaaaca aatgttttaa ctcattcaac attttataac 226620
ccctactttt atggagattt tgaaggaatt atatttcact atatttcatt gtttggacaa 226680
attgtatgca aattagaaag taattagttc tttatcactt cttttcctta aatgtatgat 226740
aacatggatt tatagtttat catatactca tattataaat tacaatggtg tatgtctttt 226800
attctatgtt ttgggcccac agagcacagg tgacaaaatt tgagttctaa catattccaa 226860
tttgattatt cctattgaag ctgtgcttct ttactaaata attggtaaaa aaattttttt 226920
tgtataaagt ttcattttgg ctccctcctt gtcctaaaat cgcatacttt cagcaatctg 226980
cattaaatat ttattaaact actgtcattc tcttagctcc tgatactgac tctggctcgc 227040
agcgggcttc tagggcaatt taaccacatt atgaattcac aacacatttt gacattaaag 227100
aaaaacttcc ctgtgtccaa agcgcatacc tatgtttata taaaatgtaa ccaaatcaat 227160
ttcactttcc ttttataaaa gaacataata ggcacagcat gaagcaatct gtatgatgga 227220
ttttcctgat atgaaaattg taagcagtgt gattttctgc tttagacagc tgaggtggcg 227280
ctagctaatc tcaagaacaa atatgaaaat gaaaaagcaa tggtgactga aaccatgacg 227340
aagcttagaa atgaactgaa ggctttgaaa gaagatgctg caaccttctc atccctgaga 227400
gcaatgtttg caacaaggta acagtatttt cttcctatga ctgggtgtgg taggtggggt 227460
aaaggcttta aaattcacag ccctgccttt gtgcatgttg agtgtattcg gtgagtagtc 227520
taggatggct aagtgtgaag aaaatctgtg gaagtccact ctgacgtatc taaaagcaag 227580
ccttctgtgc tgttttccag agccccctac tgaacactct ggatccagaa attctattac 227640
ataaaaatat tttttaagta agctaatatt aataggttgt ttctagaatt tatgcacccc 227700
aaagagagtc tccctccaaa taaaaagctt tcaataagga aaaaaacccc acttcctaga 227760
atagctaaat attatcacct ctgaaataga gttctgtgaa ggaagtacat gaaagtatat 227820
aaaagtgcct tacctttagt actgtgcgag aagatactgt cataatgaag attaataatc 227880
atcacatcag ctaattactt ataatttttt tttttttgga gacggagtct tactctgttg 227940
cccaggctag agggcagtgg tgcgatctca gctcactgca acctccgcct cccgggttct 228000
agcgattctc ctgcctcacc ctcccgagta gctgggaata caggcacctg ccaccacgcc 228060
cggctaattt tttgtacttt tagcagagac ggggtttcac cctgttagcc aggatggtct 228120
cgatttcctg acctcatgat ctgcccgcct cggcctccca aagtgctggg attacaggcg 228180
tgagccaccg cgcccggctg tattttgtgt ttaaacatga agtgattgtt aagaatgtat 228240
ttgatttgaa gttttcagaa tcttgagatt ttcaatatac tgttgaaata catttttttgc 228300
tgtcacaatg cagtgtcaaa aaagacctac tttttttttt ttttttttga gatagggtct 228360
cactctgtca cccaggctga agtgcagtgg cgctatctcg gttcactgca gcctggacat 228420
cctggactca agcaatcctc ccacgtcacc tcagcctccc gagtacctag gactgcaggc 228480
ttgcactacc acacccgcta atttttgtgg tttttgtgga ggcagggtct cgccatgttg 228540
cccaggctgg tctcaaactc ctgggctcaa gagatccgcc cacctcggcc tccaaaagtc 228600
ctgagatacg ggtatgagcc accatgcccg accaaatcct accaattgtg tatcttgtat 228660
```

```
gatgcaaact tggtgcaaaa ttcacgaata attactatgg ctttacttgc agatttagta 228720
aataatttac atttggctga tacatgtaaa agtgttaaaa acaaacaaaa aaagatctct 228780
tgagctttat aggagtcccc cagaaactga gatcacacca ctgtactcca gcctgggtga 228840
cagagcgaga ctccgtctca aaaataataa taattttta taaaaaggaa ttgttatccc 228900
caaattgtct attttcacag actttttttt ggcatgaaca gtatttgtta ttcatatttt 228960
agcgggtaaa taaactcaga aaaaaaacaa aacaaaattc agaatgagct ttttctccac 229020
gccacctcta ccttccaaat gtatatgtgc caggttttgc ctttggtaag gaaaaaagat 229080
cactaagctt atctttcttc ttcggcacaa gtatgaaacc tgaataaaga tgtttcggac 229140
agcctgctgt atctgtatga aaccttgtga aatcttggtt tttgcagggt tttctgtttt 229200
ttgtttttttg acaactcatt gctctgtcat ctggttgaga aatcattgaa aatactcagt 229260
tttctaattc aggcaaatca gtcaaattga caagaccaac agctgcaatc tatactaaac 229320
taaaacgtat aaatatagat aaggaaatgt tttctttata aacattatta ttttggatac 229380
tataggcata gcctataata aacttgttac attcctccaa agaatacaat gtcatacagt 229440
aaaaagagct actgtaagac acttcaggta tagtggacat tgtgtgagac ttgactgtta 229500
ttcgtctgtt acacagcagc cccacgataa ctctgtccct ggggtttaag acattgccta 229560
ttaagactgt ctccatatgg gctgggtgca gtggctgata cctgtaatcg cagcactttg 229620
ggagactgag gcaagaagat cacttgaggc caggagttcg agaccagtct gggcaacaca 229680
gtgagaccct gtctctttaa aaaataataa tgactgggcg tggtggctca tgccagtaat 229740
cccagcactt tgagaggcca aggtgggagg atcacttgag gtctggagtt caagaccagc 229800
ctggccaaca tggtgaaacc ccgtctctac taaaaaaaat acaaaaatta gcttggcatg 229860
gtggcacact cctgtaattc cagcaactcg gcaggctgag gcatgagaat cgcttgaacc 229920
tgggaggcag aggttacagt gagccaagat cacgccactg cactccagcc tgggcgatac 229980
agcgagactc agtctcaaaa aacaaataaa caaaacaaca acaacaaaat aataataaat 230040
tttttaaaaa tgtcccatat atctcattgt atggatgaac atatattcca gttttctgct 230100
attgtgggtt atctacattc tattgctaga cctttaaacc agtcttctaa atttctaaat 230160
ttcggtcaaa tttattactt ttcagcttaa ctcccaaatt cagtttcacc aagattttcc 230220
tctgaccact tctctgtttt ggttccagat gtgatgaata tgtcacccag ttggatgaga 230280
tgcagagaca gttagcagct gcagaggatg agaagaagac tctgaacact ttgttacgaa 230340
tggctatcca gcaaaaactc gccctgaccc agaggctgga ggacttagag tttgaccatg 230400
agcagtcccg acgcagcaaa ggcaaacttg gaaagagcaa gatcggcagc cctaaagtaa 230460
gtggggaggc atcagtcacc gtgcccacca tagacactta cctcctgcat agtcagggcc 230520
cacagacacc caacattcgg gtcagcagtg gcactcagag gaaaaggtat gcatgcagcg 230580
atcttcatag tacggtgcag tggccagatt ttagttaact gcaaaaaataa atgtgctctt 230640
gttgtggagg atggaggagg ggaagcaaaa gaaaaaatgg gagctggcat ataaatggtc 230700
ttgctaatgt gggtctttcc agatcaaaac ctttttgata attgtgttta tgtagtcctt 230760
tctaaccccc tgcccaatcc ctcctcttga ttaatcgtaa tataattttc aagtgtctgt 230820
taatattttt gctactcttt gtatgtgtaa atatgcctct cccttacctc caacctgaga 230880
attggtagat aaaggtggat attaagaatg aagctgtgtt ctacctgggt tataatttta 230940
aaagtcattg tacctttgga aatggtgctg tttatcagct tctctttaac ggggcaagga 231000
tatgaatatg ttctcttagg gaaacttttg tccatatgac caaaactgat gacagactga 231060
```

aaggggatgt ctatatctag ataaaatggg atggaatacg cacagtcctt ttcttgaaag 231120
caggtttttg tgctttttca tttggcatgg gaatattgcc cagagaaacc acttgtaagg 231180
tttttagggg cttgattttg tgagtcctgg ctgttgagtt acttaccctg tattttcggt 231240
taatggtaac atttttattt taggagcttt cattaaagac tcaaataata tattttctat 231300
ttgcggttca agctgactaa ctgtaataaa tctttttttcc agtatccaga acagtttcca 231360
aatagggttg tatcctgatg tggaaactaa aaaaaaaaaa agcaaaaaga ttgatttaca 231420
tatttaaaaa attaaatgcc agtataaata atgttgtcac tggtgaggcg ttaaaaggta 231480
attaaagtaa aactttttttg tttcctatat gtatttttct tggatctcct gcaagacaat 231540
tttcaccttc cctttgtgat cagagccgtc ccaggacttc aggggcttcc tacctacaga 231600
atttattaag agttcccccct gatcccacct ccacagaatc atttcttctg aagggccccc 231660
cttccatgag tgaattcatc caagggcacc ggctcagcaa ggaaaaaagg ttaaccgtgg 231720
ctccaccagg taaacatttt ttccttgggt gcatgtgatg caaatgatta gttgaataga 231780
ctctcccctt ccttccggtc actcaggctc acccagctgc agagtatacc tttgatgatg 231840
tgtaaattcc tataagtcaa gtaaaaactt ccttacactt agcttcccat ttcctccttc 231900
actcatattc cttagaatga cagacttcca tttaacagcc aaagatggca aatgagagtt 231960
ggaaggaatg ggataggtaa agggaaatta gcaacaagca caacgcacac acacttggat 232020
cctatttgca gtttggtagc tcatggcgat tccatcttgg tcagatttgg ccagttctct 232080
cttatcgttt ttaatgtaat ttccgtaaag ggagagccat atgtataaca aggcttttgg 232140
gctgatttcc ttttgtggtg actcagaacg tctcctcaat cattatattg agaataaaag 232200
taaaaccttc taagattttg ctcctcaaga acatttaggt cttagtataa tgttcttgta 232260
gattgcaggc cccccactgg ttaatgctta ccaacatgtt cacacttagc ttcactattt 232320
tgcatttttc tttcttcctt ccttcctttc attcttttta cttgttctat gaagaggcct 232380
aacttgaaaa tgtgacatat ggcaaataga gaaaattatt cttgcaaata aaaatcatcc 232440
ttttaaggaa tccctgcatg tgagtatagg gcagaagtgg caaacaagga gcccataaac 232500
caaagtaagc ttaaaggcag ctgttatttg actattgcca gaaaataaaa aataaaacta 232560
tttaagttag ttattgacag ttaaaaattc aagagatttt atatgaacat cagtatttct 232620
ggcctctttt ggaagattct gaatatctgg cagccctagg tctgcgttca cgcatgtcaa 232680
cacctgttgg agctctgtag tggctgctgc tgttagggca agcttcgcac tttgccacag 232740
tcaccactcc tccttattac ttatacccag cctgctatcc tcatttctat tctctcctgg 232800
cccctcctgt agtctttgag tttgccaccg ttgaaataga atttttttttt tcattttacc 232860
ttaattcctt tttgcaaacc tcagcctttg gatctctaat actttcctta tctgattcat 232920
gaagtcagcc tactgattgg gattaaaaga tgtggtgtag aaactgatag tgcatttcac 232980
gttctaaagg tgtttgagga aattggtagt gataatgagt tggaatggtg taatagccaa 233040
aatatacacc taagaagaaa aaaagtaaaa actgcttggt gtttttaatt tcataactga 233100
tttcctattg ttttagacct ccttggaagg taccttgaag tattctgtga atcaccaaag 233160
tggtaatgat ttatcaggat acctaactcg gataaaaccc acaagtcttc tttttagtgt 233220
tccaaatgga tttagtagca ctatctactg gaacttagaa aagaaattgg tatgattaat 233280
aaataactcc tattgctgtt taattaaaaa gataacatct caataaggtt aaaaattaat 233340
aatcaatgtt aacaacaata actgttttca tttttgtatg actggttttt gtttacatga 233400
atatatactt tatattgtta tcattacatt gtttaagcca tgaacattat atcacaagct 233460

```
tttccatgtt gctatctagt cttgttttta tttgttaaag ttattgtatc atagattttg 233520
tttcagatgc tgttatcaca ttaatcacta cttctcttct tgtccactga ggtagttttt 233580
cattatttgt tatattatag agcactgctg ggaataccct catgcattca gcttctcatc 233640
tattacattt ttctcaagag tgagatcact cagttaaaag ttgaacatcc ttatgttttt 233700
tgctccattc tgatgttgct gtcaagaagg gtatatcaat gtactaaaag cccataaaac 233760
actttccctt tttcccacat tgggaatctt tctgctactt tatccacact gtgcacatct 233820
tacaactcta aagtcagtta gcatacatga atgagagtac catatattgt cttaaactct 233880
ttagttttga ataaccagaa aataccattg accttagaaa tgattactat ttatgagatt 233940
cgaggccggc tgcagtggtt cacacctgta atcccagcac tttgggaggc caaggcaggt 234000
gaatcacttg ggctcaggag ttttagacca gccttggcaa catggtgaaa acccgtctct 234060
acaaaaatta gccaggtgtg gtagtgggca cctgtagtcc cagctactca ggaggctaaa 234120
gtgggatccc ttgagacagg gaggcggaag tttcagcgaa ccgagatcgc accactacac 234180
tccagcctgg gtgacagagt gagacactgt ctcaaaaaaa aaaaaaaaat tagagatata 234240
aggaatgtgg aattcagaat aatcaccaga ccagaaggtc atgctaatga cagcttaaca 234300
tattgataac ctttataatt ctcaccattt atgtaaagtt aaaataataa aagaggaaag 234360
gaagtaaagc tgttattata gccttaggaa tttttaatta tgtatcgtgg aatcaaccag 234420
attaacgctt agtaaattat tatcaaatca atcttagcaa cattttctaa aaggtcctag 234480
ttaaatgaat tactacagaa agtgacggac catccacacc aaataaattg tagcttctac 234540
aaatatctgc attattacca atatatgtta ttttccctca gctgaactat atagggtaag 234600
acatatcaaa catttttat gatgctttta ctatataaaa tcttttcaat aagccaagaa 234660
agagaaaata tgacatataa taccagtctt atgttctata taagaaatat cataagccca 234720
tgggaaatag tagattttat gagtattttt aaattcagga gtttaaccat tataaaattt 234780
gctagctagt aacaatatct attaatcatt ttaaaaggaa aattctctat taatgtatca 234840
gaatgttttt gataagcatt gttttacata tatatgtata tatatatgtg tgtatatata 234900
tgtgtgtata tatatgtata tatatatgtg tgtatatata tatgtgtgtg tgtgtatata 234960
tatatatata tatatatata tatgtatagt tttgggggtt tgtttttttt tctttttttt 235020
ttgagacgga gttttcctct gtcacccagg ctggagtgga gcggcgcaac cttggctcac 235080
tgcaagctct gcctcccagg ttcatgtcat tctcctgcct cagcctcccg agtagctggg 235140
actacaggcg cccgtcacca cacctggcta attttttgta tttttagtag agatggggtt 235200
tcacagtatt agccaggatg gtctcaatct cctgatcatg atccgccatc tcggcctccc 235260
aaagtgctgg gattacaggc gtgagccact gtgcccagcc taaaatatat ttttagtaca 235320
tctttttaga tgatttttaa ttattctaat aagcagatat gggctttatt tttctattga 235380
ggaccattga aacaattacc tcaactaaaa atgaaatcag tttaatttgt ttttaatcct 235440
tcagttgaag aattgagaga ggtatgtgtc gtttaaaaat ttaagacaca gaacataaaa 235500
tgttatttat tctgtacaag agttactttc aaatagattt tatttctatg agatggtaaa 235560
cagaaagcct catctcctta aatgcacaat ttctccattc tggagaatca actatagggt 235620
gaggcactga ttttcaacat tagtagaata ttgtatagta attgattaat gcattatact 235680
gatcggtttg ctgcattagt acaacctttt aagggaaaat tctggcgttt ccctctggct 235740
ggctcagctt ctgcaacctc agcccttaca attgcagtgc ttctggccat ggcttgcttg 235800
ttaactttct tgttcttgac tttatcctta tcctggcaca caaattccag tgtccttcca 235860
```

```
catgctcatc ttagttttca cagtttcagt taccagctga tctgagaagt gcctatcagc 235920
cttgatgacc ttgactcaaa agggaccctg ttgtcatcaa ggagtttgta attggacagc 235980
agattgtatg tcttcacaaa attgttgcct attttttagc cagcatttta tcttgactcc 236040
ttaactacct aggcctatat ccttctcctc ctcctccgtc ccctcttcct cttcctcctc 236100
cgtcccctct tcctcctcct cctcatcatc ttaccattta atcaataatt gcaatcagcc 236160
tgtcagaata cgtaaaggga atccatgtaa ttcacaggcg ggagttgtta tttctgtagt 236220
aaagacctga ctgcagcatt tacacatgat aaataggaaa tggcaaacct ggggaagcaa 236280
gtttgaactc aatctggaag taatagccta agcagcttgc tcttcacact gtgtttccca 236340
tgtcaccctt ttcctcttag gtatcttgct tctccctctc atttcaatct cctccttcct 236400
tctgttcctc catccttcca tccctccctc ctgtctttct ctgacacaat gactcagcta 236460
gtttaagaga atggtattat tttgaagtct gaaaatgttt ctgtgatatt ttgcttttta 236520
ctgatcttta aagcaactca cagaagtgta ttagccttag atacgtaatc acccccttgag 236580
atatatagtc aacagtacac actgacatgt tcatagtaaa aactgccttt atgtttcact 236640
gcattcaagc aagtagatat ttgtttgttt cacgtattgc aaagcctatg ttcttaagca 236700
tgtaccaaaa tcacatttat ttcattaatc catttactca ttcaccagaa tgtaacaaaa 236760
tttagtgaat atctgctatg tgtcaggcac ttttcttggc tcttgatata caatgatatt 236820
caaataaaac tcatagtctg gtaggggagg taggagacaa atatgtactg atgttaatag 236880
atattcctga aataaataaa ggaattagga tggttaggaa cgtccttcca gaagaaatgc 236940
aaggctggcc atgaaaggtg actatatcgt aataggcaga aggtggcagc gcaggtatgg 237000
gtcgtaagaa gaaccttata ggaaaggagg tcaacttgcc ccagtgccat gagctcagca 237060
ctacaacctg gtgcaggact tcgaagtaat agaaagcgag gctgcaaagg tggacaggga 237120
cctgaagaca gagggccagg ttagtgagag cagacttacc acgggcatag cttagcagtt 237180
ttaagaatag gatcagattt tcatttgata aaatcaccct gatgacaagg tggagagtgg 237240
attagatgtg ggtaacatcg aagataaaga agcaggtaca gagactcata aaatatgcag 237300
atgagaggta gtggagacca gaatcaaaac tgtgaggaat aggaatgttt aaatatgtcc 237360
caagttacaa ttcagttaca tatttcatca gccagcatgt cctgtgcaca cacgacctgc 237420
tcttactgct ttccatgttc tgtatgtgga aggagatcag tcaatcttga actcatggcc 237480
tcagtatttt gtactttata atttatattt tttcctatag aggcttttct atttatgtgt 237540
attccacttc cccatatcac taaactgtct ttttccacag gattcaattc ttgaactagt 237600
aggagtgaag ggcagtctgt tgaaacctgt aatctcttag gcttgtattt tctttgaaca 237660
tagtttccac agaattcttc cctgtagggg aaggcctggg cacttcttga tgtcagaaca 237720
tgttgtcttt agtttggaat ctgccaaaac aaaagttaaa tcaaaaatgt taattcctgt 237780
caccccagca cttcgggagg ccaaagcagg aggattgctt gagcccagga gtccgagact 237840
ggcctgggta acatagcgag acctcgtctc tacattaaaa tttaaaaatt agctggatgt 237900
gctggcatgc actcatagtc ccagctgctc aggaggctaa ggcgggagga ttgcttgagt 237960
ctgggaggtc gaggctgcag tgagccactg cactccagcg agtgatggag tgagaccctg 238020
tctcagaaaa aaaaaaaaaa agaagaaaaa atatattaat tcacaaaatt gtcaaccaca 238080
tgttgagaaa tacattttta tacttgctgt atatttttca ataggtaatg gttcaaaaat 238140
tttaaagtac aaagggtata cagtagatgg tagatttctg ccacaactgt gcccacccaa 238200
ccttttgtat ttttccagaa acattctata catatataag gaaatgcata taaatatata 238260
```

```
catatataaa aacatatgca ttttacatat gtgttaatac cattggcaca accacagaca 238320
ttatgcatgc cggttttttt cacttgatgt atctgggttc ttctttccta tacatttatc 238380
tttttgtttc ttttgagtca gaagaagtta tgaaggggaa ggaagacatg cttgagctct 238440
ttaagaaagc ttggaatgtt tctatgtgtg caatagaaat atttcttgcc aaatgataaa 238500
atgacagcta caagaatgtt tctattcaga actattcaat agaaatatga tataaaccat 238560
atatgtaaat ttaaattctc tagtagtcta gtagtcatgt tagaaaaagt aaaaagaagt 238620
caggcaccat ggctcacgcc tataatccca gcactttggg aggccaaaat gaaggatcac 238680
ttgagcccag gagttcaaga ccagcctggg caacatggcg aaaccatgtc tctacaaaaa 238740
ataaaaagat tattcgggca tagtggcatg cgcctgtact ctcagctact caggaggctg 238800
agatgggagg attgcttgag cccaggagat tgaggctgca gtgagccatg atcgtgcaac 238860
tgcactccag gctgggtgac agagcaagac cctgtttcaa aaaataaata aaaagaaaca 238920
agtgaactta attttagtag tagattttaa ttgacacact atatccataa tgtgatcatt 238980
tcaacatgga attcataggt ggctaacacc tataattcca ctttgggagg ccgaggtggg 239040
tggatccctt gaggccaaga gttcgagacc agcctgggca tcatggtgaa accctgtctc 239100
tacaaaaact acaaaaatta gccaggcatg gtggtgcatg cctgtagttc cacctactca 239160
ggaggccaag gtgtggggat cgcttgagcc caggaagcag aggttgcagt gagccaggat 239220
tgtgctagtt ctttccagcc tgggtgacag agtgagaccc tgtcaaaaaa aatatatata 239280
tacgtgtata tatatatata tatatatata tatatatata tatatatata tacgtgtata 239340
tatatatata tatatatata tacgtgtata tatatatata tatacgtgta tatatatata 239400
tatatataca cacacacacg cacacacaca catacacata catacacatt ctgtttttct 239460
tattcagtct ttgaaattca gtattatgca cttacagcat atcttgattt gaactagcca 239520
catttcaaat gctcaacagc ctaatttcgc taagggctac tgtgttggac ggtgcagttc 239580
tagaacttct tagttttaac tagatagaat ttccacacag aaatctaaat ttgaataact 239640
aatgactgat tttaaaataa aatttaagat ggcatgtatt tcggttttat ttcttttctt 239700
ttcttttttt ttttttttaa gacagaatct tgctcttgtt gcccaggctg gagtgcaatg 239760
gcacaatatt gcctcaccgc aacctccgcc tcccaggttc aagcgattct cctgcctcag 239820
cctcccaact agctaggatt acaggtatgt gccaccatgc ctggctaatt ttgtattttt 239880
agtagagaca gggtttctcc atgttggtca ggctggtctt gaattcctga cctcagttga 239940
tcctcctgcc tcagccttcc aaagtgctgg gattacaggc atgagccact gcgccctgcc 240000
ctcatttttc ttttaaactg acatagacca aagtgctatt ttgctgattc tgctttgtct 240060
ctgattggtg gcagtgcttt ttaaaataga tacatattaa atgtttgagc caggcgtggt 240120
ggctcatgcc tgtaatccca gcactttggg aggctgaggc gggcagatca caaggtcaag 240180
agatcgagac catcctggcc aacatggtga aaccccgtct ctactaaaaa tacaaaaatt 240240
agctgggcat ggtggtgcgt gcctgtaatc ccagctactt gggaggctga ggcaggagaa 240300
tcgcttgaac ccaggaggtg gaggttgcag tgagctgaga tcacgccatt gcactccagc 240360
ctgggcaaca agaacgaaac gccatctcaa ttaaaaaaaa agaaaaagtt tgtacctata 240420
taccctttc atacatctct tatttgttac tagatctcct tgtcaatata aaaacttaat 240480
tacttaggta tatcctaaca aaacatattc cttaaacatt cttaaaacag tataatgact 240540
tagtttttta attaccgtaa tgaagttgta aaagcccatg tttcttattt taagcagaga 240600
gtgccttaaa aaggtttaaa atgcatcctg ccagttttaa atagcagaat ttattgatac 240660
```

```
catatatata gactgaaaac acatcaaagt ctttcaaggt tgattatttc ttgtgccttc 240720
cttcttccca cagtaagaga gaagataaag ataatactga gtaaaccatt ccatgctaca 240780
aattggaccc attcgacaaa aatgcaatac ttagtagaac atctgatgac catggtccta 240840
ttcgtgtttt tattttgttt tatttttgtt tttgtttact gttctctcct ctgtccagta 240900
ttcctgtcca gaaattacat ttccttaaaa gatttcatat tcaaaacctg agcattgtat 240960
gcaaaataag ctatgatgaa aggatgaaac tttttaatta ctgaagagat caacatgaaa 241020
aactctgtag caagaatgtg tattttatat tagatcatac ttttcaatcc atattgacta 241080
ttttagtacc attatgtaat tttaaagtct tttagatttt gttaaaattt tattaaatcc 241140
atggaaattg aaagttcctt attttaatcc ttaggagaaa aactataatt tttctctaat 241200
atatccataa agtgaaagaa gaagtactta tttgatattc ttaattgtta catatttaag 241260
agcaagagta attagttcat acttatgttc acctaagtcc acccatacat tgctgaggat 241320
agcggccttc agaaggtggc tgtttccgga ggagtaacag ggaggaacag gtgggctgag 241380
atatacatga ggcccaggac attccaggca ataactgtct gcctctcctg actctgccca 241440
aacccgaaat gatgctttct agctcacaca aaaatatata tatatatata tatatatata 241500
tatatatata tatatatata tatatatatc agcaggcaga tactcaagct gaaagagaca 241560
ttactggggt tcgtttctag atcacagatc ctgcctcagg ctcactgaag tgaccagcct 241620
ccacccagta acaacaaact agtctaaatc cagaataaaa caattataca ttttaatctt 241680
accaccttct acctgtgtgt gctgtccacc ctcaagacag agaatagccc gtattccacc 241740
aaccagcaat cactagccta caacaccaaa tccacagttt ctttggtatc ctttgtgcca 241800
gggagttggg tgctgaacaa tctacctgta acattccctt gccttcatat cccaaagctc 241860
tgcaagcaaa gaagagttct ggtgggcagc tagggccatt tgttgtagtc cagaggaaga 241920
gagccatccg tatcttctgt gctgtactca tacctattta atccaatctg ctggcaccag 241980
tctattatat tcaactgttt gcccccactg taactacata acaaccacct ctattacaac 242040
agtgattata aggcattatc tgagagggta tatccaaact gtaccttgca aagggacttc 242100
tatctgcaaa gaatactaag aaaacatatt atgagaaagt cacaataggt acccagagaa 242160
gccaatctct aggttaacca actacttccc tgtccatttc tccttataaa tgtgaaagga 242220
gagcctacaa tgaagaaatc ctggaagggc atctcccagc tctgagactc tctgatgcta 242280
tgaattcaag ttattctgtc catgactggg tctggaggtc actgtgtaaa atctacgctt 242340
ctaaataaat gttatgatat ctcagcatac tataccatac ttataacatg tatgcttata 242400
acagcatact ataccatata gtatagttcc caagaaaagg gaatgtttct tccccccctaa 242460
aaaaaggaaa attcccatta tctaatatat aaaacaaact tttttgatga tttaaagtga 242520
ctgtgtgttg tgaactgagt agacaaggca ggaaggagta gtgatgttcc tgagttcttg 242580
ctgaattctg acaacgtgcc aacactttga tttctctgtc aaaatgggtg ggatttgata 242640
tctaaaaaag tataccatta catatctaaa agtatattgt tacatggaat atggaagcca 242700
ctgatttaat tctggaatgt ccgtcaacat gacagccacc taaactcctc tgaggcattg 242760
taaacggtta ggaaaattga cctttctaca cactaaatct ggcttcagtg gctctcctga 242820
gctctaaggg agttgggcag gggcagcctg agctccggct gtgagcatag ctcaactgat 242880
gtgtagttag aatgttcatg gaaggcccag gcttgctact tcccattcct ttattttaaa 242940
tgatgtagtg agccaggcgt ggtggctcat gcctgtaatc cccgcacttt gggaggccga 243000
ggtgggtgga tcacttgagc ccaggagttc aagaccagcc tgggcaacat ggtgaaaccc 243060
```

```
tgtctctaca aaaaaaacaa aaattagcca ggcatgatgg tgtgtgcctg tagtttcagg 243120
ggaggctgag gtgggagaat tgcttgagcc caggaggtgg gggctgcagt gagctgtgat 243180
tgcaccactg cactctagcc tgggtgacag tgcctacata aataaataaa aagaaagaaa 243240
gaaatgatgt agtgaaaata tagttacata gcacttatac ctagactact taaagtgacc 243300
tagtaattaa acttatatag ctcatcaacc agcaaagatt cctagtgcac cacactcgtt 243360
atagagcagg gaagcatcgc tgccaccctc agggattcct cttgcatatc tctgtgttct 243420
gtcctccaca cacccatctc tttagtcatc tattgatttt attcaatttt cctggcagtt 243480
tccccagtgt attttacctg aaaggtatga gaggaaaaag gaaaagcaca actcaaaatg 243540
gttgactatt ccattctttg ttttcttcaa aaagtgtaaa gtcataaaga tgccatagaa 243600
ccactaaatt cattgtcctt tgtcacctct cagccaataa tagtcattga tatactctcc 243660
ataccacaaa tttaaagttt tttgtgaact gtacatgcaa tagccaagtt tattttaact 243720
ttagtcatta ctggatccca gagattttct ttctcttttt tggcatatag attatttatg 243780
tcacttcagt atgcccagtc cacagatgag atcttctgag ggactgcttc tggagccggc 243840
cctcttgtgt gattgaatta gtcagtgatg gttctcagga ctagattaga ttgttactct 243900
taaaataatt acttaaaaaa aaaaaaaaaa cttccataac ttgaaaattt tgtggccagg 243960
tgtggtggct cacgcctgta atcccagcac tttgggaagc cgaggtgggc ggatcgcttg 244020
aggtcaggag ttcaagagca gcctggccaa catggtgaaa ccctgtctct actaaaaata 244080
caaaaattag ccgggcatgg tggcgcacgc ctgtaatttc agctactcag gaggctgagg 244140
caggagaatt cgcttgaacc tgggaggtgg aggctgcagt gagccaagat ggtacccact 244200
gcacttcagc ctgggcaaca gagcaagact ctgtctcaaa aaaaaaaaaa aaaaaaaaaa 244260
agaaaggaga aaaagaaaag aaaaatttgc atttaagact tatatgaaaa tacataattt 244320
attttgcaga atgatctaga gcaggactgt cattttaact aaagttattt ttggccaggt 244380
gtggtggctt atgtctgtaa tcccagcact ttgggaggcc gaggcaggtg gatcacgagg 244440
tcaggagttc aagaccagcc tggtcaatat ggtaaaaccc catctctact aaaaatacaa 244500
aaattagctg ggcatggtgg tgcattcctg taatcccagc tactcaggag gctgaggcag 244560
gataattgct tgaaccagga cgcgggaggc agaggttgca gtgagccaag atggcgccac 244620
tgcactccag cctggactac agagcgagac tctgtctcga aaaaaaaaaa agttggccag 244680
gcacagtggc tcacacctgt aatcccagca ctttgggagg ccaaggcggg tggatcacaa 244740
ggtcaggagt ttgagaccag cctggccaag atggtgaaac cccatctcta ctaaaaatac 244800
aaaaattagc tgggcacagt ggcgggcgcc tgtaatccca gctactcagg aggctgaggc 244860
aggacaatca cttgaacctg ggaggtggag gttgcagtga gccgagatcg tgcctctgca 244920
ctctagcctg ggtgacagag caagactctg tctcaaaaaa aaaaaagtta ttcttagtgg 244980
atataaaaat tggtgttttt ggccgggcgt ggtggctcat gtctgtaatc ccagcacttt 245040
gggaggccga ggcgggtgga tcacgaggtc aagagatgga gaccattctg gccaacatgg 245100
tgacacgcac ctgtaatccc aggtactcgg gaggctgagg caggagaatc acttgaatct 245160
aggaagcgga ggctgcagtg agatgagatt gcgccactgc actctggcct ggcgacagag 245220
taagatgccg tctcaaaaaa aaaaaaaaat tggtgttttc ttggtttgtt ttgtgtttta 245280
gtttaaggag acacatttcc tcatcttaag gactttttttg ctgctctgat gctggtcatc 245340
tagtccattc ttttgctcta aactgagcct tgcctcccag ttcttcattg cacttcagat 245400
tgtgtcttac tacaaagaga aaattagtct gtgatcagtt tggatcagaa gaactgaaaa 245460
```

```
tgtacattta gaatagaagc cagggatgtg atgcacaccc gtgatcccag ctactcagga 245520
ggctgagatg ggaggatcac ttgagcctgg gagttagagg ctgcagtgag ccgagatcgt 245580
gccactgcat tccggcctgg gtgacagaac aagaccctgt ctctaaaaaa taaaaagaag 245640
aaaagaaaga aatttaaagt aggaagggct accgtttgct tctggccaag cttcacctct 245700
aaccatagga tcttttaaaa gactagttct gaggtccttt actctgagta ggtatttatg 245760
gaataagcca ttatgtattg acattagaat cagttaaaca taaatttttt tctcttttta 245820
tgcactactt gacatcaaaa gcaaaaagag gtaagttggc tataaacctg taggtgaacc 245880
ttatttttct tagtagattt gttcctgagt agctttgctt caattaaatt tctgtgaatc 245940
aaatactttt acattaggaa gattgtcatt ggaaattctt attcttttct ttgaaaatga 246000
ataagcatct tctgtaaact tagattttca agatatctag tatttaaaca ttttgctttt 246060
cctttaatca agttatactt acggtttaat ttgcttgtga agacaaggca ttttcaaaca 246120
cttggtttag ttttgagata actgaattgt ttctcccacc agaaatgtgg attacatgtt 246180
ataagtcttt cctattttct taaaaatgaa aaaaaaagcc aagaaacaac tgacattggt 246240
gaaagtctgt aattttcaga tccattgatt tacagaagaa gatgccctga acctctcaga 246300
atattttcta gtgtgatttt ttttaatgat taaaaaaaat gaagaaaata ttaaacaaga 246360
agatcaaaca catttcattg agtggtgtct catatgtttt tcttgtttgg gatctatttt 246420
tataattgat ctttttagtg gattcttgat tgtagtttaa cttatttctc ttttgtttct 246480
ttttgatgat gcatcaattc tgacatttca aaggtacagc tggtcttcat tagatatgtg 246540
ctgttattga ctttgcttaa caagaacaga ccatcatcgt accaccttga gttaactctg 246600
tgccagctgg ccttgctctt gagaaggtca tttctaaaca gaaggttatt ttttgaaaga 246660
tttttaactg gtgtaagaat ctggcagcag aatgtacttt tacctcttgg tgccactgta 246720
tttaattacc ctctccccat ttatcctcca tgtctttcct accataagct attgataaca 246780
cacatgctca tggtttaatt gtaagttgtt cagaaataga aagctgactg tactgcaggg 246840
cgtttttata tttctctttt gcaagatttg aaataaaaat agatttttgc atgaatatta 246900
ctttgtttta tcagctagtc atctgatatt catcaggaca gcaaatggga agatgggtga 246960
aaggttttgt caaatctata accactgaaa aatctaaaaa tgctccctct ctacttagca 247020
aggcatgctc tcattctaca tcgctgaaga cgactttcat gcttgtcact gaagtgtgat 247080
gaactatatg cagttgtcat ttatgtgaag gaggaaccag atgcttttta agatttgtca 247140
ccaggtctta tttttgcatt gtctatattg aaattttttg atgtgtttca acaattcctt 247200
ctttttgttc tctggaaatt tttaacgaag aatgattgtt tctatcaaga gtatacgcta 247260
taatggactt tgctgtgtta aagactgatg taaatatgtc tgaagtgttt ggtgatataa 247320
attagcagat ttcacccgat aagtcagaaa ttacactatc atctgtgggt acttttagaa 247380
taactgatgt tttaacaggg gatgtaatac gtttggtgaa aagggatgag atagccaact 247440
ctatgtgttt gattataaaa tgctgacagt gcttcacagc tctccatttt tattcatatc 247500
agtgtaccat taaattcatc attagatttt tgaaaatagt tattttccta gctactgtta 247560
atatttatgt aaatgtttct atctcatgct cttcttttat atataatatt tctttctcag 247620
tttttcctta ttatttctaa attctctact ctatatgtgt gtttttcagt ttatttgttt 247680
aggaattcat aggactgttt aaatgttcaa gttgttacta caaggagaat gtattttgat 247740
gcttctttcc attaaccttt ctgttaattc actaacatta ttaatcattt tgtagattta 247800
gtgaggaata atttactggt tatgttattt ggcacatctt aaatgatggc aatttaaaaa 247860
```

```
ttattttcaa gacttatata ttaaagtcct acagttacca aagaagaata attgatcatc 247920
tgataacact aaattaacct taaaatcttt atcagataat atttatccat tcttattcct 247980
tttgttagaa agatgttgtt acaatgacag ggatgtctaa attgtaaact ctcctttcaa 248040
gtgaattaat taaacagtga cattgatgat actaataaat aaatccaagg attttttta 248100
agggaggtgg tttgcaccac ataaattccc tagcaaagtg ttgtggggaa ttgaagaatt 248160
ataaggcagg gtcctgcctg ctctcaagga gctgcatagt gtggctagag agaatagata 248220
tactgcaagg gaagcagggg tctagaattc tgtaagaaat gccaaaggaa gctgggcgca 248280
gtggctcaca cctgtaatct cagcactttg ggaggctgag gcaggcggat tgcttgaggt 248340
caggagtatg agactagcct gggcaacacg gtgaaactct gtctctacta aaaatacaaa 248400
aattagctgg gcgtggtagc atgcacgtgt aatcccagct actcgggagg ctgaggcata 248460
agaatcactt gaacctggga ggtgaagatt gcagtgagcc gagatggaga tcacgccact 248520
gcactccagc ctgggtgacg gagcaagact ctgtctcaaa aaaaaaaaag aaatgccgaa 248580
ggagatgaga gaagtgctaa aggagtttgc aggaagcaga cacctccttt tgggatggcc 248640
agaaataatg actgaaattt gactttgcat agtctgatag acaagagcat ttccgatgaa 248700
tataatgata gcttgttgaa atgaatttct cctatgatcc attttgacct ttcttatttc 248760
cttgttgtta atagcattta ctttgtttct cgaagctgaa aaccttaagg gccttcgact 248820
cctccctttc ctttgtccat catgtctaat tgatggactc agagctgcat gctttcacaa 248880
acattctctc acctgatctt cacgtgaacc ctgcaagatt ggtatttaat gttctcactt 248940
aaacggatag aaaaactgag gctaagaaca gttaagtcac ttcttcagtg tccctagcta 249000
ctggttgttg gaactggtat ctaaaagaga gacagagatc tttctgatgg actctaaatt 249060
tcatgctgaa atggagaaga gctgaagagc acagaggaga gagaatagag aataaagagg 249120
gccaggcgcg gtggctcatg cctgtaatcc cagcgctttg ggaggctgag gcgagcggat 249180
cgtttgagtg caggagttca agagcagcct tggcaacatg gcaaaaccct gtctctacaa 249240
aagttttaaa aaattagctg ggcgtagtgg cactggggag gctgaggtgg gaggatcgcc 249300
tgaacccggg aagcagaggt tgcaatgagc cgagagcaca ctactgcact ccagcctggg 249360
tgacagagtg agactccatc tcaaaaaaaa aagaaagaag aaagctgaga tgccatagga 249420
aatggctgca gaagcatcat tggcaaatgc aaggaaatta ttgtgatgta ccctcactta 249480
agactccagt gcatctaagt gtgttagtaa ctgattatgg agagcacctt tgtgctatta 249540
tcagaattcc tgggtgtggg aaacttctat aactgtgcaa cttttctatc tccacgtcag 249600
tgcacagtat atggacattt atattttcta ctaacacaac tgacattcca ctcccgtcag 249660
tttagtttcc cccagtacca ctgttttgac cactttcaca cttctgtcta tagtgctttt 249720
gctaagaagg aatctgctaa attcgaatgc agattctcct gcttttttt ttttttttt 249780
gatggagttt cgctcttgtt gcccaagctg gagtgtgatg gcgcgatctc ggctcattgc 249840
aacctccacc ccccgggttc aagcaattct tctgcctcag cctcctgagt agctgggatt 249900
acaggcgcac gccaccacgc ccggataatt ttttgtattt ttagtagaaa tggggtttca 249960
ccatgttggc caggctggtc tcgaactcct gacctcaggt ggtccaccca ccttggcctc 250020
ctaaagtgct gggattacag gcatgagcaa ccacacccag ccccagatta tccttcttaa 250080
tttgtgcttc ttgcctttcg tatatatctt tttcattttg agtttccttg aattaaaact 250140
ttttaattca actcttggat tgcttaattt tgaataattt gagagaattt gggctgttct 250200
tggtttattt agactgaaga agtactctcg gcagagtaag aaggagcact aactgcttct 250260
```

```
actttggagc aagtatcaaa ggctgtgtta gtctgctggg gcttccatca tgaatgacca 250320
cagactggat gccttaaaca acagaagtta attttctcac agttctggag gcccgaagtt 250380
caaaatcaag gtgtccgcag gtctgttttc tcctgaggtc tccgtccttg gattgcagaa 250440
ggccaccttc tcactgtcct cgcatctctg tgcactgcat ccctggtgtc tctctgcatg 250500
tattaatcct ctcttcttta caaggacacc aatcagattg gattagggcc aactctaaca 250560
gtgtcacttt aatttagtca cctcttgtaa aggtcctgtc ttcaaataca gttgcattct 250620
aaggttctga gagttagggc ttcaatatat gaatttaggg gaacacaatt cagtctataa 250680
catcatgggc cattccactg aaagggcgtg ggtggacagt cagaaacctg ggcacaagtt 250740
ctcactctgc cactctctcc atgggcccta agaaaatcac ttaacccttc tgatcctcag 250800
tgttctaatc tgtaaaatgg gcattatgac taccaatctc agttgagttt ggtttgtttg 250860
tttgtttttg agacagagtc tcgctctgtt gctcaggctg gagtgcagtg gtgtgatctc 250920
agctcactgc aacctccacc tcccgggttc aagagttctc atggctcagc ttcccaagta 250980
gctgggacta caggcacgcc ctaccatgcc cagctaattt ttgttatttt agtagagatg 251040
agttttcacc atgttggcca ggctggtctt gaactcctga actgaagcta tctgccagcc 251100
tcagtttccc aaagtgctgg gattacaggc atgagccact gcgcctggac tcacttgagt 251160
tttctaggca ctaaaaagct tttgttcatt ataaaagcca tacagaggcc aggcacagtg 251220
gctcacgcct gtaatcccag cactttggga ggctgaggca ggcggatcac gaggtcaaga 251280
gatggagacc atcctggcca acatggcgaa accccgtctc tactaaaaat acaaaagtta 251340
actgggcgtg gtggtgcatg cctgtagtcc cagctactta ggaggctgag gcaggagaat 251400
cacttgaacc cgggaggcgg aggttgcagt gagccgagat tgcaccactg cactccagcc 251460
tggcgacaga gtgagactcc acctcagaaa aaaaagtaat acagaaagtg accttgcata 251520
aacttagttt ctcatttcta aacaaaaata aaatgtatct catagagttt ttacaaggat 251580
tcaagagctt ttgcatgcaa attgtctgca aatatatata tatagcactt tttataagca 251640
ttacatatta ccattatttc tcatccttct ttcttctaca tttcttctgc ccgctcttcc 251700
ttttctgtca ttgcctaaaa tccctattaa tgaatagttt gaaagaacat ggccaggttt 251760
gcagaaagaa gaaagagaga tatccttttc cctcccataa ggactaaaag aggatgtctc 251820
tgtgctttga tcattaacca tggcgtgttg attttaggac aatctataac tctctgtcaa 251880
tttcctactt aacagctttc aaaattaaat gttcttgctt ttctactaac tgttaatcat 251940
ctgttcttat tgaaaggtct ttaatgaata ttgactgttt actccaagtt tataagattt 252000
ttggtctaaa gtggttgtct tagtccattt tctgttcctt ataacagaat acttgaaact 252060
gggtgattta taaagaaaag gaatttgtca tttgcagtta tggaggctga gaagtccaag 252120
gtcacggtga gagccttctt gctggtgggg actctgcaga gtcccaaagt ggtgcagggc 252180
atcacatggc aagggggctg tacatgctaa gtcaggtctg tcttcctctt atagagccac 252240
caatttcact cccatcataa cccatgaatc cattaaccca tgaatccatt aatccatgaa 252300
tggatttatc cattcatgag agcagacctt tatgatccaa tcacctctta aaaagttcca 252360
cctttcaata ctgccacatt ggagattaag tatcaacatg aattttggag gggatattca 252420
aaccatagca gtggtatcta tttaaatcta tttactttca aatagataat agcagcatgt 252480
tctatgatag caattgttca aagaaattta ttaaaccttt tttatagaca gtcttgggaa 252540
gaatacagca agttagcaaa gataataact aagagtctca tcaagaggcg tgtgtgttcc 252600
ttatatcatc aacttccatt tctcctgcct atttttaagg atatgagtat gtgggctggg 252660
```

cgcaatggct cacacctgta atcccagcac tttgggaggc cgaggcaggc agatcacgag 252720
gtcaggggat cgagaccatc ctggctaaca cggtgaaacc ccgtctctac taaaaataca 252780
aaaaattagc caggcgtggt ggtgggtgcc tgtagtccca gctactcggg aggctgaggc 252840
aggagaatgg tgtgaaccca ggagggggag cttgccgaga tcacaccact gcactccagc 252900
ctgtgcgaca gagtgagact ccatctcaaa aaaaaaaaag aatatatgag ttgcccattt 252960
tcaaaacagg aaaggaaaag aagaaagcac acgtcccttt ttttctcact tgttgaagga 253020
aagagactga aaaatcatga acttatgaaa gatagaggaa gaggtgccta aggagaaaga 253080
gaatatttaa gtaagaggat taatacctat atatgtcaga agaagaaatg tagaaatata 253140
gtttttacac ggtggaaaag aaaagtttct ctaaactgta gaccaacaaa ctttgcctca 253200
tcctcggcaa atttctggaa atggatgaat tacaaatgct ctctatagaa tggggattgt 253260
taaaagccag tgtgagttca tcaagaatga cttgaactgg actacccaca ttctctatct 253320
cataagacca gggaaatggt aaaataatgt gtctgaactt gggcaagcaa ttaaccaggc 253380
attttttttt aatattcttg agacaaatag agaaatcaat tctagaggat aatataattg 253440
tgtagactca taactaattg aatgatatgt gcaaagggtc caaattcatt gacttatatt 253500
tatgaaatat ggtcttcact tagcctgacc ttattattaa ttgctaatct tacataaagc 253560
tatcgaggtc atgattctca tattttctga tttaagagag aaataaatgc taaatgacgg 253620
aataggatcc aaaatattca tcagatagga agaggcgaaa tatttcacat gtattttaaa 253680
cataaagttt aaatggatat gaaatattgt gctggaattc caagcactgt aagatggagg 253740
aaaaatgact ttatagcact acctgtaaac aaagctcaat ggaaatagca gtgtgatgtg 253800
gctgcccaaa aatgccatga ggtttctgct gttttaatag gactgggatg tctcagataa 253860
gacaagacag tgccactgta ctcttcactg ggcatatctt accacacatg atttcctttc 253920
ttatcacctc atttttagaa ggatgtgcac aaaccggaac aaggtcagag agcaaggaga 253980
cgagtgaggg aaattgacat cacgtcttaa aaggaagaaa tggggttggg cctgatggct 254040
cacacctata attccagcac tttcagaggc cggggcgggt agatcatttg aggccaggag 254100
ttcgagacca gcctggccat ggtgaaaccc catctccacc aaacatacaa aaattagcca 254160
ggcatggcag cacatgcctg taatcccagc tactctggag gctgtaacac aagagtcact 254220
taaacctggg aagtggagtt tgcaatgagc caagatcacg tcacttcact ccagcctggg 254280
caacagagcg agactccatc tcaaaaaaaa aaaaaaaaga aagaaagata agaaaaaaag 254340
gaagaacttg gatacttggc ctgaggagaa ctcagaggac agagatagtt ttcatgggaa 254400
cacgtggagc atccggaggt tgtttatggt catgagggaa agagatgtgg tgtggaaaat 254460
acgatcttgt gaaaaagtag ggatgcatta gttctcaagt caggaaaatg aggaggtgga 254520
gtcaagcgat gctacaggag actgtttgcc acaaagagtt gctgctgtgc ctgccccaga 254580
gcacttgggc ccaaagaagc cacctctgca gcctcactac tcatcgtggc tgggtttggt 254640
ctccacagat gggctttcac tcacatggtg ctcaccagtg cccactgctg ccatctgggc 254700
caggtgtgga gccaaaacat agaagtgttc cttgtctcct acatgagctg ttccttccca 254760
tcccaaacag ccaccagtgg gctcctggac tccctaaggc attgactttt agaaaattgg 254820
gtagtttggc tgggcgcagt ggctcacgcc tataatccca gcactttggg aggccgaggc 254880
aggcagatca cctgaggtca ggagtttgag accagcctgg ccaacatggc gataccccat 254940
ctctactaaa attataaaaa ttggccgggc atggtggtgc atgcctgtaa tcccagctac 255000
ttgggaggct gaggcaggag aattgcttga acccgcgagg cggaggttgc agtgagctga 255060
gatcatgcca ttgcactcca gcctgggcaa caagagcgaa actctgtctc aaagaaaaaa 255120
aaagaaaatt ggttagtttt ctaaattgca ttgaaaattt tataaataat agaagcccga 255180
gagaaagcca cacagcaaaa ctttctctct ctgccaatga aatgtattat tttcagccac 255240
ctctttttaa aaacaatatt atcttcattc ctgtaccctt cattttgctt tgtatttttg 255300
agagcgctgg ttgccttaaa atcagtatct caaatctctg gcaaagttcc ttctgtttct 255360
ttgactctat gaccctgata ttttctagag gtagctggtg tcaatttgag aagcatccag 255420
aggagtgaat agaaaagagg ccttagcatt aaaaagacta aatttaaatc cttgttccgc 255480
cacttcctaa ctgtgtgacc ttgggcaagt taatacacat gctgagcttg gattaatcag 255540
tggaggcttg taggacacct actgtgatgg caaattctgt gtttgtttct agcaggagag 255600
attttaaaaa gaagttaaag aaaaaaatat gtgagactat gatattctcc catattatca 255660
aaaacactta ttttcctcaa tgtaggaata gtgcaagcct gtcgacccag ctattttaga 255720
ggctgaagtg ggagcatcac atgagcccag gagttcaaga ccaggcttta agagaccctg 255780
tctcttaaaa cagataacaa atgtaaagtt tataggaaag attacatcat gttgattcag 255840
caaatatttt cctctcttat ttctcccttt cttttctatc ttcccttcta cgtgaggccc 255900
ttgtttatgg aggaatgtca tacaagggta ctcttcttgt gcatatcgag acagacctat 255960
agatgctttg agctataata ttccatattc atccctgccc tggaggcatt agtaatctct 256020
tgagccaggc acagtgtaca cacttgtagt cccatctact caggagattg aggcaggagg 256080
attacttgaa ctcactgcat tacagcctga gcgacatagc aagacctggc ctctaaaaaa 256140
aatacataaa taatctcttg agtatgctat gacatttccc aagcctgtgg ccttatcata 256200
taaacgtaca gcattttcta attccattct gatcatttca aataaacact ttaattttat 256260
gataaaatgt cttattactg ttactaaaga ccataaaaag tttgtagtta caaagaagtt 256320
atttgactaa ctcattatgt tagatgtcag cctagatatc acaacctcca ggaagcactc 256380
cctaaccact tagatttagt tgtgtttggt tagttagatt tagttatgtt tgattagtta 256440
gattcagtct aatttaattt aattaacttc cgctgtgagg tcctgtaaca ccctacactt 256500
tccctatcat aggaggcaat acagtgatac ttctgcaagt tcagctcagc ccttggacca 256560
tacaatcctg gattcaaatt gcacctctac ctcctagtgg agtttgtcaa gttacttaac 256620
ctaagttccc ctttccttat agatgaagtg agattaataa aacagggtta tagaagagca 256680
tgtatattaa gtgcctatac agtgcctgag acatcgtaaa caataaataa gtactagatg 256740
ctgtcatcat caccatcacc atcaccatca ccaccatcat caccatcacc atcacacttc 256800
aatgtagttg cttattaaat atgcttatct tccttgataa aacagagacc acattttctc 256860
tgttcacctt tttcccccctg ctgcctaaca cagtttctga cacaaaatag gagtttagta 256920
acttgactgt tgaatggttt agacaaaccc tggtggccaa acaacagcaa tggctttgtg 256980
ggttctacaa tgcctgctcc ttcatgcaca tagttgtcat cttttattcc ccccaaagca 257040
acgagatgtg gtctagttcc ttcaagggtg agcctagcag aatagatcct agacggagca 257100
ggggagatca ctcagagcct gcagcatctc agagctacaa gggacttcct cagcctccca 257160
acctacctcc ttcattttac aaagtacatc ctaagacaca tccgtggctc agccaggcta 257220
caattgacac aactggaggg ctgtagaccc gagaagaggg atttagaaga caactgagtc 257280
agagcaatgt agctacattt tagtttaatt ttttaagtcc atcaccattt tatctatgaa 257340
atttgttttt tattctttaa ggataacacg tagctaagtg cttataaata ataaatgaaa 257400
aataatcatc attagcttgg ctaggagcag tggctcacac ctacaatccc cacatcttgg 257460

```
gaggccgagg caggaagact gcttgaggcc cggagttcaa gaccagccta ggcaaaatag 257520
ctagaacctg tctctacaaa aatttaaaaa attagcaggg tgtggtggtg tgtgcctgtg 257580
gtcccagcta ctcaagaggc tgaggcagga ggatcacttg agcccaggcg ttggatgctg 257640
aagtgagcta tgatagccac ctaggcaaca gcatgacatc ctgtctcaaa aactaaataa 257700
ataggccgag tgcagtggct cacacctgta atcccagcac tctgagaggc caaggtgggt 257760
ggatcacccg aagtcaggag ttagagacca gcctggttaa cacggtgaaa ccccgtctct 257820
actaaaaata caaacaatta gctgggcgtg gtggcgcacg cttgtaatcc caactactcg 257880
ggaggctgag gcaggagaat tgcatgaacc caggaggcgg agattgcagt gagccgagat 257940
tgtgccattg cactccagcc tgggcaacaa gagcaaaact cttgtctcaa aaataaaata 258000
aaataaaaaa taaatattag ccagagatga tgttacttct aatgaaggaa aaagtgatat 258060
tcactacaaa taagaagaat gtctaccacc tctctagcat ttcattaagg gagtacactg 258120
tggttctgat cacctgctgt ctgaatttta ccataaatta tattttgaat gaataataat 258180
ctgtgactgt attggcaaaa caaagtcaaa tatatgagat atttttaaaa gatgtaagcc 258240
attttaatac tctagttact ctaattctaa ggatcgctat tccacagagg ccactactct 258300
gctttagaag agtttcatta tacctccctg gcaatgtaag acataaggaa tccagagtgg 258360
tttttacatc cattgcattt acccaaatac accatcggag ggcagcacac acctggttga 258420
cttaactgcc tgtctggtgg ccttatcaaa atagttgtca aattagtcta agacattcct 258480
aaattaccac tcagataggc aggaaagctg ttggagaaga caaaaggagc aaagattttt 258540
aaaagacaaa agaatgcatt ccttaagact ctgagtttct acaaaaggga atctggagct 258600
aatcaatgct gcaaaatggg aaaacggagt taaaaaagga atttcctcaa tctgagaaaa 258660
cagatttgtt atatttgaaa gatttttact gagtatgatc atccgaacac cagctactaa 258720
acaaaaatca gatctccttg ttcctattaa gatgcgctaa ttaataagat ggcaacaaag 258780
accaccatat aaaagggttc cttcagtaat gttttcttga gtgaacaaaa atcaagcctg 258840
ccttatattg tattctactt tgcatcacaa acagttttag tgtatttctg gaaaagcatc 258900
agcagttttt tcgaatttta aattctggag ttatgtaact atataggcag gcttttttat 258960
aacagaatat aacagtgata cttaaataga agacttcaaa tgtaaatatc agtagagcct 259020
cgttaaggct ataaatccag actttgtgat aatgtggatt aaatattatt tacataacat 259080
ataaggaggc cgggtgcagt ggctcacgcc tgtaatccca gcactttggg aggccgaggc 259140
aggtggatca cctgaggtca ggagttcaag accagcctga ccaatatggt gaaaccctgt 259200
ctctactaaa aatacaaaat tagccgggtg tggtggcaca tgcctgtaat ccctgctcct 259260
tgggaggctg aggcaggaga atcacctcgg gaggctgagg caggagaatc gcctgaaccc 259320
aggaggcgga ggttgcagtg agctgagatt gcaccattgc actccagcct gggcaacaag 259380
agcaaaactc tgtctcaaat aaacaaacaa acaaacacat ataaggaaag ggatttgcta 259440
agcaaataca gtctaagcag ttggcaagag gaaatgcttc aattatttaa gaataatttt 259500
taagtttaat tccaatttta acttgtttgc aaaaatcttt ttggagaaat atgacgtata 259560
tgcatttcta accagcttct tgcatgattc taatatagtc acctagtacc agtaaacaga 259620
ctgctctttg attttttttt agaacaccag gcactacttt cttggagtag atgattaacc 259680
cagctaaagc ttgattttta ctagctagca ctttattaac ctagtgtgtt atattgtgac 259740
tttaaaatgg taaaaacaat tacaaagtgg agttctcatt caggttagct ttctagtcca 259800
agtcactaac aatttactat gtaatagaca ttctaagatt tctgccaaca attctattgt 259860
```

caatatataa aatcaatttt cagaaaactg taaagattat ttccttgttt aattaagatt 259920
ctactaatca tagaaaagat tatattgcac acttttctca agttacctat gggactgaca 259980
atatgtccat gtgtcctgat agtaaagtca gttatctgaa tgcgttccat tttggaataa 260040
gagatctaag tgctaagcaa gtaaccacca ccacattcag gtttagaatt ggaagatctt 260100
tcattatatt aatagaccct ttatttttag atataacaaa ataccaaaga caaatggcca 260160
catatatcct aatgtacttg agaaatctcg ctactaatgc tgtgtcacta attttttaat 260220
actgtattta agaaaaaaaa aaaagcctgt cttttctatt ggcatcattc aagaagaaaa 260280
aaaaaaagct gaatcaggat atttctgtgt gaatgcacat tcctcactaa atctctcagg 260340
cagctgcttt agtcactgtt actaacacct tgctctgtca tctctttgta cacatgtcta 260400
atttatcagt ttcttgtaga ttgtcagcag cctgctgcct ccgtaccgcc acagtgctca 260460
caactagccg ggaggcaaga ctgcccaact gtcaggtaaa ttcagatgtc ctttcccttc 260520
cacccagctg catgtcagat ccatagaccc cagctcccct ttccgacacc tgaactgcct 260580
acgcatcatt gtattttgct gtattttatt tcaagtgtgg gctacataga cacacattgg 260640
acacctgcag tccctgcgtt cccagtagga atacaagaga gctggggttt attttgctgg 260700
ctgccagctg gtagactcta caggctgcct tcagcccctt tgtctgtgta aatacttgga 260760
ttagtccact gtttcattcc tttccaaaaa ataaaagctg gaattgttat gatgtttgtc 260820
ctacttttta ttttcttttg tctttaaaat atatttattt tcctggggaa tctgagggat 260880
accaatatac taattgacct gatttgattc ctgtacttta tatgtattaa aacatcacta 260940
tatactccat gaatatgtac aattattatt tgtcaattta aaaaaataaa atccccgcta 261000
ctcaggaggc tgaggtagga ggatcaatcg cttgagcctg ggagttcaag gctgcagcga 261060
gctatgatac cactgcacac ctgcctggtg agtaagaacc tgttgctaaa aaacaaaaca 261120
aaacaaaaaa cacagtaaaa taaaacttaa agtgtttaaa taggccaggc atgatggctc 261180
acacccgtaa tcccagcact gtggaaggcc gaggcagagg gattacctga ggtcaggagt 261240
ttgagaccag cctgggcaac atggtgaaac cccgtctcta ctaaaaatac aaaaattagc 261300
tgggtgtggt ggcacatgcc tctaatccca cctactcagg aggctgaggc aggagaatca 261360
cttgaaccca ggaggtggag gttgcagtga gctgagctgg tgccactgca ctccagccta 261420
ggtgacagag agagattcca tctaaaaaaa aataaaaaat taaaaaatat atatctcagg 261480
ccaacaaaca ggaagaatat aaagaattag atataaaggc tgggtgcagt ggctcatgct 261540
ggtaatctca gcactttggg aggctgaggc aggaggattg cttgagtcca tgaatttgtg 261600
gttacagtga gtaaaatcac atcactgcac tccagcctgg gtaacagagc aagaccctgt 261660
ctctagataa atagatagat agacagacag atagaacagc tgtataaaag tgtttctgtg 261720
tttctgttct ctgtccactc agtagccttg gtaaaactga atttgaaagg tggagaaaaa 261780
cattgtagtt agcattcaaa agataatatt tgctgtgaca gtgaccttta tgtgagatta 261840
cttgaaaaat tgttaaaaca ggtttgcaca gtcctgaaca ctgaactgga gagtttgctg 261900
acaattccga ttccaaagga aagctttcca aatcagtcat gaattgccct ccatcctggt 261960
gaacctccac acagcgtctc agcgttccat caggacctca cctccatcct ggaatgcttc 262020
atctccagcc acctggcctc tgatggtgcc agacctcagt agtccggttg tggttttcat 262080
catctgctca gtgttctctc cttatcacag ctgttgccct tctaccaggg gaaggcttct 262140
tttgagcagg ggcaggccca aacactttcc atgtgtgtct gaggagtaga tgtcagtagc 262200
aagctacatg tggtcagggg tcagagccag gggacctggg gtgccacaag tgtggaaaca 262260
cagtggcagc tgaagcccaa gtgtcacatg gtctcagagg cggttgtgca gccagctgta 262320
tcagtggaac attgagttag cacagaaagg tacattattg gccaggtgtg gtggcttacg 262380
cctgtaatcc cagcagtttg ggaggctgag gcgggaggat ggcttgaacc cagaacttca 262440
agaccagcct ggggaacaca gggagacctc cacccccgac ctctaccaaa ttttttttt 262500 tttaaattag ccaggtataa tggcacatgg ctgtagtccc agctatttgg gaagctgagg 262560
ttggagggtc acttgagctc gggaggtcaa gactgcagca agctgtgatt gcatcactgc 262620
actccagcct gggtaacaga gtgagaccct gtctcaaaaa acaaataaat aaataaaaag 262680
aaaaatacat tataaaatag gttgctagcc agcagtttcc aattggtgtg tgttagttga 262740
ttgttcccac caccttcagc aacagggctt taagaaaggt tttcgctaa tgccatttta 262800 caacagcact aatttcggtt agaaataata atgataggtc aggcgtggtg gcgcaggcct 262860
gtaatcccag cactttggga ggccaaggcc ggtggatcac aaggtcaaga gatcgagacc 262920
accttggcca acatggtgaa accccgtctc tactaaaaat acaaaaatta gctgggcatg 262980
gtgatgtgcg cctgtaatct caggttctcg ggaggctgag gcaggagaat cacttgaacc 263040
tgggaggcgg aggttgcagt gagctgagat cacgccactg cattacagcc tggcgacaga 263100
gcaaaaaaga aaaaaaaaa agaaataatg taattataga tttatctcaa ttatataagt 263160
aacaatataa atattcaaac tcgtctcagt gggattctga atttgtagcg gttaagaaca 263220
gggctcttca cctacagtcc attctccacc aagcaccccc agcccttacc ccaaggcctg 263280
ggtcagtgct gggcacatga cagctgtgca ctaaatattg attatacctg agagagtgaa 263340
tgagctctgg aatcagattg cttgggttga attcccactt ctaataccca ctggttgttt 263400
aactttggaa aatttctttt gctggctaag attccatttc ttcacttgta aagttcagat 263460
gacaatagat actgagggaa ttcagcgagg cacgctcctg gcttggagtg tctgctcagt 263520
atctgttatc aatacttttt tagtatctta ccattcctca agacaaagat ctgcaatctc 263580
ttaacctctc taatttgctg aagaaagcgt ggagcgggct gctgttttgt ttgcttcaga 263640
gattgggtct ggctatgttg cccaaactgg acttgaaccc tgggctcgag caaccttcct 263700
gcctcagaag actactgctt gaagtgtttc cattaagtag gaaatggaaa ggctggcagg 263760
agattttttt aacttttttt tttccacctt gcttgttttt tgagaaccag tttgactaaa 263820
caattatgta gtctagttcc atctgttctg agattaataa atttaggttg cttactacta 263880
ccacagggat gatttacttt aaagaaaagc aatttaatga attacaaaca tttccagctt 263940
ctcaaatgtt tccagtttct acccacatga atacagcctg gtctagagcc caattctact 264000
actgttcccc atcgtggtct acgtaaagaa atgattaaat gcatatagat ctgaaaagac 264060
tcttttccaa aattgctggg atgatgactg actcttttcc cacccataca cactgccaaa 264120
tgggtcaatg ttaatacctt cattgccctt tttactcctt cttggcagaa aagttaacac 264180
atagccaaca ttcgaattct tagtataaac cagacaaggg ttcatttctt tacacatatt 264240
aaacattaca gccttccata agggataagc acagttatta cacccatttt tgttgttgtt 264300
tttgtttgtt tggtttagtt ttttggcgtt tttttgtttg tttttgtttt tgtttgagac 264360
agagtctccc tctgttgccc aggctggagt gcagtggcgt gatcttggct cactggcacc 264420
tccacctcct gggttcaagc aattcttctg cctcagccac ccgagtagct gggattacag 264480
gtgtgtgcca ccacacccag ctaatttttg tatttttagt agagacaggg tttcaccatg 264540
ttggccaggc tgcccttgaa ctcctgacct ccagtgatct gcctgcctca gcctcctaaa 264600
gtactggggt tacaagcatg agccaccaca cctggtctta cacccatttt tatgtgacga 264660
aattgaggtt tgggaaggta aaatgacttg ttcaaggtca catatcctga acacaactga 264720
gcctagtgac tcctacctac caccacaggt ggctgcactg cagaggagaa atctatttca 264780
gttacactgt gaggagcaaa gtcagagtat gtaaatcacc caccatgatt ccttttccct 264840
caaactgaag aggaatgttt gtttaatgag aaacagaaga tgtgctaaga atgttgagtt 264900
atttcacatc aggtgttctg tttctcattt tgaaaaatga ttttgagtgc tgggcccagt 264960
ggctcatgcc tgtaatccca gcactttggg aggccaaggt gggcagatca cctgaggtca 265020
ggagttcgag accagcctgg ccaatatggt gaaacggcat ctctactaaa aatacagaaa 265080
ttagccaggc atggtggcag gcacctgtaa tcccagctcc tcaggaggct gaggcaggag 265140
aatcacttgg aacagggagg cggaggttgc agtgaaccaa gatcacgctt ggacaactcc 265200
agcttgggca acagagtgag actccatctt aaaaaaaaaa ttattttgta cttccctcgg 265260
tttatacata tattcaaaca gcttttaagg tgaatgattt tttaataaaa gagcattttc 265320
tcacctttaa caatgtagaa cttttcagcc ggacatggtg actcacctct gtagtcccag 265380
cactttggaa ggctgaggtg ggaagattgc ttgagcccag gatttctaga tcagcctagg 265440
caacttggtg aaaccctgtc ctttaaaaca aaatacaaga attaggcatg gtggcctgca 265500
tctgtagtcc cagctactca ggaggctgcg gtgggaggat cgtttcagcc taggagttca 265560
aggcagcagt gagccgagat tgtgccactg cgctccggcc tgggtggcag aagaggaccc 265620
tgtctccaaa aacagaaaaa aagtagaact tttccatgta tactttttac aggctaattc 265680
cattgtagag ctaaattatc aaaattgttt atagataata ggtattataa tatgaaagga 265740
atgcccaagg tatatagcct tggatataat attgaaatat atagagttgt ttggtattta 265800
gcacttccct tctatcaagt agttttctac ttgggaaaaa aaaagaaact tcctgaagat 265860
gtatccaatt ttatatctta gtaacagctt cctaaacttg ccatttacaa catgatctac 265920
ctatgtaaag taaaatcaat ggtaaatgtt gaataacaag tggactcttg aaaatattta 265980
gcaatcacaa ctgaaactga attcattcta tgccttaaat gattataatt tatcaaatat 266040
ttatatccaa gaaatagtat cttaacctgt aagccaagaa tgtgtgtctt acaggttaat 266100
ttacacataa tatacaccat gtgattgcag cattttatgc aaattaaaaa tattaatact 266160
atagataata actttatgta agaaatctat ctaaaggaat gaaaaaaatt taaatcatca 266220
cgaatgatgt aatgtcaagg tgttaggcaa agtgagttgt aacccatatt taagctatag 266280
ctacacactt cagctggtca ggaagaaata tttgtcttcc tttatcaaaa agagtattgg 266340
ggccaggtgc agcggctcac gcctgtaatc ccaacacttt gggaggctga ggcgggtgga 266400
tcacaaggtc aggagttcga gactgtcatg gctaacacag tgaaaccccg tctctactaa 266460
aaaaaaaaaa atacaaaaaa ttagccaggt gttgtggcat gtgcctgtag tcccagctac 266520
tcgggaggct gagacaggag aatcacttga acccggaagg tggaggtggc agtgagccaa 266580
gatcgcgcca gtgcactcca ggctgggcga cagtttgaga ctgtctcaaa aaaaaaaaaa 266640
agtattggat tacacaaggt cttcaaaaac atatctttct tgggtggaca cagtggctca 266700
tgcctgtaat ccttgcgctt tgggaagcag aggcaggctg atcacttgag gtcaggagtt 266760
cgagaccagc ctgggcaaca tggtgaaact ctgtctctac taaaaataca aaaattagcc 266820
aggtgtggtg gcgcaggcct gtaatcccag ctactcagga ggctgaggca ctagaattgc 266880
ttgaacctgg gaggcagagg ttgcagtgag ctgggatcgt gccactgcac tccagcctgg 266940
gcgacaaagt gagattctgc tcaaaaaaaa aaagaaaaga aaagaaaaga aaaaaaagcc 267000
atatctttct tgtgtaatgt gacgattctg cattacttgc cataaatcac attgcataat 267060
atgtttagtt ccctaaaaag aaattagttc tggtgctgac ttccacagca cgtatagtaa 267120
aattggagtt ttttttacta tatgtgctgt ggaagtcagc agtctaagtc atgcatattt 267180
gcagaaaaac tgttaggtcg atgggaaagt ctggcctata acctgctgtt taccaggccg 267240
tcaaactctg tttggagggt caagtgtgaa tcttgccata cattattttc tgttttaaat 267300
attttctttt ctttcttctt tttttttttt ttttgagacg gagttttgct cttgttaccc 267360
aggctggagt gcaatggcgt gatctcagct caccgcaacg tctgcctccc gggttcaagc 267420
gattctcctg cctcagcctc ctgagtagct gggattacag gcatgtgcca ccacgcccgg 267480
ctaatttttt tttttttttt tttttttgt atttttagta gagacagggt ttctccatgt 267540
tggtcaggat ggtcttgaac tcccaaccac aggtgatccg cctgcctcgg cctcccaaag 267600
tgctgggatt gcaggcgtga gccactatgc ttggcctaag attttcttca tttattttcc 267660
tttttttttt tttttttttt ttttttgaga cggagtctcg ctctgtcgtc caggctggag 267720
tgcaatggcg cgatctcggc tcactgcaag ctccgcctcc cgggttcacg ccattctcct 267780
acctcagcct ccggagtagc tgggactaca ggcgcccgcc accacgccca gctaattttt 267840
ttttttaatt atttttagta gagacggggt ttcaccatgt tggccaggat ggtctctatc 267900
tcctgagctc atgatccgcc cgccttggcc tcctgaagtg ctgggattac aggcgtgcgc 267960
caccgcgccc aggcttattt tccaatttat aaatgaggcc gggcacggtg gctcgtgtgt 268020
gtaatctcag cactttgaga ggccgaggtg ggcagatcac ttgaagtcag gagttcgaga 268080
ccagcctggc caaaatggtg aaagtccgtc tctactaaaa atacaaaaaa ttagccggac 268140
gcggtggtgg gcccttgtaa tcccagctac tcgggaggct gaagcaggag aattgcttga 268200
acccaggagg cagaggttgc agtgagccga gatcgtgcca ctgcactcct gcctgggcga 268260
cagtgagatt ccatatcaaa aaaatttaca aatgaaacta tgcgctattt tcttaggctt 268320
tttgttgaag gtccagttct cccatgttta cataccacat tttaaaaata ggtaggaaaa 268380
acaattttta tcactgcttg tcttaaccag tacagaacag caaagcttct tttaaactat 268440
atttacagca cttcaaagag tttgggaaga aagaataacc tcaagccagt cagatatttt 268500
ccataattat gattttgtat taaaatgcaa gagatatagg tagaggataa tttcagtacc 268560
aaagataaaa attatttaat actaatttta atgactccat tacattttaa actccattaa 268620
atttaaagct aattttaatt agctttaaaa agctatgctt aaattaatag taataatgag 268680
ccttgaattg ttctctcaaa catcacttct ggtagaaatg aattatatag tactgacttt 268740
catagtttaa gggaatataa cagagtttta gaaaaatact cttttctaat taaaaaaaca 268800
aatctccatg ttgtgattcc cccattgcta gtcacatttt tttttttttt ttgagacgga 268860
gtctcgccct gttgccaaac tggagtacag tggcgccatc ttggctcgct gcaacctctg 268920
cctcccatgt tcaagtgatt ctcctgcctc agcctcccga atagctggga ctacaggcac 268980
acgccaccat acccagctaa tttttttttt gtatttttag tagagacagg gtttcaccat 269040
gttggccagg atggtctcaa tctcttgacc tcataatcct cctgccttgg cctcccaaag 269100
tgctgggatt acaggtgtga gccaccgcgc ccggccgcta gtcaaatttt aaaaggccca 269160
aacccaaatg tgttttgtca ttttaccta ggaaactcaa tgattttgct tctttattct 269220
tcaagattat tcatccagac cctgataggc ctgagcacag gttcatttaa actagaggct 269280
atcacaggcg tcgtttggaa agttacatta tacacttaac aaatgggaaa tgttaggctg 269340
ggctcggtgg ctcacgcctg taatcccaac acttggggag gccgaggcag gtggatcacc 269400
agaggtcagg agttcgagac cagcctggcc aacatagcaa aaccccatca ctactgaaaa 269460

-continued

```
tacaaaaatt ggcagggcat ggtagtgcat gcatgtaatc ccagctgctc gggaggctga 269520

ggcaggagaa tcgcttgaac tcgggaggcg gaggctgcag tgagctgaga tggagccact 269580

gcacaccagc ctgggcaaaa caacgagact ccatctaaaa aaaaaagggg ggggggggtg 269640

aaatataaaa ctcttcctta tacctccaag cccaagcagg tagggggaat tcttagagca 269700

aattagactt ccacaggcaa attctttatc ctagtgaatc tggatctacc agataactat 269760

agaatcctct aaactccaaa gccttggtca acctgtcagt accatcagca tcactgggag 269820

ctcattaaaa atgtagaatc tcagatctca ccccacacct aatgaatccg aatctgccct 269880

ttatactgag ctccccaggt aatttgcatg catattaaag tttgaaaaga actgatctca 269940

tgaaatctta cagctaacac agagacctag gagaacaaga ccgtgcaaaa attgagaaga 270000

acttctgtaa aatgctgggg gcaagaaaat agggaaaaca agaaaagaga agagtgactt 270060

tgagggaaga gtgcatatat catttcctta atacatttca tttttctttt ttatgccttg 270120

ttttgaaaag ctaccattat cttggcatgc tttagatgga aaccatttac tgtgcagatt 270180

tctgttcttg ttctcaaaat ctatgcaaaa atatctcgtc taacccctac cattgtgcct 270240

ggccctttga aatgtgtttc ttgctgacgt gcttgtttct cctttccagt cctgacacag 270300

ctctccctga ggagcagcca cattccagct cccagtgcgc ccctctccac tgtctctcca 270360

agcctcctca cccctagtct tcatctcctg tggacgaaca tctggggtgg aagttttgta 270420

gccacacaca ggatactgcc caagatccag cgggtgtttt cttctcggtt gttagatgta 270480

caattggatt aatgtccatc gttttggaag acgagagaaa gttgagaaga acacgaagca 270540

cagaccctga tgtgataaaa cattttgtgg tttctctgag tcacagataa acttctgcca 270600

tcaaatggct acagttcatt taaatttaaa aaaaagaaaa aagaaacaga aaacgtgtct 270660

cagatggctg gctttacctc gatagcataa gagagaccta agacatgtaa aatacgtata 270720

ttgcagtatc atctttcctc acactccaaa ttcagctagg gaagttgatt ccaatatgtt 270780

tgtcattgat atttattttg tactttattt gctacatgat ttatgtctat acaaataatt 270840

tctctgaggt gaatttaatt catttatttt caaataagca taatttgctc aattaagtat 270900

gagtttgaat ttagtttgaa atctggaatt ggccagactg tggtcatttt tcttgca    270957
```

USING GENETIC POLYMORPHISMS OF THE BICD1 GENE AS A METHOD FOR DIAGNOSING AND TREATING MYOPIA

BACKGROUND OF THE INVENTION

1. Field of the Invention

The present invention relates to a method for diagnosing myopia, and in particular relates to a method for diagnosing myopia and/or myopia related complications by determining SNP (single nucleotide polymorphism) genotype in the BICD1 gene. Further, the present invention relates to a method for screening a material for treating myopia and/or myopia related complications.

2. Description of the Related Art

Myopia, also called near- or short-sightedness, is a refractive defect of the eye in which collimated light produces image focus in front of the retina when accommodation is relaxed. Those with myopia see nearby objects clearly but distant objects appear blurred. With myopia, the eyeball is too long, or the cornea is too steep, so images are focused in the vitreous inside the eye rather than on the retina at the back of the eye.

Myopia is a common eye condition worldwide. The prevalence of the condition varies widely among populations, genders, and ages (Invest Ophthalmol Vis Sci 1997; 38:334-40; Optom Vis Sci 2001; 78:234-9; J Formos Med Assoc 2001; 100:68-91). In the USA, the prevalence of myopia was estimated to be approximately 25% between ages of 12 to 54 years (Arch Ophthalmol 1983; 101:405-7). In the Baltimore Eye Survey, myopia was less common in blacks (19.4%) compared with whites (28.1%) (Invest Ophthalmol Vis Sci 1997; 38:334-40). High myopia (defined as refractive dioptric power≦−5.0 D in this study) accounted for 27% to 33% of all myopic eyes, corresponding to a prevalence of 1.7% to 2% in the general population in the USA (Arch Ophthalmol 1983; 101:405-7). Taiwan is among the highest risk areas in the world for myopia. Using the definition of less than −6.0 D for high myopia, high myopia is much more common in Asia. The percentage of myopia in Taiwan is 18% among Taiwanese school boys and 24% among Taiwanese school girls (J Formos Med Assoc 2001; 100:684-91). The totals are even higher than the 13.1% reported among young men in Singapore (Optom Vis Sci 2001; 78:234-9). Furthermore, the prevalence of myopia is increasing in Taiwan based on two large nationwide surveys (participant number>10,000) conducted in 1995 and 2000.

High myopia is associated with potential blinding conditions such as retinal detachment, macular degeneration, and glaucoma. It has been estimated that 5.6% of blindness among school children in the USA is attributable to myopia. Substantial resources are required for optical correction of myopia such as spectacles, contact lenses, orthokeratology, photorefractive keratectomy and laser in situ keratomileusis (LASIK). However, these corrections do not prevent the ocular complications mentioned above. Furthermore, complications arising from the use of contact lenses (Curr Opin Ophthalmol 1998; 9:66-71), orthokeratology (Cornea 2003; 22:262-4) and surgical procedures (J Refract Surg 2003; 19:S247-9) also impose additional risks to myopes. In the USA, treatment of myopia costs an estimated $250 million per year (Arch Ophthalmol 1994; 112:1526-30).

While studies have found that several risks were attributed to environmental factors, twin studies have indicated a strong genetic influence on myopia with the estimates of heritability ranging from 58 to 90% (Invest Ophthalmol Vis Sci 2001; 42:1232-6; Genet Epidemiol 1988; 5:171-81; Hum Hered 1991; 41:151-6; Br J Ophthalmol 2001; 85:1470-6). Using family data, it has been reported that a family history was a significant risk factor for high myopia (Invest Ophthalmol Vis Sci 2004; 45:3446-52). Several studies also demonstrated a similar finding (Optom Vis Sci 1996; 73:279-82; JAMA 1994; 271:1323-7; Invest Ophthalmol Vis Sci 2002; 43:3633-40; Optom Vis Sci 1999; 76:387-92; Invest Ophthalmol Vis Sci 2004; 45:2873-8). However, while few papers reported identifying susceptible myopia genes, none of the studies have been replicated, thus making the identification highly questionable.

Accordingly, what is needed in the art, is a method for diagnosing, treating, preventing or ameliorating myopia and/or myopia related complications.

BRIEF SUMMARY OF THE INVENTION

The present invention provides a method for diagnosing myopia and/or myopia related complications in a subject, comprising, obtaining a biological sample from a subject; and determining at least one SNP genotype in the BICD1 gene in the biological sample, wherein the presence of the SNP genotype indicates that the subject is susceptible to myopia.

The present invention also provides a method for screening a material for treating myopia and/or myopia related complications in a subject, comprising, contacting a test material with a cell expressing the BICD1 gene, and selecting a material that modulates the expression of the BICD1 gene as compared with a control.

The present invention further provides a method for treating, preventing or ameliorating myopia and/or myopia related complications, comprising, administering to a subject a pharmaceutically effective amount of the material obtained by the method disclosed above.

The present invention further provides a method of assessing a subject for probability of response to a myopia therapeutic agent, comprising detecting at least one SNP genotype in the BICD1 gene, wherein the presence of the SNP genotype is indicative of a probability of a positive response to a myopia therapeutic agent.

The present invention further provides a kit for assaying a sample to detect a susceptibility for myopia, comprising one or more reagents for detecting one or more SNP genotype in the BICD1 gene.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
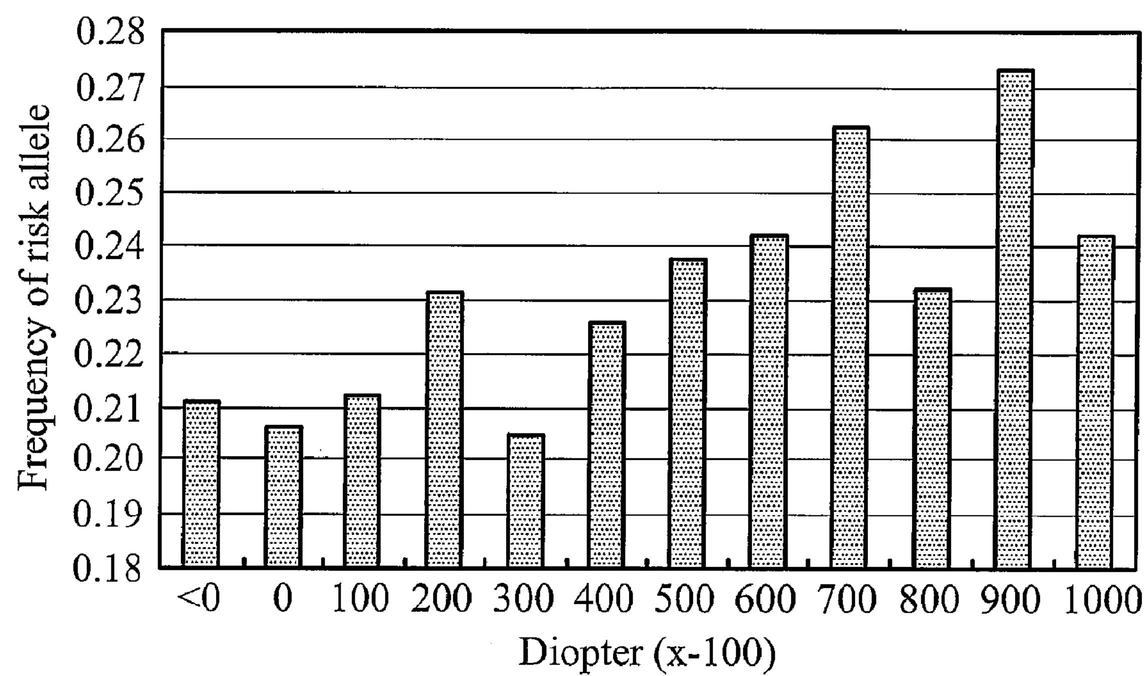
FIG. 1 shows the frequency of the risk T allele of SNP rs1151029 separated by different diopters.

The following description is of the best-contemplated mode of carrying out the invention. This description is made for the purpose of illustrating the general principles of the invention and should not be taken in a limiting sense. The scope of the invention is best determined by reference to the appended claims.

In one aspect of the invention, the present invention provides a novel method for diagnosing myopia and/or myopia related complications in a subject, comprising, obtaining a biological sample from the subject, and determining at least one SNP genotype in the BICD1 gene in the biological sample, wherein the presence of a particular allele in the SNP genotype indicates that the subject is susceptible to myopia. The diagnosis of the present invention is made by detecting a polymorphism in a BICD1 nucleic acid, such as the alleles in SNPs rs7966276, rs1151029, rs2650122, and rs10771923. The polymorphism can be a change in the BICD1 sequence, such as the change of a single nucleotide, which may cause a difference in the polypeptide encoded by the BICD1 gene, or may cause a different transcription activity.

In the method for diagnosing myopia and/or myopia related complications of the present invention, primer extension (PinPoint assay, Massextend™, SPC-SBE, or GOOD assay), hybridization (TaqMan assay, bead arry, or SNP chip), ligation (combinatorial fluorescence energy transfer (CFET) tags), and enzymatric cleavage (RFLP, Invader® assay), PCR-SSCP (single-strand conformation polymorphism), MRD (mismatch repair dection), BeadArray™, or SNPlex™ can be used. Firstly, a biological sample containing nucleic acid (DNA) is collected from a subject. The subject can be a mammalian, preferably, a human or an individual having myopia and/or myopia related complications. Examples of the subject include, but are not limited to, an adult, child, or fetus. The biological sample can be isolated or collected from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs. The DNA sample is then examined to determine whether a polymorphism of the BICD1 gene is present, and/or to determine the presence of the risk genotype in the BICD1 gene. In one embodiment, the presence of the polymorphism in the BICD1 gene can be indicated by TaqMan assay. Briefly, the PCR primers and TaqMan MGB probes are designed with Primer Express version 2.0. Reactions can be performed in 96-well microplates with GeneAmp 9700 thermal cyclers. Fluorescence can be measured with an ABI Prism 7500 sequence detection system and analyzed with the ABI Prism 7500 SDS software version 1.0. In another embodiment, the presence of SNP can be determined by genotyping as described in Mutat Res 2005; 573:70-82. Genotyping can be performed by the Illumina BeadArray technology (Sentrix® Array Matrix) [Shen, 2005 #135]. DNA is annealed to allelic-specific oligonucleotides and amplified by polymerase chain reaction (PCR). Array-based hybridization takes place and genotyping are achieved by Cy-3 and Cy-5 labeled primers. Alternately, a commercial gene chip also can be used to determine presence of SNP in BICD1 gene. The Affymetrix GeneChip® Human Mapping 500K Array Set includes two arrays, each capable of genotyping on average 250,000 SNPs (approximately 262,000 for Nsp arrays and 238,000 for Sty arrays). Genomic DNA is hybridized in accordance with the manufacturer's standard recommendations. Genotypes are determined using BRLMM clustering algorithm.

In addition, if the polymorphism results in the creation or elimination of a restriction site, a restriction digestion can be used to determine the polymorphism in the BICD1 gene. Firstly, the PCR can be used to amplify the BICD1 gene in the biological sample of genomic DNA from the subject. Next, an RFLP analysis is performed. The digestion pattern of the relevant DNA fragment indicates the presence or absence of a particular allele (or genotype) in the BICD1 gene, and therefore indicates the presence or absence for a susceptibility to myopia or a decreased susceptibility to myopia. In another embodiment, a sequence analysis can be used to determine the polymorphism in the BICD1 gene. PCR or other appropriate methods can be used to amplify the gene or nucleic acid, and/or its flanking sequences, if desired. The sequence of a BICD1 nucleic acid, or a fragment of the nucleic acid, or the BICD1 genomic DNA, or fragment of the BICD1 genomic DNA is determined, using standard methods. The sequence of the nucleic acid, nucleic acid fragment, genomic DNA, or genomic DNA fragment is compared with the known nucleic acid sequence of the gene. The presence a particular allele or genotype of a polymorphism indicates that the subject has a susceptibility to myopia and/or myopia related complications.

There are many methods for determining whether a polymorphism in the BICD1 gene is present. One of ordinary skill in the art will select the appropriate method and protocol to use. These and many other methods will be readily apparent to those of ordinary skill in the art, and are considered as equivalents within the scope of the present invention.

The term "susceptibility to myopia" of the invention refers to either an increased risk or a decreased risk of myopia, when a certain allele or SNP genotype is present. The term "decreased susceptibility to myopia" of the invention indicates that the relative risk has accordingly decreased, when a certain other allele or SNP genotype is present. The term "increased susceptibility to myopia" of the invention indicates that the relative risk has accordingly increased when a certain other allele or SNP genotype is present. In one embodiment, when the G allele in SNP rs10771923 or the T allele in SNP rs1151029 is preset, it indicates that the subject has increased susceptibility to myopia. The increased susceptibility is characterized by a relative risk of at least 1.2. In another embodiment, when the A allele in SNP rs7966276 is present, it indicates that the subject has decreased susceptibility to myopia. The decreased susceptibility is characterized by a relative risk of at least 0.6. It is understood however, that identifying whether an increased or decreased risk is medically significant may also depend on a variety of factors, including the specific disease, the marker and environmental factors.

In another aspect of the invention, the present invention also provides a method for screening a material (candidate therapeutic agents) for treating myopia and/or myopia related complications, comprising, contacting a test material with a cell expressing the BICD1 gene, and selecting a material that modulates the expression of the BICD1 gene as compared to a control.

The polymorphisms of the BICD1 gene (e.g. SNP rs7966276, rs1151029, rs2650122, and rs10771923) can also be used to identify candidate therapeutic agents for treating myopia and/or myopia related complications. The method is based on screening a candidate therapeutic agent to determine if it alters an expression profile of the BICD1 gene. For example, a cell is exposed to a test material or a combination of test materials (sequentially or consequentially) and the expression of the BICD1 gene in the cell is measured. The expression profile of the BICD1 gene in the test cell population is compared to an expression level of the BICD1 gene in a reference cell population that is not exposed to the test material. The test material can be a compound not previously described or can be a previously known compound which is not known to be an anti-myopia agent. Examples of the test materials include, but are not limited to, chemical compounds, small molecule pharmaceutical substances, carbohydrates, nucleotides, proteins, or a peptide, etc. For example, the materials can be a small interfering RNA. In one embodiment, the test material can influence or modulate the expression of the BICD1 gene through the effect of SNP rs10771923, SNP rs1151029, or SNP rs7966276 leading to prevent, reduce and/or treat myopia and/or myopia related complications.

In yet another aspect of the invention, the present invention further provides a method for treating, preventing or ameliorating myopia and/or myopia related complications, comprising, administering to a subject a pharmaceutically effective amount of the myopia therapeutic agents.

As discussed in detail above, by controlling the expression levels or activities of the BICD1 gene, the prevention, progression of myopia and/or myopia related complications can be controlled. Thus, candidate agents, which are potential targets in the treatment or prevention of myopia and/or myopia related complications, can be identified by screening test compounds using the expression levels and/or activities of the BICD1 gene.

In yet another aspect of the invention, the present method further provides a method of assessing a subject for probability of response to a myopia therapeutic agent, comprising detecting a SNP genotype in the BICD1 gene, wherein the presence of a particular allele or genotype in the SNP is indicative of a probability for a positive response to a myopia therapeutic agent.

In this method, genetic markers relating to the BICD1 gene are assessed, as described above in relation to assessing an individual for susceptibility to myopia and/or myopia related complications. The presence of an allele or SNP genotype associated with increased risk for myopia (e.g., the G allele in SNP rs10771923 or the T allele in SNP rs1151029), indicates a probability for a positive response to a myopia therapeutic agent. The term "Probability of a positive response" of the present invention refers to the concept that the subject is more likely to have a positive response to a myopia therapeutic agent than a subject not having an allele or SNP, and the subject is associated with an increased risk for myopia and/or myopia related complications.

In yet another aspect of the invention, the present invention further provides a kit for assaying a biological sample from a subject to detect susceptibility for myopia, comprising one or more reagents for detecting one or more SNP genotypes in the BICD1 gene.

The terms "kits" as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits can optionally include various electronic hardware components; for example, arrays (DNA chips) and microfluidic systems ("lab-on-a-chip" systems) provided by various manufacturers typically comprise hardware components. Other kits (e.g., probe/primer sets) may not include electronic hardware components, but may be comprised of, for example, one or more SNP detection reagents (along with, optionally, other biochemical reagents) packaged in one or more containers.

A SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment, kits are provided which contain the necessary reagents to carry out one or more assays to detect one or more SNPs disclosed herein. In another embodiment, SNP detection kits are in the form of nucleic acid arrays, or compartmentalized kits, including microfluidic/lab-on-a-chip systems.

Any number of probes, such as allele-specific probes, can be implemented in an array, and each probe or pair of probes can hybridize to a different allele position. Polynucleotide probes can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

In the present invention, the kits include for example, one or more reagents for detecting one or more SNP genotypes in the BICD1 gene, wherein the reagent includes at least one material or instrument to discriminate and detect the SNP genotypes, a buffer, and an enzyme. Examples of the materials include, but are not limited to, a nucleotide sequence that is completely complementary to a region comprising at least one SNP genotype in the BICD1 gene, a restriction enzyme (e.g. endonuclease enzyme) for recognizing a specific sequence, a labeled sequence primer, or a labeled allele-specific probe. In one embodiment, the kit for diagnosing a susceptibility to myopia can comprise primers for nucleic acid amplification of a region in the BICD1 gene comprising the SNPs rs7966276, rs1151029, rs2650122, and/or rs10771923 where the risk alleles or genotypes are more frequently present in a subject having myopia. The primers can be designed using portions of the nucleic acids flanking SNPs rs7966276, rs1151029, rs2650122, and/or rs10771923. Further, after the analysis for allelic differences, mass the mass spectrometry, fluorescence, or chemiluminescence can be used to detect the allelic differences.

EXAMPLES

Example 1

Genome Scan in the Initial Step

A total of about 4000 subjects were recruited for the myopia study. There were multiple sources for participants, whom included the following: (1) young men in military conscripts, (2) university students, (3) hospital personnel, and (4) patients from ophthalmology clinics. Individuals with spherical refraction≧−6.0 D in one eye and ≦−4.0 D in the other eye were classified as high myopia. A subject was defined as a control if the worse eye had a spherical refraction≧—1.5 D. All subjects were between the ages of 17-45 years old. All the participants were of Chinese descent. All participants gave informed consents. The study was approved by the Institutional Review Board at the Kaohsiung Medical University, Kaohsiung, Taiwan.

In the initial step, Affymetrix GeneChip® Human Mapping 500K Array Set was used. It comprised two arrays, each capable of genotyping on average 250,000 SNPs (approximately 262,000 for Nsp arrays and 238,000 for Sty arrays). To ensure the quality of DNA sample, all DNA were required to have the OD 260/280 between 1.7 and 2.0, and 260/230>1.0. About 1.5 μg (30 μl of 50 ng/μl) genomic DNA was required for genotyping. The images were analyzed using BRLMM algorithm to obtain the genotyping data. To remove an SNP or a sample which might have genotyping problems, the following criteria was used: per sample call rate of at least 90%, per SNP call rate of at least 90%, an SNP with the minor allele frequency of at least 1%, and genotypes in Hardy-Weinberg equilibrium (p>0.001). Taken together, 380619 SNPs were considered for further analysis.

To test for allelic and genotypic association between each SNP and the high myopia status, PLINK program (*Am J Hum Genet* 2007; 81:559-75) was used to calculate genotype and allele frequencies, and to perform $\chi^2$ test. To investigate the genotypic association under different inheritance models, genotype data were further encoded into dominant, recessive, and additive modes. In addition, the trend test was also performed. The genetic effect along with covariates (sex and age) was included in the logistic regression. A linear regression model was applied to test for the association between each SNP and the refraction errors. Since the refraction errors greater than −3 D were common in the Taiwanese population, the subjects as normal/mild myopia (≧−3 D) and high myopia (≦−6 D) was also dichotomized, and the discrete phenotype was tested in the logistic regression model. For logistic regression analysis, subjects with refraction between −3 and −6 D were not included in the analysis. Hap-clustering was employed to perform haplotype analysis.

For the Affymetrix 500K SNP chips, the average call rate was 98.7 (ranging from 97.4 to 99.5). The initial analysis indicated that the best 10 SNPs had the highest p value=0.0002. The 10 SNPs are on chromosome 1, 2, 4, 6, 12, 16, 17 and 21, and none of them are closely located.

Example 2

Genome Scan in the Second Step

In the second step, firstly the 10 best SNPs as the centers was used, and a genomic region of 200 kb surrounding each of the 10 best SNPs as our candidate region was selected. A total of 384 tagging SNPs were selected for follow-up fine mapping in independent 1536 subjects whose refraction errors were either <−6 D or >−1.5 D. Genotyping was performed by the Illumina BeadArray technology (Sentrix® Array Matrix) (Mutat Res 2005; 573:70-82). DNA was annealed to allelic-specific oligonucleotides and amplified by polymerase chain reaction. Array-based hybridization took place and genotyping were achieved by Cy-3 and Cy-5 labeled primers. Thirty replicates of each SNP were done to ensure the highest quality of genotype calling.

The overall call rate in the second stage was 97.1%. The most significant SNP (rs7966276) was at the BICD1 gene on chromosome 12p11 with a p value <$1.13\times10^{-4}$. Another three SNPs at BICD1 were also significant (SNP rs1151029, p=$4.78\times10^{-4}$; SNP rs2650122, p=$3.65\times10^{-2}$; SNP rs10771923, p=$2.70\times10^{-2}$).

Example 3

Genome Scan in the Third Step

In the third step, the most promising SNPs based on the stage II result were genotyped by using the TaqMan technology (Applied Biosystems [ABI], Foster City, USA). Briefly, PCR primers and TaqMan MGB probes were designed with Primer Express version 2.0. Reactions were performed in 96-well microplates with GeneAmp 9700 thermal cyclers. Fluorescence was measured with an ABI Prism 7500 sequence detection system and analyzed with the ABI Prism 7500 SDS software version 1.0. The subjects with refraction errors between −6 D and −1.5 D were used in the stage III study.

In the third step, the BICD1 gene was focused and the genetic effect was analyzed using different inheritance models for the three SNPs in a larger dataset including, SNP rs10771923 in 3273 subjects, SNP rs1151029 in 3917 subjects and SNP rs7966276 in 2962 subjects. The allele frequencies of the three SNPs are listed in Table 1. Referring to Table 2, the most significant results were from the dichotomized phenotype (>−3 D as control and ≦6 D as case) when minor G allele of rs10771923 had an additive effect (p=0.00088, OR=1.22) or the minor allele T of rs1151029 had a dominant deleterious effect (p=0.00088, OR=1.3). SNP rs7966276 had less significant results when compared with the other two SNPs. When the phenotype was treated as a continuous trait, the three SNPs showed different significant results as illustrated in Table 3. Referring to FIG. 1, the frequency of the risk T allele of rs1151029 separated by different diopters was calculated. The a-x-axis is the negative diopter (×100).

TABLE 1

Allele frequency and the number of genotyped individuals for the BICD1 gene

| | rs10771923 | | rs1151029 | | rs7966276 | |
|---|---|---|---|---|---|---|
| Refraction errors | sample size | MAF | sample size | MAF | sample size | MAF |
| ≧−3 D | 1305 | 0.375 | 0630 | 0.211 | 1215 | 0.040 |
| −3 D to −6 D | 941 | 0.400 | 1148 | 0.228 | 953 | 0.027 |
| ≦−6 D | 1027 | 0.423 | 1139 | 0.247 | 794 | 0.025 |
| Total | 3273 | 0.397 | 3917 | 0.226 | 2962 | 0.032 |

MAF: minor allele frequency

TABLE 2 results of the dichotomized trait (normal/mild vs. high myopia) from logistic regression

| | Genotype | | | | OR (p value) | | |
|---|---|---|---|---|---|---|---|
| | N (%) | N (%) | N (%) | Total | Additive | Dominant | Recessive |
| rs10771923 | AA | AG | GG | | | | |
| ≧−3 D | 509 (39.0) | 614 (47.1) | 182 (14.0) | 1305 | 1.22 (0.00088) | 1.30 (0.0024) | 1.30 (0.021) |
| ≦−6 D | 338 (32.9) | 510 (49.7) | 179 (17.4) | 1027 | | | |

TABLE 2-continued results of the dichotomized trait (normal/mild vs. high myopia) from logistic regression

| rs1151029 | AA | AT | TT | | | | |
|---|---|---|---|---|---|---|---|
| ≧−3 D | 1027 (63.0) | 519 (31.8) | 84 (5.15) | 1630 | 1.22 (0.0017) | 1.30 (0.00088) | 1.21 (0.263) |
| ≦−6 D | 646 (56.7) | 423 (37.1) | 70 (6.14) | 1139 | | | |
| **rs7966276** | **TT** | **AT** | **AA** | | | | |
| ≧−3 D | 1122 (92.3) | 90 (7.40) | 3 (0.24) | 1215 | 0.61 (0.0114) | 0.62 (0.0161) | |
| ≦−6 D | 755 (95.0) | 39 (4.91) | 0 (0) | 794 | | | |

TABLE 3

Results based on the refractive errors in the linear regression model

| | Genotype (categorical) | Additive | | Dominant | | Recessive | |
|---|---|---|---|---|---|---|---|
| | p value | beta × 100 | p value | beta × 100 | p value | beta × 100 | p value |
| rs10771923 | 0.0128 | 48.4 | 0.0032 | 29.2 | 0.0115 | 35.4 | 0.0230 |
| rs1151029 | 0.020 | 46.9 | 0.0060 | 28.8 | 0.0060 | 29.6 | 0.181 |
| rs7966276 | 0.022 | −125.1 | 0.0060 | −62.7 | 0.0077 | −173.8 | 0.260 |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of determining an increased risk of developing myopia in a human, comprising detecting in a sample from the human the SNP rs7966276 (A/T) in the BICD1 gene, and determining the risk of developing myopia in the human, wherein the presence of the TT genotype is detected at the SNP rs7966276 (A/T) and indicates that the human has an increased risk of developing high myopia, and wherein the high myopia comprises a spherical refraction ≦−6 D.

2. The method as claimed in claim 1, wherein the sample comprises blood, amniotic fluid, cerebrospinal fluid, tissue from skin, muscle, buccal or conjunctival mucosa, placenta, or gastrointestinal tract.

* * * * *